US011352357B2

(12) United States Patent
Ideue et al.

(10) Patent No.: US 11,352,357 B2
(45) Date of Patent: Jun. 7, 2022

(54) CYCLOALKYLUREA DERIVATIVE

(71) Applicant: Sumitomo Dainippon Pharma Co., Ltd., Osaka (JP)

(72) Inventors: Eiji Ideue, Osaka (JP); Masafumi Komiya, Osaka (JP); Shoukou Lee, Osaka (JP); Shunichiro Uesugi, Osaka (JP); Yuta Funakoshi, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 17/526,722

(22) Filed: Nov. 15, 2021

(65) Prior Publication Data

US 2022/0081441 A1 Mar. 17, 2022

Related U.S. Application Data

(63) Continuation of application No. 17/610,291, filed as application No. PCT/JP2020/044047 on Nov. 26, 2020.

(30) Foreign Application Priority Data

Nov. 27, 2019 (JP) .............................. JP2019-213860

(51) Int. Cl.
| C07D 471/04 | (2006.01) |
| C07D 519/00 | (2006.01) |
| C07D 487/04 | (2006.01) |

(52) U.S. Cl.
CPC .................................. *C07D 471/04* (2013.01)

(58) Field of Classification Search
CPC ... C07D 471/04; C07D 519/00; C07D 487/04
USPC .................................................... 514/213.01
See application file for complete search history.

(56) References Cited

U.S. PATENT DOCUMENTS 7,700,591 B2 * 4/2010 Goble .................... A61P 37/00
514/229.5

FOREIGN PATENT DOCUMENTS

| EP | 3029024 A1 | 8/2016 |
| JP | 2007-534638 A | 11/2007 |
| JP | 2008-531542 A | 8/2008 |
| JP | 2016-537324 A | 12/2016 |
| JP | 2018-500280 A | 1/2018 |
| JP | 2019-504098 A | 2/2019 |
| JP | 2019-527688 A | 10/2019 |
| WO | WO 2005/105802 A1 | 11/2005 |
| WO | WO 2006/090261 A1 | 8/2006 |
| WO | WO 2015/055994 A1 | 4/2015 |
| WO | WO 2016/069374 A1 | 5/2016 |
| WO | WO 2017/135306 A1 | 8/2017 |
| WO | WO 2019/027058 A1 | 2/2019 |

OTHER PUBLICATIONS

International Search Report dated Jan. 7, 2021 in PCT/JP2020/044047.
Takeshi Sakurai, et al.,"Orexins and Orexin Receptors: A Family of Hypothalamic Neuropeptides and G Protein-Coupled Receptors that Regulate Feeding Behavior", Cell, vol. 92, 573-585, 1998.
Michihiro Mieda, et al., "Orexin peptides prevent cataplexy and improve wakefulness in an orexin neuron-ablated model of narcolepsy in mice", Proc. Natl. Acad. Sci. USA, vol. 101, 4649-4654, 2004.
Richard M. Chemelli, et al., "Narcolepsy in orexin Knockout Mice:Molecular Genetics of Sleep Regulation", Cell, vol. 98, 437-451, 1999.
Seiji Nishino, et al.. "Hypocretin (orexin) deficiency in human narcolepsy", The Lancet, vol. 355, 39-40, 2000.
Ling Lin, et al., "The Sleep Disorder Canine Narcolepsy Is Caused by a Mutation in the *Hypocretin* (*Orexin*) *Receptor* 2 Gene", Cell, vol. 98, 365-376, 1999.
Jon T. Willie, et al., "Distinct Narcolepsy Syndromes in *Orexin Receptor*-2 and *Orexin* Null Mice: Molecular Genetic Dissection of Non-REM and REM Sleep Regulatory ProcessesNeuron", vol. 38, 715-730, 2003.
Rolf Fronczek, et al., "Hypocretin (orexin) loss in Parkinson's disease", Brain, vol. 130, 1577-1585, 2007.
Koji Kasanuki, et al., "Neuropathological investigation of hypocretin expression in brains of dementia with Lewy bodies", Neuroscience Letters, vol. 569, 68-73, 2014.

* cited by examiner

*Primary Examiner* — Niloofar Rahmani
(74) *Attorney, Agent, or Firm* — Oblon, McClelland, Maier & Neustadt, L.L.P.

(57) ABSTRACT

The present invention relates to a medicament for treating or preventing a disease related to orexin receptor, especially orexin type 2 receptor, comprising a new compound having a urea structure or a pharmaceutically acceptable salt thereof as an active ingredient. In more detail, the present invention relates to a medicament for treating or preventing narcolepsy, idiopathic hypersomnia, hypersomnia, sleep apnea syndrome, etc.

28 Claims, No Drawings

CYCLOALKYLUREA DERIVATIVE

RELATED APPLICATIONS

This application is a continuation of U.S. application Ser. No. 17/610,291, filed Nov. 10, 2021, which is a national stage application of PCT/JP2020/044047, filed Nov. 26, 2020 and claims benefit of Japanese application 2019-213860, filed Nov. 27, 2019, The entire contents of all three applications is incorporated herein by reference.

TECHNICAL FIELD

The present invention relates to a medicament for treating or preventing a disease related to orexin receptor, especially orexin type 2 receptor, comprising a new compound having a urea structure or a pharmaceutically acceptable salt thereof as an active ingredient. In more detail, the present invention relates to a medicament for treating or preventing narcolepsy, idiopathic hypersomnia, hypersomnia, sleep apnea syndrome, etc.

BACKGROUND ART

Orexin is a neuropeptide which is specifically produced in a specific neuron spreading across lateral hypothalamus and its adjacent region. Orexin is an endogenous ligand of orexin receptor that is a G-protein-coupled receptor existing mainly in brain, which binds to orexin receptor. It is known that orexin receptor has two subtypes, type 1 and type 2 (Non-patent Reference 1).

It was reported that a narcolepsy-like symptom in a transgenic mouse whose orexin neuron was denatured could be improved by intraventricular injection of an orexin peptide (Non-patent Reference 2), and a narcolepsy-like symptom could be initiated by knocking out prepro-orexin which is a precursor protein of orexin (Non-patent Reference 3), furthermore the orexin concentration in cerebrospinal fluid of narcolepsy patients was markedly lowered (Non-patent Reference 4). Thus, it is suggested that narcolepsy can be initiated due to lack of orexin.

In addition, it was reported that there was a mutation of orexin 2 receptor in a dog suffering from hereditary narcolepsy (Non-patent Reference 5), which suggests that orexin 2 receptor is involved in sleep-wake function. Furthermore, it was revealed that narcolepsy-like symptom was initiated in a KO mouse of orexin 2 receptor (Non-patent Reference 6), which strongly suggests that the stimulation on orexin 2 receptor is involved in sleep-wake function. Thus, an orexin 2 receptor agonist is expected to be a hopeful therapy for a patient presenting with hypersomnia-like symptom such as narcolepsy.

Recently, a compound having orexin 2 receptor agonistic action has been reported (Patent Reference 1).

PRIOR ART

Patent Reference

[Patent Literature 1] WO 2017/135306

Non-Patent Reference

[Non-patent Literature 1] Cell, Vol. 92, 573-585, 1998
[Non-patent Literature 2] Proc. Natl. Acad. Sci. USA, Vol. 101, 4649-4654, 2004
[Non-patent Literature 3] Cell, Vol. 98, 437-451, 1999
[Non-patent Literature 4] THE LANCET, Vol. 355, 39-40, 2000
[Non-patent Literature 5] Cell, Vol. 98, 365-376, 1999
[Non-patent Literature 6] Neuron, Vol. 38, 715-730, 2003
[Non-patent Literature 7] Brain, Vol. 130, 1577-1585, 2007
[Non-patent Literature 8] Neuroscience Letters, Vol. 569, 68-73, 2014

SUMMARY OF INVENTION

Technical Problem

The purpose of the present invention may be to provide a medicament for treating or preventing a disease related to orexin type 2 receptor, for example, narcolepsy, idiopathic hypersomnia, hypersomnia, sleep apnea syndrome, etc.

Solution to Problem

The present inventors have extensively studied to reach the above purpose, and then have found that a compound of the following formula (1) or a pharmaceutically acceptable salt thereof (hereinafter, it may be referred to as "the present compound") has therapeutic and preventive effect for a disease related to orexin type 2 receptor, for example, narcolepsy, idiopathic hypersomnia, hypersomnia, sleep apnea syndrome, etc. Based upon the new findings, the present invention has been completed.

The present invention can show as follows.

ITEM A1

A compound of formula (1):

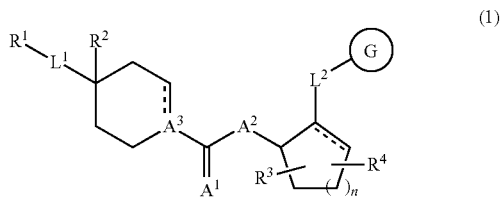

or a pharmaceutically acceptable salt thereof wherein
$R^1$ is optionally-substituted $C_{6-10}$ aromatic carbocyclyl group, optionally-substituted 5- to 10-membered aromatic heterocyclyl group, optionally-substituted $C_{3-6}$ saturated carbocyclyl group, optionally-substituted 4- to 10-membered saturated heterocyclyl group, or cyano;
$L^1$ and $L^2$ are each independently single bond, —$CH_2$—, or oxygen atom;
$R^2$ is hydrogen atom, hydroxy group, halogen atom, cyano, or optionally-substituted $C_{1-4}$ alkyl; or
when $L^1$ is single bond, $R^1$ and $R^2$ may be combined together as a spiro ring to form optionally-substituted $C_{3-6}$ saturated carbocyclic ring or optionally-substituted 4- to 10-membered saturated heteroring;
$R^3$ and $R^4$ are each independently hydrogen atom, halogen atom, cyano, —(C=O)$NR^5R^6$, carboxy group, —(C=O)O—$R^7$, optionally-substituted $C_{1-4}$ alkyl, or optionally-substituted $C_{1-4}$ alkoxy, wherein $R^3$ and $R^4$ may bind to the same carbon atom if chemically possible; or
when $R^3$ and $R^4$ bind to different ring carbon atoms, $R^3$ and $R^4$ may be taken together via $C_{1-6}$ alkylene to form a fused ring or a bridged ring;

$R^5$ to $R^7$ are each independently hydrogen atom, halogen atom, or optionally-substituted $C_{1-4}$ alkyl;

n is an integer of 1 or 2;

Ring G is optionally-substituted $C_{6-10}$ aromatic carbocyclyl group, optionally-substituted 5- to 10-membered aromatic heterocyclyl group, optionally-substituted $C_{3-6}$ saturated carbocyclyl group, or optionally-substituted 4- to 10-membered saturated heterocyclyl group;

$A^1$ is oxygen atom or sulfur atom;

$A^2$ is oxygen atom or —NH—;

$A^3$ is —CH—, nitrogen atom, or carbon atom; and the bond accompanied with broken line is each independently single bond or double bond.

ITEM A2

The compound of Item A1 or a pharmaceutically acceptable salt thereof, wherein in $R^2$-$R^7$, the optional substituent of "optionally-substituted $C_{1-4}$ alkyl" is the same or different one or more substituents selected from the group consisting of halogen atom, hydroxy group, $C_{1-4}$ alkoxy, and $C_{3-7}$ cycloalkyl; and the optional substituent of "optionally-substituted $C_{1-4}$ alkoxy" is the same or different one or more substituents selected from the group consisting of halogen atom, hydroxy group, $C_{1-4}$ alkyl, and $C_{3-7}$ cycloalkyl;

in $R^1$, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of hydrogen atom, halogen atom, hydroxy group, $C_{6-10}$ aromatic carbocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-4}$ alkyl (which may be optionally substituted with the same or different one or more substituents selected from the group consisting of halogen atom, hydroxy group, $C_{1-4}$ alkoxy, and $C_{3-7}$ cycloalkyl), $C_{3-7}$ cycloalkyl (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{3-7}$ cycloalkoxy (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), cyano, $C_{1-4}$ alkoxy (which may be optionally substituted with the same or different one or more substituents selected from the group consisting of halogen atom, hydroxy group, $C_{1-4}$ alkyl optionally-substituted with the same or different one or more halogen atoms, and $C_{3-7}$ cycloalkyl), and 5- to 10-membered aromatic heterocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl); and in Ring G, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of halogen atom, $C_{1-6}$ alkyl (which may be optionally substituted with the same or different one or more substituents selected from the group consisting of halogen atom, hydroxy group, $C_{1-4}$ alkoxy, and $C_{3-7}$ cycloalkyl), $C_{6-10}$ aromatic carbocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-4}$ alkoxy (which may be optionally substituted with the same or different one or more substituents selected from the group consisting of halogen atom, hydroxy group, $C_{1-4}$ alkyl, and $C_{3-7}$ cycloalkyl), $C_{3-7}$ cycloalkyl (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), and $C_{3-7}$ cycloalkoxy (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl); or when there are plural optional substituents, two of them may be taken together via $C_{1-6}$ alkylene to form a chemically-possible bicyclic structure selected from a fused ring, a spiro ring, and bridged ring.

ITEM A3

The compound of Item A1 or A2 or a pharmaceutically acceptable salt thereof, wherein in $R^2$-$R^7$, the optional substituent of "optionally-substituted $C_{1-4}$ alkyl" is the same or different one or more substituents selected from the group consisting of halogen atom and $C_{1-4}$ alkoxy; and the optional substituent of "optionally-substituted $C_{1-4}$ alkoxy" is the same or different one or more substituents selected from the group consisting of halogen atom and $C_{1-4}$ alkyl;

in $R^1$, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of hydrogen atom, halogen atom, hydroxy group, $C_{6-10}$ aromatic carbocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-4}$ alkyl (which may be optionally substituted with the same or different one or more substituents selected from the group consisting of halogen atom, hydroxy group, $C_{1-4}$ alkoxy, and $C_{3-7}$ cycloalkyl), $C_{3-7}$ cycloalkyl (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), cyano, $C_{1-4}$ alkoxy (which may be optionally substituted with the same or different one or more substituents selected from the group consisting of halogen atom, hydroxy group, $C_{1-4}$ alkyl optionally-substituted with the same or different one or more halogen atoms, and $C_{3-7}$ cycloalkyl), and 5- to 10-membered aromatic heterocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl); and in Ring G, the optional substituent of "optionally substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated; heterocyclyl group" is each independently at least one substituent selected from the group consisting of halogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), and $C_{3-7}$ cycloalkoxy (which may be optionally substituted with the same or different one or more substituents selected from the group consisting of halogen atom, $C_{4-4}$ alkyl, and $C_{1-4}$ alkoxy); or when there are plural optional substituents, two of them may be taken together via $C_{1-6}$ alkylene to form a chemically-possible bicyclic structure selected from a fused ring, a spiro ring, and bridged ring.

ITEM A4

The compound of any one of Items A1 to A3 or a pharmaceutically acceptable salt thereof, wherein $R^1$ is selected from the following formulae (1a-1) to (1a-4):

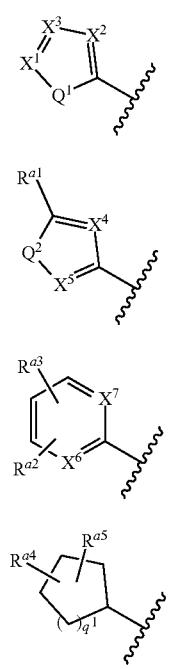

wherein $X^1$-$X^7$ are each independently nitrogen atom or $CR^{a6}$;

$Q^1$ and $Q^2$ are oxygen atom, $-NR^{a7}-$, or sulfur atom;

$R^{a1}$-$R^{a7}$ are each independently (if there are plural $CR^{a6}$, each $R^{a6}$ is also independently), hydrogen atom, halogen atom, $C_{6-10}$ aromatic carbocyclyl group (which may be optionally substituted with the same or different one or more substituents selected from the group consisting of halogen atom, hydroxy group, $C_{1-4}$ alkyl, and $C_{1-4}$ alkoxy), $C_{1-4}$ alkyl (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), cyano, $C_{1-4}$ alkoxy (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkoxy (which may be optionally substituted with the same or different one or more substituents selected from the group consisting of halogen atom, hydroxy group, $C_{1-4}$ alkyl, and $C_{1-4}$ alkoxy), or 5- to 10-membered aromatic heterocyclyl group; wherein $R^{a4}$ and $R^{a5}$ may bind to the same carbon atom if chemically possible; and when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$; and $q^1$ is an integer of 1 or 2.

ITEM A5

The compound of any one of Items A1 to A4 or a pharmaceutically acceptable salt thereof, wherein Ring G is selected from the following (1b-1) to (1b-4):

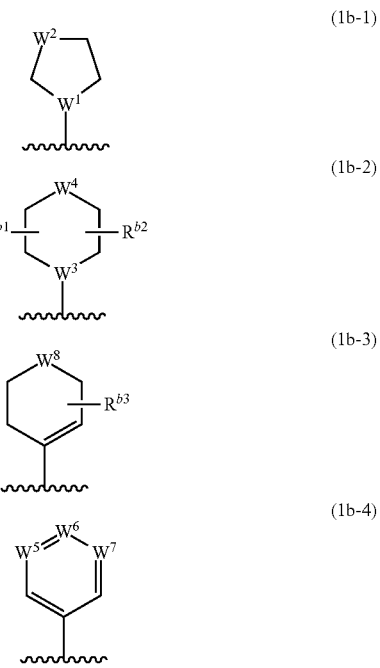

wherein $W^1$, $W^3$, $W^5$, $W^6$, and $W^7$ are each independently nitrogen atom or $CR^{b4}$;

$W^2$, $W^4$, and $W^8$ are $NR^{b5}$, oxygen atom, or $CR^{b6}R^{b7}$;

$R^{b1}$-$R^{b7}$ are each independently (if there are plural $CR^{b4}$, each $R^{b4}$ is also independently), hydrogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a chemically-possible bicyclic structure selected from a fused ring, a spiro ring, and bridged ring.

ITEM A6

The compound of any one of Items A1 to A5 of formula (2):

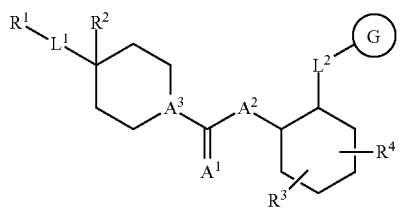

(2)

or a pharmaceutically acceptable salt thereof, wherein
$R^1$ is selected from the following formulae (1a-1) to (1a-4):

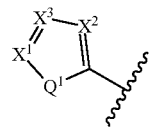

(1a-1)

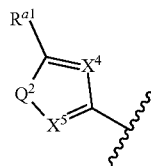

(1a-2)

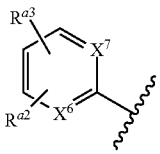

(1a-3)

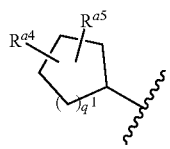

(1a-4)

wherein
$X^1$-$X^7$ are each independently nitrogen atom or $CR^{a6}$;
$Q^1$ and $Q^2$ are oxygen atom, —$NR^{a7}$—, or sulfur atom;
$R^{a1}$-$R^{a7}$ are each independently (if there are plural $CR^{a6}$, each $R^{a6}$ is also independently), hydrogen atom, halogen atom, $C_{6-10}$ aromatic carbocyclyl group (which may be optionally substituted with the same or different one or more substituents selected from the group consisting of halogen atom, hydroxy group, $C_{1-4}$ alkyl, and $C_{1-4}$ alkoxy), $C_{1-4}$ alkyl (which may be optionally substituted with the same or different one or more substituents selected from the group consisting of halogen atom, hydroxy group, $C_{1-4}$ alkyl, and $C_{1-4}$ alkoxy), $C_{3-6}$ cycloalkyl (which may be optionally substituted with the same or different one or more substituents selected from the group consisting of halogen atom, hydroxy group, $C_{1-4}$ alkyl, and $C_{1-4}$ alkoxy), cyano, $C_{1-4}$ alkoxy (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkoxy (which may be optionally substituted with the same or different one or more substituents selected from the group consisting of halogen atom, hydroxy group, $C_{1-4}$ alkyl, and $C_{1-4}$ alkoxy), or 5- to 10-membered aromatic heterocyclyl group; wherein $R^{a4}$ and $R^{a5}$ may bind to the same carbon atom if chemically possible; and when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$; and $q^1$ is an integer of 1 or 2;

$L^1$ and $L^2$ are each independently single bond, —$CH_2$—, or oxygen atom;

$R^2$ is hydrogen atom, hydroxy group, halogen atom, cyano, or optionally-substituted $C_{1-4}$ alkyl;

$R^3$ and $R^4$ are each independently hydrogen atom, halogen atom, $C_{1-4}$ alkyl (which may be optionally substituted with the same or different one or more substituents selected from the group consisting of halogen atom, hydroxy group, $C_{1-4}$ alkoxy, and $C_{3-7}$ cycloalkyl), or $C_{1-4}$ alkoxy (which may be optionally substituted with the same or different one or more substituents selected from the group consisting of halogen atom, hydroxy group, $C_{1-4}$ alkyl, and $C_{3-7}$ cycloalkyl); wherein $R^3$ and $R^4$ may bind to the same carbon atom if chemically possible; and when $R^3$ and $R^4$ bind to different carbon atoms on the ring, $R^3$ and $R^4$ may be taken together via $C_{1-6}$ alkylene to form a fused ring or bridged ring;

Ring G is selected from the following (1b-1) to (1b-4):

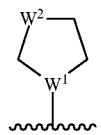

(1b-1)

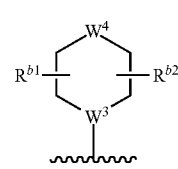

(1b-2)

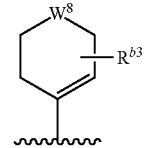

(1b-3)

-continued (1b-4)

wherein
$W^1$, $W^3$, $W^5$, $W^6$, and $W^7$ are each independently nitrogen atom or $CR^{b4}$;
$W^2$, $W^4$, and $W^8$ are $NR^{b5}$, oxygen atom or $CR^{b6}R^{b7}$;
$R^{b3}$-$R^{b7}$ are each independently (if there are plural $CR^{b4}$, each $R^{b4}$ is also independently), hydrogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{4-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a chemically-possible bicyclic structure selected from a fused ring, a spiro ring, and bridged ring;
$A^1$ is oxygen atom or sulfur atom;
$A^2$ is oxygen atom or —NH—; and
$A^3$ is —CH—, nitrogen atom, or carbon atom.

ITEM A7

The compound of Item A6 or a pharmaceutically acceptable salt thereof, wherein
$R^1$ is selected from the following formulae (1a-1), (1a-2), and (1a-3-1):

(1a-1)

(1a-2)

(1a-3-1)

wherein
$X^1$-$X^6$ are each independently nitrogen atom or $CR^{a6}$;
$Q^1$ and $Q^2$ are oxygen atom, —$NR^{a7}$—, or sulfur atom; and
$R^{a1}$-$R^{a3}$, $R^{a6}$, and $R^{a7}$ are each independently (if there are plural $CR^{a6}$, each $R^{a6}$ is also independently), hydrogen atom, halogen atom, $C_{6-10}$ aromatic carbocyclyl group (which may be optionally substituted with the same or different one or more substituents selected from the group consisting of halogen atom, hydroxy group, $C_{1-4}$ alkyl, and $C_{1-4}$ alkoxy), $C_{1-4}$ alkyl (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), cyano, $C_{1-4}$ alkoxy (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkoxy (which may be optionally substituted with the same or different one or more substituents selected from the group consisting of halogen atom, hydroxy group, $C_{1-4}$ alkyl, and $C_{1-4}$ alkoxy), or 5- to 10-membered aromatic heterocyclyl group; wherein when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$.

ITEM A8

The compound of Items A6 or A7 or a pharmaceutically acceptable salt thereof, wherein
Ring G is selected from the following (1b-1), (1b-2), and (1b-4):

(1b-1)

(1b-2)

(1b-4)

wherein
$W^1$, $W^3$, $W^5$, $W^6$, and $W^7$ are each independently nitrogen atom or $CR^{b4}$;
$W^2$ and $W^4$ are $NR^{b5}$ or $CR^{b6}R^{b7}$; and
$R^{b1}$, $R^{b2}$, and $R^{b4}$-$R^{b7}$ are each independently (if there are plural $CR^{b4}$, each $R^{b4}$ is also independently), hydrogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{4-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a bridged bicyclic structure.

ITEM A9

The compound of any one of Items A6 to A8 or a pharmaceutically acceptable salt thereof, wherein Ring G is selected from the following (1b-1) and (1b-2):

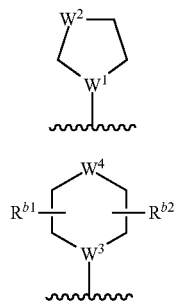

wherein $W^1$ and $W^3$ are nitrogen atom or $CR^{b4}$;

$W^2$ and $W^4$ are $NR^{b5}$ or $CR^{b6}R^{b7}$; and $R^{b1}$, $R^{b2}$, and $R^{b4}$-$R^{b7}$ are each independently hydrogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a bridged bicyclic structure.

ITEM A10

The compound of any one of Items A1 to A9 of formula (3):

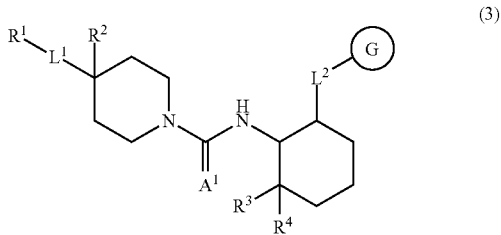

or a pharmaceutically acceptable salt thereof, wherein
$R^1$ is the following formula (1a-1), (1a-2), or (1a-3-1):

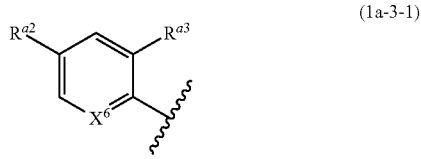

wherein
$X^1$-$X^6$ are each independently nitrogen atom or $CR^{a6}$;

$Q^1$ and $Q^2$ are oxygen atom or sulfur atom;

$R^{a1}$-$R^{a3}$ and $R^{a6}$ are each independently (if there are plural $CR^{a5}$, each $R^{a6}$ is also independently), hydrogen atom, halogen atom, $C_{1-4}$ alkyl (which may be optionally substituted with the same or different one or more substituents selected from the group consisting of halogen atom, hydroxy group, and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), cyano, or $C_{1-4}$ alkoxy (which may be optionally substituted with the same or different one or more substituents selected from the group consisting of halogen atom, hydroxy group, $C_{1-4}$ alkyl, and $C_{1-4}$ alkoxy); wherein when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$;

$L^1$ and $L^2$ are each independently single bond or oxygen atom;

$R^2$ is hydrogen atom, halogen atom, or $C_{1-4}$ alkyl which may be optionally substituted with the same or different one or more substituents selected from the group consisting of halogen atom and hydroxy group;

$R^3$ and $R^4$ are each independently halogen atom;

Ring G is the following (1b-1), (1b-2-1), (1b-2-2), or (1b-2-3):

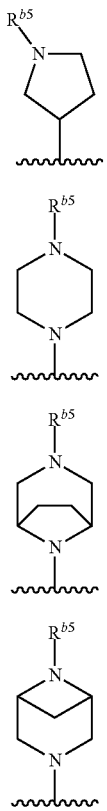

wherein
$R^{b5}$ is hydrogen atom, or $C_{1-6}$ alkyl which may be optionally substituted with the same or different one or more substituents selected from the group consisting of halogen atom and $C_{1-4}$ alkoxy; and
$A^1$ is oxygen atom or sulfur atom.

ITEM A11

The compound of any one of Items A4 to A10 or a pharmaceutically acceptable salt thereof, wherein
$R^1$ is formula (1a-2), and
$R^{a1}$ is hydrogen atom, halogen atom, $C_{1-4}$ alkyl (which may be optionally substituted with the same or different one or more substituents selected from the group consisting of halogen atom and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), or t $C_{1-4}$ alkoxy (which may be optionally substituted with the same or different one or more substituents selected from the group consisting of halogen atom and $C_{1-4}$ alkyl).

ITEM A12

The compound of Item A10 or A11 or a pharmaceutically acceptable salt thereof, wherein
$R^1$ is formula (1a-2), and
$X^4$ and $X^5$ are both nitrogen atom.

ITEM A13

The compound of any one of Items A10 to A12 or a pharmaceutically acceptable salt thereof, wherein
Ring G is formula (1b-1-1), and
$R^{b5}$ is $C_{1-4}$ alkyl which may be optionally substituted with the same or different one or more halogen atoms.

ITEM A14

The compound of any one of Items A10 to A12 or a pharmaceutically acceptable salt thereof, wherein
Ring G is formula (1b-2-1), and
$R^{b5}$ is hydrogen atom, or $C_{1-4}$ alkyl which may be optionally substituted with the same or different one or more substituents selected from the group consisting of halogen atom and $C_{1-4}$ alkoxy.

ITEM A15

The compound of any one of Items A1 to A12 of formula (4):

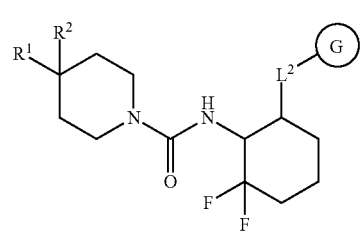

or a pharmaceutically acceptable salt thereof, wherein
$R^1$ is the following (1a-2-1):

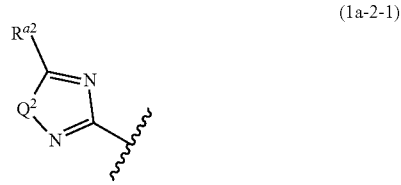

wherein
$Q^2$ is oxygen atom or sulfur atom;
$R^{a2}$ is $C_{3-7}$ cycloalkyl group (which may be optionally substituted with the same or different one or more substituents selected from the group consisting of halogen atom, $C_{1-4}$ alkyl, and $C_{1-4}$ alkoxy) or cycloalkoxy group (which may be optionally substituted with the same or different one or more substituents selected from the group consisting of halogen atom, $C_{1-4}$ alkyl, and $C_{1-4}$ alkoxy);
$R^2$ is $C_{1-4}$ alkyl;
Ring G is the following (1b-1-1) or (1b-2-1):

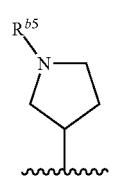

-continued (1b-2-1)

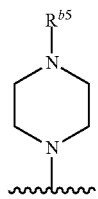

wherein

R$^{b5}$ is C$_{1-4}$ alkyl which may be optionally substituted with the same or different one or more substituents selected from the group consisting of halogen atom and C$_{1-4}$ alkyl; and L$^2$ is single bond or oxygen atom.

ITEM A16

The compound of Item A15 or a pharmaceutically acceptable salt thereof, wherein

R$^{a2}$ is C$_{3-7}$ cycloalkyl group which may be optionally substituted with the same or different one or more substituents selected from halogen atoms, and R$^2$ is methyl group.

ITEM A17

The compound of Item A15 or A16 or a pharmaceutically acceptable salt thereof, wherein R$^{a2}$ is cyclopropyl group which may be optionally substituted with the same or different one or more substituents selected from halogen atoms, and R$^2$ is methyl group.

ITEM A18

The compound of any one of Items A15 to A17 or a pharmaceutically acceptable salt thereof, wherein Ring G is formula (1b-2-1), and R$^{b8}$ is isopropyl group.

ITEM A19

The compound of any one of Items A15 to A17 or a pharmaceutically acceptable salt thereof, wherein Ring G is formula (1b-1-1), R$^{b5}$ is isopropyl group, and L$^2$ is oxygen atom.

ITEM A20

The compound of any one of Items A15 to A19 or a pharmaceutically acceptable salt thereof, wherein Q$^2$ is oxygen atom.

ITEM A21

The compound of Item A1 or a pharmaceutically acceptable salt thereof, which is selected from the following compound names or structures:

Example 22: 4-(5-cyclopropyl-1,2-oxazol-3-yl)-N-{(1S,6R)-2,2-difluoro-6-[4-(propan-2-yl)piperazin-1-yl]cyclohexyl}-4-methylpiperidine-1-carboxamide

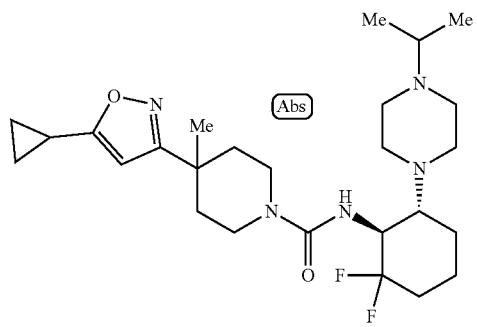 [SMILES: CC(C)N1CCN([C@@H]2CCCC(F)(F)[C@H]2NC(=O)N2CCC(C)(c3cc(C4CC4)on3)CC2)CC1]

Example 23: 4-(5-cyclopropyl-1,2,4-oxadiazol-3-yl)-N-{(1S,6R)-2,2-difluoro-6-[4-(propan-2-yl)piperazin-1-yl]cyclohexyl}-4-methylpiperidine-1-carboxamide

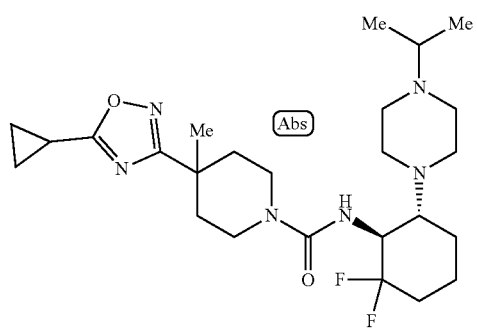 [SMILES: CC(C)N1CCN([C@@H]2CCCC(F)(F)[C@H]2NC(=O)N2CCC(C)(c3noc(C4CC4)n3)CC2)CC1]

Example 24: 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide

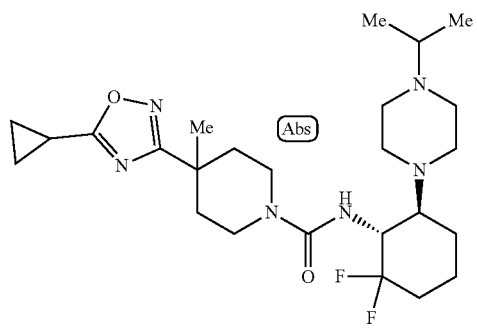 [SMILES: CC(C)N1CCN([C@H]2CCCC(F)(F)[C@@H]2NC(=O)N2CCC(C)(c3noc(C4CC4)n3)CC2)CC1]

Example 25: 4-(5-cyclopropyl-1,2-oxazol-3-yl)-N-{(1R,6S)-2,2-difluoro-6-[4-(propan-2-yl)piperazin-1-yl]cyclohexyl}-4-methylpiperidine-1-carboxamide

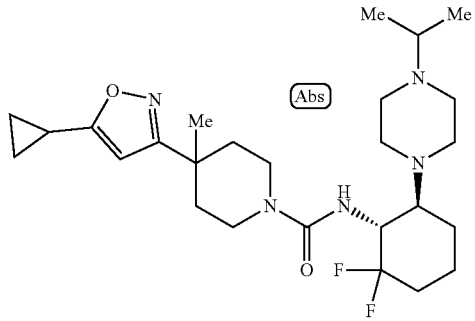 [SMILES: CC(C)N1CCN([C@H]2CCCC(F)(F)[C@@H]2NC(=O)N2CCC(C)(c3cc(C4CC4)on3)CC2)CC1]

Example 62: 4-(5-cyclopropyl-1,2,4-oxadiazol-3-yl)-N-{(1R,6S)-2,2-difluoro-6-[3-(propan-2-yl)-3,8-diazabicyclo[3.2.1]octan-8-yl]cyclohexyl}-4-methylpiperidine-1-carboxamide

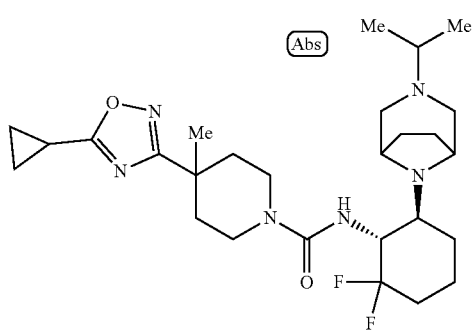 [SMILES: CC(C)N1CC2CCC(C1)N2[C@H]1CCCC(F)(F)[C@@H]1NC(=O)N1CCC(C)(c2noc(C3CC3)n2)CC1]

Example 63: N-{(1R,6S)-2,2-difluoro-6-[3-(propan-2-yl)-3,8-diazabicyclo[3.2.1]octan-8-yl]cyclohexyl}-4-methyl-4-(4-methylphenyl)piperidine-1-carboxamide

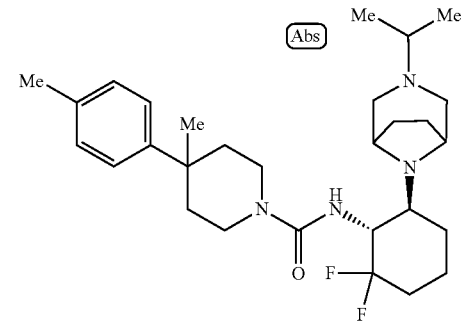 [SMILES: Cc1ccc(C2(C)CCN(C(=O)N[C@@H]3[C@@H](N4C5CCC4CN(C(C)C)C5)CCCC3(F)F)CC2)cc1]

Example 65: 4-(5-cyclopropyl-1,2-oxazol-3-yl)-N-{(1R,6S)-2,2-difluoro-6-[3-(propan-2-yl)-3,8-diazabicyclo[3.2.1]octan-8-yl]cyclohexyl}-4-methylpiperidine-1-carboxamide

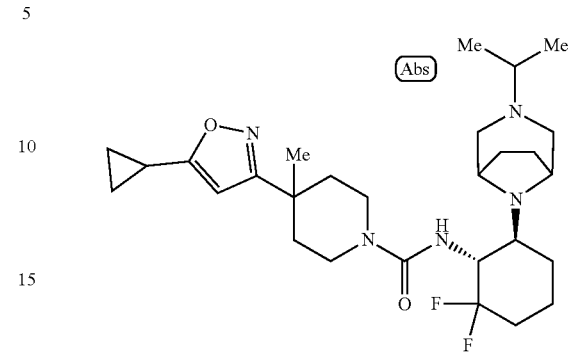

Example 66: N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide

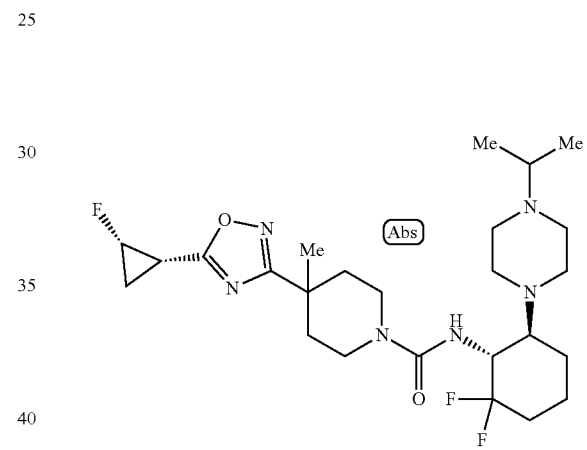

Example 68: N-{(1R,6S)-2,2-difluoro-6-[4-(propan-2-yl)piperazin-1-yl]cyclohexyl}-4-methyl-4-{5-[(1S,2R)-2-methylcyclopropyl]-1,2,4-oxadiazol-3-yl}piperidine-1-carboxamide

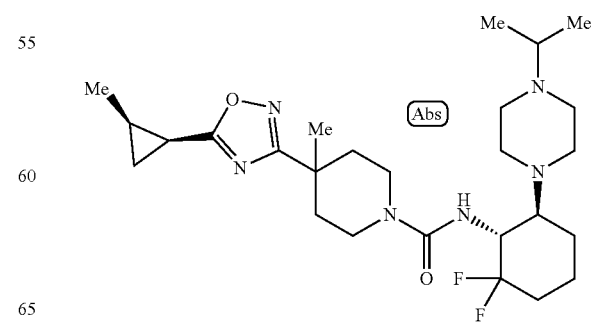

Example 69: N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide

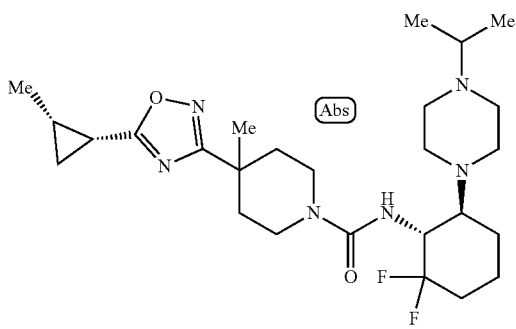 [SMILES: CC(C)N1CCN([C@H]2CCCC(F)(F)[C@@H]2NC(=O)N2CCC(C)(c3noc([C@@H]4C[C@@H]4C)n3)CC2)CC1]

Example 79: rac-4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carbothioamide

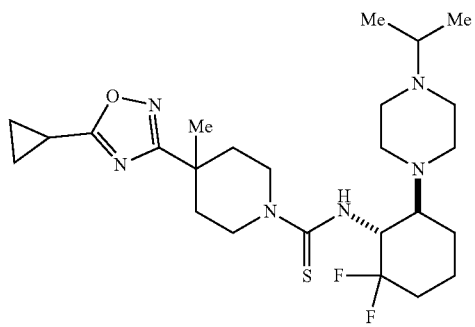

Example 80: 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carbothioamide

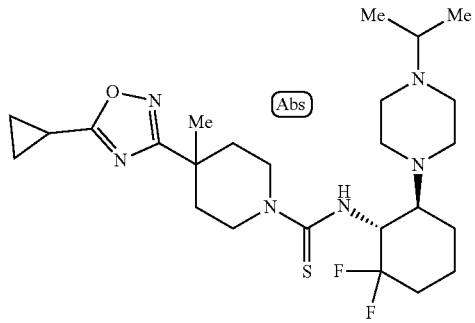 [SMILES: CC(C)N1CCN([C@H]2CCCC(F)(F)[C@@H]2NC(=S)N2CCC(C)(c3noc(C4CC4)n3)CC2)CC1]

ITEM A22

The compound of Item A1 or a pharmaceutically acceptable salt thereof, which is selected from the following compound names or structures:

Example 64: 4-(5-cyclopropyl-1,2,4-oxadiazol-3-yl)-N-[(1R,6S)-2,2-difluoro-6-{[(3R)-1-(propan-2-yl)pyrrolidin-3-yl]oxy}cyclohexyl]-4-methylpiperidine-1-carboxamide

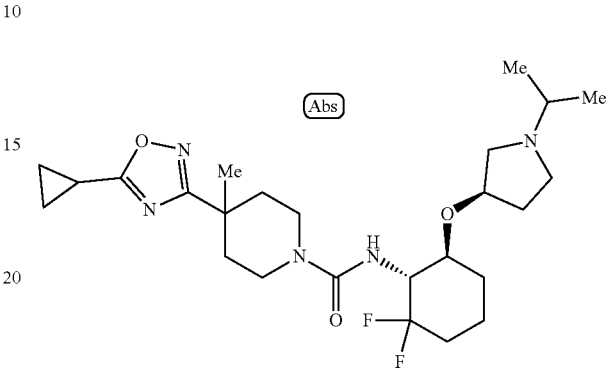

Example 67: N-[(1R,6S)-2,2-difluoro-6-{[(3R)-1-(propan-2-yl)pyrrolidin-3-yl]oxy}cyclohexyl]-4-methyl-4-(4-methylphenyl)piperidine-1-carboxamide

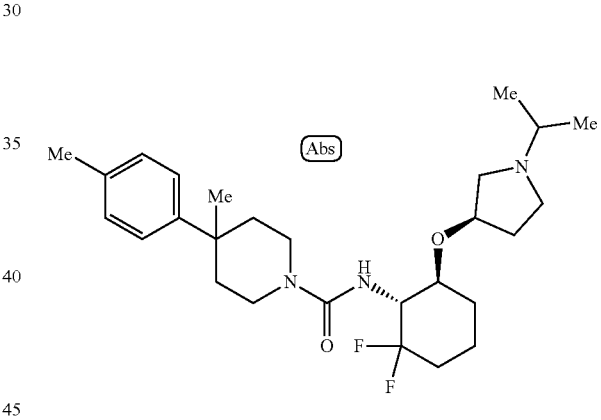

Example 71: 4-(5-cyclopropyl-1,2,4-oxadiazol-3-yl)-N-[(1R,6S)-2,2-difluoro-6-{[(3S)-1-(propan-2-yl)pyrrolidin-3-yl]oxy}cyclohexyl]-4-methylpiperidine-1-carboxamide

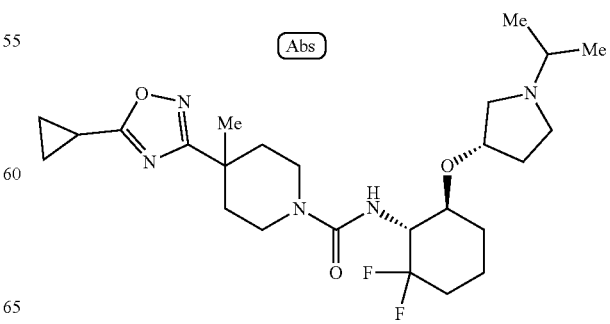

Example 72: N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide

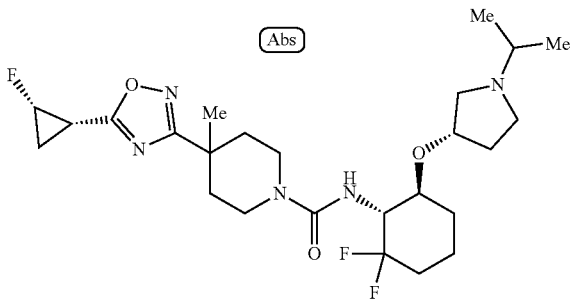 [SMILES: CC(C)N1CC[C@H](O[C@H]2CCCC(F)(F)[C@@H]2NC(=O)N2CCC(C)(c3noc([C@@H]4C[C@@H]4F)n3)CC2)C1]

Example 73: N-[(1R,6S)-2,2-difluoro-6-{[(3R)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide

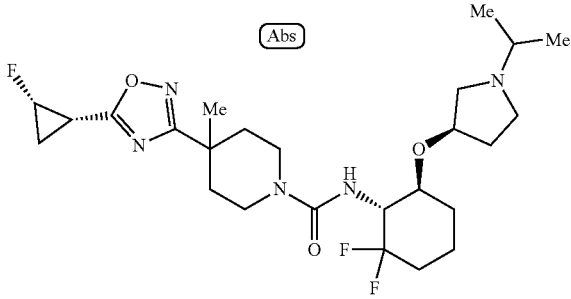 [SMILES: CC(C)N1CC[C@@H](O[C@H]2CCCC(F)(F)[C@@H]2NC(=O)N2CCC(C)(c3noc([C@@H]4C[C@@H]4F)n3)CC2)C1]

Example 74: N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide

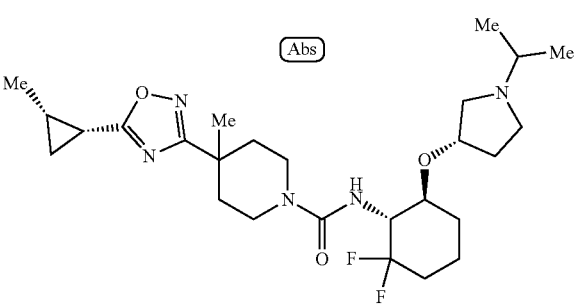 [SMILES: CC(C)N1CC[C@H](O[C@H]2CCCC(F)(F)[C@@H]2NC(=O)N2CCC(C)(c3noc([C@@H]4C[C@@H]4C)n3)CC2)C1]

Example 75: 4-(5-cyclopropyl-1,2,4-oxadiazol-3-yl)-N-[(1R,6S)-2,2-difluoro-6-{[(3S,4S)-4-fluoro-1-(propan-2-yl)pyrrolidin-3-yl]oxy}cyclohexyl]-4-methylpiperidine-1-carboxamide

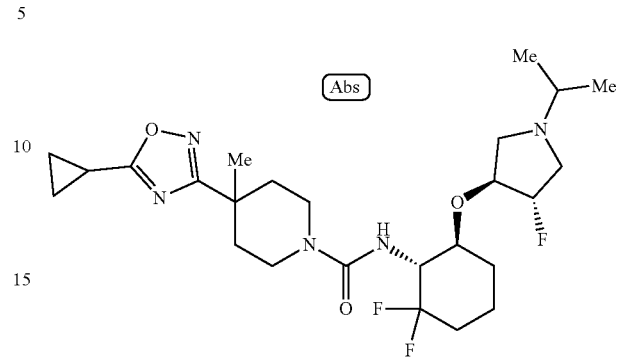

Example 76: 4-(5-cyclopropyl-1,2,4-oxadiazol-3-yl)-N-[(1R,6S)-6-{[(3R)-4,4-difluoro-1-(propan-2-yl)pyrrolidin-3-yl]oxy}-2,2-difluorocyclohexyl]-4-methylpiperidine-1-carboxamide

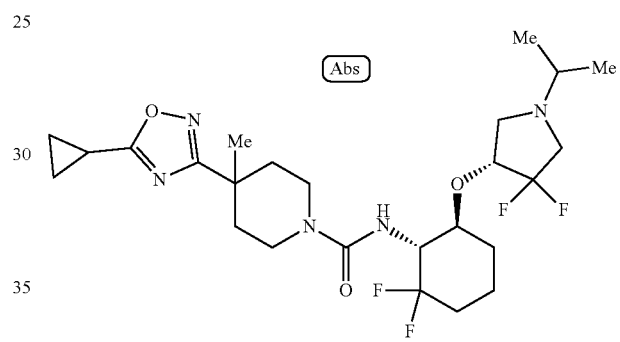

ITEM A23

A medicament for treating a disease related to orexin receptor, comprising the compound of any one of Items A1 to A22 or a pharmaceutically acceptable salt thereof.

ITEM A24

A medicament for treating narcolepsy, idiopathic hypersomnia, hypersomnia, sleep apnea syndrome, narcolepsy syndrome involving narcolepsy-like symptom, hypersomnia associated with Parkinson's disease, hypersomnia associated with dementia with Lewy body, hypersomnia syndrome involving daytime hypersomnia (e.g. Kleine-Levin syndrome, major depression accompanied by hypersomnia, dementia with Lewy body, Parkinson's disease, progressive supranuclear palsy, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalopathy, limbic encephalitis, Hashimoto encephalopathy), coma, loss of consciousness, obesity (e.g. malignant mast cell, extrinsic obesity, hyperinsulinar obesity, hyperplasmic obesity, hypophysial obesity, hypoplasmic obesity, hypothyroid obesity, hypothalamic obesity, symptomatic obesity, childhood obesity, upper body obesity, alimentary obesity, gonadal obesity, systemic mastocytosis, primary obesity, central obesity), insulin resistance syndrome, Alzheimer, impaired consciousness such as coma, side effect or complication caused by anesthesia, sleep problem, insomnia, intermittent sleep, night myoclonus, REM sleep interruption, jet lag, jet lag syndrome, sleep disorder of shift workers, dyssomnia, sleep terror, depression, major depression, sleepwalking, enuresis, sleep disorder, Alzheimer's sundown syndrome, disease associated with circadian rhythm, fibromyalgia, condition resulting from decrease in sleeping quality, bulimia, obsessive eating disorder, obesity-related diseases, hypertension, diabetes, elevated plasma insulin level/insulin resistance, hyperlipemia, hyperlipidaemia, endometrial cancer, breast cancer, prostate cancer, colon cancer, cancer, osteoarthritis, obstructive sleep apnea, cholelithiasis, gallstone, heart disease, abnormal heartbeat, arrhythmia, myocardial infarction, congestive heart failure, heart failure, coronary heart disease, cardiovascular disease, sudden death, polycystic ovary, craniopharyngioma, Prader-Willi syndrome, Froehlich syndrome, growth hormone deficiency, normal variant short stature, Turner syndrome, children suffering from acute lymphoblastic leukemia, syndrome X, reproductive hormone abnormality, decrease of fecundability, infertility, hypogonadism in men, sexual/reproductive-function dysfunction such as hirsutism in women, fetal defect associated with maternity obesity, gastrointestinal motility disorder such as obesity-related gastroesophageal reflux, obesity hypoventilation syndrome (Pickwickian syndrome), respiratory disease such as respiratory distress, inflammation such as vascular systemic inflammation, arteriosclerosis, hypercholesterolemia, hyperuricemia, low back pain, gallbladder disease, gout, renal cancer, secondary risk of obesity such as risk of left ventricle hypertrophy, migraine, headache, neuropathic pain, Parkinson's disease, psychosis, schizophrenia, facial flushing, night sweat, disease in genitalium/urinary system, disease associated with sexual function or fecundability, dysthymic disorder, bipolar disorder, bipolar I disorder, bipolar II disorder, cyclothymic disorder, acute stress disorder, agoraphobia, generalized anxiety disorder, obsessive-compulsive disorder, panic attack, panic disorder, posttraumatic stress disorder, separation anxiety disorder, social phobia, anxiety disorder, acute neurological and psychiatric disorder such as cerebral deficiency developed after heart bypass surgery or heart transplant, stroke, ischemic stroke, cerebral ischemia, spinal cord trauma, head injury, periparturient hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorder associated with muscle spasm, delirium, amnestic disorder, age-associated cognitive decline, schizoaffective disorder, paranoia, drug addiction, movement disorder, chronic fatigue syndrome, fatigue, medication-induced; parkinsonian syndrome, Gilles de la Tourette syndrome, chorea, myoclonus, tic, restless legs syndrome, dystonia, dyskinesia, attention deficit hyperactivity disorder (ADHD), conduct disorder, urinary incontinence, withdrawal symptom, trigeminal neuralgia, hearing loss, tinnitus, nerve injury, retinopathy, macular degeneration, vomiting, cerebral edema, pain, bone pain, arthralgia, toothache, cataplexy, or traumatic brain injury, comprising the compound of any one of Items A1 to A22 or a pharmaceutically acceptable salt thereof.

ITEM A25

A medicament for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body, comprising the compound of any one of Items A1 to A22 or a pharmaceutically acceptable salt thereof.

ITEM A26

A method for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body, comprising administering a therapeutically effective amount of the compound of any one of Items A1 to A22 or a pharmaceutically acceptable salt thereof to a patient in need thereof.

ITEM A27

Use of the compound of any one of Items A1 to A22 or a pharmaceutically acceptable salt thereof, in the manufacture of a medicament for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body.

The present invention can also show as follows.

ITEM 1

A compound of formula (1):

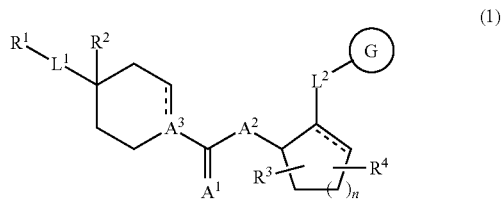

or a pharmaceutically acceptable salt thereof
wherein
$R^1$ is optionally-substituted $C_{6-10}$ aromatic carbocyclyl group, optionally-substituted 5- to 10-membered aromatic heterocyclyl group, optionally-substituted $C_{3-6}$ saturated carbocyclyl group, optionally-substituted 4- to 10-membered saturated heterocyclyl group, or cyano;

$L^1$ and $L^2$ are each independently single bond, methylene (which may be optionally substituted with the same or different one or more $C_{1-4}$ alky), —$NR^8$—, —C(=O)—, —OC(=O)—, —SO—, —$SO_2$—, —S—, or oxygen atom;

$R^2$ is hydrogen atom, hydroxy group, halogen atom, cyano, or optionally-substituted $C_{1-4}$ alkyl; or when $L^1$ is single bond, $R^1$ and $R^2$ may be combined together as a spiro ring to form optionally-substituted $C_{3-6}$ saturated carbocyclic ring or optionally-substituted 4- to 10-membered saturated heteroring;

$R^3$ and $R^4$ are each independently hydrogen atom, halogen atom, cyano, —(C=O)$NR^5R^6$, carboxy group, —(C=O) O—$R^7$, optionally-substituted $C_{1-4}$ alkyl, or optionally-substituted $C_{1-4}$ alkoxy, wherein $R^3$ and $R^4$ may bind to the same carbon atom if chemically possible; or when $R^3$ and $R^4$ bind to different ring carbon atoms, $R^3$ and $R^4$ may be taken together via $C_{1-6}$ alkylene to form a fused ring or a bridged ring;

$R^5$ to $R^7$ are each independently hydrogen atom, halogen atom, or optionally-substituted $C_{1-4}$ alkyl;

$R^8$ is each independently hydrogen atom or optionally-substituted $C_{1-4}$ alkyl;

n is an integer of 1, 2, 3, or 4;

Ring G is optionally-substituted $C_{6-10}$ aromatic carbocyclyl group, optionally-substituted 5- to 10-membered aromatic heterocyclyl group, optionally-substituted $C_{3-6}$ saturated carbocyclyl group, or optionally-substituted 4- to 10-membered saturated heterocyclyl group;

$A^1$ is oxygen atom or sulfur atom;

$A^2$ is oxygen atom or —$NR^8$—;

$A^3$ is —CH—, nitrogen atom, or carbon atom; and the bond accompanied with broken line is each independently single bond or double bond.

ITEM 2

The compound of Item 1 or a pharmaceutically acceptable salt thereof, wherein in $R^2$-$R^8$, the optional substituent of "optionally-substituted $C_{1-4}$ alkyl" is the same or different one or more substituents selected from the group consisting of halogen atom, hydroxy group, $C_{1-4}$ alkoxy, $C_{6-10}$ aromatic carbocyclyl group, and $C_{3-7}$ cycloalkyl; and the optional substituent of "optionally-substituted $C_{1-4}$ alkoxy" is the same or different one or more substituents selected from the group consisting of halogen atom, $C_{1-4}$ alkyl, and $C_{3-7}$ cycloalkyl;

in $R^1$, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of hydrogen atom, halogen atom, hydroxy group, $C_{6-10}$ aromatic carbocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-4}$ alkyl (which may be optionally substituted with the same or different one or more substituents selected from the group consisting of halogen atom, hydroxy group, $C_{1-4}$ alkoxy, and $C_{3-7}$ cycloalkyl), $C_{3-7}$ cycloalkyl (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-6}$ alkylamino (the alkyl group of which may be optionally substituted with halogen atom, hydroxy group, or $C_{3-7}$ cycloalkyl), $C_{3-7}$ cycloalkoxy (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), cyano, $C_{1-4}$ alkoxy (which may be optionally substituted with the same or different one or more substituents selected from the group consisting of halogen atom, hydroxy group, $C_{1-4}$ alkyl optionally-substituted with the same or different one or more halogen atoms, and $C_{3-7}$ cycloalkyl), and 5- to 10-membered aromatic heterocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl); and in Ring G, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of halogen atom, $C_{1-6}$ alkyl (which may be optionally substituted with the same or different one or more substituents selected from the group consisting of halogen atom, hydroxy group, $C_{1-4}$ alkoxy, and $C_{3-7}$ cycloalkyl), $C_{6-10}$ aromatic carbocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-4}$ alkoxy (which may be optionally substituted with the same or different one or more substituents selected from the group consisting of halogen atom, hydroxy group, $C_{1-4}$ alkyl, and $C_{3-7}$ cycloalkyl), $C_{1-6}$ alkylamino (the alkyl group of which may be optionally substituted with halogen atom, hydroxy group, or $C_{3-7}$ cycloalkyl), $C_{3-7}$ cycloalkyl (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), and $C_{3-7}$ cycloalkoxy (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl); or when there are plural optional substituents, two of them may be taken together via $C_{1-6}$ alkylene to form a chemically-possible bicyclic structure selected from a fused ring, a spiro ring, and bridged ring.

ITEM 3

The compound of Item 1 or 2 or a pharmaceutically acceptable salt thereof, wherein in $R^2$-$R^7$, the optional substituent of "optionally-substituted $C_{1-4}$ alkyl" is the same or different one or more substituents selected from the group consisting of halogen atom and $C_{1-4}$ alkoxy; and the optional substituent of "optionally-substituted $C_{1-4}$ alkoxy" is the same or different one or more substituents selected from the group consisting of halogen atom and $C_{1-4}$ alkyl;

in $R^1$, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of hydrogen atom, halogen atom, hydroxy group, $C_{6-10}$ aromatic carbocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), $C_{1-4}$ alkyl (which may be optionally substituted with the same or different one or more substituents selected from the group consisting of halogen atom, hydroxy group, $C_{1-4}$ alkoxy, and $C_{3-7}$ cycloalkyl), $C_{3-7}$ cycloalkyl (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl), cyano, $C_{1-4}$ alkoxy (which may be optionally substituted with the same or different one or more substituents selected from the group consisting of halogen atom, hydroxy group, $C_{1-4}$ alkyl optionally-substituted with the same or different one or more halogen atoms, and $C_{3-7}$ cycloalkyl), and 5- to 10-membered aromatic heterocyclyl group (which may be optionally substituted with the same or different one or more substituents selected from the group consisting of halogen atom, hydroxy group, $C_{1-4}$ alkyl, $C_{1-4}$ alkoxy, and $C_{3-7}$ cycloalkyl); and in Ring G, the optional substituent of "optionally-substituted $C_{6-10}$ aromatic carbocyclyl group", "optionally-substituted 5- to 10-membered aromatic heterocyclyl group", "optionally-substituted $C_{3-6}$ saturated carbocyclyl group", and "optionally-substituted 4- to 10-membered saturated heterocyclyl group" is each independently at least one substituent selected from the group consisting of halogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), $C_{1-6}$ alkylamino (the alkyl group of which may be optionally substituted with halogen atom, hydroxy group, or $C_{3-7}$ cycloalkyl), and $C_{3-7}$ cycloalkoxy (which may be optionally substituted with the same or different one or more substituents selected from the group consisting of halogen atom, $C_{1-4}$ alkyl, and $C_{1-4}$ alkoxy); or when there are plural optional substituents, two of them may be taken together via $C_{1-6}$ alkylene to form a chemically-possible bicyclic structure selected from a fused ring, a spiro ring, and bridged ring.

ITEM 4

The compound of any one of Items 1 to 3 or a pharmaceutically acceptable salt thereof, wherein
$R^1$ is selected from the following formulae (1a-1) to (1a-4):

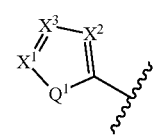
(1a-1)

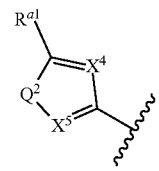
(1a-2)

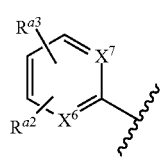
(1a-3)

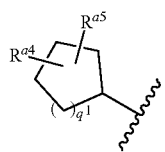
(1a-4)

wherein
$X^1$-$X^7$ are each independently nitrogen atom or $CR^{a6}$;
$Q^1$ and $Q^2$ are oxygen atom, —$NR^{a7}$—, or sulfur atom;
$R^{a1}$-$R^{a7}$ are each independently (if there are plural $CR^{a6}$, each $R^{a6}$ is also independently), hydrogen atom, halogen atom, $C_{6-10}$ aromatic carbocyclyl group (which may be optionally substituted with the same or different one or more substituents selected from the group consisting of halogen atom, hydroxy group, $C_{1-4}$ alkyl, and $C_{1-4}$ alkoxy), $C_{1-4}$ alkyl (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), cyano, $C_{1-4}$ alkoxy (which may be optionally substituted with the same or different one or more substituents selected from the group consisting of halogen atom, hydroxy group, $C_{2-4}$ alkyl, and $C_{1-4}$ alkoxy), $C_{3-7}$ cycloalkoxy (which may be optionally substituted with the same or different one or more substituents selected from the group consisting of halogen atom, hydroxy group, $C_{1-4}$ alkyl, and $C_{1-4}$ alkoxy), or 5- to 10-membered aromatic heterocyclyl group; wherein $R^{a4}$ and $R^{a5}$ may bind to the same carbon atom if chemically possible; and when $X^1$ and $X^3$ are both $CR^{a5}$, the two $R^{a6}$ may be taken together with the carbon atoms to which they are each attached to form 6-membered carbon ring that is fused with the 5-membered ring comprising $X^1$, $X^2$, and $X^3$; and
$q^1$ is an integer of 1 or 2.

ITEM 5

The compound of any one of Items 1 to 4 or a pharmaceutically acceptable salt thereof, wherein
Ring G is selected from the following (1b-1) to (1b-14):

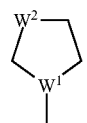
(1b-1)

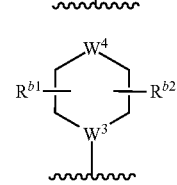
(1b-2)

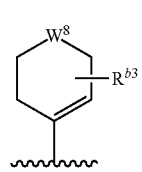
(1b-3)

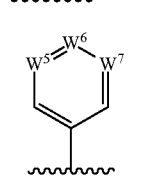
(1b-4)

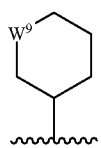
(1b-5)

-continued

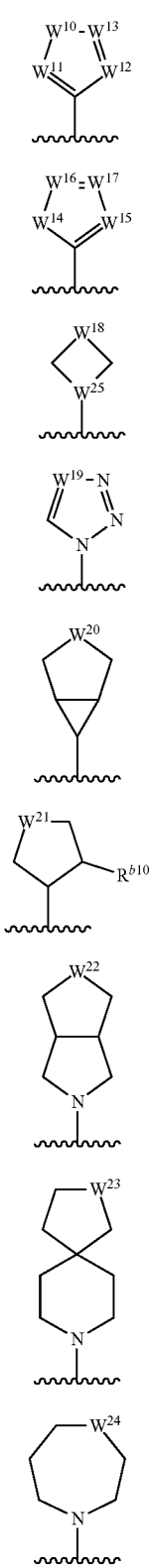

(1b-6)

(1b-7)

(1b-8)

(1b-9)

(1b-10)

(1b-11)

(1b-12)

(1b-13)

(1b-14)

wherein $W^1$, $W^3$, $W^5$, $W^6$, $W^7$, $W^{11}$, $W^{12}$, $W^{13}$, $W^{15}$, $W^{16}$, $W^{17}$, $W^{19}$, and $W^{25}$ are each independently nitrogen atom or $CR^{b4}$;

$W^2$, $W^4$, $W^8$, $W^9$, $W^{10}$, $W^{14}$, $W^{18}$, $W^{20}$, $W^{23}$, $W^{22}$, $W^{23}$, and $W^{24}$ are $NR^{b5}$, oxygen atom, or $CR^{b6}R^{b7}$;

$R^{b1}$-$R^{b7}$ are each independently (if there are plural $CR^{b4}$, each $R^{b4}$ is also independently), hydrogen atom, $N(R^{b8})R^{b9}$, $C_{1-6}$ alkyl (which may be optionally substituted with the same or different one or more substituents selected from the group consisting of halogen atom, $C_{3-7}$ cycloalkyl which may be optionally substituted with the same or different one or more substituents selected from the group consisting of halogen atom and $C_{1-4}$ alkyl (said $C_{1-4}$ alkyl may be substituted with halogen atom), and $C_{1-4}$ alkoxy), $C_{6-10}$ aromatic carbocyclyl group (which may be optionally substituted with the same or different one or more substituents selected from the group consisting of halogen atom, $C_{2-4}$ alkyl, and $C_{1-4}$ alkoxy), 5- to 10-membered aromatic heterocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a chemically-possible bicyclic structure selected from a fused ring, a spiro ring, and bridged ring; and $R^{b8}$ and $R^{b9}$ are each independently hydrogen atom, $C_{1-6}$ alkyl (which may be optionally substituted with the same or different one or more substituents selected from the group consisting of halogen atom, $C_{1-4}$ alkoxy, $C_{3-7}$ cycloalkyl which may be optionally substituted with the same or different one or more substituents selected from the group consisting of halogen atom and $C_{1-4}$ alkyl (said $C_{1-4}$ alkyl may be substituted with halogen atom), and 5- to 10-membered aromatic heterocyclyl group), $C_{1-4}$ alkoxy (which may be optionally substituted with the same or different one or more substituents selected from the group consisting of halogen atom and $C_{1-4}$ alkyl), 5- to 10-membered aromatic heterocyclyl group (which may be optionally substituted with the same or different one or more substituents selected from the group consisting of halogen atom, $C_{4-4}$ alkyl, and $C_{1-4}$ alkoxy), or $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy); or $R^{b8}$ and $R^{b9}$ may be taken together with the nitrogen atom to which they are attached to form 3- to 7-membered nitrogen-containing saturated heterocycle.

ITEM 6

The compound of any one of Items 1 to 5 of formula (2):

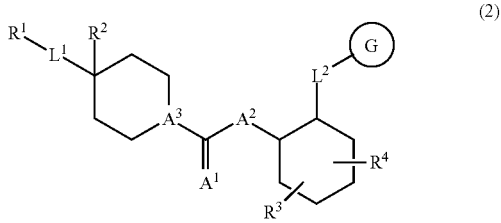

(2)

or a pharmaceutically acceptable salt thereof, wherein
$R^1$ is selected from the following formulae (1a-1) to (1a-4):

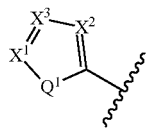

(1a-1)

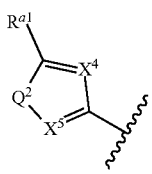

(1a-2)

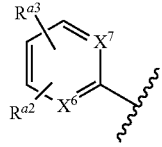

(1a-3)

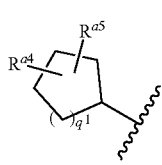

(1a-4)

wherein
$X^1$-$X^7$ are each independently nitrogen atom or $CR^{a6}$;
$Q^1$ and $Q^2$ are oxygen atom, —$NR^{a7}$—, or sulfur atom;
$R^{a1}$-$R^{a7}$ are each independently (if there are plural $CR^{a6}$, each $R^{a6}$ is also independently), hydrogen atom, halogen atom, $C_{6-10}$ aromatic carbocyclyl group (which may be optionally substituted with the same or different one or more substituents selected from the group consisting of halogen atom, hydroxy group, $C_{1-4}$ alkyl, and $C_{1-4}$ alkoxy), $C_{1-4}$ alkyl (which may be optionally substituted with the same or different one or more substituents selected from the group consisting of halogen atom, hydroxy group, $C_{1-4}$ alkyl, and $C_{1-4}$ alkoxy), $C_{3-6}$ cycloalkyl (which may be optionally substituted with the same or different one or more substituents selected from the group consisting of halogen atom, hydroxy group, $C_{1-4}$ alkyl, and $C_{1-4}$ alkoxy), cyano, $C_{1-4}$ alkoxy (which may be optionally substituted with the same or different one or more substituents selected from the group consisting of halogen atom, hydroxy group, $C_{1-4}$ alkyl, and $C_{1-4}$ alkoxy), $C_{3-7}$ cycloalkoxy (which may be optionally substituted with the same or different one or more substituents selected from the group consisting of halogen atom, hydroxy group, $C_{1-4}$ alkyl, and $C_{1-4}$ alkoxy), or 5- to 10-membered aromatic heterocyclyl group; wherein $R^{a4}$ and $R^{a5}$ may bind to the same carbon atom if chemically possible; and when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$; and
$q^1$ is an integer of 1 or 2;
$L^1$ and $L^2$ are each independently single bond, —$CH_2$—, or oxygen atom;
$R^2$ is hydrogen atom, hydroxy group, halogen atom, cyano, or optionally-substituted $C_{1-4}$ alkyl;

$R^3$ and $R^4$ are each independently hydrogen atom, halogen atom, $C_{1-4}$ alkyl (which may be optionally substituted with the same or different one or more substituents selected from the group consisting of halogen atom, hydroxy group, $C_{1-4}$ alkoxy, and $C_{3-7}$ cycloalkyl), or $C_{1-4}$ alkoxy (which may be optionally substituted with the same or different one or more substituents selected from the group consisting of halogen atom, hydroxy group, $C_{1-4}$ alkyl, and $C_{3-7}$ cycloalkyl); wherein $R^3$ and $R^4$ may bind to the same carbon atom if chemically possible; and when $R^3$ and $R^4$ bind to different carbon atoms on the ring, $R^3$ and $R^4$ may be taken together via $C_{1-6}$ alkylene to form a fused ring or bridged ring;
Ring G is selected from the following (1b-1) to (1b-4):

(1b-1)

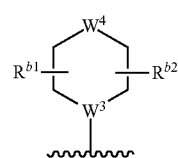

(1b-2)

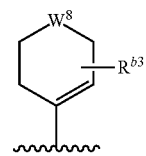

(1b-3)

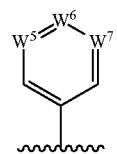

(1b-4)

wherein
$W^1$, $W^3$, $W^5$, $W^6$, and $W^7$ are each independently nitrogen atom or $CR^{b4}$;
$W^2$, $W^4$, and $W^8$ are $NR^{b5}$, oxygen atom or $CR^{b6}R^{b7}$;
$R^{b1}$-$R^{b7}$ are each independently (if there are plural $CR^{b4}$, each $R^{b4}$ is also independently), hydrogen atom, $C_{1-6}$ alkyl (which may be optionally substituted with the same or different one or more substituents selected from the group consisting of halogen atom and $C_{1-4}$ alkoxy), $C_{6-10}$ aromatic 1 carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a chemically-possible bicyclic structure selected from a fused ring, a spiro ring, and bridged ring;
$A^1$ is oxygen atom or sulfur atom;
$A^2$ is oxygen atom or —NH—; and
$A^3$ is —CH—, nitrogen atom, or carbon atom.

ITEM 7

The compound of Item 6 or a pharmaceutically acceptable salt thereof, wherein
$R^1$ is selected from the following formulae (1a-1), (1a-2), and (1a-3-1):

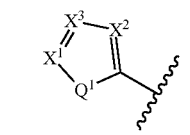
(1a-1)

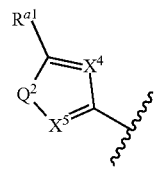
(1a-2)

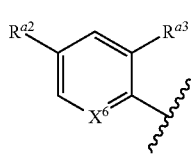
(1a-3-1)

wherein
$X^1$-$X^6$ are each independently nitrogen atom or $CR^{a6}$;
$Q^1$ and $Q^2$ are oxygen atom, —$NR^{a7}$—, or sulfur atom; and
$R^{a1}$-$R^{a3}$, $R^{a5}$, and $R^{a7}$ are each independently (if there are plural $CR^{a6}$, each $R^{a6}$ is also independently), hydrogen atom, halogen atom, $C_{6\text{-}10}$ aromatic carbocyclyl group (which may be optionally substituted with the same or different one or more substituents selected from the group consisting of halogen atom, hydroxy group, $C_{1\text{-}4}$ alkyl, and $C_{1\text{-}4}$ alkoxy), $C_{1\text{-}4}$ alkyl (which may be optionally substituted with the same or different one or more substituents selected from the group consisting of halogen atom, hydroxy group, $C_{1\text{-}4}$ alkyl, and $C_{1\text{-}4}$ alkoxy), $C_{3\text{-}7}$ cycloalkyl (which may be optionally substituted with the same or different one or more substituents selected from the group consisting of halogen atom, hydroxy group, $C_{1\text{-}4}$ alkyl, and $C_{1\text{-}4}$ alkoxy), cyano, $C_{1\text{-}4}$ alkoxy (which may be optionally substituted with the same or different one or more substituents selected from the group consisting of halogen atom, hydroxy group, $C_{1\text{-}4}$ alkyl, and $C_{1\text{-}4}$ alkoxy), $C_{3\text{-}7}$ cycloalkoxy (which may be optionally substituted with the same or different one or more substituents selected from the group consisting of halogen atom, hydroxy group, $C_{1\text{-}4}$ alkyl, and $C_{1\text{-}4}$ alkoxy), or 5- to 10-membered aromatic heterocyclyl group; wherein when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$.

ITEM 8

The compound of Items 6 or 7 or a pharmaceutically acceptable salt thereof, wherein Ring G is selected from the following (1b-1), (1b-2), and (1b-4);

(1b-1)

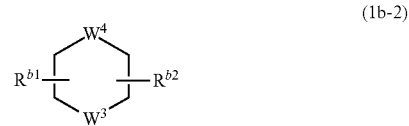
(1b-2)

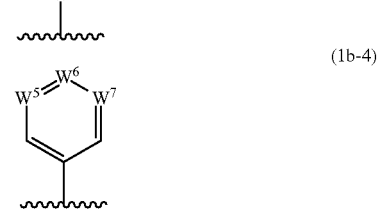
(1b-4)

wherein
$W^1$, $W^3$, $W^5$, $W^6$, and $W^7$ are each independently nitrogen atom or $CR^{b4}$;
$W^2$ and $W^4$ are $NR^{b5}$ or $CR^{b6}R^{b7}$; and
$R^{b1}$, $R^{b2}$, and $R^{b4}$-$R^{b7}$ are each independently (if there are plural $CR^{b4}$, each $R^{b4}$ is also independently), hydrogen atom, $C_{1\text{-}6}$ alkyl (which may be optionally substituted with the same or different one or more substituents selected from the group consisting of halogen atom and $C_{1\text{-}4}$ alkoxy)-, $C_{6\text{-}10}$ aromatic carbocyclyl group (which may be optionally substituted with the same or different one or more substituents selected from the group consisting of halogen atom, $C_{1\text{-}4}$ alkyl, and $C_{1\text{-}4}$ alkoxy), $C_{1\text{-}4}$ alkoxy (which may be optionally substituted with the same or different one or more substituents selected from the group consisting of halogen atom and $C_{1\text{-}4}$ alkyl), $C_{3\text{-}7}$ cycloalkyl (which may be optionally substituted with the same or different one or more substituents selected from the group consisting of halogen atom, $C_{1\text{-}4}$ alkyl, and $C_{1\text{-}4}$ alkoxy), or $C_{3\text{-}7}$ cycloalkoxy (which may be optionally substituted with the same or different one or more substituents selected from the group consisting of halogen atom, $C_{1\text{-}4}$ alkyl, and $C_{1\text{-}4}$ alkoxy); wherein $R^{b1}$ and $R^{b2}$ may bind to the same carbon atom if chemically possible; or $R^{b1}$ and $R^{b2}$ may be taken together via $C_{1\text{-}6}$ alkylene to form a bridged bicyclic structure.

ITEM 9

The compound of any one of Items 6 to 8 or a pharmaceutically acceptable salt thereof, wherein
Ring G is selected from the following (1b-1) and (1b-2):

(1b-1)

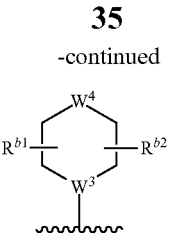

(1b-2)

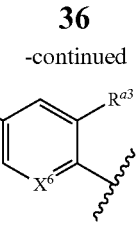

(1a-3-1)

wherein
  $W^1$ and $W^3$ are nitrogen atom or $CR^{b4}$;
  $W^2$ and $W^4$ are $NR^{b5}$ or $CR^{b6}R^{b7}$; and
  $R^{b1}$, $R^{b2}$, and $R^{b4}$-$R^{b7}$ are each independently hydrogen atom, $C_{1-6}$ alkyl (which may be optionally substituted with the same or different one or more substituents selected from the group consisting of halogen atom and $C_{1-4}$ alkoxy), $C_{6-10}$ aromatic carbocyclyl group (which may be optionally substituted with the same or different one or more substituents selected from the group consisting of halogen atom, $C_{1-4}$ alkyl, and $C_{1-4}$ alkoxy), $C_{1-4}$ alkoxy (which may be optionally substituted with the same or different one or more substituents selected from the group consisting of halogen atom and $C_{1-4}$ alkyl), $C_{3-7}$ cycloalkyl (which may be optionally substituted with the same or different one or more substituents selected from the group consisting of halogen atom, $C_{1-4}$ alkyl, and $C_{1-4}$ alkoxy), or $C_{3-7}$ cycloalkoxy (which may be optionally substituted with the same or different one or more substituents selected from the group consisting of halogen atom, $C_{1-4}$ alkyl, and $C_{1-4}$ alkoxy); wherein $R^{b1}$ and $R^{b2}$ may bind to the same carbon atom if chemically possible; or $R^{b1}$ and $R^{b2}$ may be taken together via $C_{1-6}$ alkylene to form a bridged bicyclic structure.

ITEM 10

The compound of any one of Items 1 to 9 of formula (3):

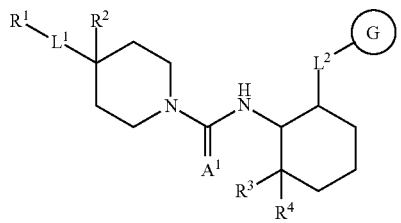

(3)

or a pharmaceutically acceptable salt thereof, wherein
  $R^1$ is the following formula (1a-1), (1a-2), or (1a-3-1):

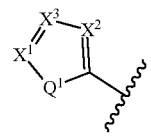

(1a-1)

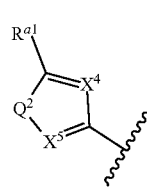

(1a-2)

wherein
  $X^1$-$X^6$ are each independently nitrogen atom or $CR^{a6}$;
  $Q^1$ and $Q^2$ are oxygen atom or sulfur atom;
  $R^{a1}$-$R^{a3}$ and $R^{a6}$ are each independently (if there are plural $CR^{a6}$, each $R^{a6}$ is also independently), hydrogen atom, halogen atom, $C_{1-4}$ alkyl (which may be optionally substituted with the same or different one or more substituents selected from the group consisting of halogen atom, hydroxy group, and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), cyano, or $C_{1-4}$ alkoxy (which may be optionally substituted with the same or different one or more substituents selected from the group consisting of halogen atom, hydroxy group, $C_{1-4}$ alkyl, and $C_{1-4}$ alkoxy); wherein when $X^1$ and $X^3$ are both $CR^{a6}$, the two $R^{a6}$ may be taken together with the carbon atoms to which they are each attached to form 6-membered carbon ring that is fused with the 5-membered ring comprising $X^1$, $X^2$, and $X^3$;

$L^1$ and $L^2$ are each independently single bond or oxygen atom;

$R^2$ is hydrogen atom, halogen atom, or $C_{1-4}$ alkyl which may be optionally substituted with the same or different one or more substituents selected from the group consisting of halogen atom and hydroxy group;

$R^3$ and $R^4$ are each independently halogen atom;

Ring G is the following (1b-1), (1b-2-1), (1b-2-2), or (1b-2-3):

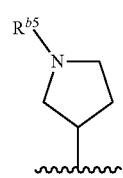

(1b-1-1)

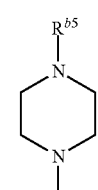

(1b-2-1)

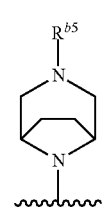

(1b-2-2)

(1b-2-3)

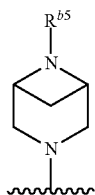

wherein $R^{b5}$ is hydrogen atom, or $C_{1-6}$ alkyl which may be optionally substituted with the same or different one or more substituents selected from the group consisting of halogen atom and $C_{1-4}$ alkoxy; and $A^1$ is oxygen atom or sulfur atom.

ITEM 11

The compound of any one of Items 4 to 10 or a pharmaceutically acceptable salt thereof, wherein $R^1$ is formula (1a-2), and $R^{a1}$ is hydrogen atom, halogen atom, $C_{1-4}$ alkyl (which may be optionally substituted with the same or different one or more substituents selected from the group consisting of halogen atom and $C_{1-4}$ alkoxy), $C_{3-7}$ cycloalkyl (which may be optionally substituted with the same or different one or more substituents selected from the group consisting of halogen atom, hydroxy group, $C_{1-4}$ alkyl, and $C_{1-4}$ alkoxy), or $C_{1-4}$ alkoxy (which may be optionally substituted with the same or different one or more substituents selected from the group consisting of halogen atom and $C_{1-4}$ alkyl).

ITEM 12

The compound of Item 10 to 11 or a pharmaceutically acceptable salt thereof, wherein $R^1$ is formula (1a-2), and $X^4$ and $X^5$ are both nitrogen atom.

ITEM 13

The compound of any one of Items 10 to 12 or a pharmaceutically acceptable salt thereof, wherein Ring G is formula (1b-1-1), and $R^{b5}$ is $C_{1-4}$ alkyl which may be optionally substituted with the same or different one or more substituents selected from halogen atoms.

ITEM 14

The compound of any one of Items 10 to 12 or a pharmaceutically acceptable salt thereof, wherein Ring G is formula (1b-2-1), and $R^{b5}$ is hydrogen atom, or $C_{1-4}$ alkyl which may be optionally substituted with the same or different one or more substituents selected from the group consisting of halogen atom and $C_{1-4}$ alkoxy.

ITEM 15

The compound of any one of Items 1 to 12 of formula (4):

(4)

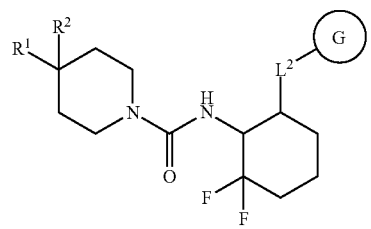

or a pharmaceutically acceptable salt thereof, wherein
$R^1$ is the following (1a-2-1):

(1a-2-1)

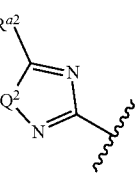

wherein $Q^2$ is oxygen atom or sulfur atom;

$R^{a2}$ is $C_{3-7}$ cycloalkyl group (which may be optionally substituted with the same or different one or more substituents selected from the group consisting of halogen atom, $C_{1-4}$ alkyl, and $C_{1-4}$ alkoxy) or cycloalkoxy group (which may be optionally substituted with the same or different one or more substituents selected from the group consisting of halogen atom, $C_{1-4}$ alkyl, and $C_{1-4}$ alkoxy);

$R^2$ is $C_{1-4}$ alkyl;

Ring G is the following (1b-1-1) or (1b-2-1):

(1b-1-1)

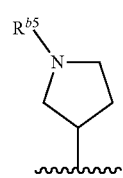

(1b-2-1)

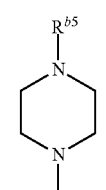

wherein $R^{b5}$ is $C_{1-4}$ alkyl which may be optionally substituted with the same or different one or more substituents selected from the group consisting of halogen atom and $C_{1-4}$ alkoxy; and $L^2$ is single bond or oxygen atom.

ITEM 16

The compound of Item 15 or a pharmaceutically acceptable salt thereof, wherein $R^{a2}$ is $C_{3-7}$ cycloalkyl group which may be optionally substituted with the same or different one or more substituents selected from halogen atoms, and
$R^2$ is methyl group.

ITEM 17

The compound of Item 15 or 16 or a pharmaceutically acceptable salt thereof, wherein
$R^{a2}$ is cyclopropyl group which may be optionally substituted with the same or different one or more substituents selected from halogen atoms, and
$R^2$ is methyl group.

ITEM 18

The compound of any one of Items 15 to 17 or a pharmaceutically acceptable salt thereof, wherein
Ring G is formula (1b-2-1), and
$R^{b5}$ is isopropyl group.

ITEM 19

The compound of any one of Items 15 to 17 or a pharmaceutically acceptable salt thereof, wherein
Ring G is formula (1b-1-1), and
$R^{b5}$ is isobutyl group.

ITEM 20

The compound of any one of Items 15 to 17 or a pharmaceutically acceptable salt thereof, wherein
Ring G is formula (1b-1-1),
$R^{b5}$ is isopropyl group, and
$L^2$ is oxygen atom.

ITEM 21

The compound of any one of Items 15 to 20 or a pharmaceutically acceptable salt thereof, wherein $Q^2$ is oxygen atom.

ITEM 22

The compound of Item 1 or a pharmaceutically acceptable salt thereof, which is selected from the following compound names or structures:
Example 22: 4-(5-cyclopropyl-1,2-oxazol-3-yl)-N-{(1S,6R)-2,2-difluoro-6-[4-(propan-2-yl)piperazin-1-yl]cyclohexyl}-4-methylpiperidine-1-carboxamide Example 23: 4-(5-cyclopropyl-1,2,4-oxadiazol-3-yl)-N-{(1S,6R)-2,2-difluoro-6-[4-(propan-2-yl)piperazin-1-yl]cyclohexyl}-4-methylpiperidine-1-carboxamide

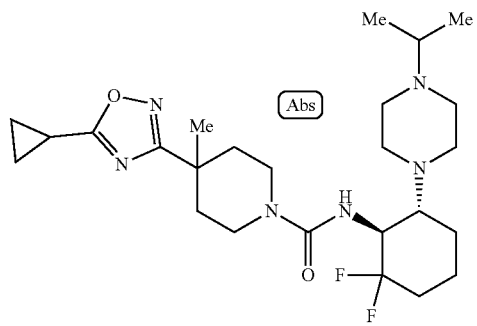 [SMILES: CC(C)N1CCN([C@@H]2CCCC(F)(F)[C@H]2NC(=O)N2CCC(C)(c3noc(C4CC4)n3)CC2)CC1]

Example 24: 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide

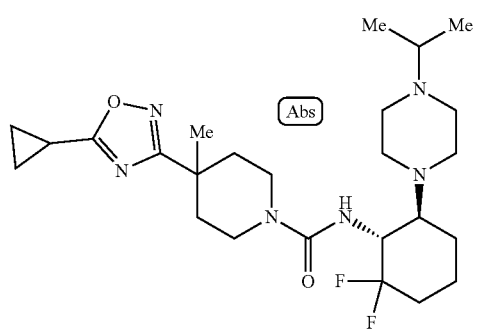 [SMILES: CC(C)N1CCN([C@H]2CCCC(F)(F)[C@@H]2NC(=O)N2CCC(C)(c3noc(C4CC4)n3)CC2)CC1]

Example 25: 4-(5-cyclopropyl-1,2-oxazol-3-yl)-N-{(1R,6S)-2,2-difluoro-6-[4-(propan-2-yl)piperazin-1-yl]cyclohexyl}-4-methylpiperidine-1-carboxamide

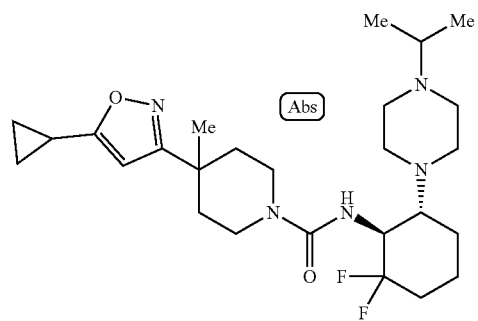

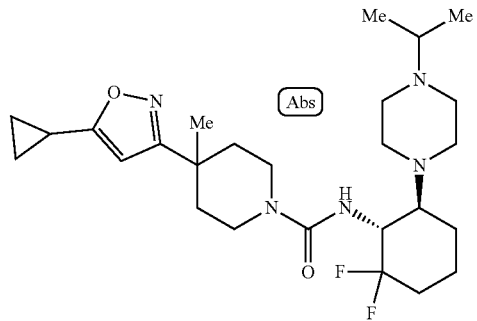 [SMILES: CC(C)N1CCN([C@H]2CCCC(F)(F)[C@@H]2NC(=O)N2CCC(C)(c3cc(C4CC4)on3)CC2)CC1]

Example 62: 4-(5-cyclopropyl-1,2,4-oxadiazol-3-yl)-N-{(1R,6S)-2,2-difluoro-6-[3-(propan-2-yl)-3,8-diazabicyclo[3.2.1]octan-8-yl]cyclohexyl}-4-methylpiperidine-1-carboxamide

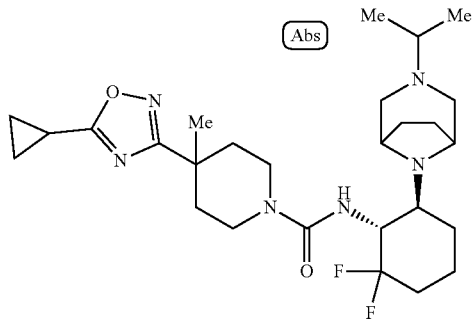 [SMILES: CC(C)N1CC2CCC(C1)N2[C@H]1CCCC(F)(F)[C@@H]1NC(=O)N1CCC(C)(c2noc(C3CC3)n2)CC1]

Example 63: N-{(1R,6S)-2,2-difluoro-6-[3-(propan-2-yl)-3,8-diazabicyclo[3.2.1]octan-8-yl]cyclohexyl}-4-methyl-4-(4-methylphenyl)piperidine-1-carboxamide

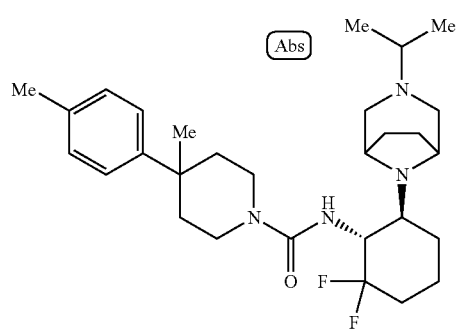 [SMILES: Cc1ccc(C2(C)CCN(C(=O)N[C@@H]3[C@@H](N4C5CCC4CN(C(C)C)C5)CCCC3(F)F)CC2)cc1]

Example 65: 4-(5-cyclopropyl-1,2-oxazol-3-yl)-N-{(1R,6S)-2,2-difluoro-6-[3-(propan-2-yl)-3,8-diazabicyclo[3.2.1]octan-8-yl]cyclohexyl}-4-methylpiperidine-1-carboxamide

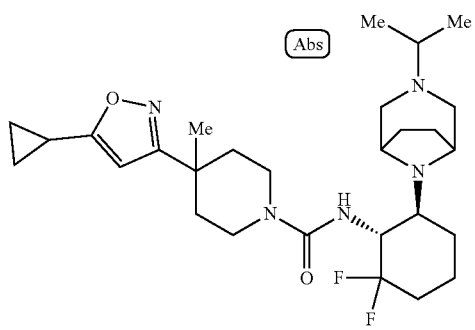 [SMILES: CC(C)N1CC2CCC(C1)N2[C@H]1CCCC(F)(F)[C@@H]1NC(=O)N1CCC(C)(c2cc(C3CC3)on2)CC1]

Example 66: N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide

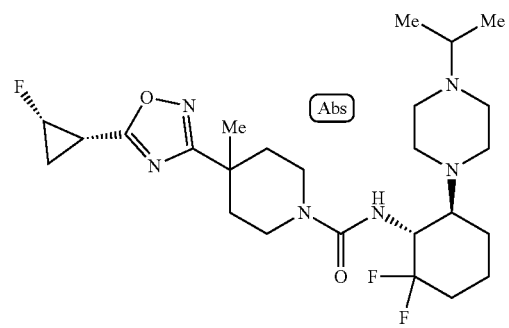 [SMILES: CC(C)N1CCN([C@H]2CCCC(F)(F)[C@@H]2NC(=O)N2CCC(C)(c3noc([C@@H]4C[C@@H]4F)n3)CC2)CC1]

Example 68: N-{(1R,6S)-2,2-difluoro-6-[4-(propan-2-yl)piperazin-1-yl]cyclohexyl}-4-methyl-4-{5-[(1S,2R)-2-methylcyclopropyl]-1,2,4-oxadiazol-3-yl}piperidine-1-carboxamide

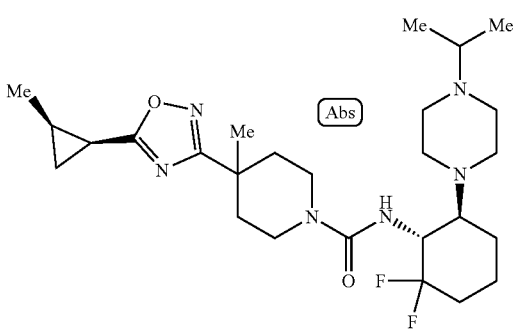 [SMILES: CC(C)N1CCN([C@H]2CCCC(F)(F)[C@@H]2NC(=O)N2CCC(C)(c3noc([C@H]4C[C@H]4C)n3)CC2)CC1]

Example 69: N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide

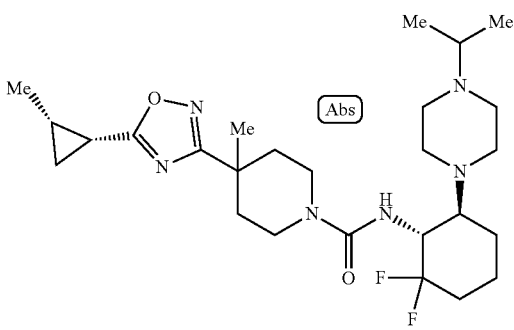 [SMILES: CC(C)N1CCN([C@H]2CCCC(F)(F)[C@@H]2NC(=O)N2CCC(C)(c3noc([C@@H]4C[C@@H]4C)n3)CC2)CC1]

Example 79: rac-4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carbothioamide

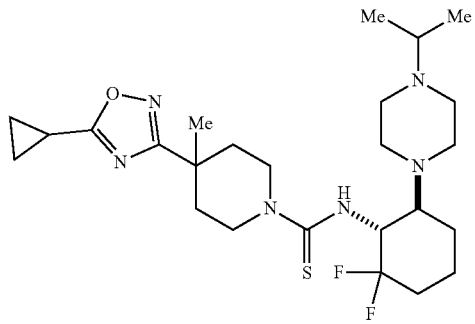 [SMILES: CC(C)N1CCN([C@H]2CCCC(F)(F)[C@@H]2NC(=S)N2CCC(C)(c3noc(C4CC4)n3)CC2)CC1]

Example 80: 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carbothioamide

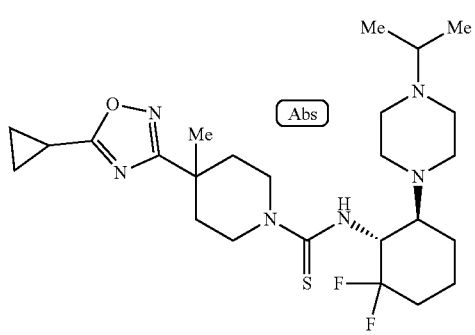 [SMILES: CC(C)N1CCN([C@H]2CCCC(F)(F)[C@@H]2NC(=S)N2CCC(C)(c3noc(C4CC4)n3)CC2)CC1]

ITEM 23

The compound of Item 1 or a pharmaceutically acceptable salt thereof, which is selected from the following compound names or structures:

Example 64: 4-(5-cyclopropyl-1,2,4-oxadiazol-3-yl)-N-[(1R,6S)-2,2-difluoro-6-{[(3R)-1-(propan-2-yl)pyrrolidin-3-yl]oxy}cyclohexyl]-4-methylpiperidine-1-carboxamide

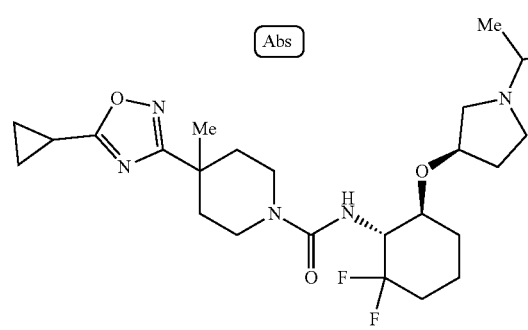

Example 67: N-[(1R,6S)-2,2-difluoro-6-{[(3R)-1-(propan-2-yl)pyrrolidin-3-yl]oxy}cyclohexyl]-4-methyl-4-(4-methylphenyl)piperidine-1-carboxamide

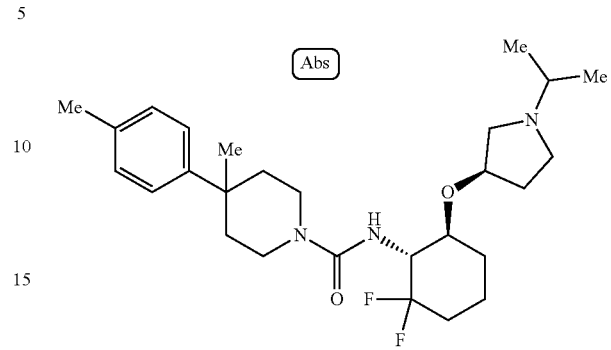

Example 71: 4-(5-cyclopropyl-1,2,4-oxadiazol-3-yl)-N-[(1R,6S)-2,2-difluoro-6-{[(3S)-1-(propan-2-yl)pyrrolidin-3-yl]oxy}cyclohexyl]-4-methylpiperidine-1-carboxamide

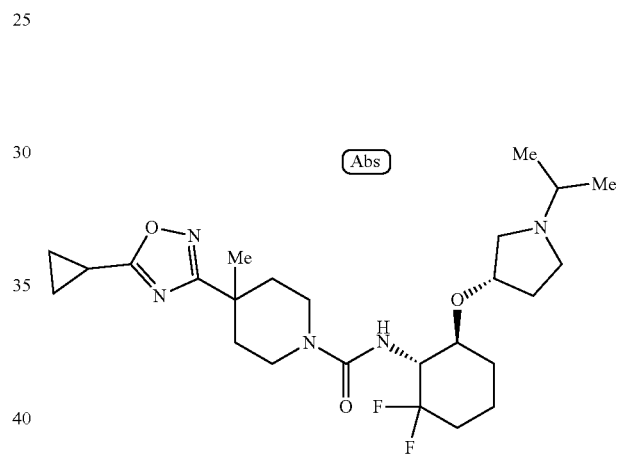

Example 72: N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide

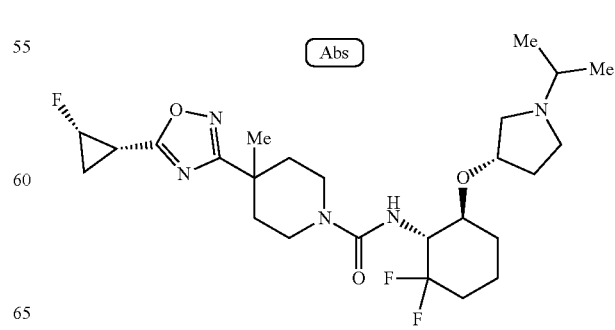

Example 73: N-[(1R,6S)-2,2-difluoro-6-{[(3R)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide

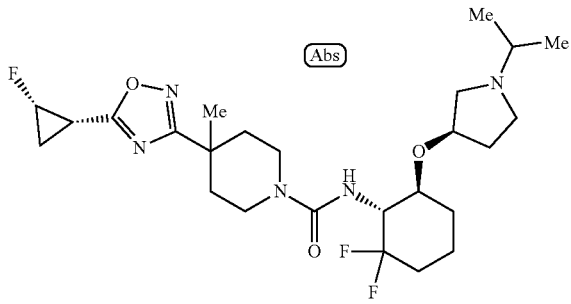 [SMILES: CC(C)N1CC[C@@H](O[C@H]2CCCC(F)(F)[C@@H]2NC(=O)N2CCC(C)(c3noc([C@@H]4C[C@@H]4F)n3)CC2)C1]

Example 74: N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide

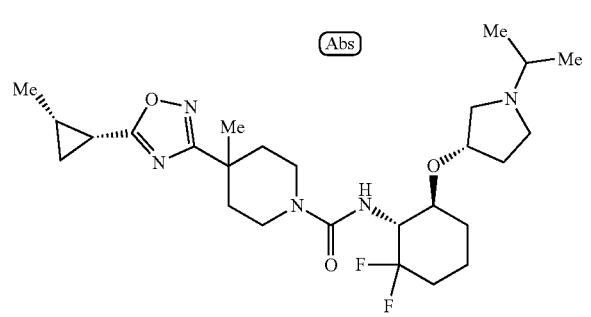 [SMILES: CC(C)N1CC[C@H](O[C@H]2CCCC(F)(F)[C@@H]2NC(=O)N2CCC(C)(c3noc([C@@H]4C[C@@H]4C)n3)CC2)C1]

Example 75: 4-(5-cyclopropyl-1,2,4-oxadiazol-3-yl)-N-[(1R,6S)-2,2-difluoro-5-{[(3S,4S)-4-fluoro-1-(propan-2-yl)pyrrolidin-3-yl]oxy}cyclohexyl]-4-methylpiperidine-1-carboxamide

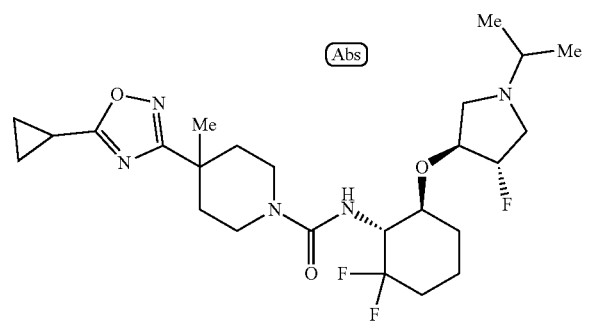 [SMILES: CC(C)N1C[C@H](O[C@H]2CCCC(F)(F)[C@@H]2NC(=O)N2CCC(C)(c3noc(C4CC4)n3)CC2)[C@@H](F)C1]

Example 76: 4-(5-cyclopropyl-1,2,4-oxadiazol-3-yl)-N-[(1R,6S)-6-{[(3R)-4,4-difluoro-1-(propan-2-yl)pyrrolidin-3-yl]oxy}-2,2-difluorocyclohexyl]-4-methylpiperidine-1-carboxamide

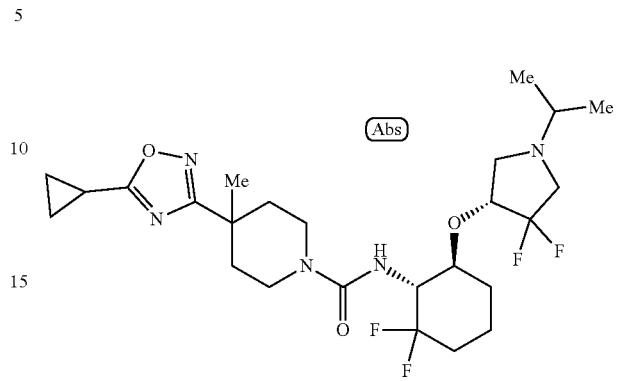

ITEM 24

The compound of Item 1 or a pharmaceutically acceptable salt thereof, which is selected from the following compound names or structures:

Example 82: N-{(1S,6R)-2,2-difluoro-6-[4-(propan-2-yl)piperazin-1-yl]cyclohexyl}-4-{5-[(1R,2R)-2-fluorocyclopropyl]-1,2,4-oxadiazol-3-yl}-4-methylpiperidine-1-carboxamide

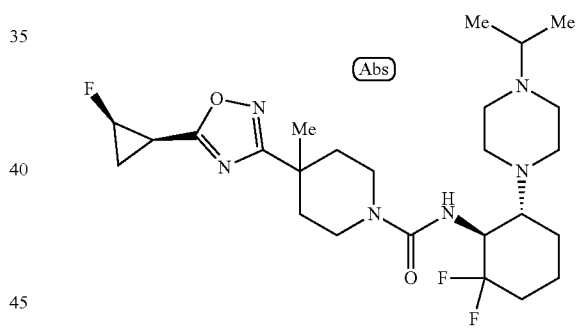

Example 95: N-[(1R,6S)-2,2-difluoro-6-{methyl[(3S)-1-(propan-2-yl)pyrrolidin-3-yl]amino}cyclohexyl]-4-{5-[(1S,2S)-2-fluorocyclopropyl]-1,2,4-oxadiazol-3-yl}-4-methylpiperidine-1-carboxamide

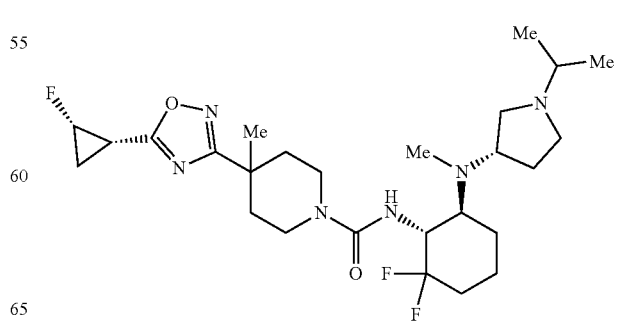

Example 96: N-[(1R,6S)-2,2-difluoro-6-{(3S)-3-[methyl(propan-2-yl)amino]pyrrolidin-1-yl}cyclohexyl]-4-{5-[(1S,2S)-2-fluorocyclopropyl]-1,2,4-oxadiazol-3-yl}-4-methylpiperidine-1-carboxamide

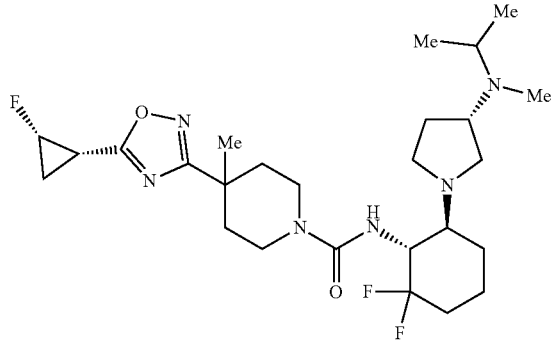 [SMILES: CC(C)N(C)[C@H]1CCN([C@H]2CCCC(F)(F)[C@@H]2NC(=O)N2CCC(C)(c3noc([C@@H]4C[C@@H]4F)n3)CC2)C1]

Example 97: 4-(5-cyclobutyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide

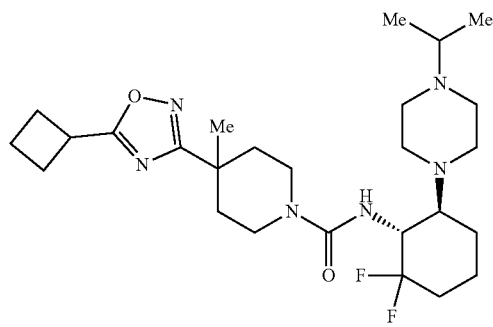 [SMILES: CC(C)N1CCN([C@H]2CCCC(F)(F)[C@@H]2NC(=O)N2CCC(C)(c3noc(C4CCC4)n3)CC2)CC1]

Example 99: 4-(5-cyclopropyl-1,2,4-oxadiazol-3-yl)-N-[(1R,6S)-2,2-difluoro-6-{(3S)-3-[methyl(propan-2-yl)amino]pyrrolidin-1-yl}cyclohexyl]-4-methylpiperidine-1-carboxamide

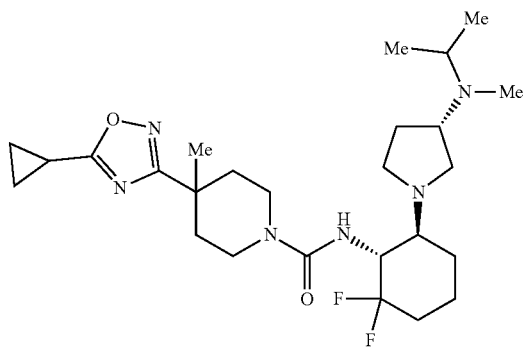 [SMILES: CC(C)N(C)[C@H]1CCN([C@H]2CCCC(F)(F)[C@@H]2NC(=O)N2CCC(C)(c3noc(C4CC4)n3)CC2)C1]

Example 110: N-{(1R,6S)-2,2-difluoro-6-[(2S)-2-methyl-4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide

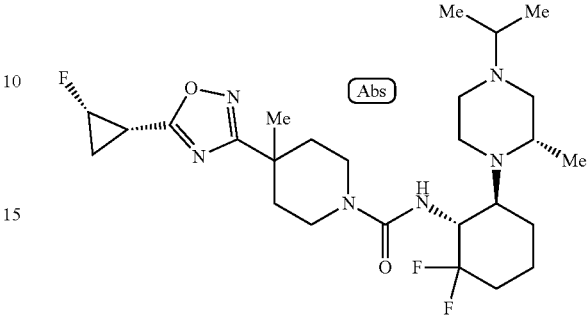

Example 111: N-{(1R,6S)-2,2-difluoro-6-[(2R)-2-methyl-4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide

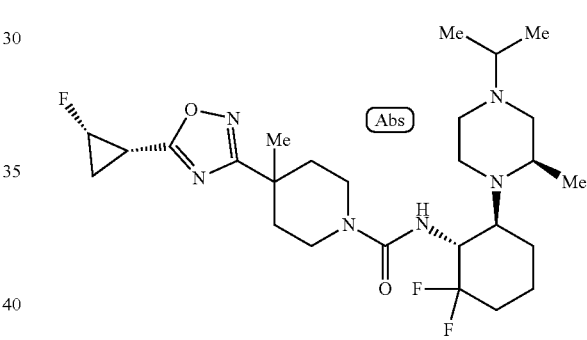

Example 112: N-[(1R,6S)-2,2-difluoro-6-{(3R)-3-[methyl(propan-2-yl)amino]pyrrolidin-1-yl}cyclohexyl]-4-{5-[(1S,2S)-2-fluorocyclopropyl]-1,2,4-oxadiazol-3-yl}-4-methylpiperidine-1-carboxamide

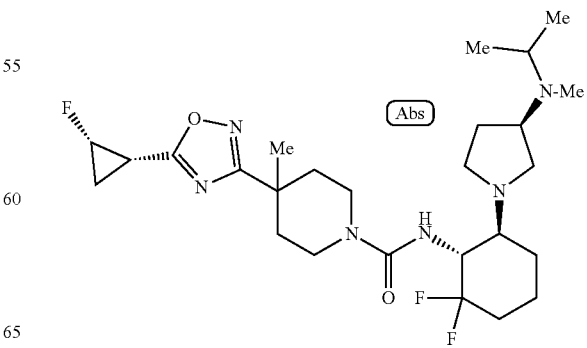

Example 114: N-[(1R,6S)-2,2-difluoro-6-{4-[methyl(propan-2-yl)amino]piperidin-1-yl}cyclohexyl]-4-{5-[(1S,2S)-2-fluorocyclopropyl]-1,2,4-oxadiazol-3-yl}-4-methylpiperidine-1-carboxamide

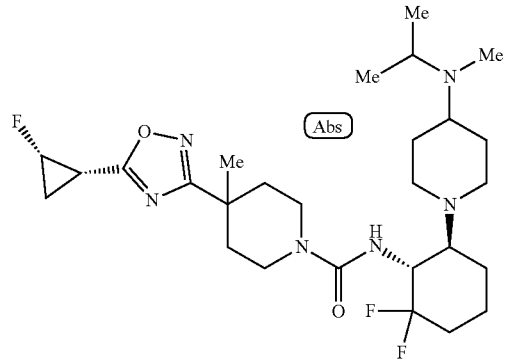 [SMILES: CC(C)N(C)C1CCN([C@H]2CCCC(F)(F)[C@@H]2NC(=O)N2CCC(C)(c3noc([C@@H]4C[C@@H]4F)n3)CC2)CC1]

Example 115: N-[(1R,6S)-6-{(3S)-3-[cyclopropyl(methyl)amino]pyrrolidin-1-yl}-2,2-difluorocyclohexyl]-4-{5-[(1S,2S)-2-fluorocyclopropyl]-1,2,4-oxadiazol-3-yl}-4-methylpiperidine-1-carboxamide

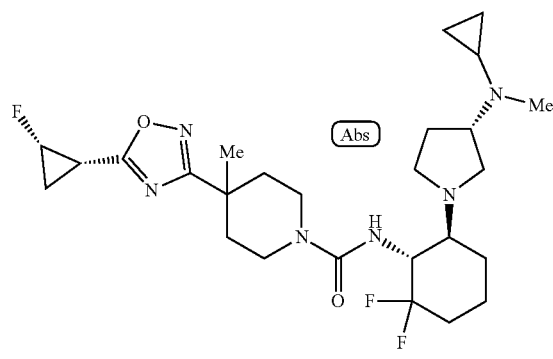 [SMILES: CN(C1CC1)[C@H]1CCN([C@H]2CCCC(F)(F)[C@@H]2NC(=O)N2CCC(C)(c3noc([C@@H]4C[C@@H]4F)n3)CC2)C1]

Example 128: N-[(1R,6S)-2,2-difluoro-6-{(3S)-3-[methyl(2-methylpropyl)amino]pyrrolidin-1-yl}cyclohexyl]-4-(5-[(1S,2S)-2-fluorocyclopropyl]-1,2,4-oxadiazol-3-yl}-4-methylpiperidine-1-carboxamide

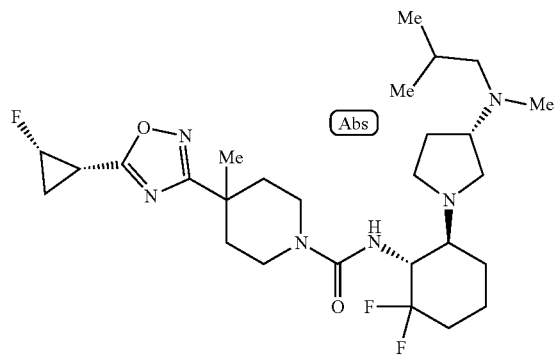 [SMILES: CC(C)CN(C)[C@H]1CCN([C@H]2CCCC(F)(F)[C@@H]2NC(=O)N2CCC(C)(c3noc([C@@H]4C[C@@H]4F)n3)CC2)C1]

Example 134: N-[(1R,6S)-2,2-difluoro-6-(4-(methyl[(1-methylcyclopropyl)methyl]amino}piperidin-1-yl)cyclohexyl]-4-{5-[(1S,2S)-2-fluorocyclopropyl]-1,2,4-oxadiazol-3-yl}-4-methylpiperidine-1-carboxamide

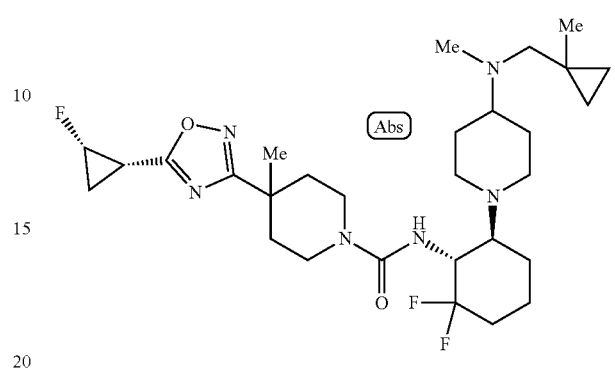

Example 136: N-[(1R,6S)-2,2-difluoro-6-(4-{[(1-fluorocyclopropyl)methyl](methyl)amino}piperidin-1-yl)cyclohexyl]-4-{5-[(1S,2S)-2-fluorocyclopropyl]-1,2,4-oxadiazol-3-yl}-4-methylpiperidine-1-carboxamide

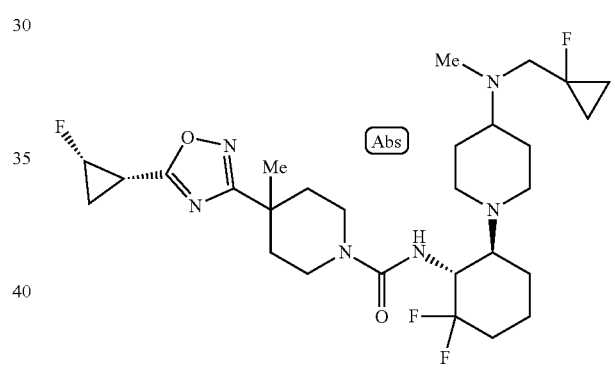

Example 137: N-[(1R,6S)-6-{(3S)-3-[(cyclopropylmethyl)(methyl)amino]pyrrolidin-1-yl}-2,2-difluorocyclohexyl]-4-{5-[(1S,2S)-2-fluorocyclopropyl]-1,2,4-oxadiazol-3-yl}-4-methylpiperidine-1-carboxamide

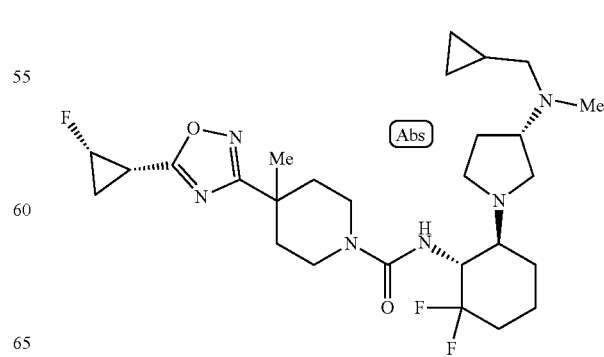

Example 138: N-[(1R/6S)-6-{(3S) 3-[(cyclopropylmethyl)(methyl)amino]pyrrolidin-1-yl}-2,2-difluorocyclohexyl]-4-(5-cyclopropyl-1,2,4-oxadiazol-3-yl)-4-methylpiperidine-1-carboxamide Example 156-A: 4-{5-[(1S,2S)-2-fluorocyclopropyl]-1,2,4-oxadiazol-3-yl}-N-{(1R,2S,6S)-2-fluoro-6-[4-(propan-2-yl)piperazin-1-yl]cyclohexyl}-4-methylpiperidine-1-carboxamide

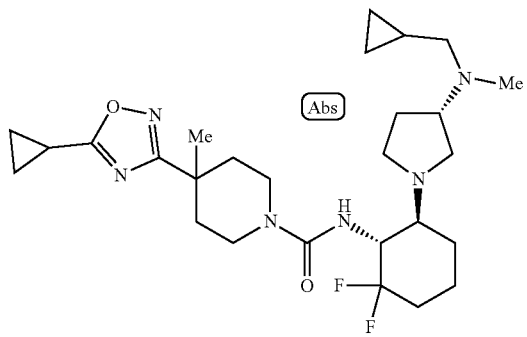 [SMILES: CN(CC1CC1)[C@H]1CCN([C@H]2CCCC(F)(F)[C@@H]2NC(=O)N2CCC(C)(c3noc(C4CC4)n3)CC2)C1]

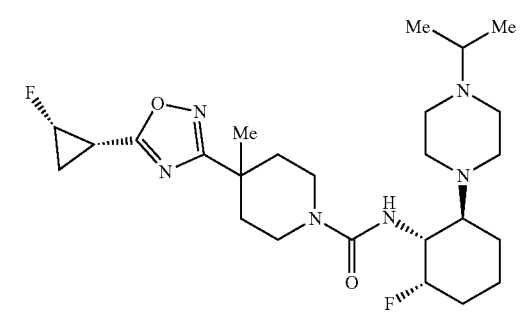

Example 139: rac-4-(5-cyclopropyl-1,2,4-oxadiazol-3-yl)-N-{(1R/2R,6S)-2-fluoro-6-[4-(propan-2-yl)piperazin-1-yl]cyclohexyl}-4-methylpiperidine-1-carboxamide Example 156-B: 4-{5-[(1S,2S)-2-fluorocyclopropyl]-1,2,4-oxadiazol-3-yl}-N-{(1S,2R,6R)-2-fluoro-6-[4-(propan-2-yl)piperazin-1-yl]cyclohexyl}-4-methylpiperidine-1-carboxamide

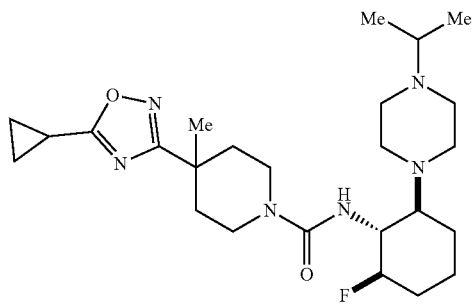 [SMILES: CC(C)N1CCN([C@H]2CCC[C@@H](F)[C@@H]2NC(=O)N2CCC(C)(c3noc(C4CC4)n3)CC2)CC1]

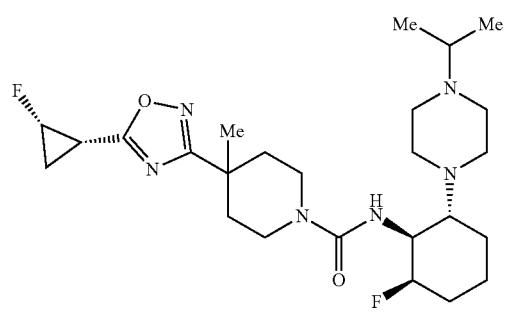

Example 152: N-{(1R,6S)-2,2-difluoro-6-[4-(propan-2-yl)-1,4-diazepan-1-yl]cyclohexyl}-4-{5-[(1S,2S)-2-fluorocyclopropyl]-1,2,4-oxadiazol-3-yl}-4-methylpiperidine-1-carboxamide Example 157: N-[(1R,6S)-2,2-difluoro-6-{4-[methyl(2-methylpropyl)amino]piperidin-1-yl}cyclohexyl]-4-{5-[(1S,2S)-2-fluorocyclopropyl]-1,2,4-oxadiazol-3-yl}-4-methylpiperidine-1-carboxamide

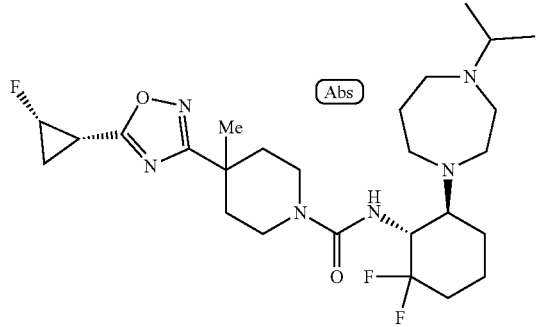 [SMILES: CC(C)N1CCCN([C@H]2CCCC(F)(F)[C@@H]2NC(=O)N2CCC(C)(c3noc([C@@H]4C[C@@H]4F)n3)CC2)CC1]

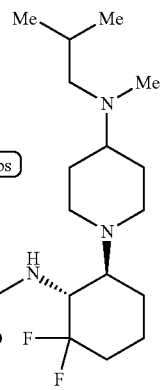

Example 158: N-[(1R,6S)-6-{4-[(cyclopropylmethyl)(methyl)amino]piperidin-1-yl}-2,2-difluorocyclohexyl]-4-{5-[(1S,2S)-2-fluorocyclopropyl]-1,2,4-oxadiazol-3-yl}-4-methylpiperidine-1-carboxamide

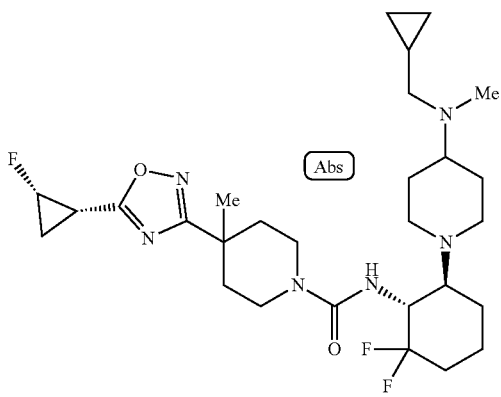 [SMILES: CN(CC1CC1)C1CCN([C@H]2CCCC(F)(F)[C@@H]2NC(=O)N2CCC(C)(c3noc([C@@H]4C[C@@H]4F)n3)CC2)CC1]

Example 159: N-[(1R,6S)-6-{4-[cyclobutyl(methyl)amino]piperidin-1-yl}-2,2-difluorocyclohexyl]-4-{5-[(1S,2S)-2-fluorocyclopropyl]-1,2,4-oxadiazol-3-yl}-4-methylpiperidine-1-carboxamide

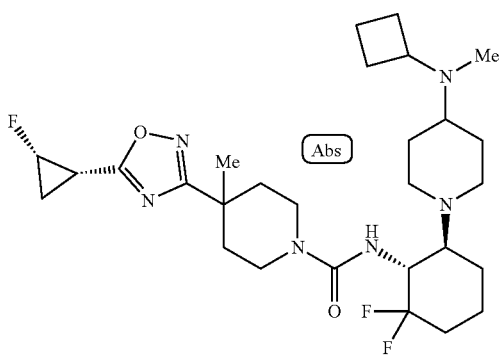 [SMILES: CN(C1CCC1)C1CCN([C@H]2CCCC(F)(F)[C@@H]2NC(=O)N2CCC(C)(c3noc([C@@H]4C[C@@H]4F)n3)CC2)CC1]

Example 161: N-[(1R,6S)-2,2-difluoro-6-{[(3S)-1-(propan-2-yl)pyrrolidin-3-yl]amino}cyclohexyl]-4-{5-[(1S,2S)-2-fluorocyclopropyl]-1,2,4-oxadiazol-3-yl}-4-methylpiperidine-1-carboxamide

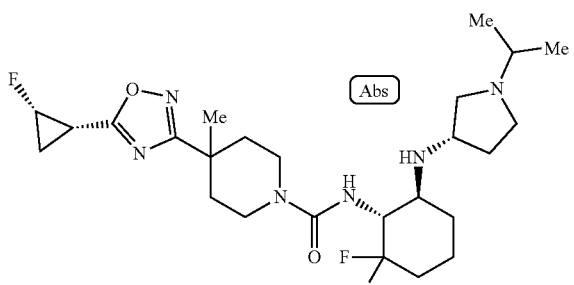

Example 83: N-[(1R,6S)-2,2-difluoro-6-{[1-(propan-2-yl)piperidin-4-yl]oxy}cyclohexyl]-4-{5-[(1S,2S)-2-fluorocyclopropyl]-1,2,4-oxadiazol-3-yl}-4-methylpiperidine-1-carboxamide

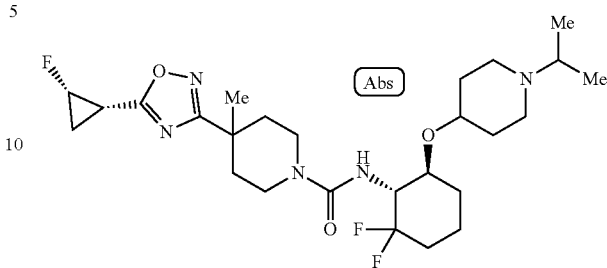

Example 84: 4-(5-cyclopropyl-1,2,4-oxadiazol-3-yl)-N-[(1R,6S)-2,2-difluoro-6-{[1-(propan-2-yl)piperidin-4-yl]oxy}cyclohexyl]-4-methylpiperidine-1-carboxamide


Example 102: 4-(5-cyclobutyl-1,2,4-oxadiazol-3-yl)-N-[(1R,6S)-2,2-difluoro-6-{[(3S)-1-(propan-2-yl)pyrrolidin-3-yl]oxy}cyclohexyl]-4-methylpiperidine-1-carboxamide

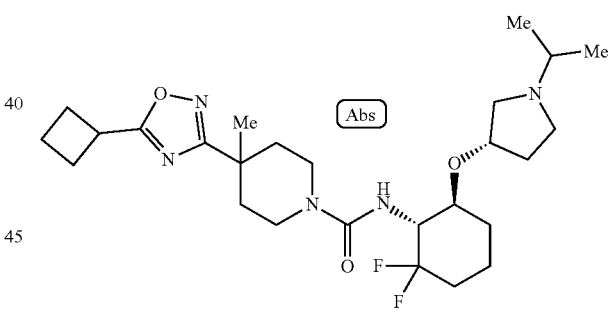

Example 103: N-[(1R,6S)-2,2-difluoro-6-{[(3S)-1-(propan-2-yl)pyrrolidin-3-yl]oxy}cyclohexyl]-4-ethyl-4-{5-[(1S,2S)-2-fluorocyclopropyl]-1,2,4-oxadiazol-3-yl}piperidine-1-carboxamide

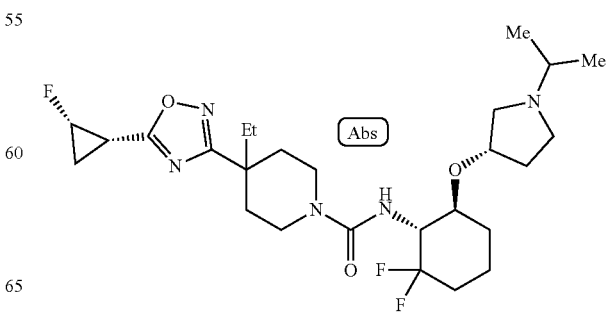

ITEM 25

The compound of Item 1 or a pharmaceutically acceptable salt thereof, which is selected from the following compound names or structures:

Example 107: N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide

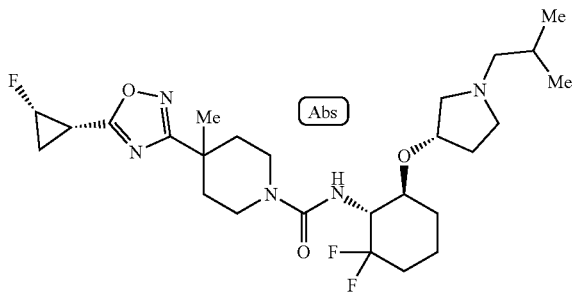 [SMILES: CC(C)CN1CC[C@H](O[C@H]2CCCC(F)(F)[C@@H]2NC(=O)N2CCC(C)(c3noc([C@@H]4C[C@@H]4F)n3)CC2)C1]

Example 116: 4-(5-cyclopropyl-1,2,4-oxadiazol-3-yl)-N-[(1R,6S)-2,2-difluoro-6-{[(3S)-1-(2-methylpropyl)pyrrolidin-3-yl]oxy}cyclohexyl]-4-methylpiperidine-1-carboxamide

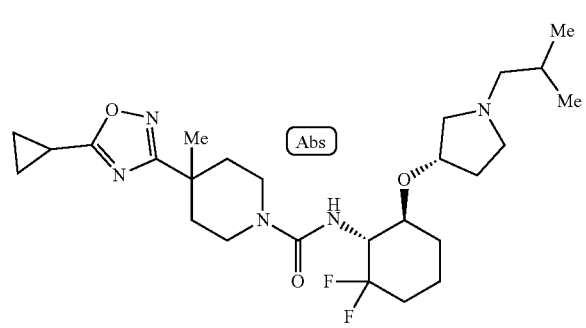 [SMILES: CC(C)CN1CC[C@H](O[C@H]2CCCC(F)(F)[C@@H]2NC(=O)N2CCC(C)(c3noc(C4CC4)n3)CC2)C1]

Example 118: N-[(1R,6S)-6-{[(3S)-1-(cyclopropylmethyl)pyrrolidin-3-yl]oxy}-2,2-difluorocyclohexyl]-4-{5-[(1S,2S)-2-fluorocyclopropyl]-1,2,4-oxadiazol-3-yl}-4-methylpiperidine-1-carboxamide

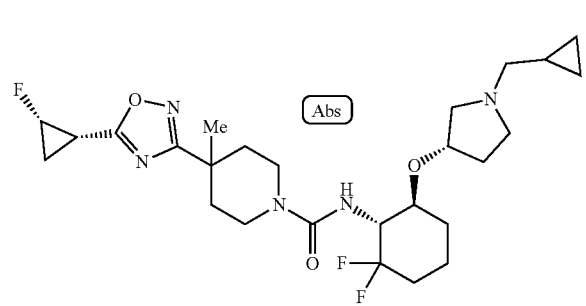 [SMILES: CC1(c2noc([C@@H]3C[C@@H]3F)n2)CCN(C(=O)N[C@@H]2[C@@H](O[C@H]3CCN(CC4CC4)C3)CCCC2(F)F)CC1]

Example 119: 4-(5-cyclopropyl-1,2,4-oxadiazol-3-yl)-N-[(1R,6S)-6-{[(3S)-1-(2,2-dimethylpropyl)pyrrolidin-3-yl]oxy}-2,2-difluorocyclohexyl]-4-methylpiperidine-1-carboxamide

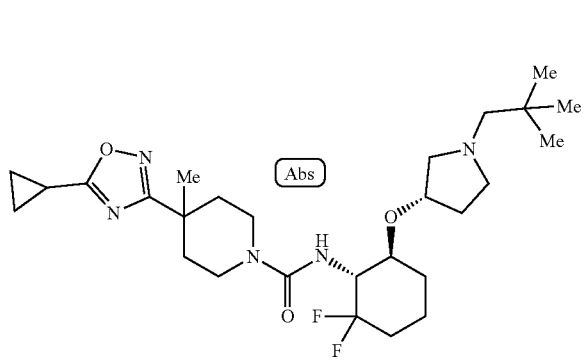 [SMILES: CC(C)(C)CN1CC[C@H](O[C@H]2CCCC(F)(F)[C@@H]2NC(=O)N2CCC(C)(c3noc(C4CC4)n3)CC2)C1]

Example 120: N-[(1R,6S)-6-{[(3S)-1-(2,2-dimethylpropyl)pyrrolidin-3-yl]oxy}-2,2-difluorocyclohexyl]-4-{5-[(1S,2S)-2-fluorocyclopropyl]-1,2,4-oxadiazol-3-yl}-4-methylpiperidine-1-carboxamide Example 121: N-[(1R,6S)-2,2-difluoro-6-({(3S)-1-[(1-methylcyclopropyl)methyl]pyrrolidin-3-yl}oxy)cyclohexyl]-4-{5-[(1S,2S)-2-fluorocyclopropyl]-1,2,4-oxadiazol-3-yl}-4-methylpiperidine-1-carboxamide

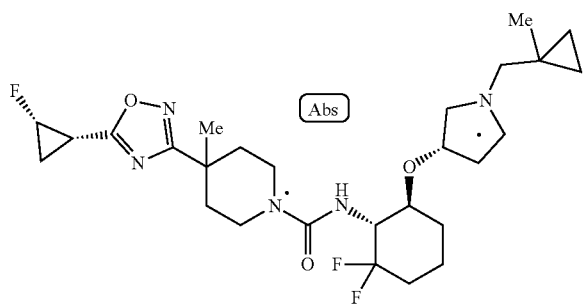

Example 122: N-[(1R,6S)-6-{[(3S)-1-(cyclopropylmethyl)pyrrolidin-3-yl]oxy}-2,2-difluorocyclohexyl]-4-(5-cyclopropyl-1,2,4-oxadiazol-3-yl)-4-methylpiperidine-1-carboxamide

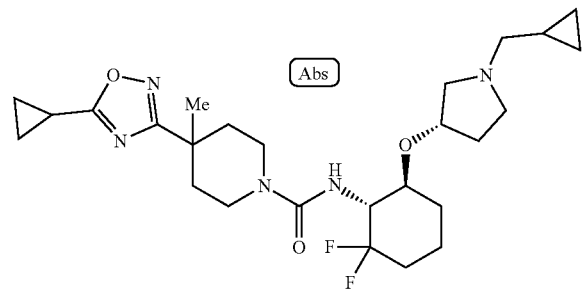 [SMILES: CC1(c2noc(C3CC3)n2)CCN(C(=O)N[C@@H]2[C@@H](O[C@H]3CCN(CC4CC4)C3)CCCC2(F)F)CC1]

Example 126: 4-(5-cyclopropyl-1,2,4-oxadiazol-3-yl)-N-[(1R,6S)-2,2-difluoro-6-({(3S)-1-[(1-methylcyclopropyl)methyl]pyrrolidin-3-yl}oxy)cyclohexyl]-4-methylpiperidine-1-carboxamide

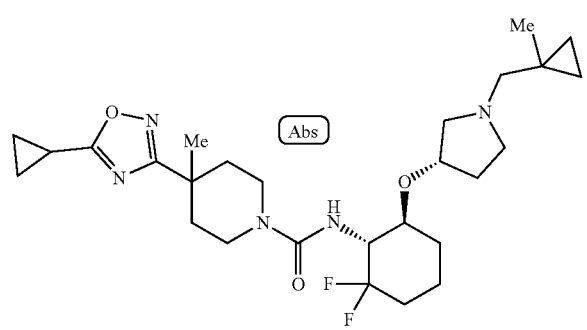 [SMILES: CC1(CN2CC[C@H](O[C@H]3CCCC(F)(F)[C@@H]3NC(=O)N3CCC(C)(c4noc(C5CC5)n4)CC3)C2)CC1]

Example 133: N-[(1R,6S)-2,2-difluoro-6-({(3S)-1-[(1-fluorocyclopropyl)methyl]pyrrolidin-3-yl}oxy)cyclohexyl]-4-{5-[(1S,2S)-2-fluorocyclopropyl]-1,2,4-oxadiazol-3-yl}-4-methylpiperidine-1-carboxamide

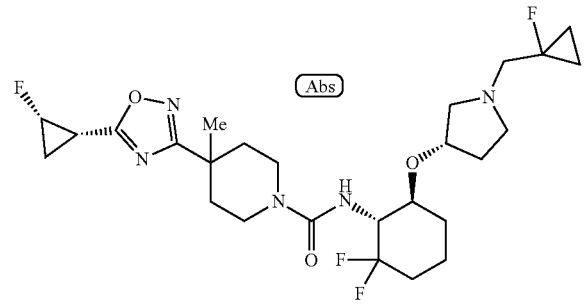 [SMILES: CC1(c2noc([C@@H]3C[C@@H]3F)n2)CCN(C(=O)N[C@@H]2[C@@H](O[C@H]3CCN(CC4(F)CC4)C3)CCCC2(F)F)CC1]

Example 134: N-[(1R,6S)-2,2-difluoro-6-(4-{methyl[(1-methylcyclopropyl)methyl]amino}piperidin-1-yl)cyclohexyl]-4-{5-[(1S,2S)-2-fluorocyclopropyl]-1,2,4-oxadiazol-3-yl}-4-methylpiperidine-1-carboxamide

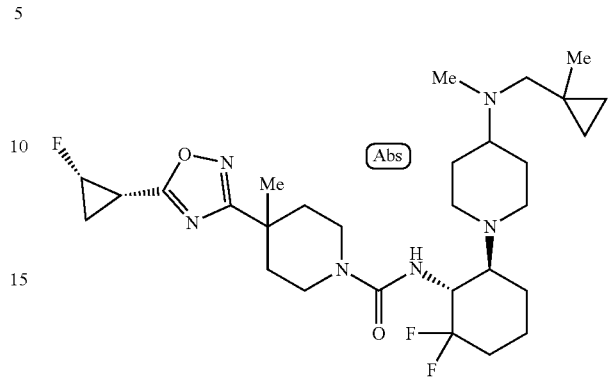

Example 143: N-[(1R,6S)-2,2-difluoro-6-{[(3S)-1-(2-fluoro-2-methylpropyl)pyrrolidin-3-yl]oxy}cyclohexyl]-4-{5-[(1S,2 S)-2-fluorocyclopropyl]-1,2,4-oxadiazol-3-yl}-4-methylpiperidine-1-carboxamide

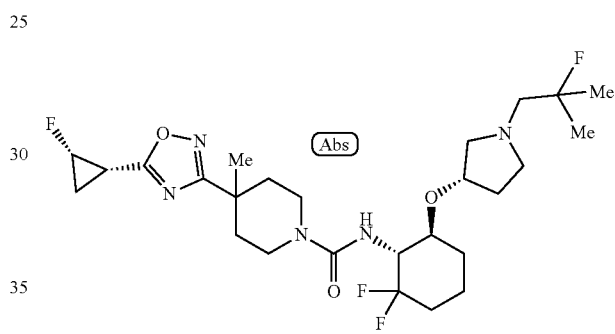

ITEM 26

A medicament for treating a disease related to orexin receptor, comprising the compound of any one of Items 1 to 25 or a pharmaceutically acceptable salt thereof.

ITEM 27

A medicament for treating narcolepsy, idiopathic hypersomnia, hypersomnia, sleep apnea syndrome, narcolepsy syndrome involving narcolepsy-like symptom, hypersomnia associated with Parkinson's disease, hypersomnia associated with dementia with Lewy body, hypersomnia syndrome involving daytime hypersomnia (e.g. Kleine-Levin syndrome, major depression accompanied by hypersomnia, dementia with Lewy body, Parkinson's disease, progressive supranuclear palsy, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalopathy, limbic encephalitis, Hashimoto encephalopathy), coma, loss of consciousness, obesity (e.g. malignant mast cell, extrinsic obesity, hyperinsulinar obesity, hyperplasmic obesity, hypophysial obesity, hypoplasmic obesity, hypothyroid obesity, hypothalamic obesity, symptomatic obesity, childhood obesity, upper body obesity, alimentary obesity, gonadal obesity, systemic mastocytosis, primary obesity, central obesity), insulin resistance syndrome, Alzheimer, impaired con sciousness such as coma, side effect or complication caused by anesthesia, sleep disturbance, sleep problem, insomnia, intermittent sleep, night myoclonus, REM sleep interruption, jet lag, jet lag syndrome, sleep disorder of shift workers, dyssomnia, sleep terror, depression, major depression, sleepwalking, enuresis, sleep disorder, Alzheimer's sundown syndrome, disease associated with circadian rhythm, fibromyalgia, condition resulting from decrease in sleeping quality, bulimia, obsessive eating disorder, obesity-related diseases, hypertension, diabetes, elevated plasma insulin level/insulin resistance, hyperlipemia, hyperlipidaemia, endometrial cancer, breast cancer, prostate cancer, colon cancer, cancer, osteoarthritis, obstructive sleep apnea, cholelithiasis, gallstone, heart disease, abnormal heartbeat, arrhythmia, myocardial infarction, congestive heart failure, heart failure, coronary heart disease, cardiovascular disease, sudden death, polycystic ovary, craniopharyngioma, Prader-Willi syndrome, Froehlich syndrome, growth hormone deficiency, normal variant short stature, Turner syndrome, children suffering from acute lymphoblastic leukemia, syndrome X, reproductive hormone abnormality, decrease of fecundability, infertility, hypogonadism in men, sexual/reproductive-function dysfunction such as hirsutism in women, fetal defect associated with maternity obesity, gastrointestinal motility disorder such as obesity-related gastroesophageal reflux, obesity hypoventilation syndrome (Pickwickian syndrome), respiratory disease such as respiratory distress, inflammation such as vascular systemic inflammation, arteriosclerosis, hypercholesterolemia, hyperuricemia, low back pain, gallbladder disease, gout, renal cancer, secondary risk of obesity such as risk of left ventricle hypertrophy, migraine, headache, neuropathic pain, Parkinson's disease, psychosis, schizophrenia, facial flushing, night sweat, disease in genitalium/urinary system, disease associated with sexual function or fecundability, dysthymic disorder, bipolar disorder, bipolar I disorder, bipolar II disorder, cyclothymic disorder, acute stress disorder, agoraphobia, generalized anxiety disorder, obsessive-compulsive disorder, panic attack, panic disorder, posttraumatic stress disorder, separation anxiety disorder, social phobia, anxiety disorder, acute neurological and psychiatric disorder such as cerebral deficiency developed after heart bypass surgery or heart transplant, stroke, ischemic stroke, cerebral ischemia, spinal cord trauma, head injury, periparturient hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorder associated with muscle spasm, delirium, amnestic disorder, age-associated cognitive decline, schizoaffective disorder, paranoia, drug addiction, movement disorder, chronic fatigue syndrome, fatigue, medication-induced parkinsonian syndrome, Gilles de la Tourette syndrome, chorea, myoclonus, tic, restless legs syndrome, dystonia, dyskinesia, attention deficit hyperactivity disorder (ADHD), conduct disorder, urinary incontinence, withdrawal symptom, trigeminal neuralgia, hearing loss, tinnitus, nerve injury, retinopathy, macular degeneration, vomiting, cerebral edema, pain, bone pain, arthralgia, toothache, cataplexy, or traumatic brain injury, comprising the compound of any one of Items 1 to 25 or a pharmaceutically acceptable salt thereof.

ITEM 28

A medicament for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body, comprising the compound of any one of Items 1 to 25 or a pharmaceutically acceptable salt thereof.

ITEM 29

A method for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body, comprising administering a therapeutically effective amount of the compound of any one of Items 1 to 25 or a pharmaceutically acceptable salt thereof to a patient in need thereof.

ITEM 30

Use of the compound of any one of Items 1 to 25 or a pharmaceutically acceptable salt thereof, in the manufacture of a medicament for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body.

DESCRIPTION OF EMBODIMENTS

Hereinafter, the present invention is explained in more detail. In the description, the number of carbon atoms in the definition of "substituents" can indicates, for example, "$C_{1-6}$". The specific definition "$C_{1-6}$ alkyl" means an alkyl group having 1 to 6 carbon atoms. In the present description, a substituent group which is not accompanied with "optionally-substituted" or "substituted" means an "unsubstituted" substituent group. For example, "$C_{1-6}$ alkyl" means "unsubstituted $C_{1-6}$ alkyl".

The substituent groups in the present description may be sometimes expressed without the term "group". In case that "optionally-substituted" is used in the definition of substituent groups, the number of the substituting groups is not limited as long as the substitutions are available, i.e., it is one or more. It means that the possible number of substituting groups is the substitution-available number on carbon atoms or carbon/nitrogen atoms in a substituent group which are acceptable for substitution. Unless otherwise specified, the definition of each substituent group also extends over the case that the substituent group is partially included in another substituent group or the case that the substituent group is attached to another substituent group.

Unless otherwise specified, the binding site of substituent groups is not limited as long as the site is available to be bound.

The "halogen" includes, for example, fluorine, chlorine, bromine, iodine, and the like. It is preferably fluorine or chlorine.

The "$C_{1-4}$ alkyl" means straight or branched chain saturated hydrocarbon group having 1 to 4 carbon atoms, and the "$C_{1-6}$ alkyl" means straight or branched chain saturated hydrocarbon group having 1 to 6 carbon atoms. The "$C_{1-4}$ alkyl" includes, for example, methyl, ethyl, propyl, isopropyl, butyl, isobutyl, sec-butyl, and tert-butyl, and the "$C_{1-6}$ alkyl" includes, for example, pentyl, isopentyl, neopentyl, 1-ethylpropyl, hexyl, and a structural isomer thereof, besides the above $C_{1-4}$ alkyl. Preferred examples of the "$C_{1-6}$ alkyl" or "$C_{1-4}$ alkyl" include methyl, ethyl, propyl, and isopropyl; more preferably methyl and isopropyl.

The "$C_{1-6}$ alkylene" means divalent straight or branched chain saturated hydrocarbon group having 1 to 6 carbon atoms. The "$C_{1-6}$ alkylene" includes preferably "$C_{1-4}$ alkylene", more preferably "$C_{1-3}$ alkylene". The "$C_{1-3}$ alkylene" includes, for example, methylene, ethylene, propylene, trimethylene, and the like. The "$C_{1-4}$ alkylene" includes, for example, butylene, 1,1-dimethylethylene, 1,2-dimethylethylene, 1 methyltrimethylene, 2-methyltrimethylene, and the like, besides the examples listed in the said "$C_{1-3}$ alkylene". The "$C_{1-6}$ alkylene" includes, for example, pentylene, 1,1-dimethyltrimethylene, 1,2-dimethyltrimethylene, 1-methylbutylene, 2-methylbutylene, 1-methylpentylene, 2-methylpentylene, 3-methylpentylene, hexylene, and the like, besides the examples listed in the said "$C_{1-4}$ alkylene".

The "$C_{3-7}$ cycloalkyl" means a non-aromatic cyclic hydrocarbon group (i.e., saturated hydrocarbon group and partially-unsaturated hydrocarbon group) having 3 to 7 carbon atoms, which includes preferably "$C_{3-6}$ cycloalkyl". The "$C_{3-7}$ cycloalkyl" also includes a bridged one. The "$C_{3-10}$ cycloalkyl" includes, for example, cyclopropyl, cyclobutyl, cyclopentyl, cyclohexyl, cyclopentenyl, cyclohexenyl, and cycloheptyl.

The "$C_{3-7}$ cycloalkyl" also includes a bi-cyclic condensed ring in which the "$C_{3-7}$ cycloalkyl" is fused with benzene or a 5- or 6-membered ring having one heteroatom selected from nitrogen, sulfur, or oxygen atom, or the same or different and two or more (for example, 2 to 4) heteroatoms thereof (for example, "5- or 6-membered monocyclic heteroaryl" mentioned below, and 5- or 6-membered ring in "4- to 10-membered saturated heterocyclyl" mentioned below).

The "$C_{1-4}$ alkoxy" means oxy group substituted with the above "$C_{1-4}$ alkyl", and the "$C_{1-6}$ alkoxy" means oxy group 1 substituted with the above "$C_{1-6}$ alkyl". The "$C_{1-4}$ alkoxy" includes, for example, methoxy, ethoxy, propoxy, isopropoxy, butoxy, isobutoxy, sec-butoxy, and tert-butoxy. Preferably, the "$C_{1-4}$ alkoxy" includes methoxy, ethoxy, and isopropoxy.

The "$C_{3-7}$ cycloalkoxy" means oxy group substituted with the above "$C_{3-7}$ cycloalkyl", which includes preferably "$C_{3-6}$ cycloalkoxy". The "$C_{3-7}$ cycloalkoxy" includes, for example, cyclopropyloxy, cyclobutyloxy, cyclopentyloxy, and cyclohexyloxy, and preferably cyclohexyloxy.

The "$C_{6-10}$ aromatic carbocyclyl group" means an aromatic hydrocarbon group having 6 to 10 carbon atoms, which is also referred to as "$C_{6-10}$ aryl". More preferably, it is phenyl. The "$C_{6-10}$ aromatic carbocyclyl group" includes, for example, phenyl, 1-naphthyl, and 2-naphthyl.

The "$C_{6-10}$ aromatic carbocyclyl group" also includes a condensed ring in which "phenyl" is fused with a 5- or 6-membered ring having one heteroatom selected from nitrogen, sulfur, or oxygen atom, or the same or different and two or more (for example, 2 to 4) heteroatoms thereof (for example, "5- or 6-membered monocyclic aromatic heterocyclyl group" mentioned below, and 5- or 6-membered ring in "4- to 10-membered saturated heterocyclyl" mentioned below), or a 5- to 7-membered cycloalkyl ring (for example, cyclopentane, cyclohexane and cycloheptane).

The "5- to 10-membered aromatic heterocyclyl group" means a 5- to 10-membered mono- or multiple-cyclic aromatic group having one heteroatom selected from nitrogen, sulfur, or oxygen atom, or the same or different and two or more (for example, 2 to 4) heteroatoms thereof, besides carbon atoms as the ring atoms, preferably, "5- or 6-membered monocyclic aromatic heterocyclyl group". The "5- or 6-membered monocyclic aromatic heterocyclyl group" means a 5- or 6-membered monocyclic aromatic group within the "5- to 10-membered aromatic heterocyclyl group".

The multiple-cyclic aromatic heterocyclyl group in the "5- to 10-membered aromatic heterocyclyl group" includes, for example, a condensed ring in which the same or different two monocyclic aromatic heterorings are fused, or a monocyclic aromatic heteroring and an aromatic ring (for example, benzene) or a non-aromatic ring (for example, cyclohexane) are fused.

The "5- to 10-membered aromatic heterocyclyl group" includes, for example, pyrazolyl, imidazolyl, pyridyl, pyrimidinyl, pyrazinyl, and pyridazinyl. Another embodiment includes, preferably, benzofuranyl in which the binding site is on the heteroaryl (furan) ring, pyridyl, pyrimidinyl, pyrazinyl, and pyridazinyl.

The "$C_{3-6}$ saturated carbocyclic ring" means a monocyclic saturated or partially-unsaturated hydrocarbon ring having 3 to 6 carbon atoms. The "$C_{3-6}$ saturated carbocyclic ring" includes, for example, cyclopropane, cyclobutane, cyclopentane, cyclohexane, cyclopropene, cyclobutene, cyclopentene, cyclohexene, and cyclohexadiene, and preferably cyclopropane and cyclobutane.

The "4- to 10-membered saturated heteroring" means a monocyclic or bicyclic saturated heteroring composed of 4 to atoms, which has the same or different and one or more (for example, 2 to 4, preferably 2 to 3, more preferably 2) heteroatoms selected from oxygen atom, nitrogen atom, and sulfur atom, besides carbon atoms as the ring atoms. The heteroring may include a partially-unsaturated one, a partially-bridged one, and a partially-spiro one. Preferred one thereof is a 5- or 6-membered saturated heteroring. The bicyclic saturated heteroring also includes a condensed ring of a monocyclic saturated heteroring, and benzene or a 5- or 6-membered monocyclic aromatic heteroring. And, the saturated heteroring may further comprise one or two carbonyl, thiocarbonyl, sulfinyl, or sulfonyl, that is, the saturated heteroring includes, for example, a cyclic group such as lactam, thiolactam, lactone, thiolactone, cyclic imide, cyclic carbamate, and cyclic thiocarbamate, wherein the number of atoms composing 4- to 10-membered ring (i.e., ring size) or the number of heteroatoms composing hetero ring does not count the oxygen atom in carbonyl, sulfinyl, and sulfonyl, and the sulfur atom in thiocarbonyl. The "4- to 10-membered saturated heteroring" includes preferably monocyclic or bicyclic "4- to 8-membered saturated heteroring", more preferably monocyclic "4- to 6-membered saturated heteroring", and even more preferably monocyclic "5- or 6-membered saturated heteroring". The "4- to 10-membered saturated heteroring" includes, for example, piperazine, oxetanyl, azetidinyl, pyranyl, tetrahydrofuryl, pyrrolidinyl, pyrazolidinyl, imidazolidinyl, piperidinyl, morpholinyl, homopiperidinyl, oxetanyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl, tetrahydropyranyl, and tetrahydropyridinyl, and preferably pyranyl, tetrahydrofuryl, pyrrolidinyl, piperidinyl, piperazinyl, and morpholinyl. The "bicyclic saturated heteroring" includes, for example, dihydroindolyl, dihydroisoindolyl, dihydropurinyl, dihydrothiazolopyrimidinyl, dihydrobenzodioxanyl, isoindolinyl, indazolyl, pyrrolopyridinyl, tetrahydroquinolinyl, decahydroquinolinyl, tetrahydroisoquinolinyl, decahydroisoquinolinyl, tetrahydronaphthyridinyl, and tetrahydropyrido-azepinyl.

The "4- to 6-membered saturated heterocyclyl group" means a monovalent substituent derived from "4- to 6-membered saturated heteroring" which belongs to the above "4- to 10-membered saturated heteroring". It includes preferably azetidinyl, pyrrolidinyl, piperidinyl, piperazinyl, morpholinyl, oxetanyl, tetrahydrofuranyl, and tetrahydropyranyl.

The "3- to 7-membered nitrogen-containing saturated heterocycle" which is formed by taking together $R^{68}$ and $R^{69}$ with the nitrogen atom to which they are attached corresponds to the above "4- to 10-membered saturated heteroring" wherein the number of atoms composing the ring is 3 to 7, and one nitrogen atom is included as an atom composing the ring besides carbon atoms.

The compound of the present invention includes various hydrate, solvate, and crystal polymorph thereof.

The compound of the present invention may include one or more isotope atoms such as D, $^{3}H$, $^{11}C$, $^{13}C$, $^{14}C$, $^{13}N$, $^{15}N$, $^{15}O$, $^{35}S$, $^{18}F$, and $^{125}I$ by substitution, and such isotope-substituted compound is also included in the compound of the present invention.

The "pharmaceutically acceptable salt" used herein means a pharmaceutically usable acid addition salt and a pharmaceutically usable base addition salt. The "pharmaceutically acceptable salt" includes, but not limited thereto, for example, an acid addition salt such as acetate, propionate, butyrate, formate, trifluoroacetate, maleate, fumarate, tartrate, citrate, stearate, succinate, ethylsuccinate, malonate, lactobionate, gluconate, glucoheptonate, benzoate, methanesulfonate, benzenesulfonate, p-toluenesulfonate (tosylate), laurylsulfate, malate, ascorbate, mandelate, saccharin, xinafoate, pamoate, cinnamate, adipate, cysteine, N-acetylcysteine, hydrochloride, hydrobromide, phosphate, sulfate, hydroiodide, nicotinate, oxalate, picrate, thiocyanate, undecanoate, polyacrylate, and carboxy vinyl polymer; an inorganic base addition salt such as lithium salt, sodium salt, potassium salt, and calcium salt; an organic base addition salt such as morpholine and piperidine; and amino acid addition salt such as aspartate and glutamate.

The present compounds can be orally or parenterally administered directly or as a suitable formulation such as drug product, medicament, and pharmaceutical composition. The formulation thereof may include, for example, tablet, capsule, powder, granule, liquid, suspension, injection, patch, gel patch, and the like, but not limited thereto. The formulation can be prepared with pharmaceutically acceptable additive agents in known means.

The additive agents can be chosen for any purpose, including an excipient, a disintegrant, a binder, a fluidizer, a lubricant, a coating agent, a solubilizer, a solubilizing agent, a thickener, dispersant, a stabilizing agent, a sweetening agent, a flavor, and the like. Specifically, they include, for example, lactose, mannitol, microcrystalline cellulose, low-substituted hydroxypropylcellulose, cornstarch, partially-pregelatinized starch, carmellose calcium, croscarmellose sodium, hydroxypropylcellulose, hydroxypropyl methylcellulose, polyvinyl alcohol, magnesium stearate, sodium stearyl fumarate, polyethylene glycol, propylene glycol, titanium oxide, talc, and the like.

The dose of the present compound should be suitably determined depending on subject animal for administration, administration route, target disease, and age, body weight, and condition of patients. For example, in the case of oral administration, about 0.01 mg as minimum to 10000 mg as maximum may be administered a day for an adult in one to several portions.

The compound of the present invention has agonist activity for orexin receptor. Thereby, the compound can be a medicament for preventing or treating a disease related to orexin receptor. The disease includes, for example, narcolepsy, idiopathic hypersomnia, hypersomnia, sleep apnea syndrome, narcolepsy syndrome involving narcolepsy-like symptom, hypersomnia associated with Parkinson's disease, hypersomnia associated with dementia with Lewy body, hypersomnia syndrome involving daytime hypersomnia (e.g. Kleine-Levin syndrome, major depression accompanied by hypersomnia, dementia with Lewy body, Parkinson's disease, progressive supranuclear palsy, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalopathy, limbic encephalitis, Hashimoto encephalopathy), coma, loss of consciousness, obesity (e.g. malignant mast cell, extrinsic obesity, hyperinsulinar obesity, hyperplasmic obesity, hypophysial obesity, hypoplasmic obesity, hypothyroid obesity, hypothalamic obesity, symptomatic obesity, childhood obesity, upper body obesity, alimentary obesity, gonadal obesity, systemic mastocytosis, primary obesity, central obesity), insulin resistance syndrome, Alzheimer, impaired consciousness such as coma, side effect or complication caused by anesthesia, sleep disturbance, sleep problem, insomnia, intermittent sleep, night myoclonus, REM sleep interruption, jet lag, jet lag syndrome, sleep disorder of shift workers, dyssomnia, sleep terror, depression, major depression, sleepwalking, enuresis, sleep disorder, Alzheimer's sundown syndrome, disease associated with circadian rhythm, fibromyalgia, condition resulting from decrease in sleeping quality, bulimia, obsessive eating disorder, obesity-related diseases, hypertension, diabetes, elevated plasma insulin level/insulin resistance, hyperlipemia, hyperlipidaemia, endometrial cancer, breast cancer, prostate cancer, colon cancer, cancer, osteoarthritis, obstructive sleep apnea, cholelithiasis, gallstone, heart disease, abnormal heartbeat, arrhythmia, myocardial infarction, congestive heart failure, heart failure, coronary heart disease, cardiovascular disease, sudden death, polycystic ovary, craniopharyngioma, Prader Willi syndrome, Froehlich syndrome, growth hormone deficiency, normal variant short stature, Turner syndrome, children suffering from acute lymphoblastic leukemia, syndrome X, reproductive hormone abnormality, decrease of fecundability, infertility, hypogonadism in men, sexual/reproductive-function dysfunction such as hirsutism in women, fetal defect associated with maternity obesity, gastrointestinal motility disorder such as obesity-related gastroesophageal reflux, obesity hypoventilation syndrome (Pickwickian syndrome), respiratory disease such as respiratory distress, inflammation such as vascular systemic inflammation, arteriosclerosis, hypercholesterolemia, hyperuricemia, low back pain, gallbladder disease, gout, renal cancer, secondary risk of obesity such as risk of left ventricle hypertrophy, migraine, headache, neuropathic pain, Parkinson's disease, psychosis, schizophrenia, facial flushing, night sweat, disease in genitalium/urinary system, disease associated with sexual function or fecundability, dysthymic disorder, bipolar disorder, bipolar I disorder, bipolar II disorder, cyclothymic disorder, acute stress disorder, agoraphobia, generalized anxiety disorder, obsessive-compulsive disorder, panic attack, panic disorder, posttraumatic stress disorder, separation anxiety disorder, social phobia, anxiety disorder, acute neurological and psychiatric disorder such as cerebral deficiency developed after heart bypass surgery or heart transplant, stroke, ischemic stroke, cerebral ischemia, spinal cord trauma, head injury, periparturient hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorder associated with muscle spasm, delirium, amnestic disorder, age-associated cognitive decline, schizoaffective disorder, paranoia, drug addiction, movement disorder, chronic fatigue syndrome, fatigue, medication-induced parkinsonian syndrome, Gilles de la Tourette syndrome, chorea, myoclonus, tic, restless legs syndrome, dystonia, dyskinesia, attention deficit hyperactivity disorder (ADHD), conduct disorder, urinary incontinence, withdrawal symptom, trigeminal neuralgia, hearing loss, tinnitus, nerve injury, retinopathy, macular degeneration, vomiting, cerebral edema, pain, bone pain, arthralgia, toothache, cataplexy, and traumatic brain injury; and preferably narcolepsy, idiopathic hypersomnia, hypersomnia, sleep apnea syndrome, narcolepsy syndrome involving narcolepsy-like symptom, hypersomnia associated with Parkinson's disease, and hypersomnia associated with dementia with Lewy body.

Hereinafter, the processes to prepare the compound of the present invention of formula (1) are exemplified along with examples, but the processes of the present invention should not be limited to the examples.

Preparation Process

The compound of the present invention may be synthesized according to each Preparation Process shown below or its combination with a known synthetic process.

Each compound in the following schemes may exist as a salt thereof, wherein the salt includes, for example, the "pharmaceutically acceptable salt" mentioned above. The following schemes are disclosed as just examples, thus it is also possible to optionally prepare the present compound by a different process based on the knowledge of a skilled person in synthetic organic chemistry field.

In each Preparation Process described below, protecting groups can be used as necessary, even if the use of protecting groups is not explicitly stated. And, the protecting groups can be deprotected after a reaction is completed or a series of reactions have been carried out to obtain the desired compound.

As such protecting groups, for example, general protecting groups described in T. W. Greene, and P. G. M. Wuts, "Protective Groups in Organic Synthesis", 3rd Ed., John Wiley & Sons, Inc., New York (1999), and the like may be used. Examples of amino-protecting groups include, for example, tert-butoxycarbonyl, benzyloxycarbonyl, p-toluenesulfonyl, o-nitrobenzenesulfonyl, tetrahydropyranyl, and the like; examples of hydroxy-protecting groups include, for example, trialkylsilyl, acetyl, benzyl, tetrahydropyranyl, methoxymethyl, and the like; examples of aldehyde-protecting groups include, for example, dialkylacetal, cyclic alkylacetal, and the like; and examples of carboxyl-protecting groups include, for example, tert-butyl ester, orthoester, amide, and the like.

The introduction and elimination of protecting groups can be carried out by a method commonly-used in synthetic organic chemistry (for example, see T. W. Greene, and P. G.

M. Wuts, "Protective Groups in Organic Synthesis", 3rd Ed., John Wiley & Sons, Inc., New York (1999)), or a similar method.

Preparation Process 1:

In compounds according to formula (1) or a pharmaceutically acceptable salt thereof, the compound of formula (s-1-1) or a pharmaceutically acceptable salt thereof which is a compound of formula (1) wherein $A^3$ is nitrogen atom can be prepared, for example, by the following process.

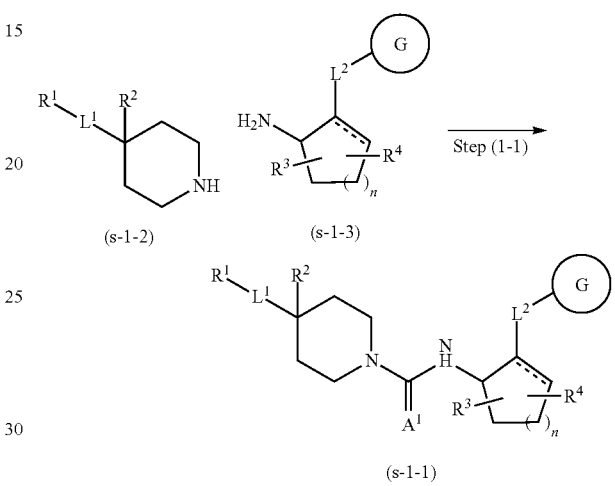

wherein $R^1$-$R^4$, $L^1$, $L^2$, n, Ring G, $A^1$, and the bond accompanied with broken line are as defined in Item 1.

Step (1-1):

Compound (s-1-1) can be prepared by reacting compound (s-1-2) and compound (s-1-3) in a suitable inert solvent under a reaction condition of urea-binding formulation. The present reaction condition includes, for example, using triphosgene, 4-nitrophenyl chloroformate, 1,1'-carbonyldiimidazole, or thiophosgene. A base is used in the present reaction, and the base used herein includes triethylamine and diisopropylethylamine. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

In Step (1-1), the intermediate such as an isocyanate may isolated, followed by transforming the intermediate.

Preparation Process 2:

In compounds according to formula (s-1-3), the compound of formula (s-2-1) which is a compound of formula (s-1-3) having no unsaturated bond in the ring can be prepared, for example, by the following process, provided that $L^2$ is oxygen atom or —$NR^{10}$—, or $L^2$ is single bond and Ring G is connected to the cycloalkyl via a nitrogen atom therein, wherein $R^{10}$ is H or $C_{1-4}$ alkyl, said definition is used below unless otherwise indicated.

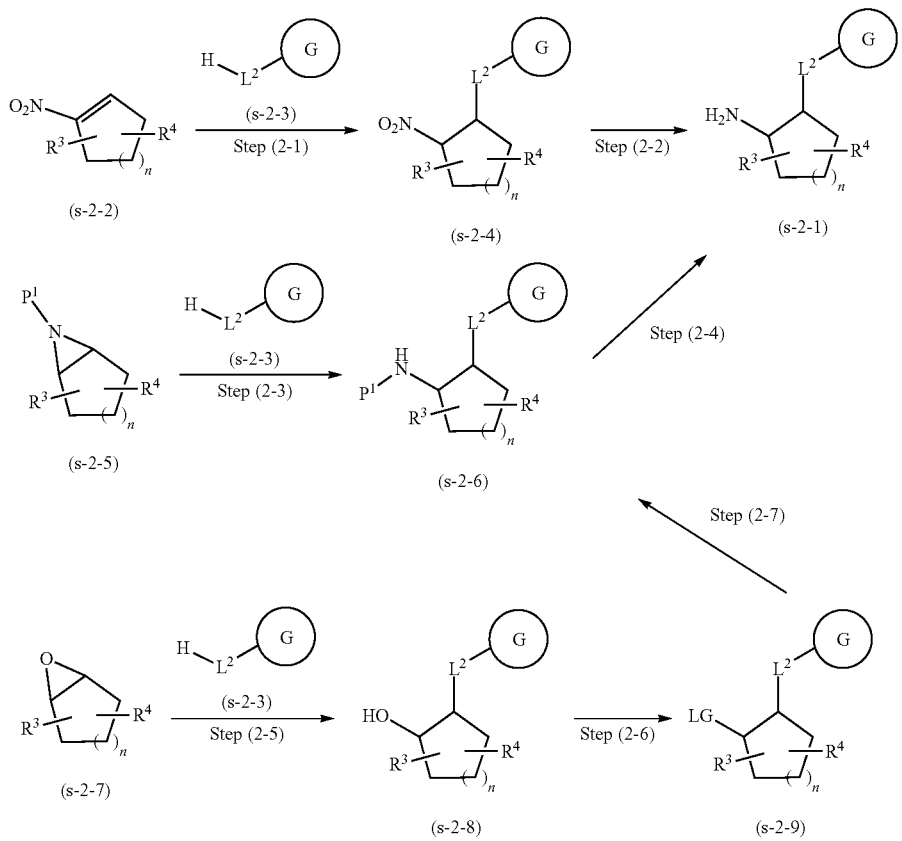

wherein $R^3$, $R^4$, $L^2$, n, and Ring G are as defined in Item 1; $P^1$ is a suitable protecting group; and LG is a suitable leaving group, said definitions are used below unless otherwise indicated.

Compound (s-2-1) can be prepared from compound (s-2-2) via Step (2-1) and Step (2-2).

Step (2-1):

Compound (s-2-4) can be prepared by reacting compound (s-2-2) and compound (s-2-3) in a suitable inert solvent without additives or in the presence of a acid or a base. The acid used herein includes, for example, a protonic acid such as hydrochloric acid, sulfuric acid, phosphoric acid, methanesulfonic acid, benzenesulfonic acid, and p toluenesulfonic; and a Lewis acid such as zinc (II) chloride, scandium (III) triflate, copper (I) chloride, boron trifluoride, boronic acid, and boronate ester. The base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (2-2):

Compound (s-2-1) can be prepared by reacting compound (s-2-4) in a suitable inert solvent or under hydrogen atmosphere as necessary, under a conventional condition of nitro-reduction. The present reaction condition includes, for example, using ferrum, zinc, tin (II) chloride, Raney nickel, palladium carbon, or palladium(II) hydroxide. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; an ester solvent such as ethyl acetate and methyl acetate; and an alcohol solvent such as methanol and ethanol. The reaction time is generally about 1 hour to 24 hours, and the reaction temperature is −20° C. to boiling point of a solvent used herein.

Compound (s-2-1) can be also prepared from compound (s-2-5) via Step (2-3) and Step (2-4).

Step (2-3):

Compound (s-2-6) can be prepared by reacting compound (s-2-5) and compound (s-2-3) in a suitable inert solvent without additives or in the presence of an acid or a base under a conventional condition of aziridine-ring-opening reaction. The acid used herein includes, for example, a protonic acid such as hydrochloric acid, sulfuric acid, phosphoric acid, methanesulfonic acid, benzenesulfonic acid, and p-toluenesulfonic; and a Lewis acid such as zinc (II) chloride, scandium(III) triflate, copper (I) chloride, boron trifluoride, boronic acid, and boronate ester. The base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (2-4):

Compound (s-2-1) can be prepared by deprotecting compound (s-2-6) in a known manner (for example, a manner described in Protective Groups in Organic Synthesis 3$^{rd}$ Edition (John Wiley & Sons, Inc.), Comprehensive Organic Transformation, edited by R. C. Larock, VCH publisher Inc., 1989, etc.) or a similar manner thereto.

Compound (s-2-1) can be also prepared from compound (s-2-7) via Step (2-5)-Step (2-7), and Step (2-4).

Step (2-5):

Compound (s-2-8) can be prepared by reacting compound (s-2-7) and compound (s-2-3) in a suitable inert solvent without additives or in the presence of a acid or a base under a conventional condition of epoxide-ring-opening reaction. The acid used herein includes, for example, a protonic acid such as hydrochloric acid, sulfuric acid, phosphoric acid, methanesulfonic acid, benzenesulfonic acid, and p-toluenesulfonic; and a Lewis acid such as boron trifluoride, zinc (II) chloride, scandium(III) triflate, copper(I) chloride, boronic acid, and boronate ester. The base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (2-6):

Compound (s-2-9) can be prepared by reacting compound (s-2-8) in a suitable inert solvent under a conventional condition of transformation reaction from hydroxy group to a leaving group. The present reaction condition includes, for example, using methanesulfonyl chloride, p-toluenesulfonyl chloride, or trifluoromethanesulfonyl chloride. A base is used in the present reaction, and the base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (2-7):

Compound (s-2-6) can be prepared in a general nucleophilic substitution reaction with compound (s-2-9), P$^1$NH$_2$, and a base. The base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The solvent used herein includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (2-6) and Step (2-7) may be carried out as one step without isolating the intermediate. And, Step (2-6) and Step (2-7) may be also carried out as one step under Mitsunobu reaction condition.

Preparation Process 3-1:

In compounds according to formula (s-2-1), the compound of formula (s-3-1) which is a compound of formula (s-2-1) wherein L$^2$ is single bond and Ring G binds to cycloalkyl via nitrogen atom therein can be also prepared, for example, by the following process.

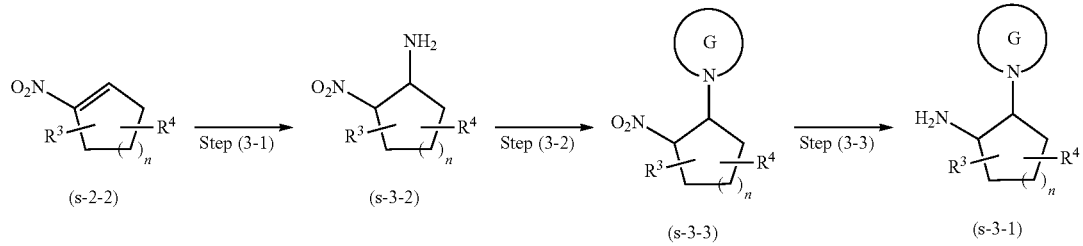

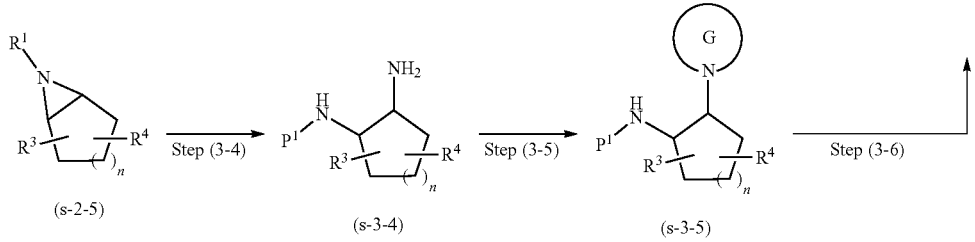

wherein R³, R⁴, n, and Ring G are as defined in Item 1.

Compound (s-3-1) can be prepared from compound (s-2-2) via Step (3-1)-Step (3-3).

Step (3-1):

Compound (s-3-2) can be prepared in a similar manner to Step (2-1) with compound (s-2-2) and ammonia or a reagent equal to ammonia that includes a protected-amine reagent which is deprotected after the amination and an azide-inducer which is reduced after the azidation.

Step (3-2):

Compound (s-3-3) can be prepared in a nitrogen-containing heteroring-formulation with compound (s-3-2). For example, compound (s-3-3) wherein Ring G is piperazine can be prepared by reacting compound (s-3-2) with N-benzyl-bis(2-chloroethyl)amine, followed by deprotection and alkylation.

Step (3-3):

Compound (s-3-1) can be prepared in a similar manner to Step (2-2) with compound (s-3-3).

Compound (s-3-1) can be also prepared from compound (s-2-5) via Step (3-4)-Step (3-6).

Step (3-4):

Compound (s-3-4) can be prepared in a similar manner to Step (2-3) with compound (s-2-5) and ammonia or a reagent equal to ammonia that includes a protected-amine reagent which is deprotected after the amination and an azide-inducer which is reduced after the azidation.

Step (3-5):

Compound (s-3-5) can be prepared in a similar manner to Step (3-2) with compound (s-3-4).

Step (3-6):

Compound (s-3-1) can be prepared in a similar deprotection to Step (2-4) with compound (s-3-5).

Preparation Process 3-2:

The compound according to formula (s-3-1) can be also prepared, for example, by the following process.

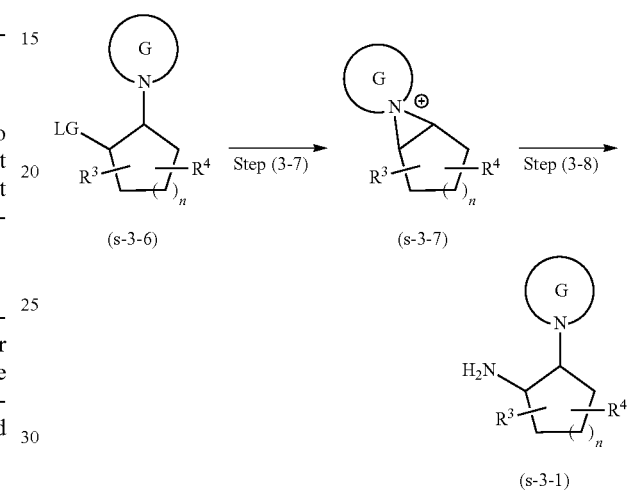

wherein R³, R⁴, n, and Ring G are as defined in Item 1.

Compound (s-3-1) can be prepared from compound (s-3-6) via Step (3-7) and Step (3-8).

Step (3-7):

Compound (s-3-6) is compound (s-2-9) in Preparation Process 2, wherein L² is single bond and Ring G is connected to the cycloalkyl via a nitrogen atom therein. Compound (s-3-7) can be prepared in a general nucleophilic substitution reaction like Step (2-7) with compound (s-3-6) and a conventional base as intramolecular reaction. Compound (s-3-7) may be used in the next step without isolation.

Step (3-8):

Compound (s-3-1) can be prepared in a general ring-opening reaction with compound (s-3-7) and ammonia or a reagent equal to ammonia that includes a protected-amine reagent which is deprotected after the amination and an azide-inducer which is reduced after the azidation.

Preparation Process 4:

In compounds according to formula (s-2-1), the compound of formula (s-4-1) which is a compound of formula (s-2-1) wherein L² is O or NR¹⁰ can be also prepared, for example, by the following process.

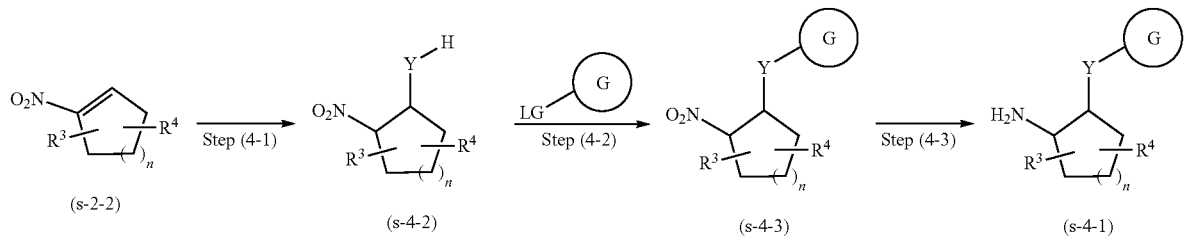

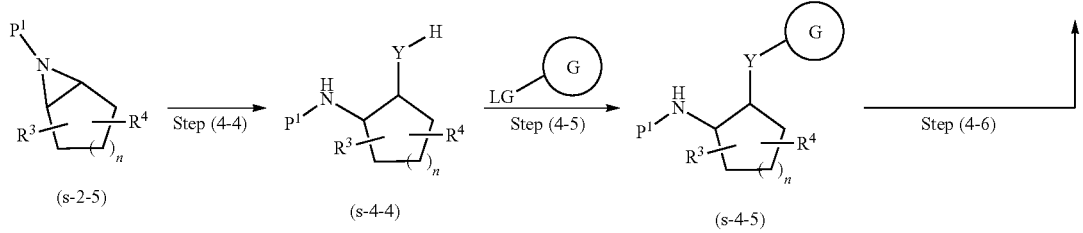

wherein $R^3$, $R^4$, n, and Ring G are as defined in Item 1; and Y is O or $NR^{10}$, said definitions are used below unless otherwise indicated.

Compound (s-4-1) can be prepared from compound (s-2-2) via Step (4-1)-Step (4-3).

Step (4-1):
Compound (s-4-2) can be prepared by reacting compound (s-2-2) in a similar manner to Step (2-1) with $YH_2$ or a reagent equal to $YH_2$ that includes a protected reagent $P^2YH$ which is deprotected after the addition reaction, wherein $P^2$ is a suitable protecting group, said definition is used below unless otherwise indicated.

Step (4-2):
Compound (s-4-3) can be prepared in a general nucleophilic substitution reaction or aromatic nucleophilic substitution reaction with compound (s-4-2), Ring G accompanied with a leaving group, and a base. The base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The solvent used herein includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (4-3):
Compound (s-4-1) can be prepared in a similar manner to Step (2-2) with compound (s-4-3).

Compound (s-4-1) can be also prepared from compound (s-2-5) via Step (4-4)-Step (4-6).

Step (4-4):
Compound, (s-4-4) can be prepared by reacting compound (s-2-5) in a similar manner to Step (2-3) with $YH_2$ or a reagent equal to $YH_2$ that includes a protected reagent $P^2YH$ which is deprotected after the addition reaction.

Step (4-5):
Compound (s-4-5) can be prepared in a similar manner to Step (4-2) with compound (s-4-4).

Step (4-6):
Compound (s-4-1) can be prepared in a similar deprotection to Step (2-4) with compound (s-4-5).

Preparation Process 5:
The compound of formula (s-2-5) can be also prepared, for example, by the following process.

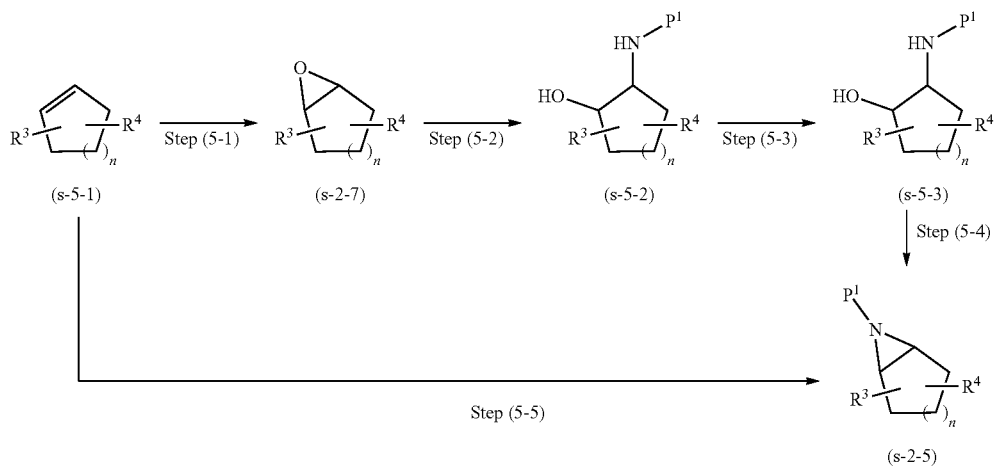

wherein $R^3$, $R^4$, and n are as defined in Item 1.

Compound (s-2-5) can be prepared from compound (s-5-1) via Step (5-1)-Step (5-4).

Step (5-1):
Compound (s-2-7) can be prepared by reacting compound (s-5-1) in a suitable inert solvent under a conventional condition of epoxide-formulation. The present reaction condition includes, for example, using an oxidizing agent such as hydrogen peroxide solution, mCPBA, tert-butyl hydroperoxide, and Oxone. In the present reaction, a metal catalyst such as V, Mo, Al, Ti, Fe, Ta, Zr, Nb, W, and Re may be used, as appropriate. The inert solvent includes a halogenated carbon solvent such as chloroform and dichloromethane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.
Step (5-2):

Compound (s-5-2) can be prepared in a similar manner to Step (2-5) with compound (s-2-7) and $P^1NH_2$ in a suitable inert solvent.

Step (5-2) may be carried out in a process comprising reacting compound (s-2-7) and ammonia or a reagent equal to ammonia that includes a protected-amine reagent which is deprotected after the amination and an azide-inducer which is reduced after the azidation, and then protecting the product with a protecting group $P^1$.
Step (5-3):

Compound (s-5-3) can be prepared in a similar manner to Step (2-6) with compound (s-5-2) in a suitable inert solvent.
Step (5-4):

Compound (s-2-5) can be prepared by reacting compound (s-5-3) in the presence of a base in a suitable inert solvent under a conventional condition of intramolecular cyclization reaction. The base used herein includes, for example, an organic base such as triethylamine, diisopropylethylamine, and DBU; an inorganic base such as sodium hydrogen carbonate, sodium carbonate, and potassium carbonate; a metal alkoxide such as potassium tert-butoxide; an organometallic reagent such as n-butyl lithium and isopropylmagnesium chloride; and a metal amide reagent such as LDA and LHMDS. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (5-3) and Step (5-4) may be carried out as one step without isolating the intermediate. And, (5-3) and Step (5-4) may be also carried out as one step under Mitsunobu reaction condition.

Compound (s-2-5) can be also prepared from compound (s-5-1) via Step (5-5).
Step (5-5):

Compound (s-2-5) can be prepared by reacting compound (s-5-1) in a suitable inert solvent under a conventional condition of aziridine-ring-formulation reaction. The present reaction condition includes, for example, using $P^1NH_2$ and an oxidizing agent such as iodosylbenzene in the presence of a metallic catalyst, and using a hydroxylamine derivative $P^1N(H)O$-LG and a metallica catalyst.
Preparation Process 6:

In compounds according to formula (s-1-1), the compound of formula (s-6-1) which has an unsaturated bond in the ring can be prepared, for example, by the following process.

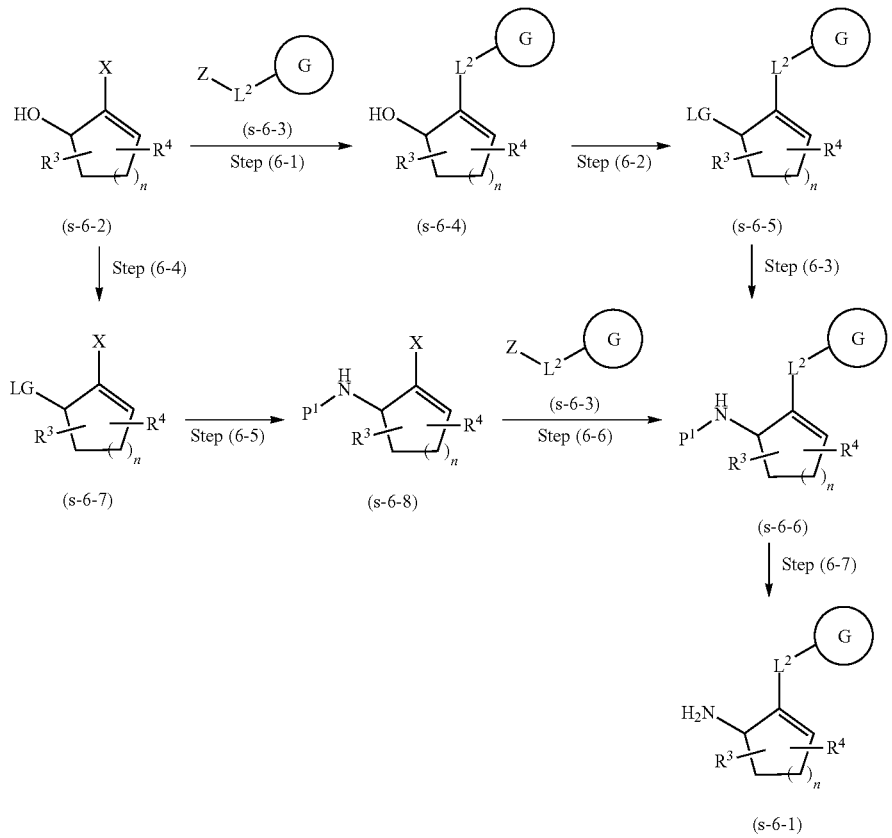

wherein $R^3$, $R^4$, $L^2$, n, and Ring G are as defined in Item 1; Z is boronic acid, boronate ester, $BF_3K$, $BF_3Na$, trialkyl tin, zinc halide, or hydrogen atom; and X is halogen.

Compound (s-6-1) can be prepared from compound (s-6-6) via Step (6-7). And, compound (s-6-6) can be prepared from compound (s-6-2) via Step (6-1)-Step (6-3), or via Step (6-4)-Step (6-6).

Step (6-1):

Compound (s-6-4) wherein $L^2$ is single bond or methylene which may be optionally substituted with the same or different one or more $C_{1-4}$ alkyl can be prepared by reacting compound (s-6-2) with compound (s-6-3) wherein Z is boronic acid, boronate ester, $BF_3K$, $BF_3Na$, trialkyl tin, or zinc halide, in the presence of palladium catalyst and phosphine ligand, and optionally in the presence of a base, in a suitable inert solvent. Compound (s-6-3) is commercially available, or can be prepared according to a known method or a similar method thereto. The palladium catalyst used herein includes, for example, tetrakis(triphenylphosphine)palladium(0), bis(dibenzylideneacetone)palladium(0), tris(dibenzylideneacetone)dipalladium(0), bis(tri-tert-butylphosphine)palladium(0), palladium(0) acetate, [1,1-bis(diphenylphosphino)ferrocene]palladium(II) dichloride, and bis(di-tert-butyl(4-dimethylaminophenyl)phosphine)dichloropalladium(II).

The phosphine ligand used herein includes, for example, o-tolylphosphine, 2-dicyclohexylphosphino-2',6'-dimethoxybiphenyl (S-Phos), 2-dicyclohexylphosphino-2',4',6'-triisopropylbiphenyl (X-Phos), 1,1'-bis(diphenylphosphino)ferrocene (DPPF), 1,2-bis(diphenylphosphino)ethane (DPPE), 1,3-bis(diphenylphosphino)propane (DPPP), 1,4-bis(diphenylphosphino)butane (DPPB), 2,2'-bis(diphenylphosphino)-1,1'-binaphthyl (BINAP), 4,5-bis(diphenylphosphino)-9,9-dimethylxanthene (XANT-Phos), and bis((2-diphenylphosphino)phenyl) ether (DPE-Phos). The base used herein includes, for example, sodium carbonate, potassium carbonate, cesium carbonate, potassium phosphate, sodium hydroxide, and potassium hydroxide. The inert solvent includes, for example, 1,4-dioxane, THF, 1,2-dimethoxyethane, acetonitrile, water, and a mixture thereof. The reaction time is generally about 1 hour to 24 hours, and the reaction temperature is $-20°$ C. to boiling point of a solvent used herein.

In addition, compound (s-6-4) wherein $L^2$ is O or $NR^{10}$ can be also prepared by reacting compound (s-6-2) with compound (s-6-3) wherein Z is hydrogen atom in the presence of palladium catalyst, phosphine ligand, and a base in a suitable inert solvent.

Step (6-2):
Compound (s-6-5) can be prepared in a similar manner to Step (2-6) with compound (s-6-4).

Step (6-3):
Compound (s-6-6) can be prepared in a similar manner to Step (2-7) with compound (s-6-5) and $P^1NH_2$.

Step (6-3) may be carried out in a process comprising reacting compound (s-6-5) and ammonia or a reagent equal to ammonia that includes a protected-amine reagent which is deprotected after the amination and an azide-inducer which is reduced after the azidation, and then protecting the product with a protecting group $P^1$.

Step (6-2) and Step (6-3) may be carried out as one step without isolating the intermediate. And, Step (6-2) and Step (6-3) may be also carried out as one step under Mitsunobu reaction condition.

Step (6-4):
Compound (s-6-7) can be prepared in a similar manner to Step (6-2) with compound (s-6-2).

Step (6-5):
Compound (s-6-8) can be prepared in a similar manner to Step (6-3) with compound (s-6-7).

Step (6-5) may be carried out in a process comprising reacting compound (s-6-7) and ammonia or a reagent equal to ammonia that includes a protected-amine reagent which is deprotected after the amination and an azide-inducer which is reduced after the azidation, and then protecting the product with a protecting group $P^1$.

Step (6-4) and Step (6-5) may be carried out as one step without isolating the intermediate. And, Step (6-4) and Step (6-5) may be also carried out as one step under Mitsunobu reaction condition.

Step (6-6):
Compound (s-6-6) can be prepared in a similar manner to Step (6-1) with compound (s-6-8).

Step (6-7):
Compound (s-6-1) can be prepared in a similar deprotection to Step (2-4) with compound (s-6-6).

Preparation Process 7:
In compounds according to formula (s-1-1), the compound of formula (s-7-1) which has no unsaturated bond in the ring can be prepared, for example, by the following process.

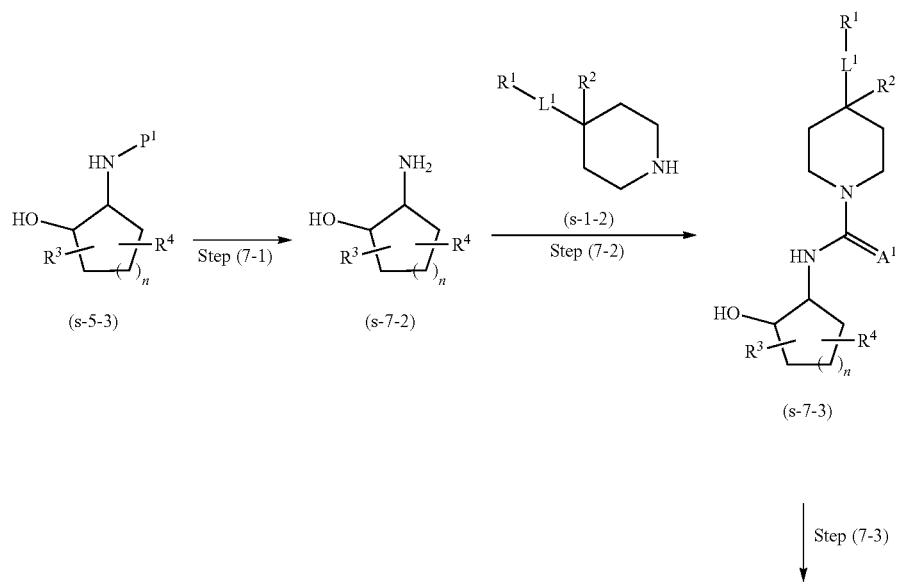

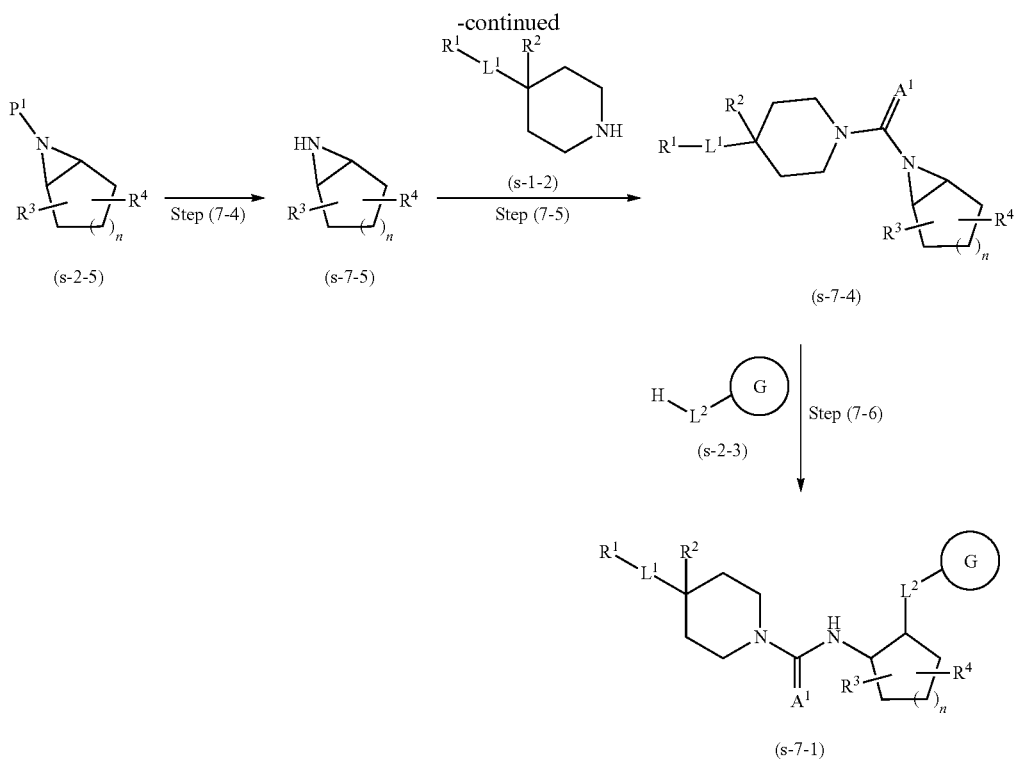

wherein $R^1$-$R^4$, $L^1$, $L^2$, n, Ring G, and $A^1$ are as defined in Item 1.

Compound (s-7-1) can be prepared from compound (s-7-4) via Step (7-6). And, compound (s-7-4) can be prepared from compound (s-5-3) via Step (7-1)-Step (7-3), or from compound (s-2-5) via Step (7-4) and Step (7-5).

Step (7-1):

Compound (s-7-2) can be prepared in a similar deprotection to Step (2-4) with compound (s-5-3).

Step (7-2):

Compound (s-7-3) can be prepared in a similar ureation to Step (1-1) with compound (s-7-2) and compound (s-1-2). In this step, the hydroxy group may be protected and deprotected, if necessary.

Step (7-3):

Compound (s-7-4) can be prepared in a similar manner to Step (5-3) and Step (5-4) with compound (s-7-3).

Step (7-4):

Compound (s-7-5) can be prepared in a similar deprotection to Step (2-4) with compound (s-2-5).

Step (7-5):

Compound (s-7-4) can be prepared in a similar urea formation to Step (1-1) with compound (s-7-5) and compound (s-1-2).

Step (7-6):

Compound (s-7-1) can be prepared in a similar aziridine-ring-open reaction to Step (2-3) with compound (s-7-4) and compound (s-2-3).

Preparation Process 8:

The compound of formula (s-1-1) can be also prepared from compound (s-8-1) via Step (8-1)-Step (8-3).

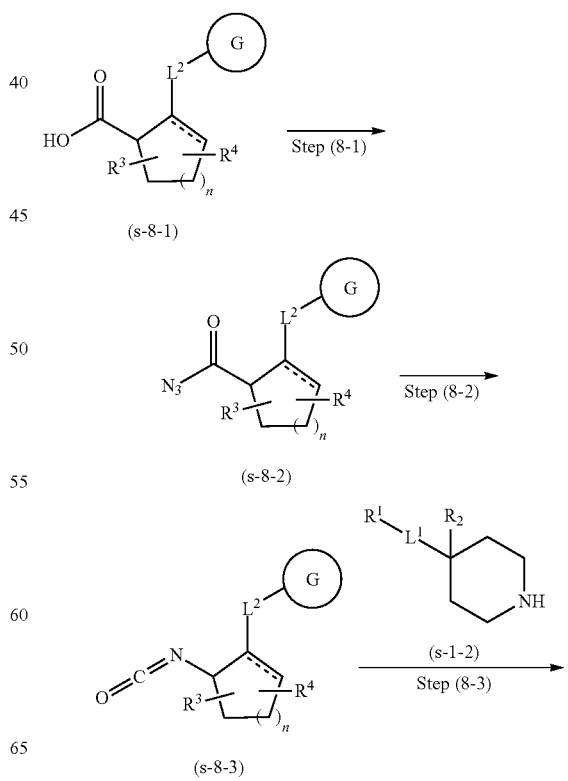

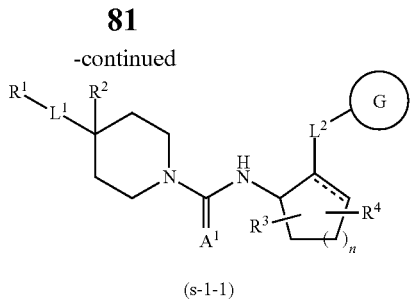

(s-1-1)

wherein $R^1$-$R^4$, $L^1$, $L^2$, n, Ring G, $A^1$, and the bond accompanied with broken line are as defined in Item 1.

Step (8-1):

Compound (s-8-2) can be prepared by reacting compound (s-8-1) in a suitable inert solvent under a conventional condition of acyl azide formulation. The present reaction condition includes, for example, using diphenylphosphoryl azide, or converting the carboxylic acid to its acid halide and then azidating the acid halide with a metallic azide. The inert solvent includes an ether solvent such as diethyl ether, diisopropyl ether, tetrahydrofuran, and 1,4-dioxane; an aromatic hydrocarbon solvent such as benzene, toluene, and xylene, an ester solvent such as ethyl acetate and methyl acetate; an aprotic polar solvent such as N,N-dimethylformamide, N,N-dimethylacetamide, N-methyl-2-pyrrolidinone, 1,3-dimethyl-2-imidazolidinone, and dimethyl sulfoxide. The reaction time is generally about 1 hour to 24 hours, and the reaction temperature is −20° C. to boiling point of a solvent used herein.

Step (8-2):

Compound (s-8-3) can be prepared by reacting compound (s-8-2) in a suitable inert solvent under a condition of Curtius rearrangement reaction. Compound (s-8-2) used herein may be the un-isolated product from the prior step.

Step (8-3):

Compound (s-1-1) can be prepared by reacting compound (s-8-3) and compound (s-1-2) in a suitable inert solvent under a conventional condition of addition reaction. Compound (s-8-3) used herein may be the un-isolated product from the prior step.

Preparation Process 9:

In compounds according to formula (s-8-1), the compound of formula (s-9-1) which has no unsaturated bond in the ring can be prepared, for example, by the following process.

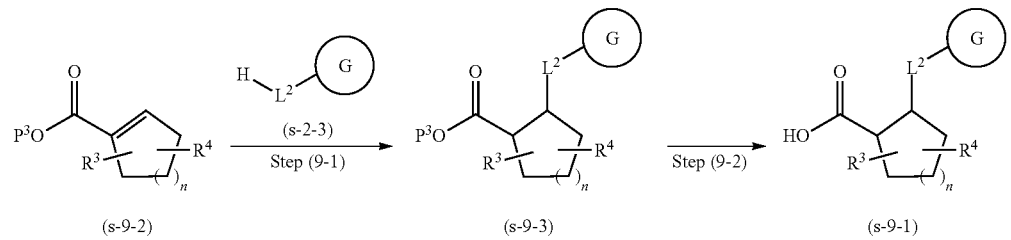

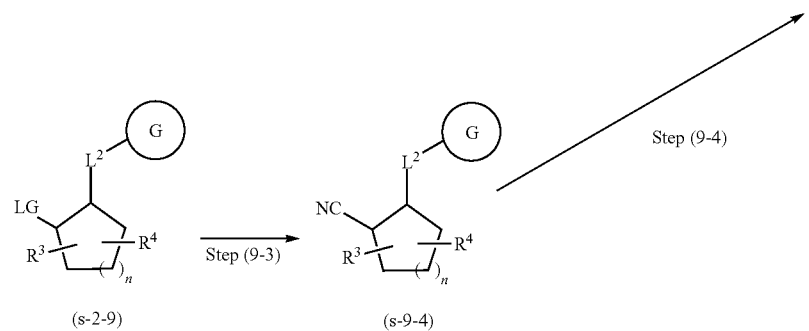

wherein R³, R⁴, L², n, and Ring G are as defined in Item 1; and P³ is a suitable protecting group or $C_{1-3}$ alkyl, said definitions are used below unless otherwise indicated.

Compound (s-9-1) can be prepared from compound (s-9-2) via Step (9-1) and Step (9-2).

Step (9-1):

Compound (s-9-3) can be prepared in a similar manner to Step (2-1) with compound (s-9-2) and compound (s-2-3).

Step (9-2):

Compound (s-9-1) can be prepared by subjecting compound (s-9-3) to a general condition of hydrolysis or deprotection.

Compound (s-9-1) can be prepared from compound (s-2-9) via Step (9-3) and Step (9-4).

Step (9-3):

Compound (s-9-4) can be prepared in a similar manner to Step (2-7) with compound (s-2-9) and a metallic cyanide.

Step (9-4):

Compound (s-9-1) can be prepared by reacting compound (s-9-4) in a suitable inert solvent under a general condition of hydrolysis.

Preparation Process 10:

In compounds according to formula (s-8-1), the compound of formula (s-10-1) which has an unsaturated bond in the ring can be prepared, for example, by the following process.

wherein R³, R⁴, L², n, and Ring G are as defined in Item 1, Z is boronic acid, boronate ester, $BF_3K$, $BF_3Na$, trialkyl tin, zinc halide, or hydrogen atom; and X is halogen.

Compound (s-10-1) can be prepared from compound (s-10-2) via Step (10-2). And, compound (s-10-2) can be prepared from compound (s-6-5) via Step (10-1), or from compound (s-6-7) via Step (10-3) and Step (10-4).

Step (10-1):

Compound (s-10-2) can be prepared in a similar manner to Step (2-7) with compound (s-6-5) and a metallic cyanide.

Step (10-2):

Compound (s-10-1) can be prepared by reacting compound (s-10-2) in a suitable inert solvent under a general condition of hydrolysis.

Step (10-3):

Compound (s-10-3) can be prepared in a similar manner to Step (10-1) with compound (s-6-7) and a metallic cyanide.

Step (10-4):

Compound (s-10-2) can be prepared in a similar manner to Step (6-1) with compound (s-10-3) and compound (s-6-3).

Preparation Process 11:

In compounds according to formula (1) or a pharmaceutically acceptable salt thereof, the compound of formula (s-11-1) which is a compound of formula (1) wherein A³ is carbon atom or a pharmaceutically acceptable salt thereof can be prepared, for example, by the following process.

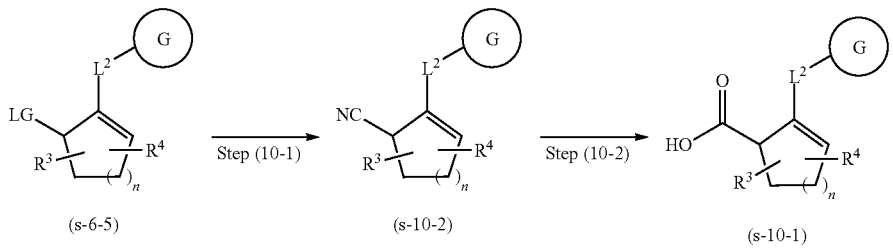

(s-6-5)     (s-10-2)     (s-10-1)

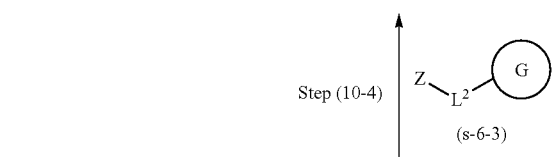

(s-6-3)

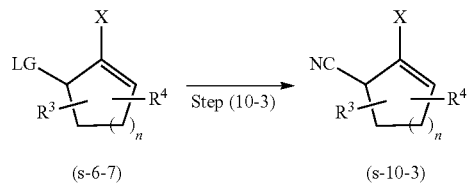

(s-6-7)     (s-10-3)

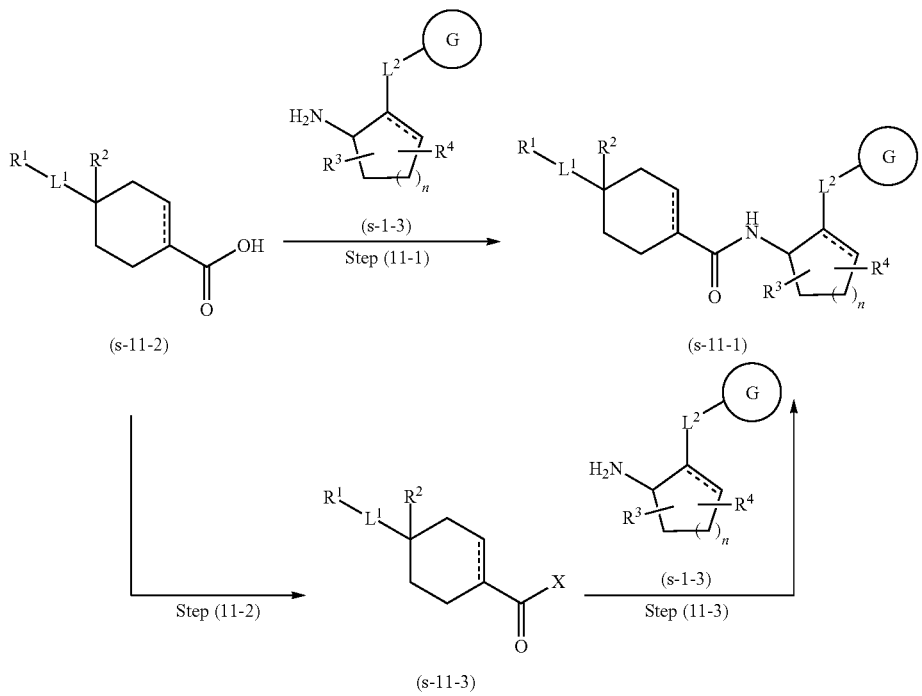

wherein $R^1$-$R^4$, $L^1$, $L^2$, n, Ring G, and the bond accompanied with broken line are as defined in Item 1.

Step (11-1):

Compound (s-11-1) can be prepared by reacting compound (s-11-2) and compound (s-1-3) in a suitable inert solvent under a conventional condition of amide-bond formulation reaction. The present reaction condition includes, for example, using a condensation agent and a base, and the condensation agent used herein includes, for example, a carbodiimide such as dicyclohexylcarbodiimide, 1,1'-carbonyldiimidazole, diphenylphosphoryl azide (DPPA), diethylphosphoryl cyanide (DEPC), dicyclohexylcarbodiimide (DCC), carbonyldiimidazole (CDI), 1-ethyl-3-(3-dimethylaminopropyl)carbodiimide hydrochloride (EDC-HCl), 0-(1H-benzotriazol-1-yl)-1,1,3,3-tetramethyl-uronium tetrahydroborate (TBTU), O-(benzotriazol-1-yl)-N,N,N',N'-tetramethyluronium hexafluorophosphate (HBTU), and O-(7-azabenzotriazol-1-yl)-N,N,N',N',-tetramethyluronium hexafluorophosphate (HATU). The base used herein includes an organic base such as triethylamine, diisopropylethylamine, tributylamine, DBU, pyridine, and dimethylaminopyridine. The inert solvent includes a halogenated hydrocarbon solvent such as dichloromethane and chloroform; an ether solvent such as diethyl ether, diisopropyl ether, tetrahydrofuran, and 1,4-dioxane; an aromatic hydrocarbon solvent such as benzene, toluene, and xylene; an ester solvent such as ethyl acetate and methyl acetate; an aprotic polar solvent such as N,N-dimethylformamide, N,N-dimethylacetamide, N-methyl-2-pyrrolidinone, 1,3-dimethyl-2-imidazolidinone, and dimethyl sulfoxide. The reaction time is generally about 1 hour to 24 hours, and the reaction temperature is −20° C. to boiling point of a solvent used herein.

Compound (s-11-1) can be also prepared from compound (s-11-2) via Step (11-2) and Step (11-3).

Step (11-2):

Compound (s-11-3) can be prepared by reacting compound (s-11-2) in a suitable inert solvent under a conventional condition of acid halide formulation reaction. The present reaction condition includes, for example, using a halogenating agent, and the halogenating agent used herein includes, for example, thionyl chloride, oxalyl chloride, phosphoryl chloride, sulfuryl chloride, phosphorus trichloride, phosphorus tribromide, and phosphorus pentachloride. The inert solvent includes a halogenated hydrocarbon solvent such as dichloromethane and chloroform; an ether solvent such as diethyl ether, diisopropyl ether, tetrahydrofuran, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (11-3):

Compound (s-11-1) can be prepared by reacting compound (s-11-3) and compound (s-1-3) in a suitable inert solvent in the presence of a base. The base used herein includes an organic base such as triethylamine, diisopropylethylamine, tributylamine, DBU, pyridine, and dimethylaminopyridine; and an inorganic base such as sodium hydrogen carbonate, sodium carbonate, and potassium carbonate. The inert solvent includes a halogenated hydrocarbon solvent such as dichloromethane and chloroform; an ether solvent such as diethyl ether, diisopropyl ether, tetrahydrofuran, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Preparation Process 12:

In compounds according to formula (1) or a pharmaceutically acceptable salt thereof, the compound of formula (s-12-1) which is a compound of formula (1) wherein $A^2$ is oxygen atom or a pharmaceutically acceptable salt thereof can be prepared, for example, by the following process.

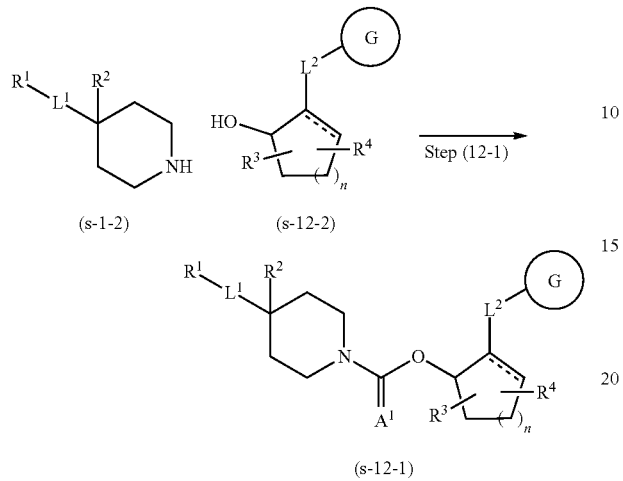

wherein $R^1$-$R^4$, $L^1$, $L^2$, n, Ring G, $A^1$, and the bond accompanied with broken line are as defined in Item 1.

Step (12-1):

Compound (s-12-1) can be prepared by reacting compound (s-1-2) and compound (s-12-2) in a suitable inert solvent under a conventional condition of carbamate formulation reaction. The present reaction condition includes, for example, using triphosgene, 4-nitrophenyl chloroformate, or thiophosgene. A base is used in the present reaction, and the base used herein includes triethylamine and diisopropylethylamine. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Compound (s-12-2) which has no unsaturated bond in the ring is prepared in the Preparation Process of compound (s 2-8). And, compound (s-12-2) which has a unsaturated bond in the ring is prepared in the Preparation Process of compound (s-6-4).

Preparation Process 13:

In compounds according to formula (s-1-2), the compound of formula (s-13-1) can be prepared, for example, by the following process.

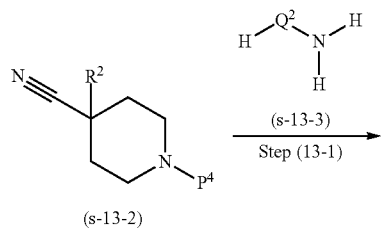

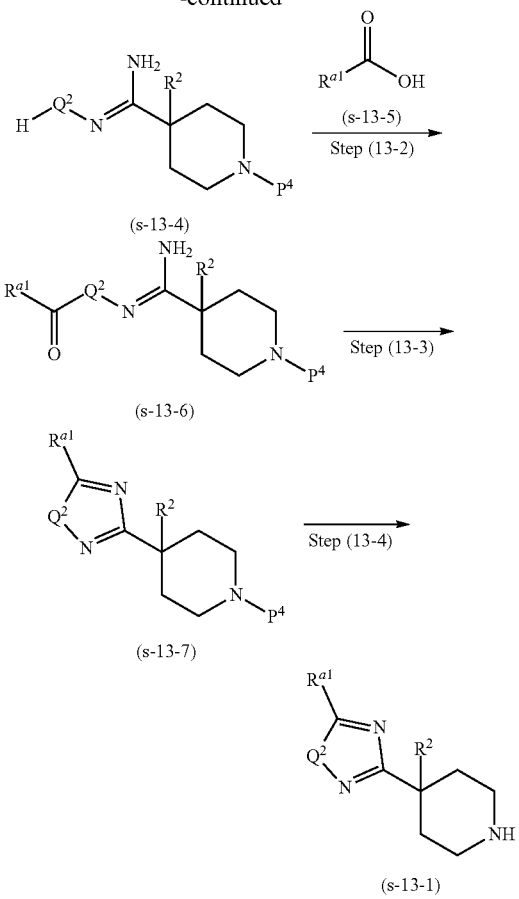

wherein $R^2$ is as defined in Item 1, $R^{a1}$ and $Q^2$ are as defined in Item 4; and $P^4$ is a suitable protecting group, said definitions are used below unless otherwise indicated.

Step (13-1):

Compound (s-13-4) can be prepared by reacting compound (s-13-2) and compound (s-13-3) in a suitable inert solvent under a conventional condition of addition reaction. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; an alcohol solvent such as methanol and ethanol; and water. The reaction time is generally about 1 hour to 24 hours, and the reaction temperature is −20° C. to boiling point of a solvent used herein.

Step (13-2):

Compound (s-13-6) can be prepared by reacting compound (s-13-4) and compound (s-13-5) in a suitable inert solvent under a conventional condition of condensation reaction. The present reaction condition includes, for example, using HATU, DCC, or CDI. A base is used in the present reaction, and the base used herein includes triethylamine and diisopropylethylamine. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (13-3):

Compound (s-13-7) can be prepared by reacting compound (s-13-6) in a suitable inert solvent under a conventional condition of dehydration reaction. In the present reaction, a base such as triethylamine and DBU may be used as appropriate. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (13-4):

Compound (s-13-1) can be prepared by deprotecting compound (s-13-7) in a known manner (for example, a manner described in Protective Groups in Organic Synthesis $3^{rd}$ Edition (John Wiley & Sons, Inc.), Comprehensive Organic Transformation, edited by R. C. Larock, VCH publisher Inc., 1989, etc.) or a similar manner thereto.

Preparation Process 14:

In compounds according to formula (s-1-2), the compound of formula (s-14-1) which is a compound of formula (s-1-2) wherein $L^1$ is single bond and $R^1$ is optionally-substituted 5-membered aromatic heterocyclyl group can be also prepared, for example, by the following process.

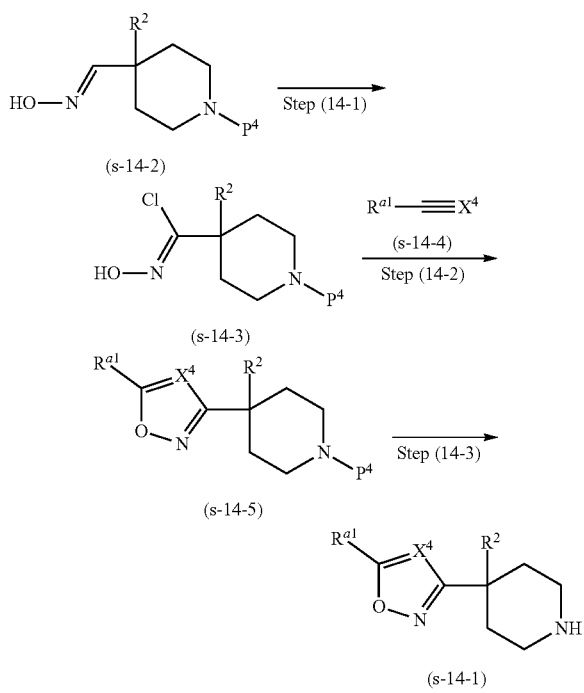

wherein $R^2$ is as defined in Item 1, $X^4$ and $R^{a1}$ are as defined in Item 4.

Compound (s-14-1) can be prepared from compound (s-14-2) via Step (14-1)-Step (14-3).

Step (14-1):

Compound (s-14-3) can be prepared by reacting compound (s-14-2) in a suitable inert solvent under a conventional condition of chlorination reaction. The present reaction condition includes, for example, using chlorine, N-succinimide, and trimethylbenzylammonium tetrachloroiodate. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; an aprotic polar solvent such as N,N-dimethylformamide, N,N-dimethylacetamide, N-methyl-2-pyrrolidinone, 1,3-dimethyl-2-imidazolidinone and dimethyl sulfoxide; water; and a mixture thereof. The reaction time is generally about 1 hour to 24 hours, and the reaction temperature is −20° C. to boiling point of a solvent used herein.

Step (14-2):

Compound (s-14-5) can be prepared by reacting compound (s-14-3) and compound (s-14-4) in a suitable inert solvent under a conventional condition of 1,3-dipolar cycloaddition reaction. The present reaction condition includes, for example, using a base, and the base used herein includes an inorganic base such as potassium carbonate, cesium carbonate, sodium carbonate, sodium hydrogen carbonate, sodium methoxide, sodium t-butoxide, sodium hydroxide, potassium hydroxide, and potassium fluoride; and an organic base such as triethylamine, diisopropylethylamine, tributylamine, DBN, DABCO, DBU, pyridine, dimethylaminopyridine, picoline, and NMM. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; and an ester solvent such as ethyl acetate and methyl acetate. The reaction time is generally about 1 hour to 24 hours, and the reaction temperature is −20° C. to boiling point of a solvent used herein.

Step (14-3):

Compound (s-14-1) can be prepared in a similar manner to Step (13-4) with compound (s-14-5).

Preparation Process 15:

In compounds according to formula (s-1-2), the compound of formula (s-15-1) can be prepared, for example, by the following process.

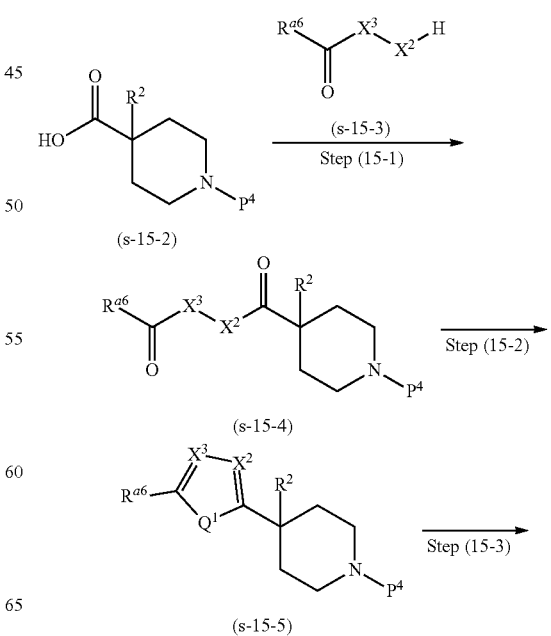

-continued

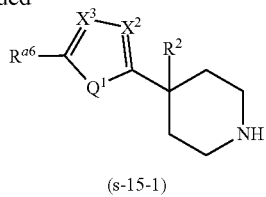

(s-15-1)

wherein $R^2$ is as defined in Item 1, $X^1$-$X^3$, $Q^1$ and $R^{a6}$ are as defined in Item 4.

Step (15-1):

Compound (s-15-4) can be prepared by reacting compound (s-15-2) and compound (s-15-3) in a suitable inert solvent under a condensation reaction like Step (13-2).

Step (15-2):

Compound (s-15-5) can be prepared by reacting compound (s-15-4) in a suitable inert solvent under a conventional condition of dehydration reaction, or a cyclization condition after the treatment with Lawesson's reagent or the like.

Step (15-3):

Compound (s-15-1) can be prepared in a similar manner to Step (13-4) with compound (s-15-5).

Preparation Process 16:

In compounds according to formula (s-1-2), the compound of formula (s-16-5) or the compound of formula (s-16-8) which is a compound of formula (s-1-2) wherein $L^1$ is single bond and $R^1$ is optionally-substituted $C_{6-10}$ aromatic carbocyclyl group or optionally-substituted 5- to 10-membered aromatic heterocyclyl group can be prepared, for example, by the following process.

sodium hydrogen carbonate, sodium methoxide, sodium t-butoxide, sodium hydroxide, potassium hydroxide, and potassium fluoride; and an organic base such as triethylamine, diisopropylethylamine, tributylamine, DBN, DABCO, DBU, pyridine, dimethylaminopyridine, picoline, and NMM. Sometimes, a base is not used depending on the coupling type. The metallic catalyst used herein includes, for example, bis(tri-tert-butylphosphine)palladium, bis(tri-o-tolylphosphine)dichloropalladium, bis(tri-o-tolylphosphine)palladium, tetrakis(triphenylphosphine)palladium, dichlorobis(acetonitrile)palladium, bis(tri-o-tolylphosphine)dichloropalladium, [1,1'-bis(diphenylphosphino)ferrocene]dichloropalladium, and PEPPSITM.IPr ((1,3-bis(2,6-diisopropylphenyl)imidazolidene) (3-chloropyridyl)palladium(II)dichloride). Palladium acetate or palladium chloride may be used herein, and a ligand described in Palladium reagents and catalysts, John Wiley & Sons Inc. (2004) or a similar ligand may be also used in place of the acetate in palladium acetate or the chloride in palladium chloride. The solvent used herein includes, for example, an ether solvent such as diethyl ether, diisopropyl ether, tetrahydrofuran, methyl cyclopentyl ether, anisole, and 1,4-dioxane; an aromatic hydrocarbon solvent such as benzene, toluene, chlorobenzene, and xylene; an ester solvent such as ethyl acetate and methyl acetate; an aprotic polar solvent such as N,N-dimethylformamide, N,N-dimethylacetamide, N-methyl-2-pyrrolidinone, 1,3-dimethyl-2-imidazolidinone, and dimethyl sulfoxide; water; and a mixture thereof. The reaction temperature should be determined depending on the starting compound to be used, which is generally about 0° C. to about 250° C., preferably about 20° C. to about 200° C. The reaction time is generally 30 minutes to 48 hours, preferably 1 to 24 hours.

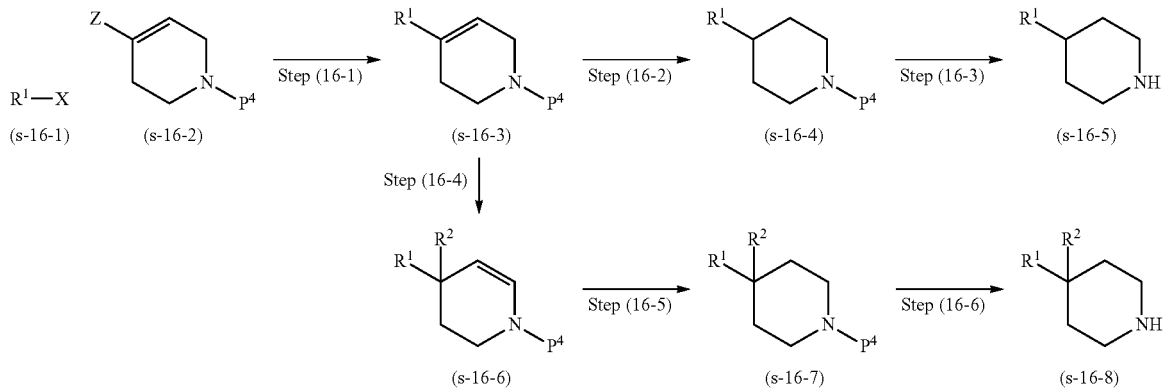

wherein $R^1$ and $R^2$ are as defined in Item 1; Z is exemplified in the following Step (16-1); and X is halogen.

Compound (s-16-5) can be prepared from compound (s-16-1) via Step (16-1)-Step (16-3).

Step (16-1):

Compound (s-16-3) can be prepared by coupling compound (s-16-1) with organic boron compound (for example, Z is B(OH)$_2$ and the like), organic zinc compound (for example, Z is ZnCl and the like), alkenyl compound, alkynyl compound, hydroxy compound (for example, Z is OH and the like), amine compound (for example, Z is NH$_2$ and the like), or metallic cyanide (for example, Z is CuCN and the like), in the presence of a base and metallic catalyst. The base used herein includes an inorganic base such as potassium carbonate, cesium carbonate, sodium carbonate, Step (16-2):

Compound (s-16-4) can be prepared by reacting compound (s-16-3) in a suitable inert solvent under a conventional condition of alkene-reduction reaction, and under hydrogen atmosphere if necessary. The present reaction condition includes, for example, using a reducing agent such as palladium carbon, palladium(II) hydroxide, platinum on carbon, platinum(IV) oxide, Raney nickel, ruthenium carbon, and tris(triphenylphosphine)rhodium(I) chloride. The inert solvent includes a halogenated carbon solvent such as chloroform and dichloromethane; a ether solvent such as diethyl ether, THF, and 1,4-dioxane; an aromatic hydrocarbon solvent such as benzene, toluene, and xylene; an alcohol solvent such as methanol and ethanol; and an ester solvent such as ethyl acetate and methyl acetate. The reaction time is generally about 1 hour to 24 hours, and the reaction temperature is −20° C. to boiling point of a solvent used herein.

Step (16-3):

Compound (s-16-5) can be prepared in a similar manner to Step (13-4) with compound (s-16-4).

Compound (s-16-8) can be prepared from compound (s-16-1) via Step (16-1), and Step (16-4)-Step (16-6).

Step (16-4):

Compound (s-16-6) can be prepared by reacting compound (s-16-3), an alkylating agent $R^2$—X, and a base in a suitable inert solvent under a condition of alkylation reaction. The base used herein includes LDA, LHMDS, and n-butyllithium. The inert solvent includes a ether solvent such as diethyl ether, THF, and 1,4-dioxane; and an aromatic hydrocarbon solvent such as benzene, toluene, and xylene. The reaction time is generally about 1 hour to 24 hours, and the reaction temperature is −20° C. to boiling point of a solvent used herein.

Step (16-5):

Compound (s-16-7) can be prepared by reacting compound (s-16-6) in a suitable inert solvent in a similar manner to Step (16-2) wherein the reducing agent may include sodium borohydride, sodium cyanoborohydride, and sodium triacetoxyborohydride.

Step (16-6):

Compound (s-16-8) can be prepared in a similar manner to Step (13-4) with compound (s-16-7).

Preparation Process 17:

In compounds according to formula (s-1-2), the compound of formula (s-17-1) can be prepared, for example, by the following process.

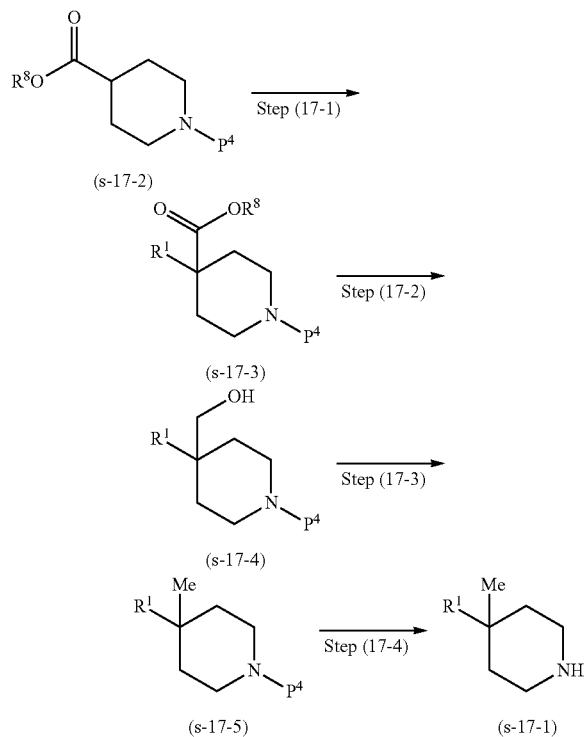

wherein $R^1$ is as defined in Item 1, and $R^8$ is $C_{1-3}$ alkyl.

Step (17-1):

Compound (s-17-3) can be prepared by reacting compound (s-17-2) and an alkylating agent $R^1$-X wherein X is halogen in a suitable inert solvent under a condition of alkylation reaction like Step (16-4).

Step (17-2):

Compound (s-17-4) can be prepared by reacting compound (s-17-3) in a suitable inert solvent under a conventional condition of reduction reaction. The present reaction condition includes, for example, using LAH or DIBAL. The inert solvent includes a halogenated carbon solvent such as chloroform and dichloromethane; a ether solvent such as diethyl ether, THF, and 1,4-dioxane; and an aromatic hydrocarbon solvent such as benzene, toluene, and xylene. The reaction time is generally about 1 hour to 24 hours, and the reaction temperature is −20° C. to boiling point of a solvent used herein.

Step (17-3):

Compound (s-17-5) can be prepared by reacting compound (s-17-4) in a suitable inert solvent under a condition of Barton-McCombie deoxygenation.

Step (17-4):

Compound (s-17-1) can be prepared in a similar manner to Step (13-4) with compound (s-17-5).

EXAMPLES

The present invention is explained in more detail in the following by referring to Reference examples, Examples, and Tests; however, the technical scope of the present invention should not be limited thereto. It should be understood that the names of compounds used in the following Reference examples and Examples do not necessarily follow the IUPAC nomenclature.

In the present specification, the abbreviations shown below may be used.

$CDCl_3$: deuterochloroform
DMSO-$d_6$: deuterodimethylsulfoxide
Rt: retention time
min: minute
HATU: 0-(7-aza-1H-benzotriazol-1-yl)-N,N,N',N'-tetramethyluronium hexafluorophosphate
DCC: N,N'-dicyclohexylcarbodiimide
CDI: carbonyldiimidazole
THF: tetrahydrofuran
TFA: trifluoroacetic acid
DMF: N,N-dimethylformamide
DMSO: dimethyl sulfoxide
CPME: cyclopentyl methyl ether
Boc: tert-butoxycarbonyl
Ns: 2-nitrobenzenesulfonyl
Tf: trifluoromethanesulfonyl
DBU: diazabicycloundecene
DBN: 1,5-diazabicyclo[4.3.0]non-5-ene
LDA: lithium diisopropylamide
LHMDS: lithium bis(trimethylsilyl)amide
mCPBA: meta-chloroperbenzoic acid
DABCO: 1,4-diazabicyclo[2.2.2]octane
NMM: N-methylmorpholine
LAH: lithium aluminium hydride
DIBAL: diisobutylaluminium hydride
Abs: Absolute Configuration; each chemical structure of compounds described along with Abs mark surrounded with a square flame is shown in absolute configuration with a wedged bond. However, not all compounds without Abs mark are shown in non-absolute configuration, i.e., the configuration should be properly judged based on the disclosure about the subject compound in the present description and its context, and a skilled person's technical knowledge, with or without Abs mark.

In the column chromatography and amino chromatography used in Reference examples and Examples, silica gel column and amino column made by YAMAZEN CORPORATION were used. The TLC (silica gel plate) used in the TLC purification was Silica gel 60F254 (Merck), and the TLC (NH silica gel plate) used therein was TLC plate NH (FujiSilysia).

In Reference examples and Examples, the reactors shown below were used. The physicochemical data described in Reference examples and Examples were obtained with the apparatuses below.
Microwave reactor: Biotage AB Initiator
$^1$H-NMR: JEOL JNM-AL400; JEOL JNM-ECS400; Brucker AVANCE 400 Spectrometer The symbols used in NMR are defined as follows, s: singlet, d: doublet, dd: doublet of doublet, ddd: doublet of doublet of doublet, dddd: doublet of doublet of doublet of doublet, t: triplet, td: triplet of doublet, q: quartet, m: multiplet, br: broad singlet or multiplet, and J: coupling constant.

The LC/MS data of each compound in Examples and Reference examples were obtained with any one of the apparatuses below.
Method A
Detection apparatus: ACQUITY™ SQ detector (Waters Corporation)
HPLC: ACQUITY™ UPLC SYSTEM
Column: Waters ACQUITY™ UPLC BEH C18 (1.7 μm, 2.1 mm×30 mm)
Method B
Detection apparatus: Shimadzu LCMS-2020
Column: Phenomenex Kinetex (C18, 1.7 μm, 2.1 mm×50 mm)
Method C
Detection apparatus: ACQUITY™ SQ detector (Waters Corporation)
HPLC: ACQUITY™ UPLC SYSTEM
Column: Waters ACQUITY™ UPLC BEH C18 (1.7 μm, 2.1 mm×30 mm)

High-performance liquid chromatograph mass spectrometer; the measurement conditions of LC/MS are as follows, wherein the observed [MS (m/z)] is denoted by [M+H]$^+$ and the retention time is denoted by Rt (min). Each measured MS value shown in the working examples is accompanied by any one of A-D which were measurement methods used in the actual measurements.
Method A
Solvent: A; 0.06% formic acid/H$_2$O, B; 0.06% formic acid/acetonitrile
Gradient condition: 0.0-1.3 min (linear gradient from B 2% to B 96%)
Flow rate: 0.8 mL/min; Detective UV: 220 nm and 254 nm; Temperature: 40° C.

Hereinafter, the LC-MS data shown below were measured by Method A, unless otherwise indicated.
Method B
Solvent: A; 0.05% TFA/H$_2$O, B; acetonitrile
Gradient condition: 0.0-1.7 min (linear gradient from B 10% to B 99%)
Flow rate: 0.5 mL/min; Detective UV: 220 nm; Temperature. 40° C.
Method C
Solvent: A; 0.05% formic acid/H$_2$O, B; acetonitrile
Gradient condition: 0.0-1.3 min (linear gradient from B 10-6 to B 95%) 1.3-1.5 min (B 10%)
Flow rate: 0.8 mL/min; Detective UV: 220 nm and 254 nm, Temperature: 40° C.

Example 1 rac-4-(4-Methylphenyl)-N-{(1S,2S)-2-[4-(propan-2-yl)piperazin-1-yl]cyclohexyl}piperidine-1-carboxamide

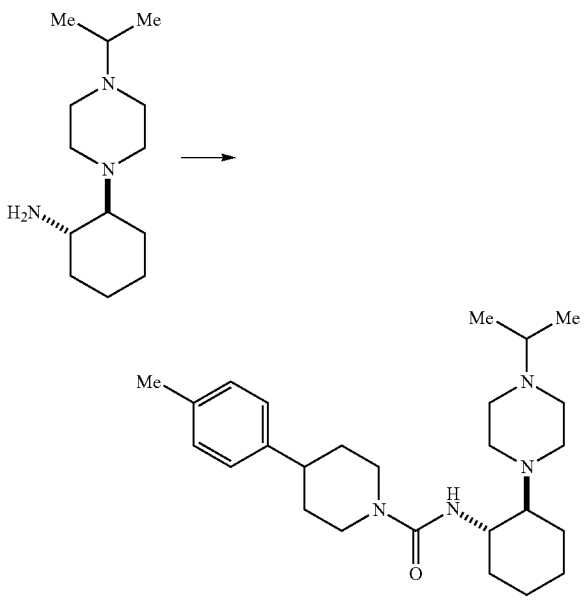

To a mixture of Reference example 1 (211 mg)(Material A), triethylamine (0.391 mL), and chloroform (3 mL) was added 4-nitrophenyl chloroformate (208 mg) at 0° C., and the mixture was stirred at the same temperature for 40 minutes. To the reaction mixture was added 4-(4-methylphenyl)piperidine hydrochloride (238 mg) (Material B) at 0° C., and the mixture was stirred at room temperature for one hour. Water was added to the reaction mixture, and the mixture was extracted with chloroform. The organic layer was dried over anhydrous sodium sulfate, concentrated in vacuo, and then the obtained residue was purified by amino silica gel column chromatography (eluate: hexane/ethyl acetate) to give the title compound (346 mg).

$^1$H-NMR (CDCl$_3$) δ: 1.02 (6H, d, J=6.7 Hz), 1.04-1.11 (1H, m), 1.12-1.40 (3H, m), 1.58-1.71 (3H, m), 1.76-1.93 (4H, m), 2.27 (1H, dd, J=10.4, 3.6 Hz), 2.32 (3H, s), 2.35-2.54 (6H, m), 2.54-2.65 (3H, m), 2.65-2.75 (2H, m), 2.78-2.91 (2H, m), 3.25-3.33 (1H, m), 4.08-4.19 (2H, m), 5.76 (1H, s), 7.09 (2H, d, J=8.8 Hz), 7.12 (2H, d, J=8.8 Hz).

Examples 2 to 16

The compounds of Examples 2 to 16 shown in the table below were prepared in the same manner as Example 1, by using commercial compounds or Reference example compounds which correspond to Material A and Material B described in Example 1.

| Example | Structure / Spectral data | Material A | Material B |
|---|---|---|---|
| 2 | 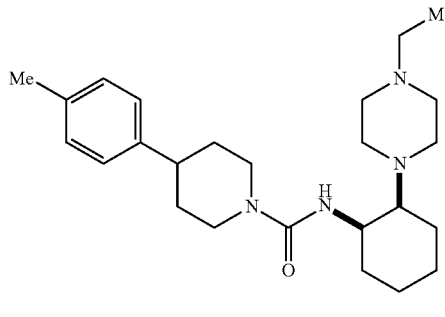<br>¹H-NMR (CDCl₃) δ: 1.07 (3H, t, J = 7.3 Hz), 1.12-1.35 (6H, m), 1.36-1.45 (2H, m), 1.56-1.69 (2H, m), 1.80-1.88 (2H, m), 1.89-1.96 (1H, m), 2.12-2.20 (1H, m), 2.30-2.58 (11H, m), 2.59-2.70 (2H, m), 2.80-2.91 (2H, m), 3.98-4.04 (1H, m), 4.07-4.15 (2H, m), 5.16 (1H, s), 7.10 (2H, d, J = 8.5 Hz), 7.13 (2H, d, J = 8.5 Hz). | Reference example 3<br>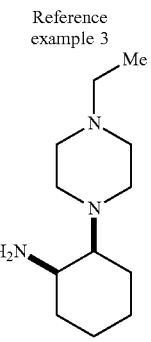 | Commercial product<br>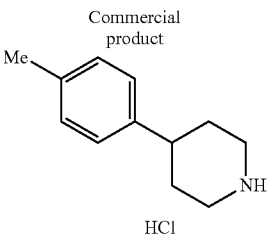 |
| 3 | 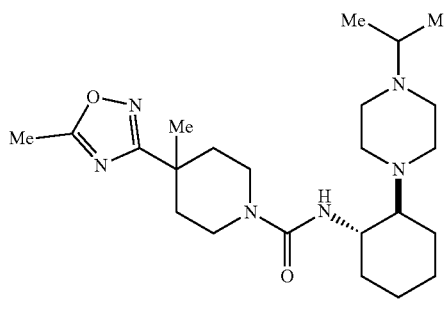<br>¹H-NMR (CDCl₃) δ: 1.03 (6H, d, J = 6.1 Hz), 1.14-1.28 (3H, m), 1.32 (3H, s), 1.58-1.68 (3H, m), 1.76-1.82 (1H, m), 1.83-1.91 (1H, m), 2.19-2.30 (3H, m), 2.34-2.53 (6H, m), 2.53-2.62 (6H, m), 2.62-2.71 (2H, m), 3.07 (2H, ddd, J = 13.2, 10.4, 2.8 Hz), 3.20-3.31 (1H, m), 3.63-3.74 (2H, m), 5.70 (1H, s). | Reference example 1<br>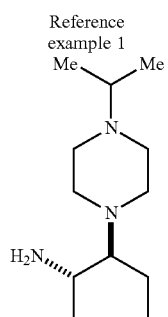 | Commercial product<br>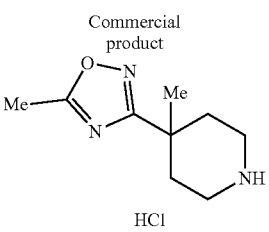 |
| 4 | 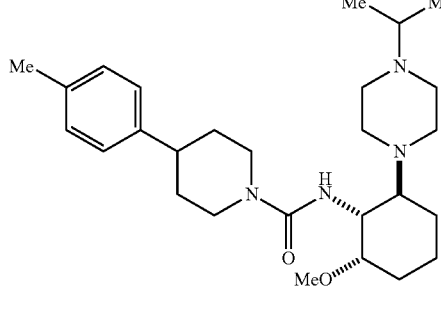<br>¹H-NMR (CDCl₃) δ: 1.01 (6H, d, J = 6.1 Hz), 1.15-1.35 (4H, m), 1.42-1.58 (2H, m), 1.58-1.71 (2H, m), 1.81-1.90 (2H, m), 1.91-2.01 (1H, m), 2.32 (3H, s), 2.38-2.63 (8H, m), 2.63-2.71 (3H, m), 2.72-2.95 (3H, m), 3.35 (3H, s), 3.50-3.57 (1H, m), 4.01-4.06 (1H, m), 4.06-4.23 (2H, m), 5.53 (1H, d, J = 3.7 Hz), 7.09 (2H, d, J = 8.2 Hz), 7.12 (2H, d, J = 8.2 Hz). | Reference example 4<br>3HCl<br>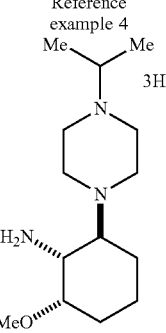 | Commercial product<br>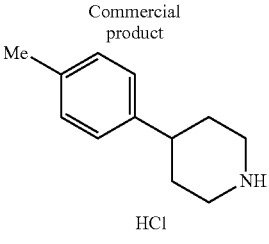 |

-continued

| Example | Structure<br>Spectral data | Material A | Material B |
|---|---|---|---|
| 5 | [Structure: 4-(4-methylphenyl)piperidine-1-carboxamide with cyclopentyl-piperazine-N(iPr)2]<br><sup>1</sup>H-NMR (CDCl₃) δ: 1.06 (6H, d, J = 6.1 Hz), 1.35-1.48 (1H, m), 1.48-1.73 (5H, m), 1.78-1.91 (2H, m), 2.12-2.25 (1H, m), 2.32 (3H, s), 2.39-2.79 (12H, m), 2.79-2.93 (2H, m), 3.96-4.12 (3H, m), 4.63 (1H, s), 7.09 (2H, d, J = 7.9 Hz), 7.12 (2H, d, J = 7.9 Hz). | Reference example 5 | Commercial product (4-(p-tolyl)piperidine·HCl) |
| 6 | [Structure: cyclopropyl-isoxazole piperidine carboxamide with cyclopentyl-piperazine-N(iPr)2]<br><sup>1</sup>H-NMR (CDCl₃) δ: 0.92-0.99 (2H, m), 0.99-1.09 (8H, m), 1.26 (3H, s), 1.35-1.45 (1H, m), 1.46-1.76 (6H, m), 1.80-1.90 (1H, m), 1.94-2.10 (3H, m), 2.10-2.21 (1H, m), 2.37-2.84 (9H, m), 3.08-3.17 (2H, m), 3.52-3.64 (2H, m), 3.98-4.08 (1H, m), 4.61 (1H, s), 5.77 (1H, s). | Reference example 5 | Reference example 20 |
| 7 | [Structure: cyclopropyl-oxadiazole piperidine carboxamide with difluorocyclohexyl-piperazine-N(iPr)2]<br><sup>1</sup>H-NMR (CDCl₃) δ: 0.80-0.91 (1H, m), 1.02 (3H, d, J = 6.0 Hz), 1.03 (3H, d, J = 6.0 Hz), 1.18-1.23 (4H, m), 1.24-1.28 (2H, m), 1.31 (3H, s), 1.53-1.70 (2H, m), 1.92-2.28 (5H, m), 2.28-2.69 (7H, m), 2.73-2.81 (2H, m), 3.02-3.14 (4H, m), 3.52-3.63 (1H, m), 3.63-3.75 (2H, m), 5.52 (1H, s). | Reference example 7 | Reference example 8 |

| Example | Structure | Material A | Material B |
|---|---|---|---|
| | Spectral data | | |
| 8 | [Structure: 4-(p-tolyl)piperidine-1-carboxamide with 2,2-difluorocyclohexyl bearing 4-(isopropyl)piperazin-1-yl]<br>¹H-NMR (CDCl₃) δ: 0.96-1.52 (11H, m), 1.70-1.93 (3H, m), 1.94-2.08 (2H, m), 2.13-2.26 (1H, m), 2.32 (3H, s), 2.42-3.27 (12H, m), 4.02-4.26 (3H, m), 4.61 (1H, d, J = 6.7 Hz), 7.08 (2H, d, J = 8.5 Hz), 7.12 (2H, d, J = 8.5 Hz). | Reference example 14<br>[Structure: 4-(isopropyl)piperazin-1-yl cyclohexylamine, difluoro] · 3HCl | Commercial product<br>[Structure: 4-(p-tolyl)piperidine] · HCl |
| 9 | [Structure: 5-cyclopropyl-1,2,4-oxadiazol-3-yl-4-methylpiperidine-1-carboxylate with difluorocyclohexyl piperazinyl isopropyl]<br>¹H-NMR (CDCl₃) δ: 1.46-1.63 (6H, m), 1.12-1.24 (4H, m), 1.24-1.39 (5H, m), 1.39-1.50 (1H, m), 1.51-1.71 (3H, m), 1.86-1.96 (1H, m), 2.07-2.29 (4H, m), 2.31-2.59 (6H, m), 2.59-2.74 (2H, m), 2.74-2.89 (2H, m), 2.93-3.17 (1H, m), 3.18-3.41 (1H, m), 3.62-3.83 (1H, m), 3.83-4.00 (1H, m), 4.82-5.00 (1H, m). | Reference example 6<br>[Structure: HO-cyclohexyl with difluoro and piperazinyl isopropyl] | Reference example 8<br>[Structure: 5-cyclopropyl-3-(4-methylpiperidin-4-yl)-1,2,4-oxadiazole] · HCl |
| 10 | [Structure: 5-methyl-1,2,4-oxadiazol-3-yl-4-methylpiperidine-1-carboxylate with difluorocyclohexyl piperazinyl isopropyl]<br>¹H-NMR (CDCl₃) δ: 0.88-1.10 (6H, m), 1.23-1.39 (1H, m), 1.33 (3H, s), 1.40-1.51 (1H, m), 1.53-2.99 (2H, m), 1.73-1.83 (1H, m), 1.83-1.96 (1H, m), 2.06-2.31 (3H, m), 2.31-2.60 (9H, m), 2.60-2.86 (3H, m), 2.90-3.16 (1H, m), 3.16-3.42 (1H, m), 3.63-3.86 (1H, m), 3.86-4.03 (1H, m), 4.83-5.00 (1H, m). | Reference example 6<br>[Structure: HO-cyclohexyl with difluoro and piperazinyl isopropyl] | Commercial product<br>[Structure: 5-methyl-3-(4-methylpiperidin-4-yl)-1,2,4-oxadiazole] · HCl |

-continued

| Example | Structure / Spectral data | Material A | Material B |
|---|---|---|---|
| 11 | (structure) <br> ¹H-NMR (CDCl₃) δ: 0.90-1.10 (10H, m), 1.15-1.37 (5H, m), 1.37-1.50 (1H, m), 1.53-1.81 (4H, m), 1.83-1.95 (1H, m), 1.95-2.24 (4H, m), 2.24-2.71 (7H, m), 2.71-2.87 (2H, m), 3.01-3.49 (2H, m), 3.60-3.81 (1H, m), 3.81-3.97 (1H, m), 4.83-5.00 (1H, m), 5.77 (1H, s). | Reference example 6 | Reference example 20 |
| 12 | (structure) <br> ¹H-NMR (CDCl₃) δ: 0.82-1.12 (6H, m), 1.23-1.50 (5H, m), 1.56-1.83 (4H, m), 1.85-1.97 (1H, m), 2.10-2.33 (3H, m), 2.33-2.73 (8H, m), 2.73-2.88 (2H, m), 2.95-3.22 (1H, m), 3.21-3.48 (1H, m), 3.65-3.84 (1H, m), 3.86-4.04 (1H, m), 4.85-5.00 (1H, m), 6.79 (1H, t, J = 52.3 Hz). | Reference example 6 | Reference example 10 |
| 13 | (structure) <br> ¹H-NMR (CDCl₃) δ: 0.83-1.15 (10H, m), 1.18-1.34 (1H, m), 1.29 (3H, s), 1.34-1.50 (1H, m), 1.52-1.72 (3H, m), 1.72-1.82 (1H, m), 1.83-1.97 (1H, m), 2.08-2.21 (1H, m), 2.21-2.60 (8H, m), 2.60-2.73 (2H, m), 2.73-2.89 (2H, m), 2.91-3.11 (1H, m), 3.14-3.37 (1H, m), 3.42-3.59 (1H, m), 3.59-3.83 (1H, m), 3.83-4.03 (1H, m), 4.79-5.02 (1H, m), 8.00 (1H, s). | Reference example 6 | Reference example 27 |

| Example | Structure | Spectral data | Material A | Material B |
|---|---|---|---|---|
| 14 | [Structure with cyclopropyl-oxadiazole-methylpiperidine-carbamate-difluorocyclohexyl-piperazine-isopropyl group, Abs] | ¹H-NMR (CDCl₃) δ: 1.46-1.63 (6H, m), 1.12-1.24 (4H, m), 1.24-1.39 (5H, m), 1.39-1.50 (1H, m), 1.51-1.71 (3H, m), 1.86-1.96 (1H, m), 2.07-2.29 (4H, m), 2.31-2.59 (6H, m), 2.59-2.74 (2H, m), 2.74-2.89 (2H, m), 2.93-3.17 (1H, m), 3.18-3.41 (1H, m), 3.62-3.83 (1H, m), 3.83-4.00 (1H, m), 4.82-5.00 (1H, m). | Reference example 42 [Structure, Abs] | Reference example 8 [Structure, HCl] |
| 15 | [Structure with cyclopropyl-isoxazole-methylpiperidine-urea-cyclohexenyl-pyridine-isopropyl group] | ¹H-NMR (CDCl₃) δ: 0.89-0.98 (2H, m), 0.98-1.06 (2H, m), 1.18 (3H, s), 1.28 (6H, d, J = 7.3 Hz), 1.32-1.41 (1H, m), 1.41-1.54 (1H, m), 1.54-1.79 (2H, m), 1.79-2.05 (5H, m), 2.12-2.32 (2H, m), 2.91-3.09 (3H, m), 3.35-3.44 (1H, m), 3.50-3.59 (1H, m), 4.37 (1H, d, J = 7.9 Hz), 4.90-4.97 (1H, m), 5.72 (1H, s), 6.26 (1H, dd, J = 3.7, 3.7 Hz), 7.10 (1H, d, J = 8.3 Hz), 7.61 (1H, dd, J = 8.3, 2.0 Hz), 8.55 (1H, d, J = 2.0 Hz). | Reference example 44 [Structure] | Reference example 20 [Structure, HCl] |
| 16 | [Structure with cyclopropyl-oxadiazole-methylpiperidine-urea-cyclohexenyl-pyridine-isopropyl group] | ¹H-NMR (CDCl₃) δ: 1.15-1.20 (4H, m), 1.23 (3H, s), 1.24-1.32 (1H, m), 1.28 (6H, d, J = 6.7 Hz), 1.37 (1H, ddd, J = 14.1, 10.3, 3.6 Hz), 1.50 (1H, ddd, J = 14.1, 10.3, 3.8 Hz), 1.69-1.79 (1H, m), 1.79-1.97 (2H, m), 2.02-2.18 (3H, m), 2.18-2.34 (2H, m), 2.84-3.09 (3H, m), 3.39-3.48 (1H, m), 3.53-3.61 (1H, m), 4.36 (1H, d, J = 7.9 Hz), 4.91-4.98 (1H, m), 6.27 (1H, dd, J = 4.0, 4.0 Hz), 7.10 (1H, d, J = 8.2 Hz), 7.61 (1H, dd, J = 8.2, 2.1 Hz), 8.56 (1H, d, J = 2.1 Hz). | Reference example 44 [Structure] | Reference example 8 [Structure, HCl] |

The chemical names of Example 2 to Example 16 are listed below.

Example 2: rac-N-[(1R,2S)-2-(4-ethylpiperazin-1-yl)cyclohexyl]-4-(4-methylphenyl)piperidine-1-carboxamide Example 3: rac-4-methyl-4-(5-methyl-1,2,4-oxadiazol-3-yl)-N-{(1S,2S)-2-[4-(propan-2-yl)piperazin-1-yl]cyclohexyl}piperidine-1-carboxamide Example 4: rac-N-{(1R,2S,6S)-2-methoxy-6-[4-(propan-2-yl)piperazin-1-yl]cyclohexyl}-4-(4-methylphenyl)piperidine-1-carboxamide Example 5: rac-4-(4-methylphenyl)-N-{(1S,2S)-2-[4-(propan-2-yl)piperazin-1-yl]cyclopentyl}piperidine-1-carboxamide Example 6: rac-4-(5-cyclopropyl-1,2-oxazol-3-yl)-4-methyl-N-{(1S,2S)-2-[4-(propan-2-yl)piperazin-1-yl]cyclopentyl}piperidine-1-carboxamide Example 7: rac-4-(5-cyclopropyl-1,2,4-oxadiazol-3-yl)-N-{(1R,2S)-3,3-difluoro-2-[4-(propan-2-yl)piperazin-1-yl]cyclohexyl}-4-methylpiperidine-1-carboxamide Example 8: rac-N-{(1R,6S)-2,2-difluoro-6-[4-(propan-2-yl)piperazin-1-yl]cyclohexyl}-4-(4-methylphenyl)piperidine-1-carboxamide Example 9: rac-(1R,6S)-2,2-difluoro-6-[4-(propan-2-yl)piperazin-1-yl]cyclohexyl 4-(5-cyclopropyl-1,2,4-oxadiazol-3-yl)-4-methylpiperidine-1-carboxylate Example 10: rac-(1R,6S)-2,2-difluoro-6-[4-(propan-2-yl)piperazin-1-yl]cyclohexyl 4-methyl-4-(5-methyl-1,2,4-oxadiazol-3-yl)piperidine-1-carboxylate Example 11: rac-(1R,6S)-2,2-difluoro-6-[4-(propan-2-yl)piperazin-1-yl]cyclohexyl 4-(5-cyclopropyl-1,2-oxazol-3-yl)-4-methylpiperidine-1-carboxylate Example 12: rac-(1R,6S)-2,2-difluoro-6-[4-(propan-2-yl)piperazin-1-yl]cyclohexyl 4-[5-(difluoromethyl)-1,2,4-oxadiazol-3-yl]-4-methylpiperidine-1-carboxylate Example 13: rac-(1R,6S)-2,2-difluoro-6-[4-(propan-2-yl)piperazin-1-yl]cyclohexyl 4-(1-cyclopropyl-1H-1,2,4-triazol-3-yl)-4-methylpiperidine-1-carboxylate Example 14: (1R,6S)-2,2-difluoro-6-[4-(propan-2-yl)piperazin-1-yl]cyclohexyl 4-(5-cyclopropyl-1,2,4-oxadiazol-3-yl)-4-methylpiperidine-1-carboxylate Example 15: rac-4-(5-cyclopropyl-1,2-oxazol-3-yl)-4-methyl-N-{2-[6-(propan-2-yl)pyridin-3-yl]cyclohex-2-en-1-yl}piperidine-1-carboxamide Example 16: rac-4-(5-cyclopropyl-1,2,4-oxadiazol-3-yl)-4-methyl-N-{2-[6-(propan-2-yl)pyridin-3-yl]cyclohex-2-en-1-yl}piperidine-1-carboxamide Example 17 rac-N-[(1S,2S)-2-(4-Ethylpiperazin-1-yl)cyclohexyl]-4-(4-methylphenyl)piperidine-1-carboxamide

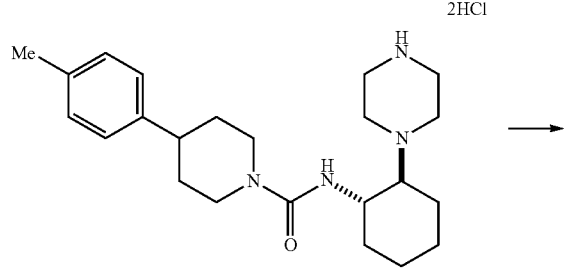

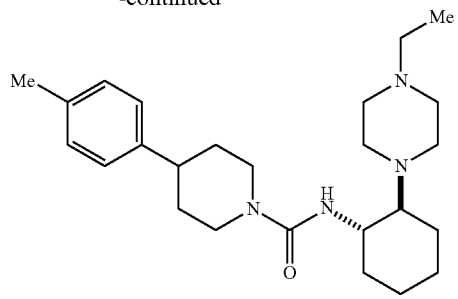

To a mixture of Reference example 2 (73.7 mg), sodium acetate (18.9 mg), acetaldehyde (0.054 ml), and dichloromethane (2 mL) was added sodium triacetoxyborohydride (122 mg) at 0° C., and the mixture was warmed to room temperature and stirred for 1.5 hours. Water was added to the reaction mixture at 0° C., and the mixture was extracted with chloroform. The organic layer was dried over anhydrous sodium sulfate, concentrated in vacuo, and then the obtained residue was purified by amino silica gel column chromatography (eluate: hexane/ethyl acetate) to give the title compound (24 mg).

$^1$H-NMR (CDCl$_3$) δ: 1.02-1.12 (1H, m), 1.07 (3H, t, J=7.3 Hz), 1.14-1.41 (3H, m), 1.57-1.71 (3H, m), 1.75-1.96 (5H, m), 2.16-2.78 (15H, m), 2.78-2.90 (2H, m), 3.24-3.39 (1H, m), 4.05-4.18 (2H, m), 5.72 (1H, s), 7.09 (2H, d, J=7.9 Hz), 7.12 (2H, d, J=7.9 Hz).

Example 18 rac-4-(5-Cyclopropyl-1,2,4-oxadiazol-3-yl)-4-methyl-N-{2-[1-(propan-2-yl)-1,2,3,6-tetrahydropyridin-4-yl]cyclohex-2-en-1-yl}piperidine-1-carboxamide

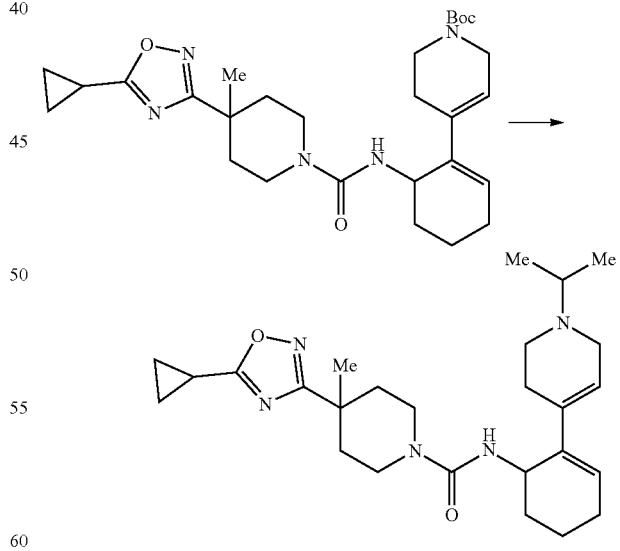

To a solution of Reference example 13 (13.5 mg) in chloroform (2 mL) was added hydrogen chloride/acetic acid solution (4 M, 0.198 mL), and the mixture was stirred at room temperature. After the reaction was terminated as judged by the consumption of the starting material, the reaction mixture was concentrated in vacuo. To the obtained residue were added sodium acetate (8.66 mg), acetone (0.058 mL), and chloroform (2 mL). To the mixture was added sodium triacetoxyborohydride (33.6 mg) at 0° C., and the mixture was warmed to room temperature and stirred. After the reaction was completed, water was added to the reaction mixture under ice temperature, and the mixture was extracted with chloroform. The organic layer was dried over anhydrous sodium sulfate, concentrated in vacuo, and then the obtained residue was purified by amino silica gel column chromatography (eluate: hexane/ethyl acetate) to give the title compound (10 mg).

$^1$H-NMR (CDCl$_3$) δ: 1.07 (6H, d, J=6.1 Hz), 1.17-1.22 (4H, m), 1.23-1.32 (2H, m), 1.29 (3H, s), 1.43-1.66 (3H, m), 1.91-1.98 (1H, m), 2.08-2.26 (6H, m), 2.26-2.41 (1H, m), 2.50 (1H, ddd, J=11.2, 7.2, 4.8 Hz), 2.63-2.76 (2H, m), 2.97-3.13 (3H, m), 3.13-3.23 (1H, m), 3.52-3.63 (2H, m), 4.43 (1H, d, J=7.3 Hz), 4.63-4.69 (1H, m), 5.78-5.84 (1H, m), 5.85-5.91 (1H, m).

Example 19 rac-4-(5-Cyclopropyl-1,2,4-oxadiazol-3-yl)-N-{(1R,6S)-2,2-difluoro-6-[4-(propan-2-yl)piperazin-1-yl] cyclohexyl}-4-methylpiperidine-1-carboxamide

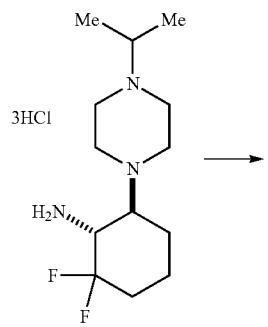

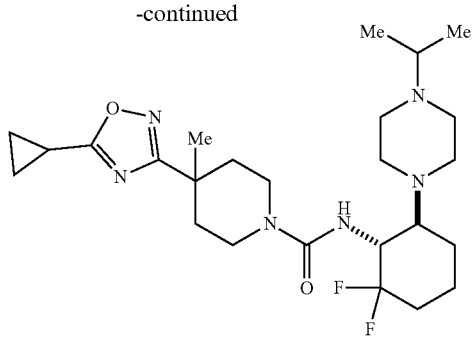

To a mixture of Reference example 14 (84.6 mg) (Material A), triethylamine (0.318 mL), and chloroform (2 mL) was added triphosgene (27.1 mg) at 0° C., and the mixture was stirred at the same temperature for 40 minutes. To the reaction mixture was added Reference example 8 (66.7 mg)(Material B) at 0° C., and the mixture was stirred at room temperature for one hour. Water was added to the reaction mixture, and the mixture was extracted with chloroform. The organic layer was dried over anhydrous sodium sulfate, concentrated in vacuo, and then the obtained residue was purified by silica gel column chromatography (eluate: chloroform/methanol) to give the title compound (99.1 mg).

$^1$H-NMR (CDCl$_3$) δ: 1.00 (3H, d, J=6.0 Hz), 1.01 (3H, d, J=6.0 Hz), 1.17-1.22 (4H, m), 1.23-1.30 (1H, m), 1.30-1.48 (2H, m), 1.31 (3H, s), 1.57-1.70 (2H, m), 1.75-1.84 (1H, m), 1.89-1.97 (1H, m), 2.10-2.27 (4H, m), 2.32-2.53 (7H, m), 2.53-2.64 (1H, m), 2.68-2.78 (2H, m), 3.08 (1H, ddd, J=13.6, 10.7, 3.1 Hz), 3.16 (1H, ddd, J=13.6, 10.7, 3.1 Hz), 3.66 (1H, ddd, J=13.6, 4.7, 4.1 Hz), 3.77 (1H, ddd, J=13.6, 4.7, 4.1 Hz), 4.10-4.21 (1H, m), 4.54 (1H, d, J=7.3 Hz).

Examples 20 to 76

The compounds of Examples 20 to 76 shown in the table below were prepared in the same manner as Example 19, by using commercial compounds or Reference example compounds which correspond to Material A and Material B described in Example 19.

| Example | Structure / Spectral data | Material A | Material B |
|---|---|---|---|
| 20 | (structure shown) $^1$H-NMR (CDCl$_3$) δ: 0.92-1.19 (10H, m), 1.27 (3H, s), 1.30-1.74 (3H, m), 1.75-1.88 (3H, m), 1.89-1.97 (1H, m), 1.97-2.04 (1H, m), 2.05-2.27 (3H, m), 2.32-2.67 (8H, m), 2.69-2.81 (2H, m), 3.12-3.29 (2H, m), 3.57-3.68 (1H, m), 3.68-3.80 (1H, m), 4.08-4.25 (1H, m), 4.54 (1H, d, J = 7.3 Hz), 5.77 (1H, s). | Reference example 14 | Reference example 20 |

-continued

| Example | Structure | Material A / Spectral data | Material B |
|---|---|---|---|
| 21 | (benzoxazole-Me-piperidine-carboxamide with difluorocyclohexyl-piperazine-N-iPr structure) | Reference example 14<br>(piperazine-iPr with difluoro-aminocyclohexyl, 3HCl)<br><br>$^1$H-NMR (CDCl$_3$) δ: 0.93 (6H, d, J = 6.1 Hz), 1.22-1.43 (2H, m), 1.45 (3H, s), 1.63-1.86 (4H, m), 1.89-1.97 (1H, m), 2.11-2.22 (1H, m), 2.28-2.54 (10H, m), 2.68-2.78 (2H, m), 3.11-3.26 (2H, m), 3.76 (1H, ddd, J = 13.5, 4.1, 4.0 Hz), 3.84 (1H, ddd, J = 13.5, 4.1, 4.0 Hz), 4.09-4.22 (1H, m), 4.56 (1H, d, J = 7.3 Hz), 7.29-7.35 (2H, m), 7.47-7.53 (1H, m), 7.67-7.72 (1H, m). | Reference example 21<br>(benzoxazole-Me-piperidine-NH) |
| 22 | (cyclopropyl-isoxazole-Me-piperidine-carboxamide with difluorocyclohexyl-piperazine-N-iPr, Abs) | Reference example 15'<br>(Abs, piperazine-iPr with difluoro-aminocyclohexyl, 3HCl)<br><br>$^1$H-NMR (CDCl$_3$) δ: 0.92-0.98 (2H, m), 1.00-1.08 (2H, m), 1.13 (6H, d, J = 6.0 Hz), 1.28 (3H, s), 1.28-1.47 (3H, m), 1.47-1.88 (5H, m), 1.90-2.25 (5H, m), 2.25-3.07 (8H, m), 3.13-3.03 (2H, m), 3.58-3.74 (2H, m), 4.07-4.23 (1H, m), 4.54 (1H, d, J = 8.0 Hz), 5.78 (1H, s). | Reference example 20<br>(cyclopropyl-isoxazole-Me-piperidine-NH, HCl) |
| 23 | (cyclopropyl-oxadiazole-Me-piperidine-carboxamide with difluorocyclohexyl-piperazine-N-iPr, Abs) | Reference example 15'<br>(Abs, piperazine-iPr with difluoro-aminocyclohexyl, 3HCl)<br><br>$^1$H-NMR (CDCl$_3$) δ: 0.97-1.16 (6H, m), 1.16-1.26 (4H, m), 1.26-1.44 (3H, m), 1.31 (3H, s), 1.47-1.75 (5H, m), 1.75-1.88 (2H, m), 1.88-2.03 (1H, m), 2.09-2.28 (4H, m), 2.28-3.01 (6H, m), 3.01-3.26 (2H, m), 3.58-3.84 (2H, m), 4.06-4.26 (1H, m), 4.54 (1H, d, J = 8.0 Hz). | Reference example 8<br>(cyclopropyl-oxadiazole-Me-piperidine-NH, HCl) |

| Example | Structure | Material A Spectral data | Material B |
|---|---|---|---|
| 24 | 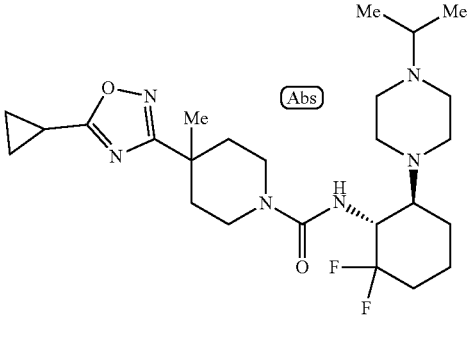 [SMILES: CC(C)N1CCN([C@H]2CCCC(F)(F)[C@@H]2NC(=O)N2CCC(C)(c3noc(C4CC4)n3)CC2)CC1] | Reference example 15<br>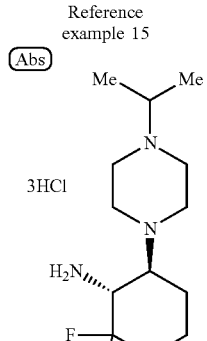<br>3HCl<br><br>¹H-NMR (CDCl₃) δ: 1.00 (3H, d, J = 6.0 Hz), 1.01 (3H, d, J = 6.0 Hz), 1.17-1.22 (4H, m), 1.23-1.30 (1H, m), 1.30-1.48 (2H, m), 1.31 (3H, s), 1.57-1.70 (2H, m), 1.75-1.84 (1H, m), 1.89-1.97 (1H, m), 2.10-2.27 (4H, m), 2.32-2.53 (7H, m), 2.53-2.64 (1H, m), 2.68-2.78 (2H, m), 3.08 (1H, ddd, J = 13.6, 10.7, 3.1 Hz), 3.16 (1H, ddd, J = 13.6, 10.7, 3.1 Hz), 3.66 (1H, ddd, J = 13.6, 4.7, 4.1 Hz), 3.77 (1H, ddd, J = 13.6, 4.7, 4.1 Hz), 4.10-4.21 (1H, m), 4.54 (1H, d, J = 7.3 Hz). | Reference example 8<br>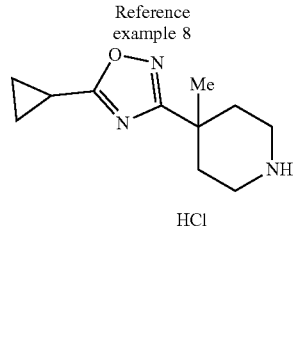<br>HCl |
| 25 | 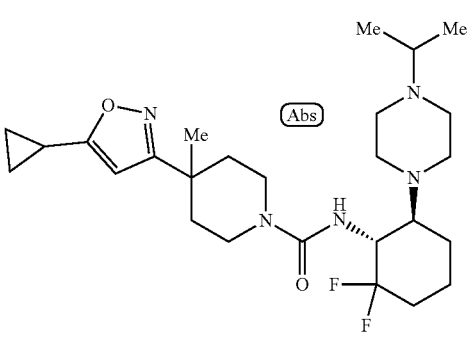 [SMILES: CC(C)N1CCN([C@H]2CCCC(F)(F)[C@@H]2NC(=O)N2CCC(C)(c3cc(C4CC4)on3)CC2)CC1] | Reference example 15<br>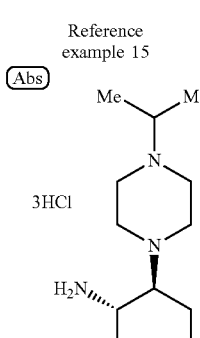<br>3HCl<br><br>¹H-NMR (CDCl₃) δ: 0.92-1.19 (10H, m), 1.27 (3H, s), 1.30-1.74 (3H, m), 1.75-1.88 (3H, m), 1.89-1.97 (1H, m), 1.97-2.04 (1H, m), 2.05-2.27 (3H, m), 2.32-2.67 (8H, m), 2.69-2.81 (2H, m), 3.12-3.29 (2H, m), 3.57-3.68 (1H, m), 3.68-3.80 (1H, m), 4.08-4.25 (1H, m), 4.54 (1H, d, J = 7.3 Hz), 5.77 (1H, s). | Reference example 20<br>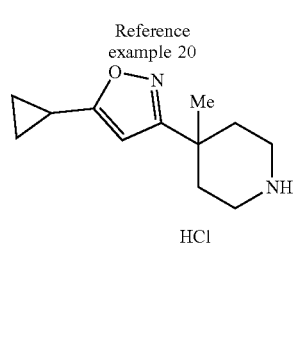<br>HCl |

| Example | Structure | Material A | Material B |
|---|---|---|---|
| | | Spectral data | |
26 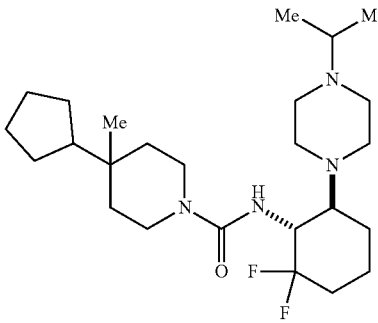 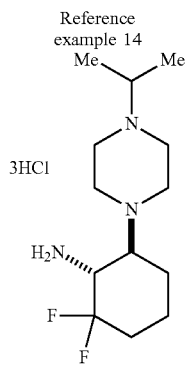 Reference example 14 · 3HCl 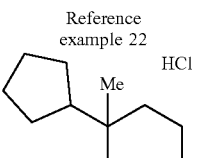 Reference example 22 · HCl
¹H-NMR (CDCl₃) δ: 0.84-0.91 (4H, m), 1.02 (6H, d, J = 6.7 Hz), 1.20-1.31 (3H, m), 1.31-1.41 (2H, m), 1.45 (3H, s), 1.46-1.59 (3H, m), 1.66-1.85 (3H, m), 1.89-1.97 (1H, m), 2.10-2.22 (1H, m), 2.35-2.55 (7H, m), 2.55-2.66 (1H, m), 2.67-2.79 (2H, m), 2.98-3.13 (2H, m), 3.18 (1H, ddd, J = 13.8, 10.5, 3.6 Hz), 3.59 (1H, ddd, J = 13.8, 4.6, 3.6 Hz), 3.63-3.79 (2H, m), 4.10-4.22 (1H, m), 4.53 (1H, d, J = 7.9 Hz).
27 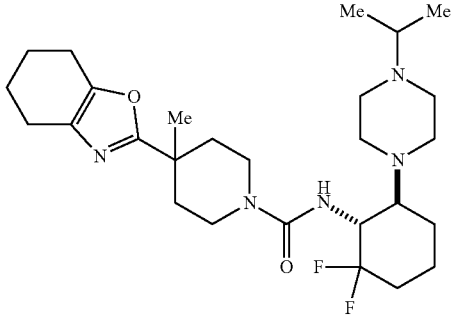 [SMILES: CC(C)N1CCN([C@H]2CCCC(F)(F)[C@@H]2NC(=O)N2CCC(C)(c3nc4c(o3)CCCC4)CC2)CC1] 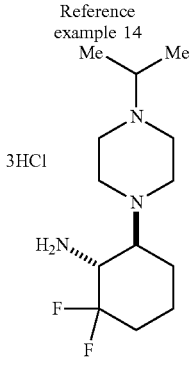 Reference example 14 · 3HCl 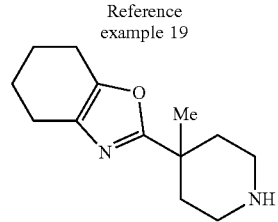 Reference example 19
¹H-NMR (CDCl₃) δ: 1.00 (6H, d, J = 6.8 Hz), 1.28-1.46 (2H, m), 1.32 (3H, s), 1.57-1.66 (2H, m), 1.74-1.88 (6H, m), 1.89-1.97 (1H, m), 2.10-2.21 (1H, m), 2.22-2.31 (2H, m), 2.35-2.54 (9H, m), 2.54-2.63 (3H, m), 2.69-2.78 (2H, m), 3.09 (1H, ddd, J = 13.8, 10.5, 2.9 Hz), 3.17 (1H, ddd, J = 13.8, 10.5, 2.9 Hz), 3.65 (1H, ddd, J = 13.8, 4.1, 4.1 Hz), 3.79 (1H, ddd, J = 13.8, 4.1, 4.1 Hz), 4.08-4.22 (1H, m), 4.53 (1H, d, J = 7.9 Hz).

| Example | Structure | Material A | Material B |
|---|---|---|---|
| | | Spectral data | |
| 28 | (structure: 5-ethyl-1,2,4-oxadiazol-3-yl attached to 4-methylpiperidine-N-carboxamide linked to NH of 2-(4-isopropylpiperazin-1-yl)-6,6-difluorocyclohexyl) | Reference example 14: 1-isopropyl-4-[2-amino-6,6-difluorocyclohexyl]piperazine · 3HCl | Reference example 9: 5-ethyl-3-(4-methylpiperidin-4-yl)-1,2,4-oxadiazole · HCl |
| | | ¹H-NMR (CDCl₃) δ: 1.00 (3H, d, J = 6.0 Hz), 1.00 (3H, d, J = 6.0 Hz), 1.20-1.43 (3H, m), 1.33 (3H, s), 1.39 (3H, t, J = 7.7 Hz), 1.61-1.74 (2H, m), 1.75-1.86 (1H, m), 1.89-1.98 (1H, m), 2.10-2.21 (1H, m), 2.21-2.30 (2H, m), 2.34-2.54 (7H, m), 2.54-2.64 (1H, m), 2.70-2.78 (2H, m), 2.89 (2H, q, J = 7.7 Hz), 3.09 (1H, ddd, J = 13.8, 10.7, 3.1 Hz), 3.17 (1H, ddd, J = 13.8, 10.7, 3.1 Hz), 3.66 (1H, ddd, J = 13.6, 4.4, 4.4 Hz), 3.79 (1H, ddd, J = 13.6, 4.4, 4.4 Hz), 4.08-4.22 (1H, m), 4.53 (1H, d, J = 7.9 Hz). | | |
| 29 | (structure: 1-cyclopropyl-1,2,4-triazol-3-yl attached to 4-methylpiperidine-N-carboxamide linked to NH of 2-(4-isopropylpiperazin-1-yl)-6,6-difluorocyclohexyl) | Reference example 14 | Reference example 27: 1-cyclopropyl-3-(4-methylpiperidin-4-yl)-1,2,4-triazole · HCl |
| | | ¹H-NMR (CDCl₃) δ: 0.94-1.15 (10H, m), 1.16-1.47 (3H, m), 1.29 (3H, s), 1.52-1.87 (5H, m), 1.87-1.99 (1H, m), 2.10-2.22 (1H, m), 2.23-2.36 (2H, m), 2.37-2.92 (8H, m), 2.97-3.08 (1H, m), 3.08-3.19 (1H, m), 3.43-3.65 (2H, m), 3.72-3.84 (1H, m), 4.07-4.23 (1H, m), 4.52 (1H, d, J = 7.9 Hz), 8.00 (1H, s). | | |

-continued

| Example | Structure | Material A | Material B |
|---|---|---|---|
| | | Spectral data | |
| 30 | (structure) | Reference example 14 (structure) 3HCl | Reference example 23 (structure) HCl |

¹H-NMR (CDCl₃) δ: 1.03 (6H, d, J = 6.1 Hz), 1.10-1.21 (1H, m), 1.22–1.51 (9H, m), 1.54-1.86 (5H, m), 1.61 (3H, s), 1.89-1.98 (1H, m), 2.08-2.23 (3H, m), 2.32-2.55 (7H, m), 2.55-2.65 (1H, m), 2.68-2.79 (2H, m), 3.01-3.19 (2H, m), 3.66 (1H, ddd, J = 13.6, 4.4, 3.2 Hz), 3.78 (1H, ddd, J = 13.6, 4.4, 3.2 Hz), 4.09-4.23 (1H, m), 4.52 (1H, d, J = 7.3 Hz).

| 31 | (structure) | Reference example 14 (structure) 3HCl | Reference example 28 (structure) |

¹H-NMR (CDCl₃) δ: 1.00 (3H, d, J = 6.1 Hz), 1.01 (3H, d, J = 6.1 Hz), 1.11-1.18 (2H, m), 1.22-1.35 (4H, m), 1.30 (3H, s), 1.35-1.47 (1H, m), 1.62-1.75 (2H, m), 1.75-1.85 (1H, m), 1.88-1.97 (1H, m), 2.10-2.22 (1H, m), 2.31-2.62 (11H, m), 2.67-2.78 (2H, m), 3.01 (1H, ddd, J = 13.8, 10.7, 3.1 Hz), 3.10 (1H, ddd, J = 13.8, 10.7, 3.1 Hz), 3.65 (1H, ddd, J = 14.0, 4.3, 4.3 Hz), 3.79 (1H, ddd, J = 14.0, 4.3, 4.3 Hz), 4.08-4.22 (1H, m), 4.53 (1H, d, J = 7.3 Hz).

| Example | Structure | Material A Spectral data | Material B |
|---|---|---|---|
| 32 | [Structure: 4-(pyridin-2-yl)piperidine-1-carboxamide linked to 2-(4-(isopropyl)piperazin-1-yl)-6,6-difluorocyclohexyl] | Reference example 14, 3HCl | Commercial product, 2HCl |

¹H-NMR (CDCl₃) δ: 1.01 (6H, d, J = 6.8 Hz), 1.21-1.49 (2H, m), 1.62-1.88 (4H, m), 1.89-2.06 (3H, m), 2.10-2.23 (1H, m), 2.34-2.66 (8H, m), 2.70-2.83 (2H, m), 2.85-3.07 (3H, m), 4.05-4.30 (3H, m), 4.60 (1H, d, J = 8.0 Hz), 7.10-7.18 (2H, m), 7.62 (1H, ddd, J = 8.0, 8.0, 1.6 Hz), 8.52 (1H, dd, J = 4.8, 1.6 Hz).

| Example | Structure | Material A | Material B |
|---|---|---|---|
| 33 | [Structure: 2-azaspiro[4.5]... spiro cyclopentane-piperidine carboxamide linked to difluorocyclohexyl-piperazinyl-isopropyl] | Reference example 14, 3HCl | Commercial product |

¹H-NMR (CDCl₃) δ: 1.03 (6H, d, J = 6.4 Hz), 1.20-1.53 (10H, m), 1.54-1.66 (4H, m), 1.66-1.86 (3H, m), 1.88-1.98 (1H, m), 2.08-2.24 (1H, m), 2.26-2.56 (6H, m), 2.56-2.69 (1H, m), 2.69-2.82 (2H, m), 3.20-3.51 (4H, m), 4.06-4.25 (1H, m), 4.52 (1H, d, J = 8.0 Hz).

| Example | Structure | Material A | Material B |
|---|---|---|---|
| 34 | [Structure: 4-(5-cyclopropyl-1,3,4-thiadiazol-2-yl)-4-methylpiperidine-1-carboxamide linked to difluorocyclohexyl-piperazinyl-isopropyl] | Reference example 14, 3HCl | Reference example 24 |

¹H-NMR (CDCl₃) δ: 1.01-1.23 (10H, m), 1.23-1.46 (4H, m), 1.43 (3H, s), 1.60-1.74 (1H, m), 1.74-1.87 (3H, m), 1.92-2.03 (1H, m), 2.11-2.29 (3H, m), 2.31-2.40 (1H, m), 2.40-3.14 (8H, m), 3.26-3.38 (2H, m), 3.58-3.71 (2H, m), 4.08-4.23 (1H, m), 4.52 (1H, d, J = 7.9 Hz).

| Example | Structure | Material A / Spectral data | Material B |
|---|---|---|---|
| 35 | [cyclohexyl-piperidine-carbonyl urea with difluorocyclohexyl piperazine bearing isopropyl group] | Reference example 14 [isopropyl piperazine difluorocyclohexyl amine] 3HCl<br><br>$^1$H-NMR (CDCl$_3$) δ: 0.82-1.07 (3H, m), 1.03 (6H, d, J = 6.8 Hz), 1.07-1.49 (11H, m), 1.49-1.86 (6H, m), 1.89-1.99 (1H, m), 2.09-2.25 (1H, m), 2.34-2.56 (7H, m), 2.56-2.67 (1H, m), 2.67-2.87 (4H, m), 3.89-3.99 (1H, m), 4.05-4.27 (2H, m), 4.49 (1H, d, J = 8.0 Hz). | Commercial product [cyclohexyl-piperidine] HCl |
| 36 | [pyrimidinyl-piperidine-carbonyl urea with difluorocyclohexyl piperazine bearing isopropyl group] | Reference example 14 [isopropyl piperazine difluorocyclohexyl amine] 3HCl<br><br>$^1$H-NMR (CDCl$_3$) δ: 0.99 (6H, d, J = 6.4 Hz), 1.21-1.49 (2H, m), 1.61-2.00 (5H, m), 2.01-2.12 (2H, m), 2.12-2.24 (1H, m), 2.29-2.64 (8H, m), 2.68-2.81 (2H, m), 2.87-3.00 (1H, m), 3.00-3.14 (2H, m), 3.97-4.09 (1H, m), 4.09-4.29 (2H, m), 4.58 (1H, d, J = 8.0 Hz), 7.13 (1H, t, J = 4.8 Hz), 8.67 (2H, d, J = 4.8 Hz). | Commercial product [pyrimidinyl-piperidine] HCl |
| 37 | [pyridinyl-hydroxy-piperidine-carbonyl urea with difluorocyclohexyl piperazine bearing isopropyl group] | Reference example 14 [isopropyl piperazine difluorocyclohexyl amine] 3HCl<br><br>$^1$H-NMR (CDCl$_3$) δ: 1.03 (6H, d, J = 6.4 Hz), 1.22-1.51 (2H, m), 1.59-1.90 (4H, m), 1.90-2.07 (3H, m), 2.10-2.24 (1H, m), 2.34-2.65 (8H, m), 2.69-2.82 (2H, m), 3.33-3.50 (2H, m), 3.92-4.10 (2H, m), 4.13-4.28 (1H, m), 4.64 (1H, d, J = 8.0 Hz), 5.30 (1H, bs), 7.23 (1H, ddd, J = 8.0, 8.0, 1.6 Hz), 7.32 (1H, dd, J = 8.0, 1.6 Hz), 7.71 (1H, ddd, J = 8.0, 8.0, 1.6 Hz), 8.51-8.55 (1H, m). | Commercial product [pyridinyl-hydroxy-piperidine] HCl |

| Example | Structure | Material A / Spectral data | Material B |
|---|---|---|---|
| 38 | [structure] | Reference example 14, 3HCl [structure] <br> ¹H-NMR (CDCl₃) δ: 1.02 (6H, d, J = 6.4 Hz), 1.22-1.50 (2H, m), 1.61-1.77 (3H, m), 1.77-2.00 (4H, m), 2.11-2.24 (1H, m), 2.31-2.64 (8H, m), 2.65-2.82 (3H, m), 2.83-3.04 (2H, m), 4.02-4.13 (1H, m), 4.13-4.33 (2H, m), 4.60 (1H, d, J = 8.0 Hz), 7.17-7.24 (3H, m), 7.27-7.34 (2H, m). | Commercial product [structure] |
| 39 | [structure] | Reference example 14, 3HCl [structure] <br> ¹H-NMR (CDCl₃) δ: 0.95 (6H, d, J = 6.4 Hz), 1.18-1.48 (4H, m), 1.60-1.86 (5H, m), 1.87-1.98 (1H, m), 2.07-2.23 (3H, m), 2.25-2.55 (8H, m), 2.66-2.78 (2H, m), 3.28-3.62 (4H, m), 4.07-4.24 (1H, m), 4.54 (1H, d, J = 8.0 Hz), 7.16-7.24 (1H, m), 7.28-7.38 (4H, m). | Commercial product [structure] |
| 40 | [structure] | Reference example 14, 3HCl [structure] <br> ¹H-NMR (CDCl₃) δ: 0.99 (6H, d, J = 6.4 Hz), 1.22-1.49 (2H, m), 1.56-1.88 (5H, m), 1.89-2.00 (1H, m), 2.01-2.24 (3H, m), 2.29-2.61 (8H, m), 2.68-2.81 (2H, m), 3.30-3.47 (2H, m), 3.85-4.05 (2H, m), 4.11-4.27 (1H, m), 4.62 (1H, d, J = 8.0 Hz), 7.25-7.31 (1H, m), 7.36 (2H, t, J = 8.0 Hz), 7.48 (2H, d, J = 8.0 Hz). | Commercial product [structure] |

| Example | Structure | Material A Spectral data | Material B |
|---|---|---|---|
| 41 | 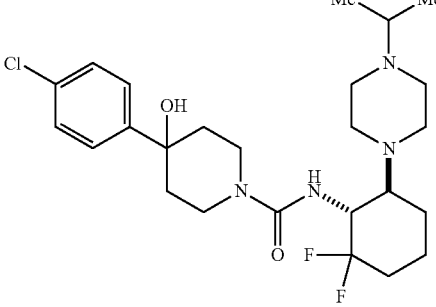 | 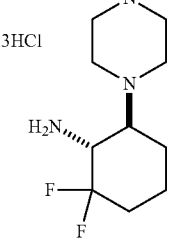 Reference example 14<br><br>¹H-NMR (CDCl₃) δ: 0.99 (6H, d, J = 6.0 Hz), 1.21-1.49 (2H, m), 1.60-1.88 (5H, m), 1.88-1.97 (1H, m), 1.97-2.09 (2H, m), 2.10-2.23 (1H, m), 2.27-2.61 (8H, m), 2.66-2.80 (2H, m), 3.25-3.43 (2H, m), 3.84-4.03 (2H, m), 4.07-4.24 (1H, m), 4.61 (1H, d, J = 8.0 Hz), 7.31 (2H, d, J = 8.8 HZ), 7.41 (2H, d, J = 8.8 Hz). | 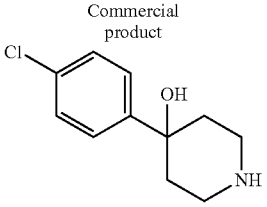 Commercial product |
| 42 | 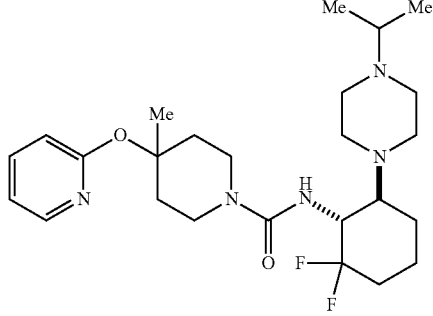 | 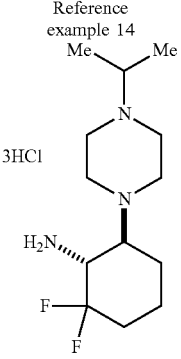 Reference example 14<br><br>¹H-NMR (CDCl₃) δ: 1.01 (6H, d, J = 6.1 Hz), 1.19-1.47 (3H, m), 1.65 (3H, s), 1.67-1.84 (3H, m), 1.90-1.97 (1H, m), 2.09-2.21 (1H, m), 2.36-2.53 (9H, m), 2.55-2.66 (1H, m), 2.70-2.80 (2H, m), 3.19-3.36 (2H, m), 3.66 (1H, ddd, J = 13.0, 4.1, 3.5 Hz), 3.76 (1H, ddd, J = 13.0, 4.1, 3.5 Hz), 4.11-4.26 (1H, m), 4.52 (1H, d, J = 7.3 Hz), 6.68 (1H, d, J = 8.3 Hz), 6.81 (1H, dd, J = 6.7, 5.5 Hz), 7.49-7.54 (1H, m), 8.10 (1H, dd, J = 5.5, 1.7 Hz). | 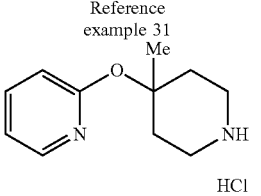 Reference example 31 |

-continued

| Example | Structure | Material A / Spectral data | Material B |
|---|---|---|---|
| 43 | [Structure: cyclopropyl-1,2,4-thiadiazole-Me-piperidine-carboxamide-NH-difluorocyclohexyl-piperazine-N-CH(Me)₂, (Abs)] | Reference example 15 [Structure with 3HCl] <br> ¹H-NMR (CDCl₃) δ: 1.00 (3H, d, J = 6.1 Hz), 1.01 (3H, d, J = 6.1 Hz), 1.11-1.18 (2H, m), 1.22-1.35 (4H, m), 1.30 (3H, s), 1.35-1.47 (1H, m), 1.62-1.75 (2H, m), 1.75-1.85 (1H, m), 1.88-1.97 (1H, m), 2.10-2.22 (1H, m), 2.31-2.62 (11H, m), 2.67-2.78 (2H, m), 3.01 (1H, ddd, J = 13.8, 10.7, 3.1 Hz), 3.10 (1H, ddd, J = 13.8, 10.7, 3.1 Hz), 3.65 (1H, ddd, J = 14.0, 4.3, 4.3 Hz), 3.79 (1H, ddd, J = 14.0, 4.3, 4.3 Hz), 4.08-4.22 (1H, m), 4.53 (1H, d, J = 7.3 Hz). | Reference example 28 [Structure] |
| 44 | [Structure: cyclopropyl-1,3,4-thiadiazole-Me-piperidine-carboxamide analog, (Abs)] | Reference example 15 [Structure with 3HCl] <br> ¹H-NMR (CDCl₃) δ: 1.01-1.23 (10H, m), 1.23-1.46 (4H, m), 1.43 (3H, s), 1.60-1.74 (1H, m), 1.74-1.87 (3H, m), 1.92-2.03 (1H, m), 2.11-2.29 (3H, m), 2.31-2.40 (1H, m), 2.40-3.14 (8H, m), 3.26-3.38 (2H, m), 3.58-3.71 (2H, m), 4.08-4.23 (1H, m), 4.52 (1H, d, J = 7.9 Hz). | Reference example 24 [Structure] |
| 45 | [Structure: MeO-thiadiazole-Me-piperidine-carboxamide analog] | Reference example 14 [Structure with 3HCl] <br> ¹H-NMR (CDCl₃) δ: 1.04-1.19 (6H, m), 1.21-1.47 (3H, m), 1.31 (3H, s), 1.53-1.87 (3H, m), 1.89-2.01 (1H, m), 2.10-2.23 (1H, m), 2.28-2.40 (2H, m), 2.40-2.74 (7H, m), 2.74-3.03 (3H, m), 3.05-3.22 (2H, m), 3.58-3.77 (2H, m), 4.05-4.22 (1H, m), 4.14 (3H, s), 4.53 (1H, s). | Reference example 29 [Structure] |

| Example | Structure | Material A | Material B |
|---|---|---|---|
| | | Spectral data | |
| 46 | 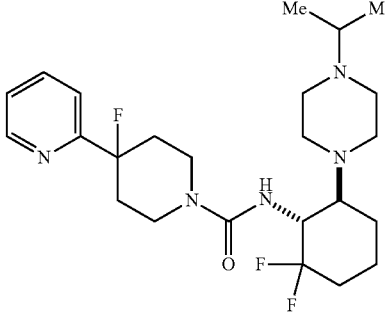 | 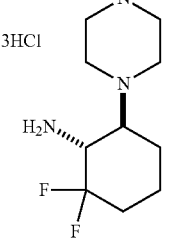 Reference example 14<br>3HCl | 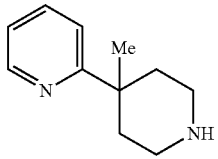 [SMILES: CC1(c2ccccn2)CCNCC1] Commercial product |
| | | ¹H-NMR (CDCl₃) δ: 1.02 (6H, d, J = 6.4 Hz), 1.22-1.49 (2H, m), 1.62-1.88 (2H, m), 1.88-2.01 (3H, m), 2.10-2.23 (1H, m), 2.23-2.66 (10H, m), 2.70-2.83 (2H, m), 3.20-3.43 (2H, m), 3.89-4.01 (1H, m), 4.06-4.27 (2H, m), 4.62 (1H, d, J = 8.0 Hz), 7.20 (1H, ddd, J = 8.0, 4.8, 1.2 Hz), 7.55 (1H, dd, J = 8.0, 1.2 Hz), 7.72 (1H, ddd, J = 8.0, 8.0, 1.2 Hz), 8.51 (1H, d, J = 4.8 Hz). | |
| 47 | 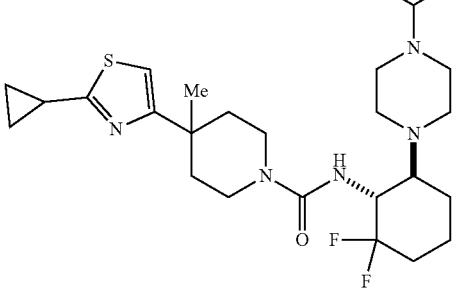 | 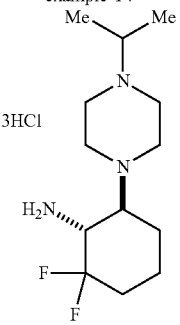 Reference example 14<br>3HCl | 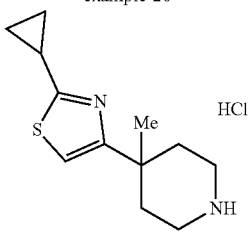 Reference example 26<br>HCl |
| | | ¹H-NMR (CDCl₃) δ: 0.96-1.02 (2H, m), 0.99 (6H, d, J = 6.0 Hz), 1.05-1.16 (2H, m), 1.18-1.48 (3H, m), 1.28 (3H, s), 1.62-1.76 (3H, m), 1.89-1.99 (1H, m), 2.08-2.23 (3H, m), 2.24-2.32 (1H, m), 2.32-2.63 (8H, m), 2.68-2.80 (2H, m), 3.24 (1H, ddd, J = 13.1, 9.2, 3.7 Hz), 3.34 (1H, ddd, J = 13.1, 9.2, 3.7 Hz), 3.43-3.52 (1H, m), 3.57-3.67 (1H, m), 4.07-4.22 (1H, m), 4.54 (1H, d, J = 7.3 Hz), 6.63 (1H, s). | |

-continued

| Example | Structure | Material A / Spectral data | Material B |
|---|---|---|---|
| 48 | [Structure: 5-cyclopropylthiazole-piperidine(Me)-C(O)NH-cyclohexane(F,F)-piperazine-N-CH(Me)₂] | Reference example 14 [Structure: piperazine(CHMe₂)-cyclohexane(NH₂,F,F)] · 3HCl<br><br>¹H-NMR (CDCl₃) δ: 0.68-0.78 (2H, m), 0.95-1.16 (8H, m), 1.22-1.50 (3H, m), 1.35 (3H, s), 1.62-1.86 (3H, m), 1.88-1.97 (1H, m), 1.97-2.08 (1H, m), 2.10-2.30 (3H, m), 2.32-2.66 (8H, m), 2.68-2.86 (2H, m), 3.23 (1H, ddd, J = 13.6, 9.6, 3.2 Hz), 3.32 (1H, ddd, J = 13.6, 9.6, 3.2 Hz), 3.55-3.66 (1H, m), 3.66-3.76 (1H, m), 4.08-4.23 (1H, m), 4.54 (1H, d, J = 7.3 Hz), 7.32 (1H, s). | Reference example 25 [Structure: 5-cyclopropylthiazol-2-yl-4-methylpiperidine] · HCl |
| 49 | [Structure: 4-methylphenyl-piperidine(Me)(Abs)-C(O)NH-cyclohexane(F,F)-piperazine-N-CH(Me)₂] | Reference example 15 [Structure: piperazine(CHMe₂)-cyclohexane(NH₂,F,F)] · 3HCl<br><br>¹H-NMR (CDCl₃) δ: 0.95 (6H, d, J = 6.4 Hz), 1.19-1.47 (3H, m), 1.25 (3H, s), 1.61-1.85 (3H, m), 1.88-1.97 (1H, m), 2.06-2.22 (3H, m), 2.28-2.53 (8H, m), 2.32 (3H, s), 2.67-2.76 (2H, m), 3.32 (1H, ddd, J = 11.6, 8.0, 3.6 Hz), 3.40-3.49 (2H, m), 3.56 (1H, ddd, J = 11.6, 8.0, 3.6 Hz), 4.09-4.22 (1H, m), 4.53 (1H, d, J = 7.8 Hz), 7.14 (2H, d, J = 8.2 Hz), 7.22 (2H, d, J = 8.2 Hz). | Commercial product [Structure: 4-(4-methylphenyl)-4-methylpiperidine] · HCl |
| 50 | [Structure: 5-methylpyridin-2-yl-piperidine-C(O)NH-cyclohexane(F,F)-piperazine-N-CH(Me)₂] | Reference example 14 [Structure: piperazine(CHMe₂)-cyclohexane(NH₂,F,F)] · 3HCl<br><br>¹H-NMR (CDCl₃) δ: 0.99 (6H, d, J = 6.0 Hz), 1.21-1.49 (2H, m), 1.62-1.89 (4H, m), 1.89-2.06 (3H, m), 2.09-2.23 (1H, m), 2.30 (3H, s), 2.34-2.63 (8H, m), 2.67-2.80 (2H, m), 2.80-3.06 (3H, m), 4.03-4.29 (3H, m), 4.59 (1H, d, J = 8.0 Hz), 7.04 (1H, d, J = 8.0 Hz), 7.42 (1H, dd, J = 8.0, 2.4 Hz), 8.34 (1H, d, J = 2.4 Hz). | Commercial product [Structure: 2-(piperidin-4-yl)-5-methylpyridine] |

| Example | Structure | Material A / Spectral data | Material B |
|---|---|---|---|
| 51 | (structure) | Reference example 14 (structure) 3HCl  <br>¹H-NMR (CDCl₃) δ: 1.01 (6H, d, J = 6.8 Hz), 1.21-1.48 (2H, m), 1.61-1.88 (4H, m), 1.88-2.04 (3H, m), 2.09-2.24 (1H, m), 2.31 (3H, s), 2.35-2.66 (8H, m), 2.69-2.81 (2H, m), 2.85-3.09 (2H, m), 3.10-3.23 (1H, m), 4.00-4.10 (1H, m), 4.10-4.33 (2H, m), 4.58 (1H, d, J = 8.0 Hz), 7.14 (1H, d, J = 11.2 Hz), 8.14 (1H, s). | Reference example 41 (structure) |
| 52 | (structure) | Reference example 14 (structure) 3HCl  <br>¹H-NMR (CDCl₃) δ: 1.00 (6H, d, J = 6.4 Hz), 1.22-1.50 (2H, m), 1.62-1.87 (4H, m), 1.90-2.06 (3H, m), 2.10-2.23 (1H, m), 2.33-2.65 (8H, m), 2.69-2.81 (2H, m), 2.85-3.06 (3H, m), 4.04-4.30 (3H, m), 4.59 (1H, d, J = 8.0 Hz), 7.15 (1H, dd, J = 8.4, 4.4 Hz), 7.33 (1H, ddd, J = 8.4, 8.4, 2.8 Hz), 8.38 (1H, d, J = 2.8 Hz). | Commercial product (structure) |
| 53 | (structure) | Reference example 14 (structure) 3HCl  <br>¹H-NMR (CDCl₃) δ: 1.00 (6H, d, J = 6.4 Hz), 1.21-1.49 (2H, m), 1.63-1.87 (4H, m), 1.88-2.03 (3H, m), 2.09-2.23 (1H, m), 2.34-2.64 (8H, m), 2.68-2.80 (2H, m), 2.80-3.06 (3H, m), 3.84 (3H, s), 4.03-4.29 (3H, m), 4.59 (1H, d, J = 8.0 Hz), 7.07 (1H, d, J = 8.4 Hz), 7.14 (1H, dd, J = 8.4, 2.8 Hz), 8.22 (1H, d, J = 2.8 Hz). | Commercial product (structure) |

| Example | Structure | Material A / Spectral data | Material B |
|---|---|---|---|
| 54 | 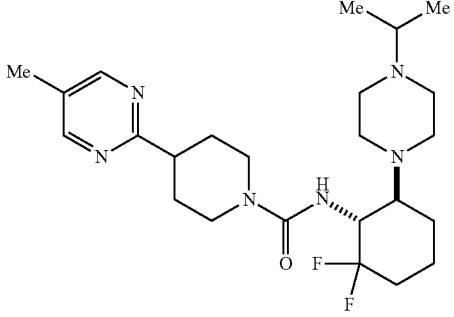 [SMILES: Cc1cnc(C2CCN(C(=O)N[C@@H]3[C@@H](N4CCN(C(C)C)CC4)CCCC3(F)F)CC2)nc1] | Reference example 14<br>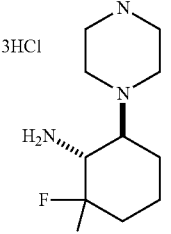<br>3HCl<br><br>¹H-NMR (CDCl₃) δ: 0.99 (6H, d, J = 6.4 Hz), 1.21-1.49 (2H, m), 1.60-1.99 (5H, m), 1.99-2.10 (2H, m), 2.10-2.22 (1H, m), 2.27 (3H, s), 2.30-2.63 (8H, m), 2.67-2.81 (2H, m), 2.85-3.11 (2H, m), 3.95-4.08 (1H, m), 4.09-4.26 (3H, m), 4.58 (1H, d, J = 8.0 Hz), 8.48 (2H, s). | Commercial product<br>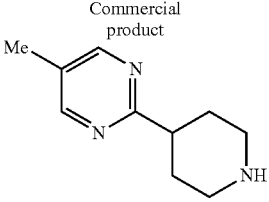 |
| 55 | 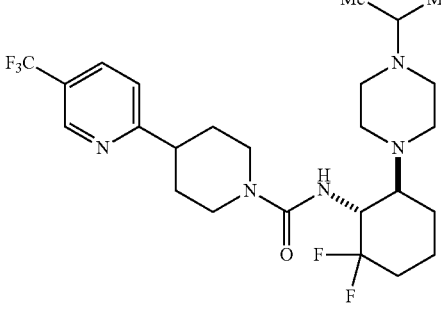 | Reference example 14<br>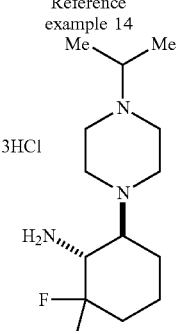<br>3HCl<br><br>¹H-NMR (CDCl₃) δ: 1.00 (6H, d, J = 6.4 Hz), 1.22-1.50 (2H, m), 1.63-1.90 (4H, m), 1.90-2.06 (3H, m), 2.10-2.25 (1H, m), 2.31-2.65 (8H, m), 2.69-2.81 (2H, m), 2.89-3.08 (3H, m), 4.06-4.32 (3H, m), 4.60 (1H, d, J = 8.0 Hz), 7.29 (1H, d, J = 8.4 Hz), 7.86 (1H, d, J = 8.4, 2.4 Hz), 8.79 (1H, s). | Commercial product<br>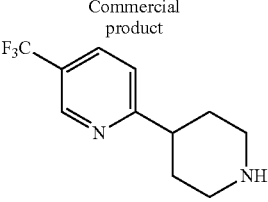 |
| 56 | 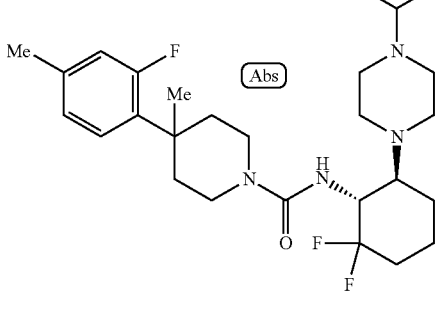 | Reference example 15<br>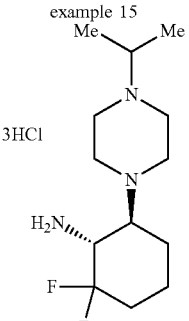<br>3HCl<br><br>¹H-NMR (CDCl₃) δ: 0.94 (6H, d, J = 6.1 Hz), 1.23-1.47 (3H, m), 1.34 (3H, s), 1.67-1.86 (3H, m), 1.88-1.97 (1H, m), 2.10-2.23 (3H, m), 2.31 (3H, s), 2.31-2.52 (8H, m), 2.67-2.76 (2H, m), 3.36 (1H, ddd, J = 11.6, 8.0, 3.6 Hz), 3.40-3.52 (2H, m), 3.53-3.59 (1H, m), 4.07-4.23 (1H, m), 4.54 (1H, d, J = 7.9 Hz), 6.81-6.91 (2H, m), 7.11 (1H, dd, J = 7.6, 7.6 Hz). | Reference example 32<br>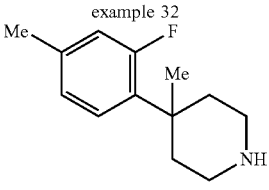 |

| Example | Structure | Material A | Material B |
|---|---|---|---|
| | | Spectral data | |
| 57 | 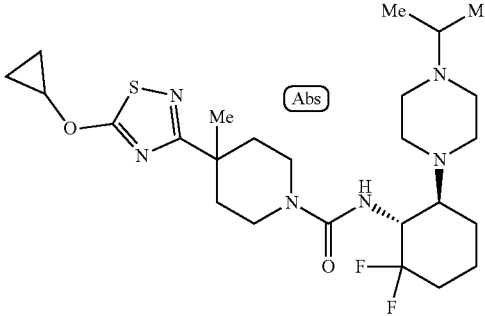 | Reference example 15<br>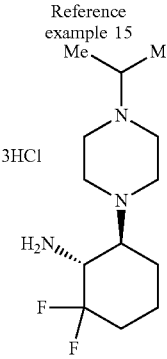<br>3HCl | Reference example 30<br>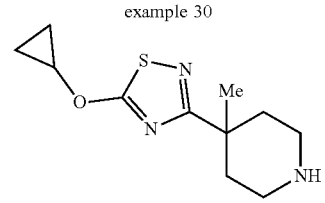 |
| | ¹H-NMR (CDCl₃) δ: 0.86-0.93 (2H, m), 0.94-1.07 (2H, m), 1.00 (3H, d, J = 6.4 Hz), 1.01 (3H, d, J = 6.4 Hz), 1.20-1.48 (3H, m), 1.30 (3H, s), 1.54-1.85 (3H, m), 1.89-1.97 (1H, m), 2.09-2.22 (1H, m), 2.31-2.54 (9H, m), 2.54-2.64 (1H, m), 2.68-2.79 (2H, m), 3.06 (1H, ddd, J = 13.8, 10.7, 3.1 Hz), 3.16 (1H, ddd, J = 13.8, 10.7, 3.1 Hz), 3.58-3.68 (1H, m), 3.74-3.84 (1H, m), 4.09-4.23 (2H, m), 4.53 (1H, d, J = 7.9 Hz). | | |
| 58 | 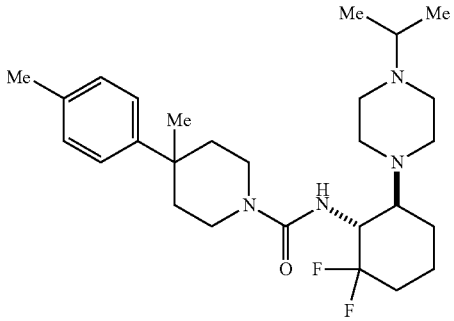 [SMILES: Cc1ccc(C2(C)CCN(C(=O)N[C@@H]3[C@@H](N4CCN(C(C)C)CC4)CCCC3(F)F)CC2)cc1] | Reference example 14<br>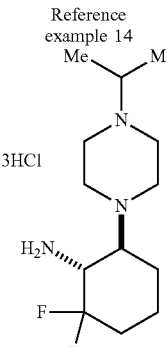<br>3HCl | Commercial product<br>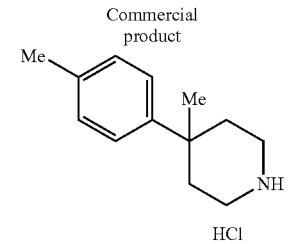<br>HCl |
| | ¹H-NMR (CDCl₃) δ: 0.95 (6H, d, J = 6.4 Hz), 1.19-1.47 (3H, m), 1.25 (3H, s), 1.61-1.85 (3H, m), 1.88-1.97 (1H, m), 2.06-2.22 (3H, m), 2.28-2.53 (8H, m), 2.32 (3H, s), 2.67-2.76 (2H, m), 3.32 (1H, ddd, J = 11.6, 8.0, 3.6 Hz), 3.40-3.49 (2H, m), 3.56 (1H, ddd, J = 11.6, 8.0, 3.6 Hz), 4.09-4.22 (1H, m), 4.53 (1H, d, J = 7.8 Hz), 7.14 (2H, d, J = 8.2 Hz), 7.22 (2H, d, J = 8.2 Hz). | | |

| Example | Structure | Material A Spectral data | Material B |
|---|---|---|---|
| 59 | (structure) | Reference example 14<br>(structure, 3HCl)<br><br>¹H-NMR (CDCl₃) δ: 0.92 (3H, d, J = 6.7 Hz), 0.93 (3H, d, J = 6.7 Hz), 1.22-1.46 (3H, m), 1.29 (3H, s), 1.64-1.85 (3H, m), 1.88-1.96 (1H, m), 2.06-2.22 (3H, m), 2.25-2.54 (8H, m), 2.66-2.76 (2H, m), 3.36 (1H, ddd, J = 11.2, 7.6, 3.6 Hz), 3.41-3.59 (3H, m), 4.08-4.22 (1H, m), 4.54 (1H, d, J = 7.9 Hz), 6.63 (1H, t, J = 56.5 Hz), 7.42 (2H, d, J = 8.5 Hz), 7.48 (2H, d, J = 7.9 Hz). | Reference example 33<br>(structure, HCl) |
| 60 | (structure, Abs) | Reference example 15<br>(structure, 3HCl)<br><br>¹H-NMR (CDCl₃) δ: 0.95 (6H, d, J = 6.7 Hz), 1.23-1.48 (2H, m), 1.52 (3H, s), 1.59-1.74 (1H, m), 1.74-1.84 (1H, m), 1.89-1.98 (1H, m), 2.00-2.10 (2H, m), 2.10-2.20 (1H, m), 2.21-2.32 (2H, m), 2.32-2.58 (8H, m), 2.35 (3H, s), 2.69-2.80 (2H, m), 3.43 (1H, ddd, J = 13.1, 9.2, 3.7 Hz), 3.48-3.61 (3H, m), 4.09-4.23 (1H, m), 4.52 (1H, d, J = 7.3 Hz), 7.29-7.36 (2H, m), 7.51 (1H, s). | Reference example 34<br>(structure) |

-continued

| Example | Structure | Material A<br>Spectral data | Material B |
|---|---|---|---|
| 61 | 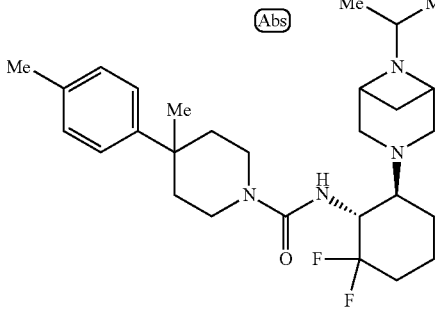 | Reference example 16<br>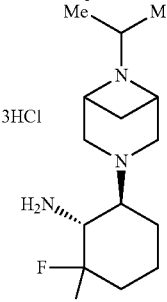<br><sup>1</sup>H-NMR (CDCl$_3$) δ: 0.95-1.14 (6H, m), 1.17-1.31 (2H, m), 1.24 (3H, s), 1.33-1.80 (5H, m), 1.80-1.88 (1H, m), 2.05-2.25 (3H, m), 2.32 (3H, s), 2.53-2.63 (1H, m), 2.63-2.73 (1H, m), 2.78-2.88 (1H, m), 2.89-3.14 (2H, m), 3.20-3.34 (3H, m), 3.34-3.54 (3H, m), 3.84-3.98 (2H, m), 4.22-4.37 (1H, m), 4.61 (1H, d, J = 8.5 Hz), 7.15 (2H, d, J = 8.5 Hz), 7.20 (2H, d, J = 8.5 Hz). | Commercial product<br>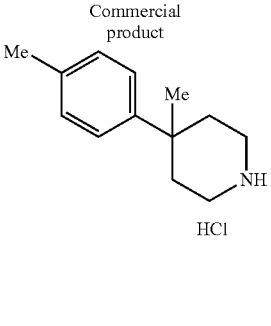 |
| 62 | 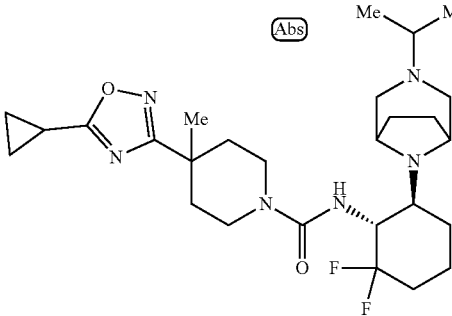 | Reference example 17<br>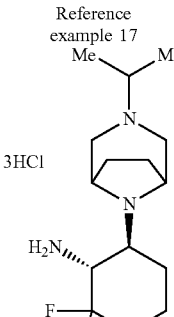<br><sup>1</sup>H-NMR (CDCl$_3$) δ: 0.89 (3H, d, J = 6.0 Hz), 0.90 (3H, d, J = 6.0 Hz), 1.15-1.22 (4H, m), 1.22-1.35 (1H, m), 1.29 (3H, s), 1.35-1.44 (1H, m), 1.44-1.53 (1H, m), 1.61-1.70 (3H, m), 1.70-1.85 (5H, m), 2.04-2.19 (3H, m), 2.20-2.29 (3H, m), 2.41-2.57 (4H, m), 3.03-3.19 (3H, m), 3.19-3.24 (1H, m), 3.68-3.83 (2H, m), 3.94-4.07 (1H, m), 4.72 (1H, d, J = 7.3 Hz). | Reference example 8<br>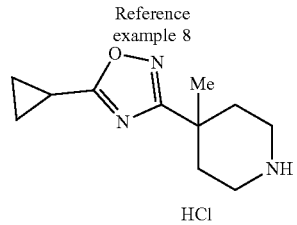 |
| 63 | 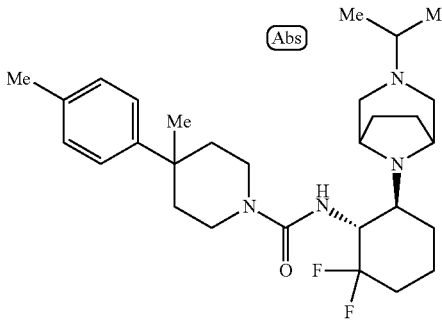 | Reference example 17<br>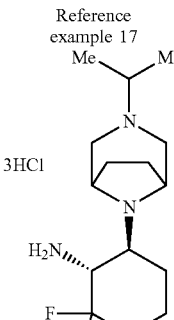<br><sup>1</sup>H-NMR (CDCl$_3$) δ: 0.84 (3H, d, J = 6.8 Hz), 0.85 (3H, d, J = 6.8 Hz), 1.19-1.35 (1H, m), 1.24 (3H, s), 1.35-1.43 (1H, m), 1.43-1.53 (1H, m), 1.59-1.85 (7H, m), 2.02-2.18 (4H, m), 2.21-2.27 (1H, m), 2.32 (3H, s), 2.34-2.59 (5H, m), 3.03-3.09 (1H, m), 3.18-3.25 (1H, m), 3.34-3.45 (2H, m), 3.46-3.59 (2H, m), 3.94-4.08 (1H, m), 4.73 (1H, d, J = 7.3 Hz), 7.13 (2H, d, J = 7.9 Hz), 7.21 (2H, d, J = 7.9 Hz). | Commercial product<br>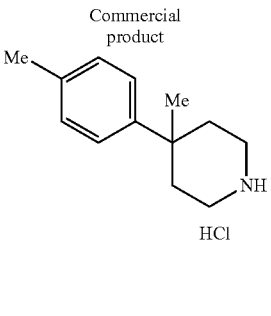 |

| Example | Structure | Material A Spectral data | Material B |
|---|---|---|---|
| 64 | 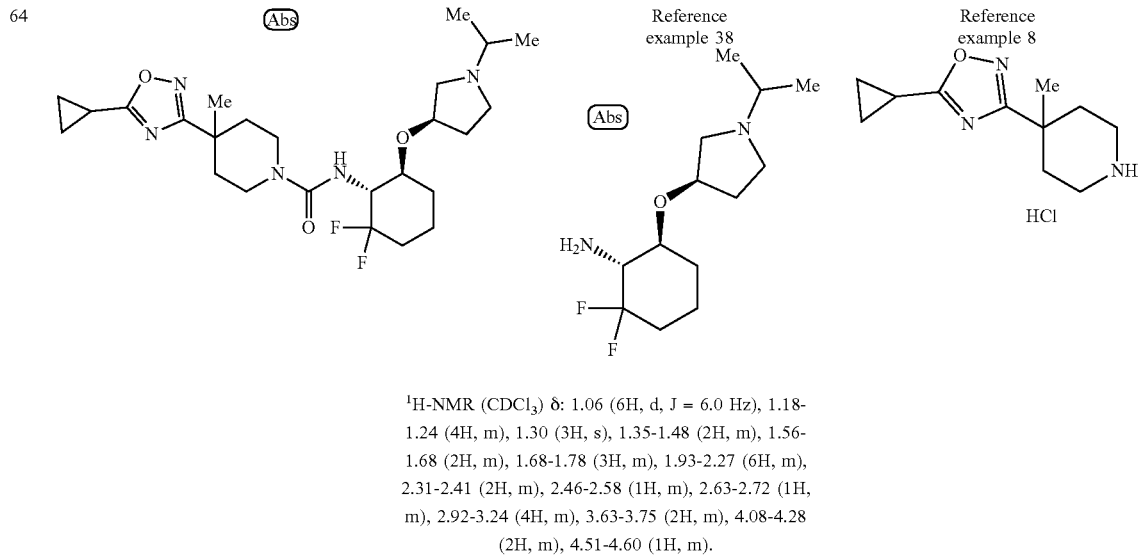 | Reference example 38 | Reference example 8 |
| | | $^1$H-NMR (CDCl$_3$) δ: 1.06 (6H, d, J = 6.0 Hz), 1.18-1.24 (4H, m), 1.30 (3H, s), 1.35-1.48 (2H, m), 1.56-1.68 (2H, m), 1.68-1.78 (3H, m), 1.93-2.27 (6H, m), 2.31-2.41 (2H, m), 2.46-2.58 (1H, m), 2.63-2.72 (1H, m), 2.92-3.24 (4H, m), 3.63-3.75 (2H, m), 4.08-4.28 (2H, m), 4.51-4.60 (1H, m). | |
| 65 | 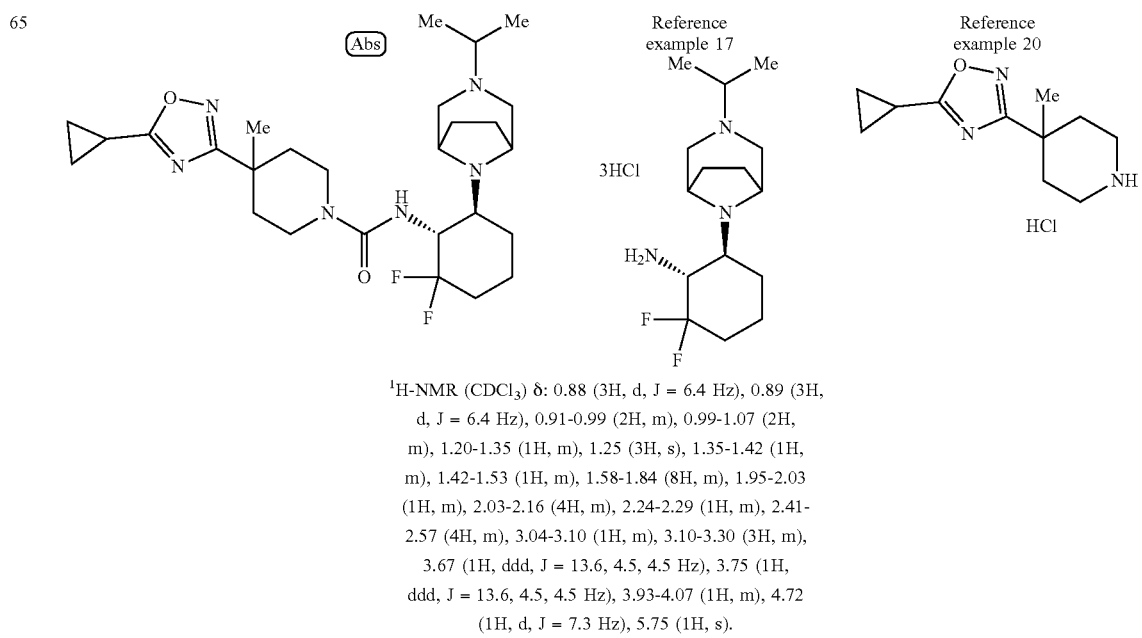 | Reference example 17 | Reference example 20 |
| | | $^1$H-NMR (CDCl$_3$) δ: 0.88 (3H, d, J = 6.4 Hz), 0.89 (3H, d, J = 6.4 Hz), 0.91-0.99 (2H, m), 0.99-1.07 (2H, m), 1.20-1.35 (1H, m), 1.25 (3H, s), 1.35-1.42 (1H, m), 1.42-1.53 (1H, m), 1.58-1.84 (8H, m), 1.95-2.03 (1H, m), 2.03-2.16 (4H, m), 2.24-2.29 (1H, m), 2.41-2.57 (4H, m), 3.04-3.10 (1H, m), 3.10-3.30 (3H, m), 3.67 (1H, ddd, J = 13.6, 4.5, 4.5 Hz), 3.75 (1H, ddd, J = 13.6, 4.5, 4.5 Hz), 3.93-4.07 (1H, m), 4.72 (1H, d, J = 7.3 Hz), 5.75 (1H, s). | |

| Example | Structure | Material A / Spectral data | Material B |
|---|---|---|---|
| 66 | (structure) | Reference example 15 / ¹H-NMR (DMSO-d6) δ: 0.87 (6H, d, J = 6.4 Hz), 1.18-1.36 (2H, m), 1.26 (3H, s), 1.47-1.66 (3H, m), 1.66-1.88 (4H, m), 1.95-2.11 (3H, m), 2.17-2.40 (6H, m), 2.43-2.63 (5H, m), 2.95-3.19 (2H, m), 3.55-3.77 (2H, m), 3.98-4.18 (1H, m), 5.16 (1H, dddd, J = 65.0, 6.0, 6.0, 3.2 Hz), 5.88 (1H, d, J = 8.0 Hz). | Reference example 11 |
| 67 | (structure) | Reference example 38 / ¹H-NMR (CDCl₃) δ: 1.02 (6H, d, J = 7.3 Hz), 1.21-1.30 (1H, m), 1.25 (3H, s), 1.35-1.48 (2H, m), 1.65-1.84 (3H, m), 1.98-2.19 (6H, m), 2.25-2.36 (2H, m), 2.32 (3H, s), 2.48 (1H, dd, J = 16.4, 8.0 Hz), 2.59-2.69 (1H, m), 2.94 (1H, dd, J = 10.1, 6.4 Hz), 3.14-3.23 (1H, m), 3.27-3.42 (2H, m), 3.42-3.56 (2H, m), 4.07-4.28 (2H, m), 4.56 (1H, d, J = 9.2 Hz), 7.14 (2H, d, J = 8.2 Hz), 7.21 (2H, d, J = 8.2 Hz). | Commercial product |
| 68 | (structure) | Reference example 15 / ¹H-NMR (CDCl₃) δ: 0.95-1.06 (8H, m), 1.13 (3H, d, J = 6.0 Hz), 1.21-1.57 (7H, m), 1.58-1.73 (2H, m), 1.73-1.87 (1H, m), 1.87-1.98 (1H, m), 2.08-2.30 (4H, m), 2.31-2.66 (8H, m), 2.66-2.83 (2H, m), 3.01-3.19 (2H, m), 3.61-3.72 (1H, m), 3.74-3.85 (1H, m), 4.03-4.24 (1H, m), 4.53 (1H, d, J = 8.0 Hz). | Reference example 12' |

| Example | Structure | Material A Spectral data | Material B |
|---|---|---|---|
| 69 | (structure) | Reference example 15 (structure, 3HCl)  ¹H-NMR (CDCl₃) δ: 0.97-1.06 (8H, m), 1.13 (3H, d, J = 6.4 Hz), 1.22-1.58 (7H, m), 1.58-1.73 (2H, m), 1.73-1.87 (1H, m), 1.89-1.99 (1H, m), 2.08-2.30 (4H, m), 2.31-2.66 (8H, m), 2.66-2.84 (2H, m), 3.00-3.22 (2H, m), 3.61-3.72 (1H, m), 3.74-3.85 (1H, m), 4.03-4.23 (1H, m), 4.53 (1H, d, J = 8.0 Hz). | Reference example 12 (structure, HCl) |
| 70 | (structure) | Reference example 15 (structure, 3HCl)  ¹H-NMR (CDCl₃) δ: 0.97-1.04 (6H, m), 1.20-1.48 (7H, m), 1.62-1.87 (3H, m), 1.89-1.98 (1H, m), 2.10-2.21 (1H, m), 2.21-2.31 (2H, m) 2.31-2.54 (6H, m) 2.58 (1H, sept, J = 6.4 Hz), 2.68-2.80 (2H, m), 3.10 (1H, ddd, J = 12.8, 10.0, 2.4 Hz), 3.17 (1H, ddd, J = 13.2, 10.4, 2.8 Hz), 3.63-3.73 (1H, m) 3.73-3.83 (3H, m), 4.08-4.23 (1H, m), 4.54 (1H, d, J = 8.0 Hz). | Commercial product (structure) |
| 71 | (structure) | Reference example 37 (structure)  ¹H-NMR (CDCl₃) δ: 1.05 (3H, d, J = 6.4 Hz), 1.06 (3H, d, J = 6.4 Hz), 1.17-1.23 (4H, m), 1.30 (3H, s), 1.36-1.47 (2H, m), 1.56-1.81 (5H, m), 1.98 (1H, ddd, J = 16.0, 13.6, 8.0 Hz), 2.03-2.26 (5H, m), 2.31-2.42 (2H, m), 2.51 (1H, dd, J = 16.0, 8.0 Hz), 2.60-2.67 (1H, m), 2.97 (1H, dd, J = 10.1, 6.4 Hz), 3.04-3.23 (3H, m), 3.63-3.75 (2H, m), 4.07-4.27 (2H, m), 4.55 (1H, d, J = 9.2 Hz). | Reference example 8 (structure, HCl) |

-continued
| Example | Structure | Material A Spectral data | Material B |
|---|---|---|---|
| 72 | 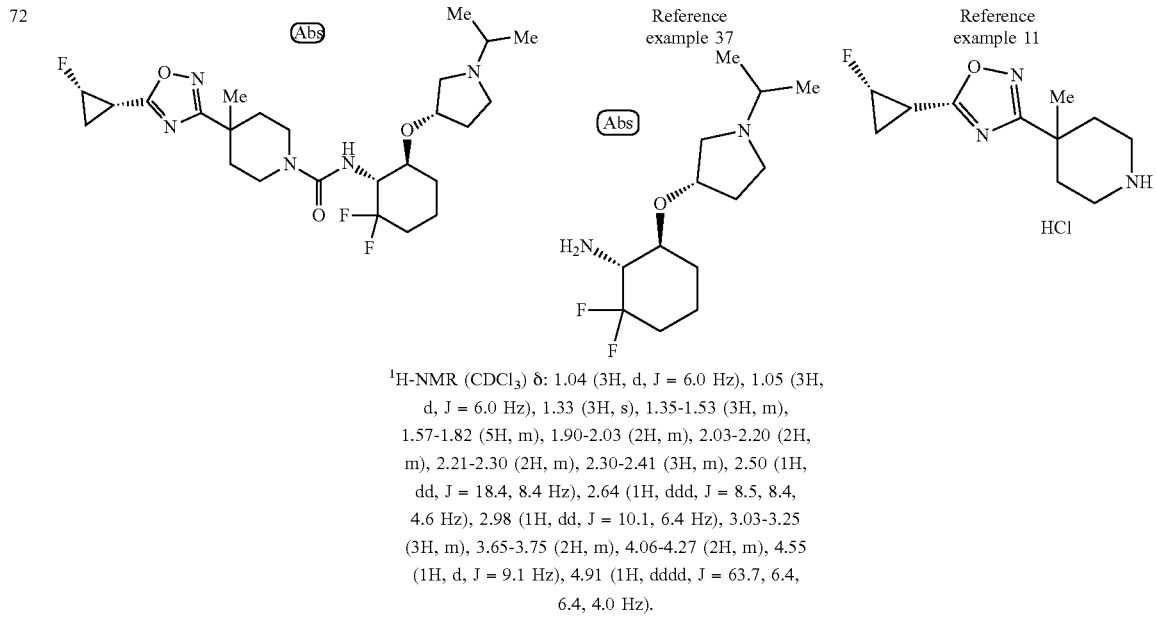 | Reference example 37 <br><br> ¹H-NMR (CDCl₃) δ: 1.04 (3H, d, J = 6.0 Hz), 1.05 (3H, d, J = 6.0 Hz), 1.33 (3H, s), 1.35-1.53 (3H, m), 1.57-1.82 (5H, m), 1.90-2.03 (2H, m), 2.03-2.20 (2H, m), 2.21-2.30 (2H, m), 2.30-2.41 (3H, m), 2.50 (1H, dd, J = 18.4, 8.4 Hz), 2.64 (1H, ddd, J = 8.5, 8.4, 4.6 Hz), 2.98 (1H, dd, J = 10.1, 6.4 Hz), 3.03-3.25 (3H, m), 3.65-3.75 (2H, m), 4.06-4.27 (2H, m), 4.55 (1H, d, J = 9.1 Hz), 4.91 (1H, dddd, J = 63.7, 6.4, 6.4, 4.0 Hz). | Reference example 11 |
| 73 | 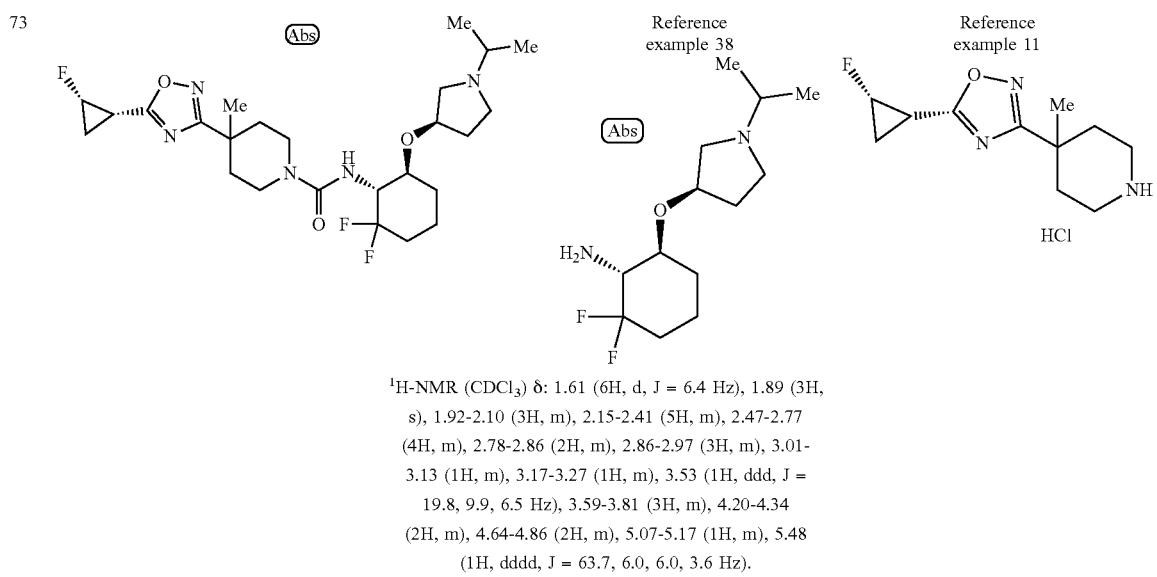 | Reference example 38 <br><br> ¹H-NMR (CDCl₃) δ: 1.61 (6H, d, J = 6.4 Hz), 1.89 (3H, s), 1.92-2.10 (3H, m), 2.15-2.41 (5H, m), 2.47-2.77 (4H, m), 2.78-2.86 (2H, m), 2.86-2.97 (3H, m), 3.01-3.13 (1H, m), 3.17-3.27 (1H, m), 3.53 (1H, ddd, J = 19.8, 9.9, 6.5 Hz), 3.59-3.81 (3H, m), 4.20-4.34 (2H, m), 4.64-4.86 (2H, m), 5.07-5.17 (1H, m), 5.48 (1H, dddd, J = 63.7, 6.0, 6.0, 3.6 Hz). | Reference example 11 |

-continued

| Example | Structure | Material A<br>Spectral data | Material B |
|---|---|---|---|
| 74 | 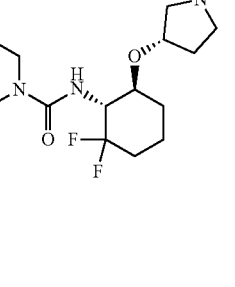 <br> ¹H-NMR (CDCl₃) δ: 1.06-1.12 (1H, m), 1.13 (3H, d, J = 6.1 Hz), 1.24-1.38 (11H, m), 1.39-1.55 (3H, m), 1.56-1.66 (2H, m), 1.67-1.79 (1H, m), 1.93-2.02 (1H, m), 2.04-2.19 (3H, m), 2.19-2.28 (3H, m), 2.78-2.84 (1H, m), 2.88 (1H, ddd, J = 10.4, 10.4, 6.8 Hz), 3.02-3.19 (3H, m), 3.20-3.36 (2H, m), 3.56-3.73 (3H, m), 4.12-4.28 (2H, m), 4.74 (1H, d, J = 9.2 Hz). | Reference example 37 <br> 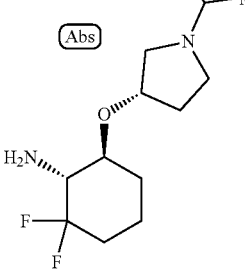 | Reference example 12 <br> 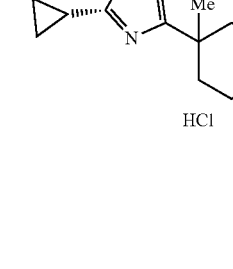 <br> HCl |
| 75 | 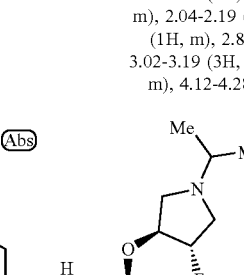 <br> ¹H-NMR (CDCl₃) δ: 1.01-1.09 (6H, m), 1.17-1.23 (4H, m), 1.30 (3H, s), 1.37-1.50 (2H, m), 1.55-1.67 (2H, m), 1.67-1.81 (2H, m), 2.05-2.27 (6H, m), 2.32-2.42 (1H, m), 2.54-2.69 (1H, m), 2.93-3.36 (5H, m), 3.63-3.76 (2H, m), 4.06-4.31 (2H, m), 4.59-4.68 (1H, m), 4.76-4.96 (1H, m). | Reference example 39 <br> 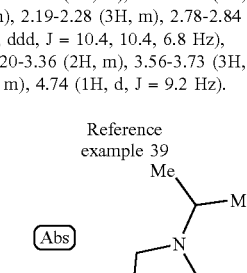 | Reference example 8 <br> 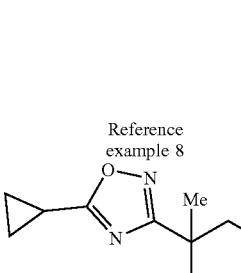 <br> HCl |
| 76 | 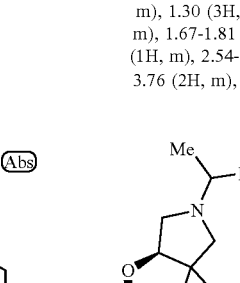 <br> ¹H-NMR (CDCl₃) δ: 1.02 (3H, d, J = 6.1 Hz), 1.04 (3H, d, J = 6.7 Hz), 1.17-1.23 (4H, m), 1.30 (3H, s), 1.32-1.51 (2H, m), 1.58-1.70 (2H, m), 1.71-1.87 (2H, m), 2.11-2.26 (5H, m), 2.35-2.50 (2H, m), 2.61-2.74 (1H, m), 3.04-3.27 (4H, m), 3.41-3.50 (1H, m), 3.62-3.75 (2H, m), 4.00-4.10 (1H, m), 4.19-4.32 (1H, m), 4.64 (1H, d, J = 8.5 Hz). | Reference example 40 <br> 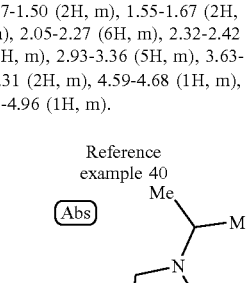 | Reference example 8 <br> 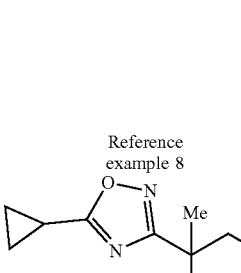 <br> HCl |

The chemical names of Example 20 to Example 76 are listed below.

Example 20: rac-4-(5-cyclopropyl-1,2-oxazol-3-yl)-N-{(1R,6S)-2,2-difluoro-6-[4-(propan-2-yl)piperazin-1-yl]cyclohexyl}-4-methylpiperidine-1-carboxamide Example 21: rac-4-(1,3-benzoxazol-2-yl)-N-{(1R,6S)-2,2-difluoro-6-[4-(propan-2-yl)piperazin-1-yl]cyclohexyl}-4-methylpiperidine-1-carboxamide Example 22: 4-(5-cyclopropyl-1,2-oxazol-3-yl)-N-{(1S,6R)-2,2-difluoro-6-[4-(propan-2-yl)piperazin-1-yl]cyclohexyl}-4-methylpiperidine-1-carboxamide Example 23: 4-(5-cyclopropyl-1,2,4-oxadiazol-3-yl)-N-{(1S,6R)-2,2-difluoro-6-[4-(propan-2-yl)piperazin-1-yl]cyclohexyl}-4-methylpiperidine-1-carboxamide Example 24: 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide Example 25: 4-(5-cyclopropyl-1,2-oxazol-3-yl)-N-{(1R,6S)-2,2-difluoro-6-[4-(propan-2-yl)piperazin-1-yl]cyclohexyl}-4-methylpiperidine-1-carboxamide Example 26: rac-4-cyclopentyl-N-{(1R,6S)-2,2-difluoro-6-[4-(propan-2-yl)piperazin-1-yl]cyclohexyl}-4-methylpiperidine-1-carboxamide Example 27: rac-N-{(1R,6S)-2,2-difluoro-6-[4-(propan-2-yl)piperazin-1-yl]cyclohexyl}-4-methyl-4-(4,5,6,7-tetrahydro-1,3-benzoxazol-2-yl)piperidine-1-carboxamide Example 28: rac-N-{(1R,6S)-2,2-difluoro-6-[4-(propan-2-yl)piperazin-1-yl]cyclohexyl}-4-(5-ethyl-1,2,4-oxadiazol-3-yl)-4-methylpiperidine-1-carboxamide Example 29: rac-4-(1-cyclopropyl-1H-1,2,4-triazol-3-yl)-N-{(1R,6S)-2,2-difluoro-6-[4-(propan-2-yl)piperazin-1-yl]cyclohexyl}-4-methylpiperidine-1-carboxamide Example 30: rac-4-(4,4-difluorocyclohexyl)-N-{(1R,6S)-2,2-difluoro-6-[4-(propan-2-yl)piperazin-1-yl]cyclohexyl}-4-methylpiperidine-1-carboxamide Example 31: rac-4-(5-cyclopropyl-1,2,4-thiadiazol-3-yl)-N-{(1R,6S)-2,2-difluoro-6-[4-(propan-2-yl)piperazin-1-yl]cyclohexyl}-4-methylpiperidine-1-carboxamide Example 32: rac-N-{(1R,6S)-2,2-difluoro-6-[4-(propan-2-yl)piperazin-1-yl]cyclohexyl}-4-(pyridin-2-yl)piperidine-1-carboxamide Example 33: rac-N-{(1R,6S)-2,2-difluoro-6-[4-(propan-2-yl)piperazin-1-yl]cyclohexyl}-8-azaspiro[4.5]decane-8-carboxamide Example 34: rac-4-(5-cyclopropyl-1,3,4-thiadiazol-2-yl)-N-{(1R,6S)-2,2-difluoro-6-[4-(propan-2-yl)piperazin-1-yl]cyclohexyl}-4-methylpiperidine-1-carboxamide Example 35: rac-4-cyclohexyl-N-{(1R,6S)-2,2-difluoro-6-[4-(propan-2-yl)piperazin-1-yl]cyclohexyl}piperidine-1-carboxamide Example 36: rac-N-{(1R,6S)-2,2-difluoro-6-[4-(propan-2-yl)piperazin-1-yl]cyclohexyl}-4-(pyrimidin-2-yl)piperidine-1-carboxamide Example 37: rac-N-{(1R,6S)-2,2-difluoro-6-[4-(propan-2-yl)piperazin-1-yl]cyclohexyl}-4-hydroxy-4-(pyridin-2-yl)piperidine-1-carboxamide Example 38: rac-N-{(1R,6S)-2,2-difluoro-6-[4-(propan-2-yl)piperazin-1-yl]cyclohexyl}-4-phenylpiperidine-1-carboxamide Example 39: rac-N-{(1R,6S)-2,2-difluoro-6-[4-(propan-2-yl)piperazin-1-yl]cyclohexyl}-4-methyl-4-phenylpiperidine-1-carboxamide Example 40: rac-N-{(1R,6S)-2,2-difluoro-6-[4-(propan-2-yl)piperazin-1-yl]cyclohexyl}-4-hydroxy-4-phenylpiperidine-1-carboxamide Example 41: rac-4-(4-chlorophenyl)-N-{(1R,6S)-2,2-difluoro-6-[4-(propan-2-yl)piperazin-1-yl]cyclohexyl}-4-hydroxypiperidine-1-carboxamide Example 42: rac-N-{(1R,6S)-2,2-difluoro-6-[4-(propan-2-yl)piperazin-1-yl]cyclohexyl}-4-methyl-4-[(pyridin-2-yl)oxy]piperidine-1-carboxamide Example 43: 4-(5-cyclopropyl-1,2,4-thiadiazol-3-yl)-N-{(1R,6S)-2,2-difluoro-6-[4-(propan-2-yl)piperazin-1-yl]cyclohexyl}-4-methylpiperidine-1-carboxamide Example 44: 4-(5-cyclopropyl-1,3,4-thiadiazol-2-yl)-N-{(1R,6S)-2,2-difluoro-6-[4-(propan-2-yl)piperazin-1-yl]cyclohexyl}-4-methylpiperidine-1-carboxamide Example 45: rac-N-{(1R,6S)-2,2-difluoro-6-[4-(propan-2-yl)piperazin-1-yl]cyclohexyl}-4-(5-methoxy-1,2,4-thiadiazol-3-yl)-4-methylpiperidine-1-carboxamide Example 46: rac-N-{(1R,6S)-2,2-difluoro-6-[4-(propan-2-yl)piperazin-1-yl]cyclohexyl}-4-fluoro-4-(pyridin-2-yl)piperidine-1-carboxamide Example 47: rac-4-(2-cyclopropyl-1,3-thiazol-4-yl)-N-{(1R,6S)-2,2-difluoro-6-[4-(propan-2-yl)piperazin-1-yl]cyclohexyl}-4-methylpiperidine-1-carboxamide Example 48: rac-4-(5-cyclopropyl-1,3-thiazol-2-yl)-N-{(1R,6S)-2,2-difluoro-6-[4-(propan-2-yl)piperazin-1-yl]cyclohexyl}-4-methylpiperidine-1-carboxamide Example 49: N-{(1R,6S)-2,2-difluoro-6-[4-(propan-2-yl)piperazin-1-yl]cyclohexyl}-4-methyl-4-(4-methylphenyl)piperidine-1-carboxamide Example 50: rac-N-{(1R,6S)-2,2-difluoro-6-[4-(propan-2-yl)piperazin-1-yl]cyclohexyl}-4-(5-methylpyridin-2-yl)piperidine-1-carboxamide Example 51: rac-N-{(1R,6S)-2,2-difluoro-6-[4-(propan-2-yl)piperazin-1-yl]cyclohexyl}-4-(3-fluoro-5-methylpyridin-2-yl)piperidine-1-carboxamide Example 52: rac-N-{(1R,6S)-2,2-difluoro-6-[4-(propan-2-yl)piperazin-1-yl]cyclohexyl}-4-(5-fluoropyridin-2-yl)piperidine-1-carboxamide Example 53: rac-N-{(1R,6S)-2,2-difluoro-6-[4-(propan-2-yl)piperazin-1-yl]cyclohexyl}-4-(5-methoxypyridin-2-yl)piperidine-1-carboxamide Example 54: rac-N-{(1R,6S)-2,2-difluoro-6-[4-(propan-2-yl)piperazin-1-yl]cyclohexyl}-4-(5-methylpyrimidin-2-yl)piperidine-1-carboxamide Example 55: rac-N-{(1R,6S)-2,2-difluoro-6-[4-(propan-2-yl)piperazin-1-yl]cyclohexyl}-4-[5-(trifluoromethyl)pyridin-2-yl]piperidine-1-carboxamide Example 56: N-{(1R,6S)-2,2-difluoro-6-[4-(propan-2-yl)piperazin-1-yl]cyclohexyl}-4-(2-fluoro-4-methylphenyl)-4-methylpiperidine-1-carboxamide Example 57: 4-[5-(cyclopropyloxy)-1,2,4-thiadiazol-3-yl]-N-{(1R,6S)-2,2-difluoro-6-[4-(propan-2-yl)piperazin-1-yl]cyclohexyl}-4-methylpiperidine-1-carboxamide Example 58: rac-N-{(1R,6S)-2,2-difluoro-6-[4-(propan-2-yl)piperazin-1-yl]cyclohexyl}-4-methyl-4-(4-methylphenyl)piperidine-1-carboxamide Example 59: rac-4-[4-(difluoromethyl)phenyl]-N-{(1R,6S)-2,2-difluoro-6-[4-(propan-2-yl)piperazin-1-yl]cyclohexyl}-4-methylpiperidine-1-carboxamide Example 60: 4-(2-cyano-4-methylphenyl)-N-{(1R,6S)-2,2-difluoro-6-[4-(propan-2-yl)piperazin-1-yl]cyclohexyl}-4-methylpiperidine-1-carboxamide Example 61: N-{(1R,6S)-2,2-difluoro-6-[6-(propan-2-yl)-3,6-diazabicyclo[3.1.1]heptan-3-yl]cyclohexyl}-4-methyl-4-(4-methylphenyl)piperidine-1-carboxamide Example 62: 4-(5-cyclopropyl-1,2,4-oxadiazol-3-yl)-N-{(1R,6S)-2,2-difluoro-6-[3-(propan-2-yl)-3,8-diazabicyclo[3.2.1]octan-8-yl]cyclohexyl}-4-methylpiperidine-1-carboxamide Example 63: N-{(1R,6S)-2,2-difluoro-6-[3-(propan-2-yl)-3,8-diazabicyclo[3.2.1]octan-8-yl]cyclohexyl}-4-methyl-4-(4-methylphenyl)piperidine-1-carboxamide Example 64: 4-(5-cyclopropyl-1,2,4-oxadiazol-3-yl)-N-[(1R,6S)-2,2-difluoro-6-{[(3R)-1-(propan-2-yl)pyrrolidin-3-yl]oxy}cyclohexyl]-4-methylpiperidine-1-carboxamide Example 65: 4-(5-cyclopropyl-1,2-oxazol-3-yl)-N-{(1R,6S)-2,2-difluoro-6-[3-(propan-2-yl)-3,8-diazabicyclo[3.2.1]octan-8-yl]cyclohexyl}-4-methylpiperidine-1-carboxamide Example 66: N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide Example 67: N-[(1R,6S)-2,2-difluoro-6-{[(3R)-1-(propan-2-yl)pyrrolidin-3-yl]oxy}cyclohexyl]-4-methyl-4-(4-methylphenyl)piperidine-1-carboxamide Example 68: N-{(1R,6S)-2,2-difluoro-6-[4-(propan-2-yl)piperazin-1-yl]cyclohexyl}-4-methyl-4-{5-[(1S,2R)-2-methylcyclopropyl]-1,2,4-oxadiazol-3-yl}piperidine-1-carboxamide Example 69: N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide Example 70: N-{(1R,6S)-2,2-difluoro-6-[4-(propan-2-yl)piperazin-1-yl]cyclohexyl}-4-methyl-4-[5-(2,2,2-trifluoroethyl)-1,2,4-oxadiazol-3-yl]piperidine-1-carboxamide Example 71: 4-(5-cyclopropyl-1,2,4-oxadiazol-3-yl)-N-[(1R,6S)-2,2-difluoro-6-{[(3S)-1-(propan-2-yl)pyrrolidin-3-yl]oxy}cyclohexyl]-4-methylpiperidine-1-carboxamide Example 72: N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide Example 73: N-[(1R,6S)-2,2-difluoro-6-{[(3R)-1-(propan-2-yl) pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide Example 74: N-[(1R,6S)-2,2-difluoro-6-{[(3S)-1-(propan-2-yl) pyrrolidin-3-yl]oxy}cyclohexyl]-4-methyl-4-{5-[(1R,2S)-2-methylcyclopropyl]-1,2,4-oxadiazol-3-yl}piperidine-1-carboxamide Example 75: 4-(5-cyclopropyl-1,2,4-oxadiazol-3-yl)-N-[(1R,6S)-2,2-difluoro-6-{[(3S,4S)-4-fluoro-1-(propan-2-yl)pyrrolidin-3-yl]oxy}cyclohexyl]-4-methylpiperidine-1-carboxamide Example 76: 4-(5-cyclopropyl-1,2,4-oxadiazol-3-yl)-N-[(1R,6S)-6-{[(3R)-4,4-difluoro-1-(propan-2-yl)pyrrolidin-3-yl]oxy}-2,2-difluorocyclohexyl]-4-methylpiperidine-1-carboxamide Example 77 rac-N-{(1R,6S)-2,2-Difluoro-6-[4-(propan-2-yl)piperazin-1-yl]cyclohexyl}-4'-methyl-1,2,3,6-tetrahydro[1,1'-biphenyl]-4-carboxamide

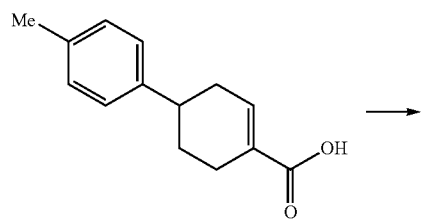

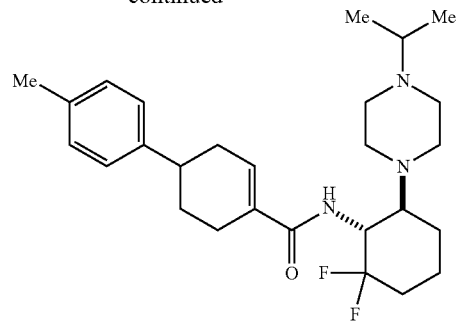

To a solution of 4-(4-methylphenyl)-cyclohex-1-ene-carboxylic acid (64.3 mg) in chloroform (2 mL) were added oxalyl chloride (0.036 mL) and DMF (5 µL), and the mixture was stirred at room temperature for 3 hours. Then, the reaction solution was concentrated in vacuo, and chloroform (2 mL), triethylamine (0.120 mL), and Reference example 14 (53.3 mg) were added to the reaction residue. The mixture was stirred. After the reaction was completed, water was added to the reaction mixture, and the mixture was extracted with chloroform. The organic layer was dried over anhydrous sodium sulfate, and concentrated in vacuo, and then the obtained residue was purified by amino silica gel column chromatography (eluate: hexane/ethyl acetate) to give the title compound (55.6 mg).

$^1$H-NMR (CDCl$_3$) δ: 1.02 (6H, d, J=6.7 Hz), 1.23-1.50 (2H, m), 1.71-1.91 (4H, m), 1.93-2.11 (2H, m), 2.13-2.68 (14H, m), 2.69-2.89 (4H, m), 4.27-4.44 (1H, m), 5.68-5.77 (1H, m), 6.67-6.77 (1H, m), 7.09-7.20 (4H, m).

Example 78 rac-(1R,6S)-2,2-Difluoro-6-[4-(propan-2-yl)piperazin-1-yl]cyclohexyl 4'-methyl-1,2,3,6-tetrahydro[1,1'-biphenyl]-4-carboxylate The compound of Example 78 shown in the table below was prepared in the same manner as Example 77, by using Reference example 6 instead of Reference example 14 in Example 77.

| Example | Structure | Instrumental analytical data |
|---|---|---|
| 78 | 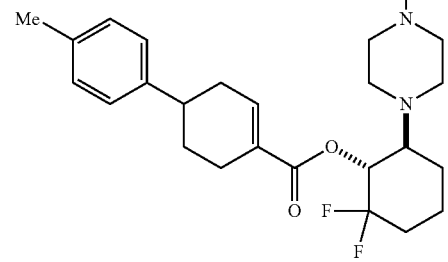 | $^1$H-NMR (CDCl$_3$) δ: 1.02 (3H, d, J = 6.0 Hz), 1.03 (3H, d, J = 6.0 Hz), 1.29-1.53 (2H, m), 1.58-1.85 (4H, m), 1.88-1.97 (1H, m), 1.98-2.08 (1H, m), 2.14-2.25 (1H, m), 2.25-2.53 (11H, m), 2.53-2.66 (2H, m), 2.67-2.83 (4H, m), 5.04-5.16 (1H, m), 7.09-7.16 (5H, m). |

Example 79 rac-4-(5-Cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carbothioamide

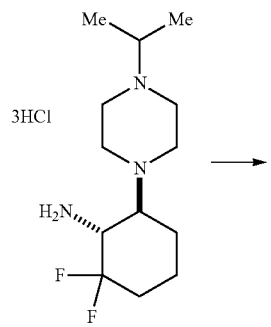

To a mixture of Reference example 14 (10.0 mg)(Material A), N,N-diisopropylamine (0.034 mL), and chloroform (0.2 mL) was added thiophosgene (4.40 mg) at 0° C., and the mixture was stirred at the same temperature for 40 minutes. To the reaction mixture was added Reference example 8 (66.7 mg)(Material B) at 0° C., and the mixture was stirred at room temperature for one hour. The mixture was directly purified by amino silica gel column chromatography (eluate: hexane/ethyl acetate) to give the title compound (9.6 mg).

$^1$H-NMR (CDCl$_3$) δ: 1.02 (6H, d, J=5.6 Hz), 1.14-1.27 (4H, m), 1.27-1.50 (2H, m), 1.50-1.91 (8H, m), 1.91-2.04 (1H, m), 2.08-2.24 (2H, m), 2.24-2.35 (2H, m), 2.35-2.55 (5H, m), 2.55-2.70 (2H, m), 2.79-3.00 (2H, m), 3.33 (1H, t, J=11.2 Hz), 3.49 (1H, t, J=11.2 Hz), 4.16 (1H, d, J=12.8 Hz), 4.49 (1H, d, J=12.8 Hz), 5.02-5.26 (1H, m), 5.42 (1H, d, J=8.0 Hz).

Example 80

4-(5-Cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carbothioamide The compound of Example 80 shown in the table below was prepared in the same manner as Example 79, by using Reference example 15 corresponding to Material A in Example 79 and Reference example 8 corresponding to Material B in Example 79.

| Example | Structure / Spectral data | Material A | Material B |
|---|---|---|---|
| 80 | 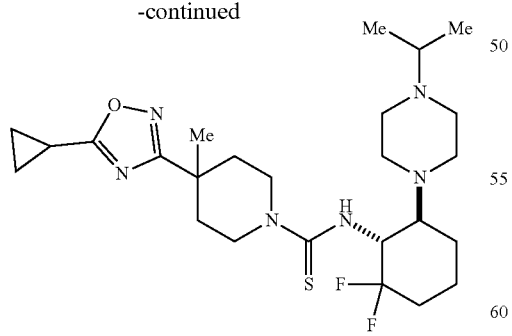 $^1$H-NMR (CDCl$_3$) δ: 1.02 (6H, d, J = 5.6 Hz), 1.14-1.27 (4H, m), 1.27-1.50 (2H, m), 1.50-1.91 (8H, m), 1.91-2.04 (1H, m), 2.08-2.24 (2H, m), 2.24-2.35 (2H, m), 2.35-2.55 (5H, m), 2.55-2.70 (2H, m), 2.79-3.00 (2H, m), 3.33 (1H, t, J = 11.2 Hz), 3.49 (1H, t, J = 11.2 Hz), 4.16 (1H, d, J = 12.8 Hz), 4.49 (1H, d, J = 12.8 Hz), 5.02-5.26 (1H, m), 5.42 (1H, d, J = 8.0 Hz). | Reference example 15 | Reference example 8 |

Example 81 rac-4-(4-Methylphenyl)-N-[(1S,4R)-3-{[4-(propan-2-yl)piperazin-1-yl]methyl}bicyclo[2.2.1]heptan-2-yl]piperidine-1-carboxamide

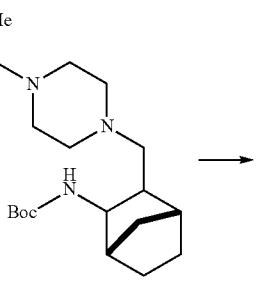

-continued

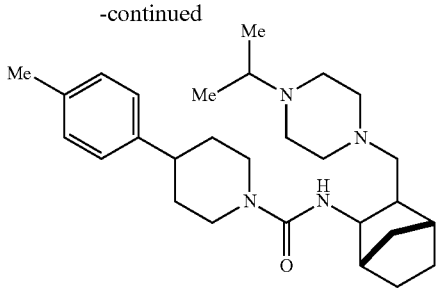

To a solution of Reference example 40 (20 mg) in chloroform (0.5 mL) was added TFA (0.057 ml) at room temperature, and the mixture was stirred at the same temperature for one hour. The reaction solution was concentrated in vacuo, and the obtained residue was purified by amino silica gel column chromatography (eluate: hexane/ethyl acetate). The obtained residue was dissolved in chloroform (0.284 mL). To the solution were added N,N-diisopropylethylamine (36.8 mg) and triphosgene (8.4 mg) at 0° C., and the mixture was stirred at the same temperature for one hour. Then, 4-(4-methylphenyl)piperidine (0.057 mL) was added to the reaction mixture, which was stirred at room temperature for one hour. The reaction mixture was directly purified by amino silica gel column chromatography (eluate: hexane/ethyl acetate) to give the title compound (8 mg).

$^1$H-NMR (CDCl$_3$) δ: 1.24 (6H, d, J=7.3 Hz), 1.31-1.49 (7H, m), 1.54-1.67 (4H, m), 1.84 (2H, m), 2.24 (1H, m), 2.32 (3H, s), 2.63 (2H, m), 2.80-2.99 (4H, m), 3.06-3.49 (8H, m), 4.05-4.14 (3H, m), 7.07-7.13 (4H, m).

Examples 82-156

The compounds of Examples 82 to 156 shown in the table below were prepared in the same manner as Example 19, by using commercial compounds or Reference example compounds which correspond to Material A and Material B described in Example 19.

| Example | Structure | Spectral data | Material A | Material B |
|---|---|---|---|---|
| 82 | 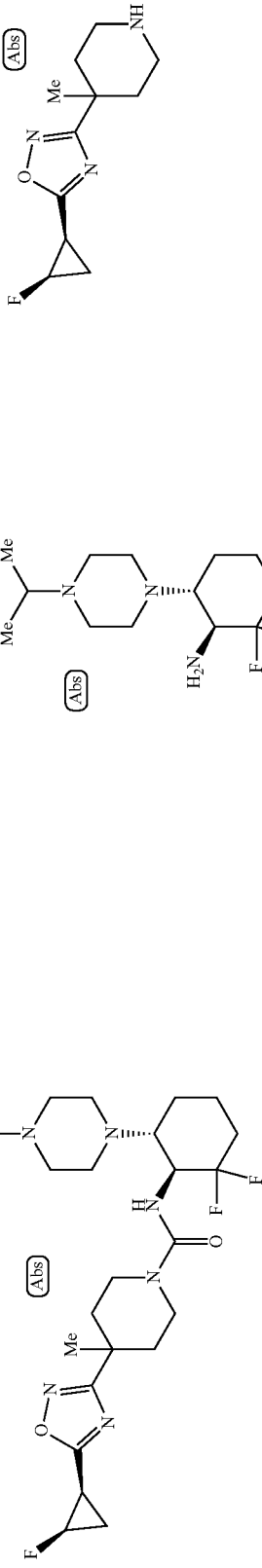 | ¹H-NMR (DMSO-d6) δ: 0.87 (6H, d, J = 6.4 Hz), 1.18-1.36 (2H, m), 1.26 (3H, s), 1.47-1.66 (3H, m), 1.66-1.88 (4H, m), 1.95-2.11 (3H, m), 2.17-2.40 (6H, m), 2.43-2.63 (5H, m), 2.95-3.19 (2H, m), 3.55-3.77 (2H, m), 3.98-4.18 (1H, m), 5.16 (1H, dddd, J = 65.0, 6.0, 6.0, 3.2 Hz), 5.88 (1H, d, J = 8.0 Hz). | Reference example 58 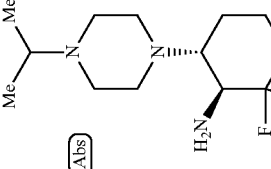 | Reference example 116 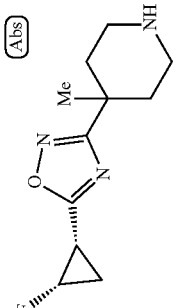 |
| 83 | 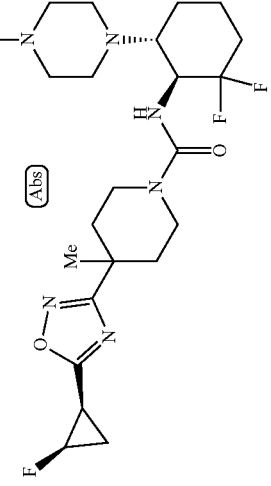 | ¹H-NMR (CDCl₃) δ: 1.00 (5H, m), 1.13 (1H, d, J = 6.4 Hz), 1.33 (3H, s), 1.38-1.85 (9H, m), 1.90-2.30 (8H, m), 2.32-2.41 (1H, m), 2.60-2.74 (4H, m), 3.03-3.15 (2H, m), 3.17-3.28 (1H, m), 3.33-3.44 (1H, m), 3.65- 3.76 (2H, m), 4.13-4.30 (1H, m), 4.51 (1H, d, J = 9.2 Hz), 4.91 (1H, dddd, J = 63.6, 6.0, 3.6 Hz). | Reference example 96 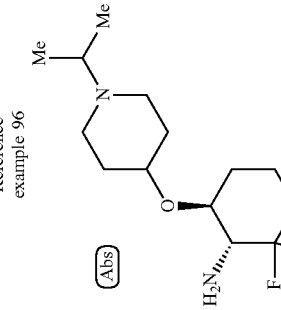 | Reference example 115  |

-continued

| Example | Structure | Spectral data | Material A | Material B |
|---|---|---|---|---|
| 84 | (structure shown) | $^1$H-NMR (CDCl$_3$) δ: 1.00 (6H, dd, J = 6.8, 1.2 Hz), 1.17-1.25 (4H, m), 1.30 (3H, s), 1.38-1.46 (2H, m), 1.50-1.69 (4H, m), 1.69-1.85 (4H, m), 2.00-2.30 (7H, m), 2.60-2.74 (3H, m), 3.03-3.15 (2H, m), 3.17-3.28 (1H, m), 3.33-3.42 (1H, m), 3.64-3.74 (2H, m), 4.13-4.30 (1H, m), 4.50 (1H, d, J = 9.2 Hz). | Reference example 96 | Reference example 8, HCl |
| 85 | (structure shown) | $^1$H-NMR (CDCl$_3$) δ: 1.16-1.23 (4H, m), 1.27 (3H, s), 1.36 (6H, d, J = 6.8 Hz), 1.44-1.58 (2H, m), 1.58-1.75 (1H, m), 1.80-2.06 (4H, m), 2.09-2.23 (3H, m), 2.23-2.35 (1H, m), 2.88-3.08 (3H, m), 3.11-3.25 (1H, m), 3.48-3.67 (2H, m), 4.41-4.57 (1H, m), 4.57-4.67 (1H, m). | Reference example 91 | Reference example 8, HCl |

| Example | Structure | Material A | Spectral data | Material B |
|---|---|---|---|---|
| 86 | (structure with oxadiazole, difluorocyclohexane, piperidine carboxamide, methyl oxadiazole, fluorocyclopropyl) | Reference example 91 | $^1$H-NMR (CDCl$_3$) δ: 1.30 (3H, s), 1.35 (6H, d, J = 6.4 Hz), 1.42-1.62 (3H, m), 1.62-1.75 (1H, m), 1.80-2.07 (5H, m), 2.11-2.22 (2H, m), 2.22-2.41 (2H, m), 2.89-3.08 (3H, m), 3.11-3.24 (1H, m), 3.50-3.66 (2H, m), 4.41-4.56 (1H, m), 4.58-4.67 (1H, m), 4.93 (1H, dddd, J = 63.6, 6.0, 6.0, 3.6 Hz). | Reference example 115 |
| 87 | (structure with thiadiazole-O linkage, difluorocyclohexane, piperidine carboxamide, methyl oxadiazole, fluorocyclopropyl) | Reference example 97 | $^1$H-NMR (CDCl$_3$) δ: 1.25 (3H, s), 1.26-1.37 (1H, m), 1.30 (3H, d, J = 6.4 Hz), 1.31 (3H, d, J = 6.4 Hz), 1.39-1.74 (4H, m), 1.74-2.01 (3H, m), 2.10-2.19 (2H, m), 2.19-2.30 (1H, m), 2.30-2.39 (2H, m), 2.86 (1H, ddd, J = 14.0, 11.0, 3.1 Hz), 2.96-3.08 (2H, m), 2.96-3.08 (2H, m), 3.41-3.50 (1H, m), 3.63-3.72 (1H, m), 4.41 (1H, dddd, J = 64.0, 6.0, 6.0, 3.6 Hz), 4.46-4.60 (1H, m), 4.78-4.86 (1H, m), 5.06-5.15 (1H, m). | Reference example 115 |

-continued
| Example | Structure | Spectral data | Material A | Material B |
|---|---|---|---|---|
| 88 | 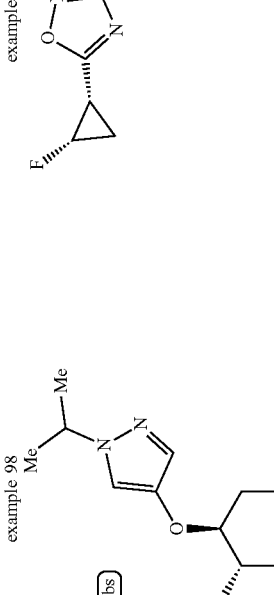 | $^1$H-NMR (CDCl$_3$) δ: 1.30 (3H, s), 1.41-1.89 (14H, m), 1.90-2.02 (1H, m), 2.13-2.30 (4H, m), 2.31-2.41 (1H, m), 2.99-3.13 (2H, m), 3.60-3.78 (2H, m), 4.32-4.50 (2H, m), 4.63 (1H, d, J = 9.2 Hz), 4.91 (1H, dddd, J = 63.6, 6.0, 6.0, 3.6 Hz), 7.17 (1H, s), 7.21 (1H, s). | Reference example 98  | Reference example 115  |
| 89 | 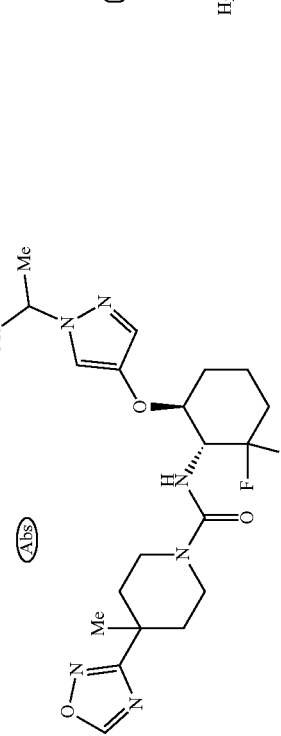 | $^1$H-NMR (CDCl$_3$) δ: 1.13 (6H, d, J = 6.0 Hz), 1.32 (3H, s), 1.42-1.83 (5H, m), 1.87-2.04 (2H, m), 2.06-2.17 (2H, m), 2.18-2.28 (4H, m), 2.31-2.41 (1H, m), 2.60-2.73 (2H, m), 2.88-3.17 (5H, m), 3.30-3.80 (6H, m), 4.80-5.04 (1H, m). | Reference example 99  | Reference example 115 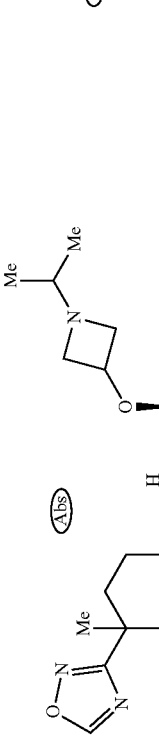 |

| Example | Structure | Spectral data | Material A | Material B |
|---|---|---|---|---|
| 90 | 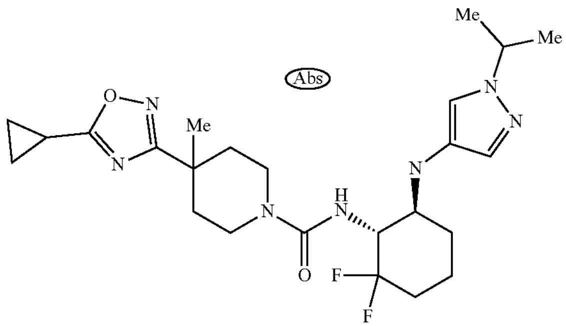 [SMILES: CC(C)n1cc(N[C@H]2CCCC(F)(F)[C@@H]2NC(=O)N2CCC(C)(c3noc(C4CC4)n3)CC2)cn1] | ¹H-NMR (CDCl₃) δ: 1.17-1.23 (4H, m), 1.27 (3H, s), 1.44 (3H, d, J = 6.7 Hz), 1.45 (3H, d, J = 6.7 Hz), 1.46-1.65 (4H, m), 1.69-1.91 (2H, m), 2.12-2.30 (5H, m), 2.99-3.12 (2H, m), 3.59-3.69 (2H, m), 3.69-3.77 (1H, m), 4.31-4.50 (2H, m), 4.63 (1H, d, J = 9.2 Hz), 7.16 (1H, s), 7.20 (1H, s). | Reference example 98 | Reference example 8 · HCl |
| 91 | 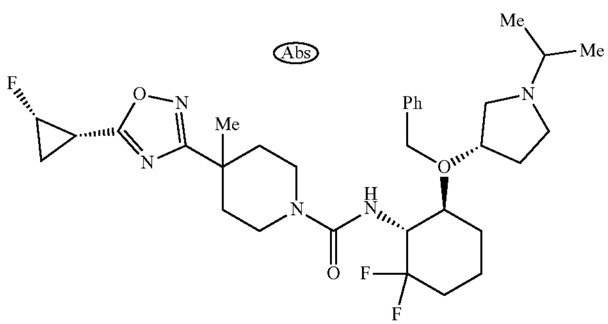 | ¹H-NMR (CDCl₃) δ: 1.09-1.43 (11H, m), 1.43-1.56 (2H, m), 1.56-1.76 (3H, m), 1.76-2.24 (7H, m), 2.24-2.48 (5H, m), 2.48-2.75 (1H, m), 2.75-3.06 (1H, m), 3.06-3.45 (4H, m), 3.45-3.71 (1H, m), 3.71-3.87 (1H, m), 3.87-4.13 (1H, m), 4.13-4.50 (1H, m), 4.94 (1H, dddd, J = 64.4, 6.0, 6.0, 4.0 Hz), 7.13-7.44 (5H, m), 11.97 (1H, brs). | Reference example 89 | Reference example 115 |

| Example | Structure | Spectral data | Material A | Material B |
|---|---|---|---|---|
| 92 | 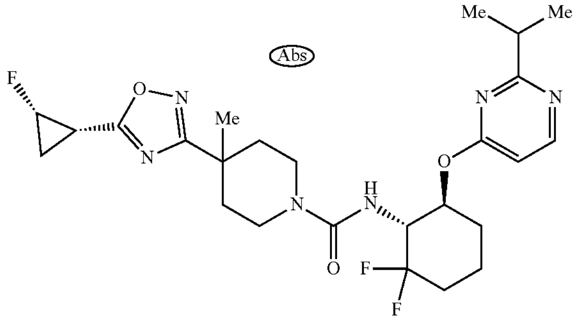 [SMILES: CC(C)c1nccc(O[C@H]2CCCC(F)(F)[C@@H]2NC(=O)N2CCC(C)(c3noc([C@@H]4C[C@@H]4F)n3)CC2)n1] | ¹H-NMR (CDCl₃) δ: 1.18-1.29 (1H, m), 1.22 (3H, s), 1.30 (3H, d, J = 6.4 Hz), 1.31 (3H, d, J = 6.4 Hz), 1.40-1.53 (3H, m), 1.58-1.71 (1H, m), 1.78-2.03 (3H, m), 2.05-2.12 (2H, m), 2.17-2.28 (1H, m), 2.30-2.40 (2H, m), 2.81 (1H, ddd, J = 13.6, 10.8, 2.9 Hz), 2.93-3.06 (2H, m), 3.37-3.47 (1H, m), 3.54-3.61 (1H, m), 4.41-4.54 (1H, m), 4.74 (1H, d, J = 9.2 Hz), 4.91 (1H, dddd, J = 63.6, 6.0, 6.0, 3.6 Hz), 5.40-5.48 (1H, m), 6.53 (1H, d, J = 5.5 Hz), 8.35 (1H, d, J = 5.5 Hz). | Reference example 119 | Reference example 115 |
| 93 | 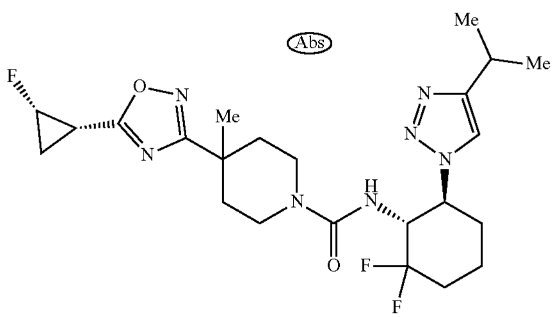 [SMILES: CC(C)c1cn([C@H]2CCCC(F)(F)[C@@H]2NC(=O)N2CCC(C)(c3noc([C@@H]4C[C@@H]4F)n3)CC2)nn1] | ¹H-NMR (CDCl₃) δ: 1.24-1.30 (9H, m), 1.35-1.53 (3H, m), 1.65-2.04 (6H, m), 2.07-2.20 (2H, m), 2.27-2.40 (2H, m), 2.83 (1H, ddd, J = 14.0, 11.6, 3.2 Hz), 2.95-3.10 (2H, m), 3.40-3.49 (1H, m), 3.57-3.67 (1H, m), 4.60-4.71 (3H, m), 4.90 (1H, dddd, J = 64.0, 6.0, 6.0, 4.0 Hz), 7.42 (1H, s). | Reference example 92 | Reference example 115 |

| Example | Structure | Spectral data | Material A | Material B |
|---|---|---|---|---|
| 94 | 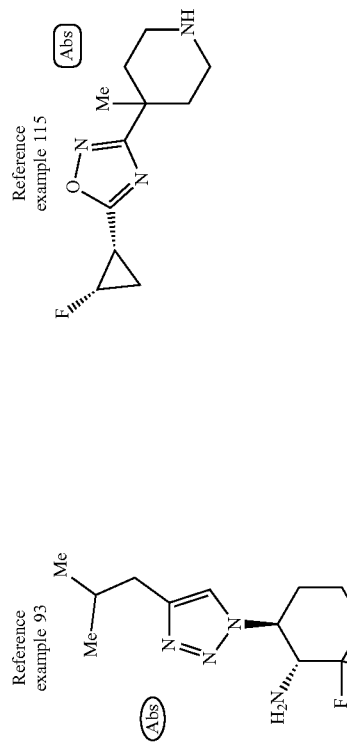 | $^1$H-NMR (CDCl$_3$) δ: 0.89 (6H, t, J = 6.8 Hz), 1.27 (3H, s), 1.36-1.53 (3H, m), 1.64-2.04 (6H, m), 2.07-2.20 (2H, m), 2.27-2.40 (3H, m), 2.48-2.63 (2H, m), 2.84 (1H, ddd, J = 14.0, 11.2, 3.2 Hz), 2.98 (1H, ddd, J = 14.0, 11.2, 3.2 Hz), 3.40-3.50 (1H, m), 3.54-3.65 (1H, m), 4.60-4.76 (3H, m), 4.90 (1H, dddd, J = 64.0, 6.0, 6.0, 3.6 Hz), 7.43 (1H, s). | Reference example 93 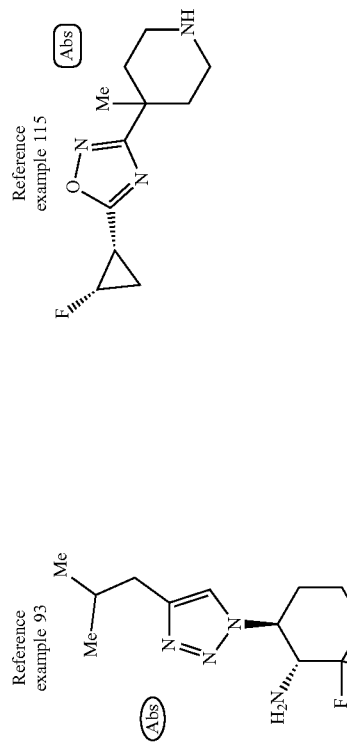 | Reference example 115 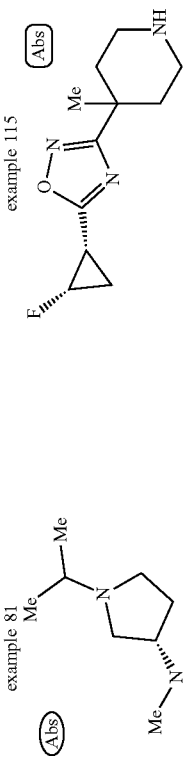 |
| 95 | 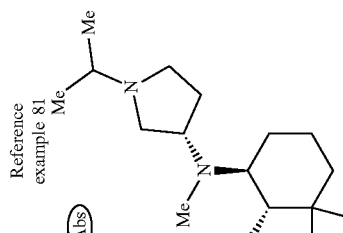 | | Reference example 81 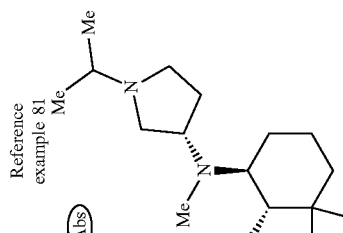 | Reference example 115 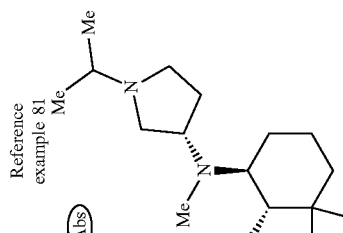 |

-continued

| Example | Structure | Spectral data | Material A | Material B |
|---|---|---|---|---|
| 96 | (structure shown) | ¹H-NMR (CDCl₃) δ: 1.00-1.11 (6H, m), 1.15-1.54 (7H, m), 1.54-1.75 (4H, m), 1.75-2.07 (5H, m), 2.15 (3H, s), 2.20-2.30 (3H, m), 2.30-2.42 (2H, m), 2.42-2.57 (1H, m), 2.59-2.70 (1H, m), 2.73-2.85 (1H, m), 2.90 (1H, tt, J = 8.0 Hz), 3.02-3.18 (2H, m), 3.23 (1H, tt, J = 15.2, 7.2 Hz), 3.63-3.79 (2H, m), 4.07-4.22 (1H, m), 4.54 (1H, d, J = 7.6 Hz), 4.91 (1H, dddd, J = 63.6, 6.0, 6.0, 3.6 Hz). | Reference example 59 | Reference example 115 |

| Example | Structure | Spectral data | Material A | Material B |
|---|---|---|---|---|
| 97 | (structure shown) | ¹H-NMR (CDCl₃) δ: 1.00 (6H, d, J = 6.4 Hz), 1.22-1.48 (2H, m), 1.34 (3H, s), 1.49-1.60 (1H, m), 1.61-1.75 (2H, m), 1.75-1.87 (1H, m), 1.87-1.98 (1H, m), 1.98-2.22 (3H, m), 2.22-2.33 (2H, m), 2.33-2.54 (11H, m), 2.54-2.64 (1H, m), 2.68-2.81 (2H, m), 3.14 (2H, dddd, J = 32.4, 14.0, 10.8, 3.2 Hz), 3.62-3.84 (3H, m), 4.16 (1H, dddd, J = 23.6, 11.2, 8.0, 3.6 Hz), 4.54 (1H, d, J = 8.0 Hz). | Reference example 18 | Reference example 117 |
| 98 | (structure shown) | ¹H-NMR (CDCl₃) δ: 1.00-1.11 (6H, m), 1.33 (3H, s), 1.36-1.84 (13H, m), 1.85-2.07 (4H, m), 2.07-2.20 (1H, m), 2.22-2.31 (2H, m), 2.31-2.41 (1H, m) , 2.90 (1H, sep, J = 6.4 Hz), 3.03-3.26 (3H, m), 3.42-3.52 (2H, m), 3.59- 3.78 (3H, m), 4.10-4.24 (1H, m), 4.50 (1H, d, J = 9.2 Hz), 4.91 (1H, dddd, J = 63.6, 6.0, 6.0, 3.6 Hz). | Reference example 100 | Reference example 115 |

| Example | Structure | Spectral data | Material A | Material B |
|---|---|---|---|---|
| 99 | 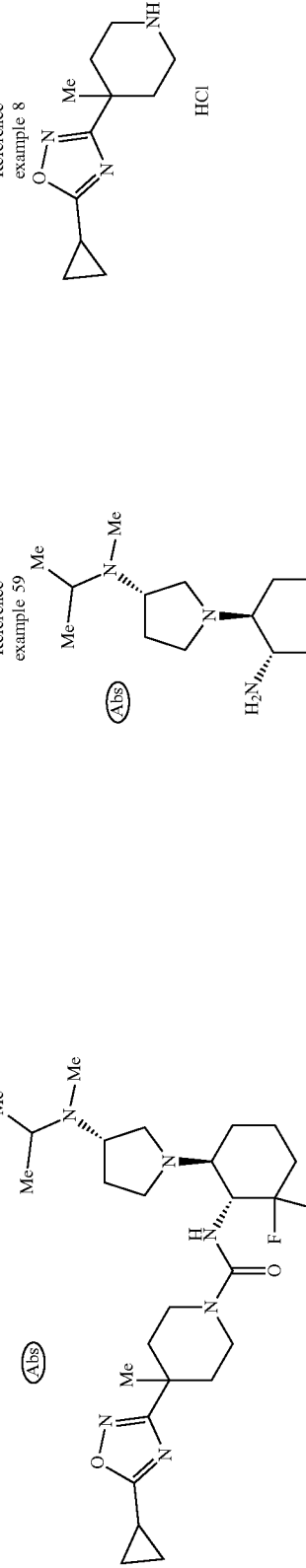 | ¹H-NMR (CDCl₃) δ: 0.92-1.00 (6H, m), 1.13 (2H, d, J = 6.0 Hz), 1.17-1.24 (4H, m), 1.30 (3H, s), 1.32-1.50 (2H, m), 1.56-1.70 (2H, m), 1.70-1.86 (1H, m), 1.86-1.97 (2H, m), 2.08 (3H, s), 2.11-2.26 (4H, m), 2.44 (1H, t, J = 7.6 Hz), 2.60-2.70 (2H, m), 2.76-2.86 (1H, m), 2.86-2.92 (2H, m), 2.92-3.17 (3H, m), 3.60-3.77 (2H, m), 4.07-4.23 (1H, m), 4.53 (1H, d, J = 7.6 Hz). | Reference example 59 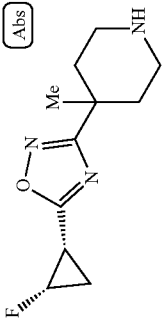 | Reference example 8 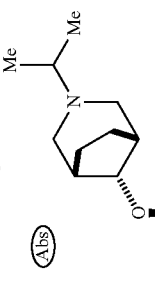 HCl |
| 100 | 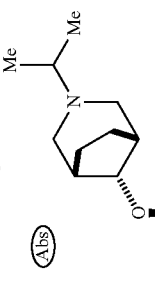 | ¹H-NMR (CDCl₃) δ: 0.91-0.97 (6H, m), 1.32 (3H, s), 1.37-1.86 (11H, m), 1.90-2.04 (3H, m), 2.07-2.21 (2H, m), 2.21-2.41 (5H, m), 2.49 (1H, sep, J = 6.0 Hz), 2.62 (2H, dd, J = 15.6, 10.8 Hz), 3.02-3.16 (2H, m), 3.21-3.32 (2H, m), 3.59 (1H, t, J = 4.4 Hz), 3.63-3.78 (2H, m), 4.22-4.37 (1H, m), 4.56 (1H, d, J = 8.8 Hz), 4.91 (1H, dddd, J = 63.6, 6.0, 6.0, 4.0 Hz). | Reference example 101 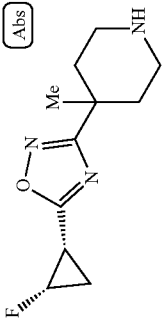 | Reference example 115 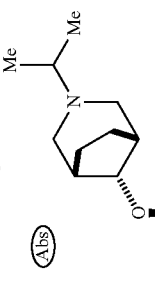 |

| Example | Structure | Spectral data | Material A | Material B |
|---|---|---|---|---|
| 101 | (structure with oxadiazole-cyclopropyl-F, piperidine-Me, difluorocyclohexane, piperidine-O-CHMe-Me) [Abs] | ¹H-NMR (CDCl₃) δ: 1.11 (6H, d, J = 6.4 Hz), 1.20-1.54 (8H, m), 1.60-1.74 (2H, m), 1.74-1.85 (4H, m), 1.85-2.04 (2H, m), 2.09-2.20 (2H, m), 2.21-2.30 (2H, m), 2.32-2.42 (1H, m), 2.46-2.63 (3H, m), 2.76-2.85 (1H, m), 3.01-3.17 (2H, m), 3.28 (1H, sep, J = 4.4 Hz), 3.61-3.82 (3H, m), 4.08-4.23 (1H, m), 4.56 (1H, d, J = 7.2 Hz), 4.92 (1H, dddd, J = 64.0, 6.0, 6.0, 3.6 Hz). | Reference example 60 (structure) [Abs] | Reference example 115 (structure) [Abs] |
| 102 | (structure with oxadiazole-cyclobutyl, piperidine-Me, difluorocyclohexane, pyrrolidine-O-CHMe-Me) [Abs] | ¹H-NMR (CDCl₃) δ: 1.05 (3H, d, J = 6.0 Hz), 1.06 (3H, d, J = 6.0 Hz), 1.33 (3H, s), 1.36-1.51 (2H, m), 1.59-1.86 (5H, m), 1.92-2.12 (5H, m), 2.69 (2H, d, J = 13.2 Hz), 2.31-2.40 (2H, m), 2.40-2.55 (5H, m), 2.61-2.73 (1H, m), 2.95-3.27 (4H, m), 3.62-3.80 (3H, m), 4.06-4.30 (2H, m), 4.54 (1H, d, J = 9.2 Hz). | Reference example 37 (structure) [Abs] | Reference example 117 (structure) HCl |

| Example | Structure | Spectral data | Material A | Material B |
|---|---|---|---|---|
| 103 | 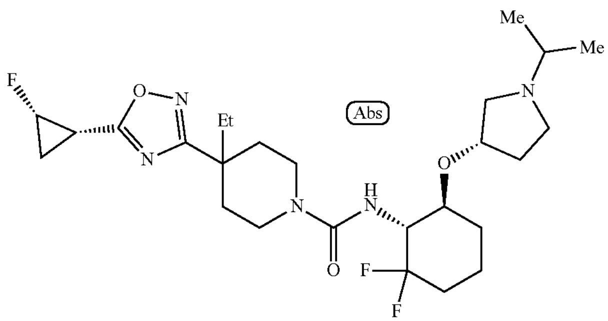 [SMILES: CCC1(c2noc([C@@H]3C[C@@H]3F)n2)CCN(C(=O)N[C@@H]2[C@@H](O[C@H]3CCN(C(C)C)C3)CCCC2(F)F)CC1] | ¹H-NMR (CDCl₃) δ: 0.71 (3H, t, J = 7.2 Hz), 1.05 (3H, d, J = 6.0 Hz), 1.06 (3H, d, J = 6.0 Hz), 1.32-1.54 (3H, m), 1.54-1.87 (7H, m), 1.91-2.04 (2H, m), 2.04-2.21 (2H, m), 2.30 (2H, d, J = 18.0 Hz), 2.33-2.42 (3H, m), 2.47 (1H, dd, J = 16.4, 8.0 Hz), 2.60-2.76 (1H, m), 2.88-3.11 (3H, m), 3.14-3.26 (1H, m), 3.79 (2H, d, J = 13.6 Hz), 4.06-4.29 (2H, m), 4.53 (1H, d, J = 9.2 Hz), 4.92 (1H, dddd, J = 63.6, 6.0, 6.0, 3.6 Hz). | Reference example 37 | Reference example 118 |
| 104 | 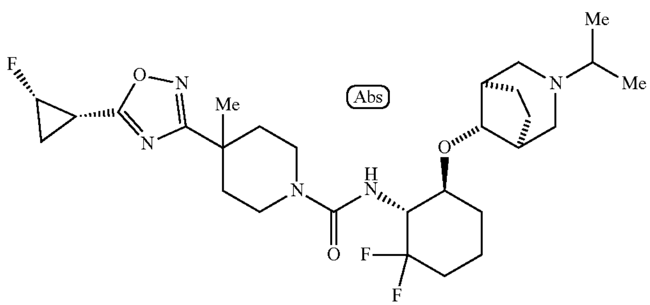 | ¹H-NMR (CDCl₃) δ: 0.95 (6H, d, J = 6.1 Hz), 1.29-1.87 (12H, m), 1.33 (3H, s), 1.90-2.04 (1H, m), 2.04-2.31 (8H, m), 2.31-2.43 (1H, m), 2.52-2.67 (2H, m), 3.00-3.31 (3H, m), 3.35-3.43 (1H, m), 3.63-3.79 (2H, m), 4.12-4.29 (1H, m), 4.49 (1H, d, J = 9.2 Hz), 4.80-5.02 (1H, m). | Reference example 102 | Reference example 115 |

| Example | Structure | Spectral data | Material A | Material B |
|---|---|---|---|---|
| 105 | [Structure with Abs label] | ¹H-NMR (CDCl₃) δ: 1.12 (6H, br s), 1.29-1.42 (2H, m), 1.33 (3H, s), 1.42-1.53 (2H, m), 1.54-1.85 (8H, m), 1.90-2.21 (6H, m), 2.21-2.30 (2H, m), 2.32-2.41 (1H, m), 2.59-2.71 (1H m), 3.03-3.20 (3H, m), 3.25-3.60 (2H, m), 3.61-3.74 (3H, m), 4.17-4.30 (1H, m), 4.56 (1H, d, J = 9.2 Hz), 4.91 (1H, dddd, J = 63.6, 6.0, 6.0, 3.6 Hz). | Reference example 103 | Reference example 115 |
| 106 | [Structure with Abs label] | ¹H-NMR (CDCl₃) δ: 1.01 (6H, d, J = 5.5 Hz), 1.24-1.84 (8H, m), 1.33 (3H, s), 1.90-2.03 (1H, m), 2.07-2.30 (5H, m), 2.30-2.47 (4H, m), 2.96-3.17 (4H, m), 3.22-3.30 (1H, m), 3.49-3.57 (1H, m), 3.66-3.75 (2H, m), 4.10-4.24 (1H, m), 4.56 (1H, d, J = 8.5 Hz), 4.91 (1H, dddd, J = 63.6, 6.0, 6.0, 3.6 Hz). | Reference example 104 | Reference example 115 |

| Example | Structure | Spectral data | Material A | Material B |
|---|---|---|---|---|
| 107 | 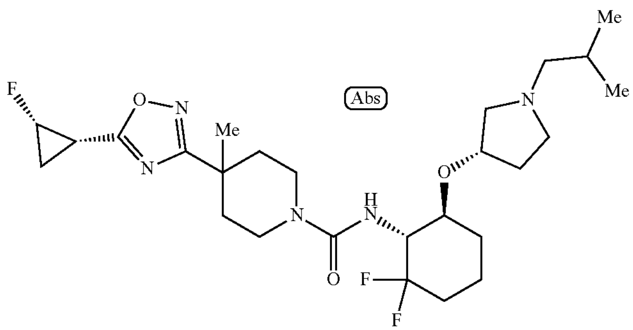 [SMILES: CC(C)CN1CC[C@H](O[C@H]2CCCC(F)(F)[C@@H]2NC(=O)N2CCC(C)(c3noc([C@@H]4C[C@@H]4F)n3)CC2)C1] | ¹H-NMR (CDCl₃) δ: 0.92 (3H, d, J = 4.3 Hz), 0.94 (3H, d, J = 4.3 Hz), 1.34 (3H, s), 1.36-1.54 (3H, m), 1.58-1.84 (7H, m), 1.91-2.21 (4H, m), 2.22-2.46 (6H, m), 2.46-2.58 (1H, m), 2.97-3.24 (4H, m), 3.65-3.74 (2H, m), 4.15-4.25 (2H, m), 4.58 (1H, d, J = 9.2 Hz), 4.92 (1H, dddd, J = 63.6, 6.0, 6.0, 3.6 Hz). | Reference example 105 | Reference example 115 |
| 108 | 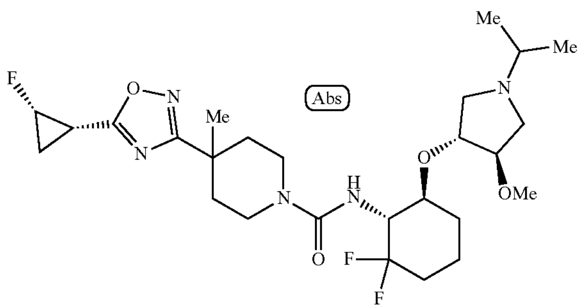 [SMILES: CO[C@@H]1CN(C(C)C)C[C@H]1O[C@H]1CCCC(F)(F)[C@@H]1NC(=O)N1CCC(C)(c2noc([C@@H]3C[C@@H]3F)n2)CC1] | ¹H-NMR (CDCl₃) δ: 1.10 (6H, br s), 1.34 (3H, s), 1.39-1.54 (3H, m), 1.54-1.85 (6H, m),? 1.91-2.04 (1H, m), 2.04-2.21 (2H, m), 2.21-2.31 (2H, m), 2.32-2.58 (2H, m), 2.62-2.80 (1H, m), 3.05-3.19 (3H, m), 3.24-3.35 (1H, m), 3.29 (3H, s), 3.61-3.79 (3H, m), 3.92-4.01 (1H, m), 4.15-4.30 (1H, m), 4.65 (1H, d, J = 9.2 Hz), 4.92 (1H, dddd, J = 63.6, 6.0, 6.0, 3.6 Hz). | Reference example 106 | Reference example 115 |

| Example | Structure | Spectral data | Material A | Material B |
|---|---|---|---|---|
| 109 | 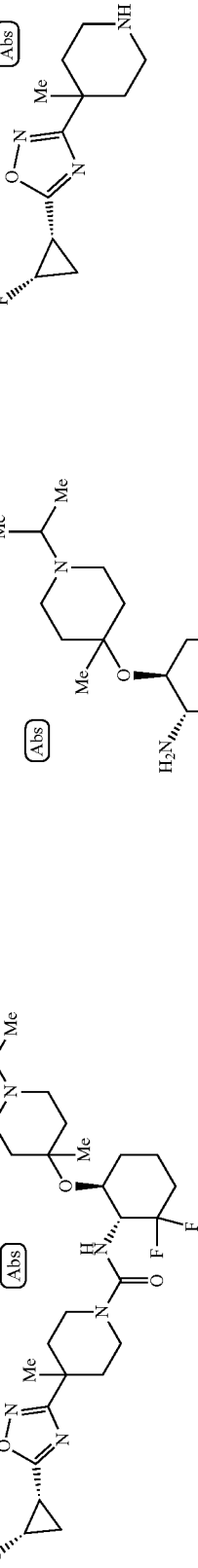 | $^1$H-NMR (CDCl$_3$) δ: 0.94-1.29 (8H, m), 1.33 (3H, s), 1.38-1.86 (14H, m), 1.89-2.18 (2H, m), 2.18-2.31 (2H, m), 2.31-2.75 (4H, m), 2.98-3.51 (4H, m), 3.57-3.79 (2H, m), 4.08-4.26 (1H, m), 4.51 (1H, d, J = 8.4 Hz), 4.91 (1H, dddd, J = 63.6, 6.4, 6.4, 4.0 Hz). | Reference example 107 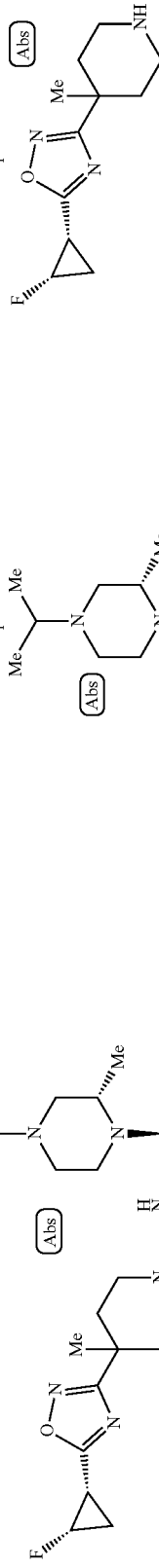 | Reference example 115 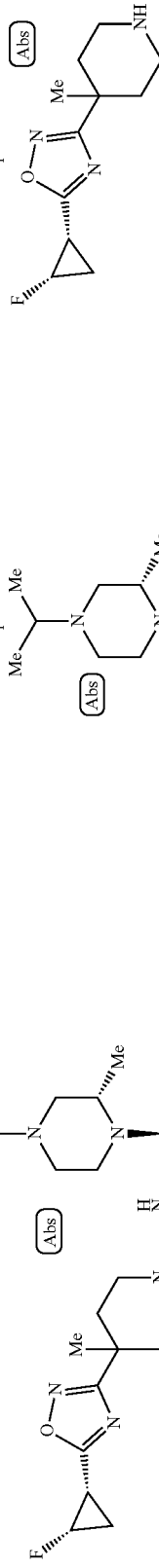 |
| 110 | 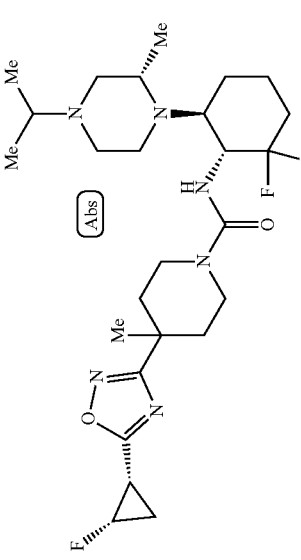 | $^1$H-NMR (CDCl$_3$) δ: 0.93-1.04 (9H, m), 1.23-1.53 (6H, m), 1.61-1.75 (2H, m), 1.75-1.87 (4H, m), 1.90-2.04 (2H, m), 2.10-2.22 (1H, m), 2.22-2.30 (2H, m), 2.30-2.41 (2H, m), 2.54 (1H, sep, J = 6.4 Hz), 2.62-2.81 (4H, m), 2.88 (1H, t, J = 11.0 Hz), 3.02-3.12 (1H, m), 3.12-3.22 (1H, m), 3.62-3.72 (1H, m), 3.74-3.84 (1H, m), 4.10-4.24 (1H, m), 4.48 (1H, d, J = 7.4 Hz), 4.91 (1H, dddd, J = 63.6, 6.0, 6.0, 3.6 Hz). | Reference example 61 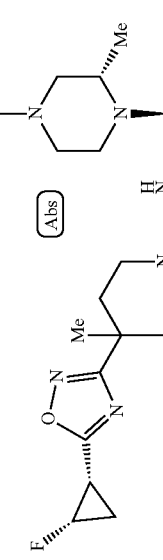 | Reference example 115 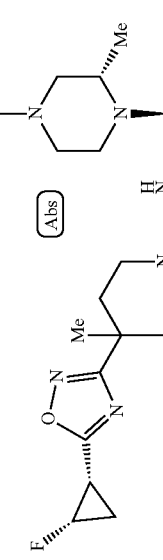 |

| Example | Structure | Spectral data | Material A | Material B |
|---|---|---|---|---|
| 111 | 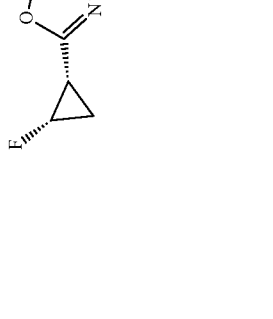 | ¹H-NMR (CDCl₃) δ: 0.92-1.00 (6H, m), 1.09 (3H, d, J = 6.0 Hz), 1.33 (3H, s), 1.42-1.54 (3H, m), 1.60-1.89 (5H, m), 1.90-2.22 (3H, m), 2.22-2.42 (4H, m), 2.42-2.67 (4H, m), 2.68-2.79 (2H, m), 2.83-2.94 (4H, m), 3.03-3.18 (2H, m), 3.64-3.77 (2H, m), 4.10-4.27 (1H, m), 4.53 (1H, d, J = 8.4 Hz), 4.91 (1H, dddd, J = 64.0, 6.0, 6.0, 3.6 Hz). | Reference example 62 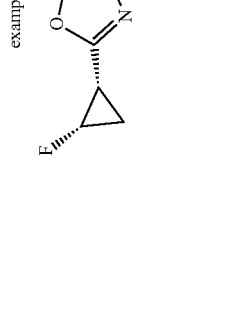 | Reference example 115  |
| 112 | 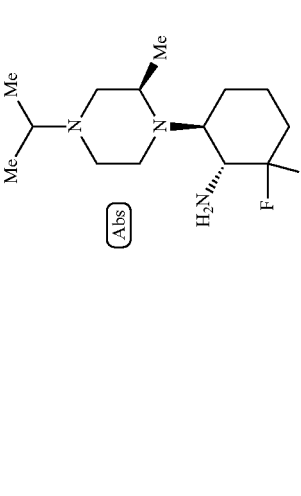 | ¹H-NMR (CDCl₃) δ: 0.92-1.02 (6H, m), 1.33 (3H, s), 1.35-1.53 (3H, m), 1.54-1.85 (5H, m), 1.86-2.04 (3H, m), 2.08 (3H, s), 2.10-2.20 (1H, m), 2.20-2.28 (2H, m), 2.31-2.42 (1H, m), 2.56-2.68 (2H, m), 2.70-2.80 (3H, m), 2.85-2.97 (1H, m), 3.02-3.16 (3H, m), 3.66-3.77 (2H, m), 4.05-4.20 (1H, m), 4.59 (1H, d, J = 7.2 Hz), 4.92 (1H, dddd, J = 64.0, 6.0, 6.0, 4.0 Hz). | Reference example 82 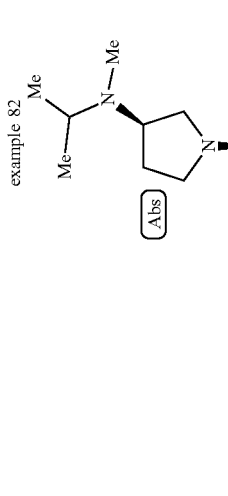 | Reference example 115 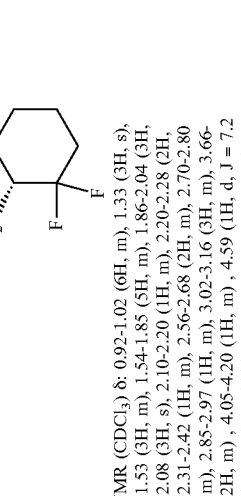 |

| Example | Structure | Spectral data | Material A | Material B |
|---|---|---|---|---|
| 113 | 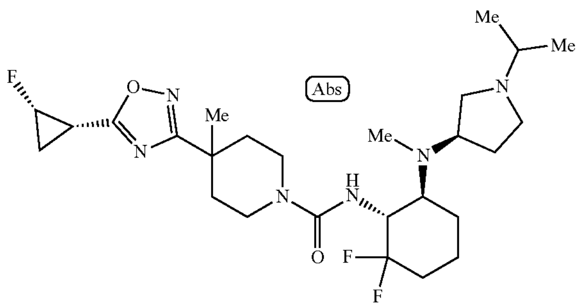 [SMILES: CC(C)N1CC[C@@H](N(C)[C@H]2CCCC(F)(F)[C@@H]2NC(=O)N2CCC(C)(c3noc([C@@H]4C[C@@H]4F)n3)CC2)C1] | $^1$H-NMR (CDCl$_3$) δ: 1.02-1.12 (6H, m), 1.30-1.54 (6H, m), 1.58-1.89 (6H, m), 1.89-2.04 (2H, m), 2.09-2.29 (7H, m), 2.29-2.4 (2H, m), 2.42-2.52 (1H, m), 2.52-2.62 (1H, m), 2.72-2.87 (2H, m), 3.03-3.18 (2H, m), 3.23 (1H, quint, J = 7.6 Hz), 3.63- 3.78 (2H, m), 4.07-4.22 (1H, m), 4.55 (1H, d, J = 7.2 Hz), 4.91 (1H, dddd, J = 64.0, 6.0, 6.0, 3.6 Hz). | Reference example 83 | Reference example 115 |
| 114 | 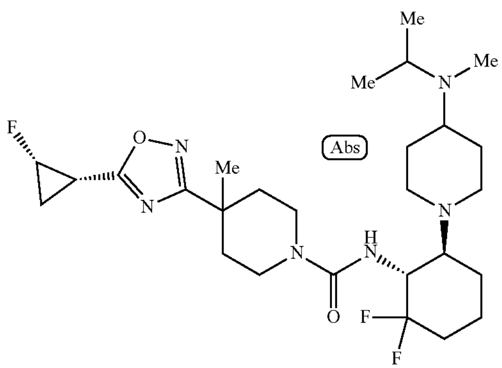 [SMILES: CC(C)N(C)C1CCN([C@H]2CCCC(F)(F)[C@@H]2NC(=O)N2CCC(C)(c3noc([C@@H]4C[C@@H]4F)n3)CC2)CC1] | | Reference example 84 | Reference example 115 |

| Example | Structure | Spectral data | Material A | Material B |
|---|---|---|---|---|
| | | ¹H-NMR (CDCl₃) δ: 0.93-1.05 (6H, m), 1.19-1.30 (2H, m), 1.33 (3H, s), 1.37-1.53 (3H, m), 1.60-1.84 (6H, m), 1.85-2.04 (2H, m), 2.05-2.21 (5H, m), 2.21-2.30 (2H, m), 2.30-2.42 (2H, m), 2.46-2.58 (2H, m), 2.61-2.69 (1H, m), 2.76-2.86 (1H, m), 2.91-3.03 (1H, m), 3.03-3.17 (2H, m), 3.68-3.80 (2H, m), 4.07-4.22 (1H, m), 4.55 (1H, d, J = 7.2 Hz), 4.91 (1H, dddd, J = 64.0, 6.0, 6.0, 3.6 Hz). | 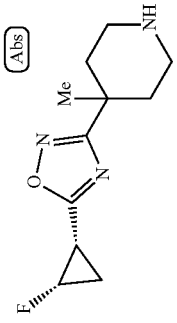 Reference example 85 | 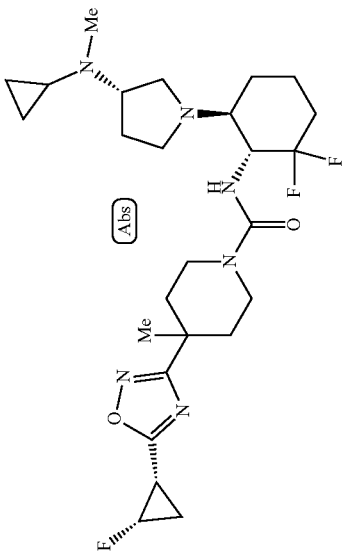 Reference example 115 |
| 115 | 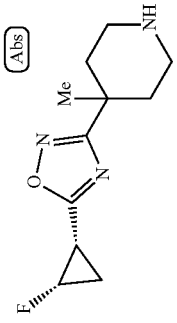 | ¹H-NMR (CDCl₃) δ: 0.36-0.43 (2H, m), 0.43-0.50 (2H, m), 1.33 (3H, s), 1.34-1.53 (3H, m), 1.55-1.77 (5H, m), 1.77-1.86 (1H, m), 1.86-2.04 (3H, m), 2.10-2.30 (6H, m), 2.31-2.42 (1H, m), 2.52-2.73 (3H, m), 2.81 (1H, td, J = 8.4, 4.4 Hz), 2.89 (1H, t, J = 7.6 Hz), 2.98-3.17 (3H, m), 3.62-3.77 (2H, m), 4.09-4.23 (1H, m), 4.54 (1H, d, J = 8.0 Hz), 4.91 (1H, dddd, J = 64.0 6.0, 6.0, 4.0 Hz). | | |

| Example | Structure | Spectral data | Material A | Material B |
|---|---|---|---|---|
| 116 | 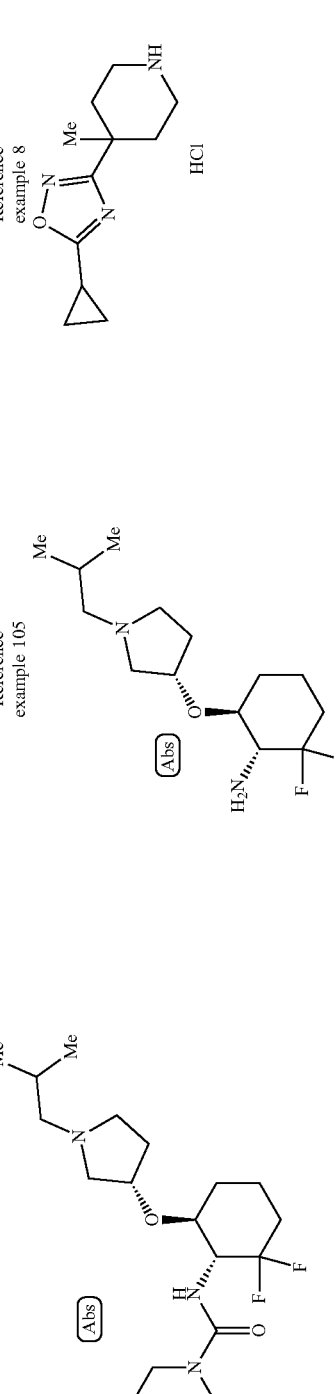 | ¹H-NMR (CDCl₃) δ: 0.89 (3H, d, J = 6.8 Hz), 0.90 (3H, d, J = 6.8 Hz), 1.17-1.24 (4H, m), 1.30 (3H, s), 1.35-1.49 (2H, m), 1.56-1.85 (6H, m), 1.93-2.28 (8H, m), 2.28-2.37 (1H, m), 2.40-2.49 (3H, m), 2.56-2.68 (1H, m), 2.89-2.99 (1H, m), 3.02-3.24 (3H, m), 3.61-3.76 (2H, m), 4.08-4.28 (2H, m), 4.55 (1H, d, J = 9.2 Hz). | Reference example 105 | Reference example 8 HCl |
| 117 | 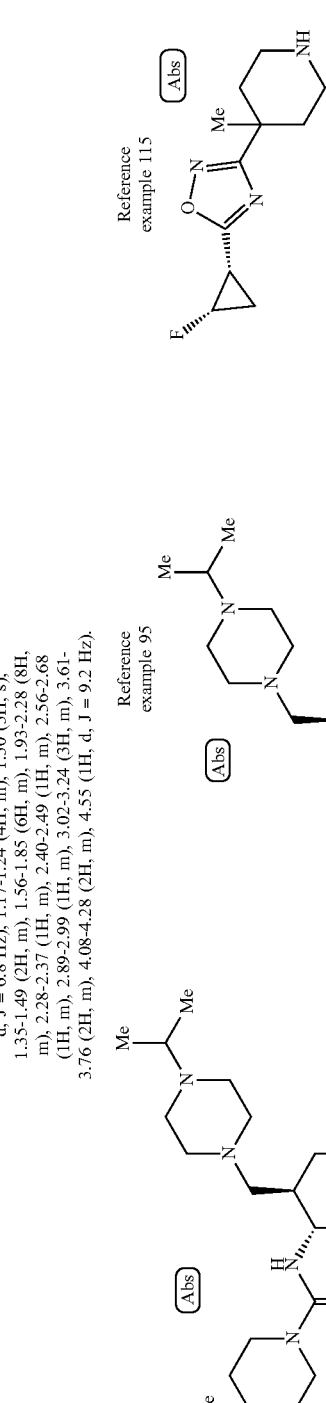 | ¹H-NMR (CDCl₃) δ: 1.05 (6H, d, J = 6.7 Hz), 1.33 (3H, s), 1.43-1.54 (2H, m), 1.57-1.84 (7H, m), 1.88-2.03 (2H, m), 2.10-2.22 (2H, m), 2.22-2.30 (2H, m), 2.31-2.71 (10H, m), 3.02-3.17 (2H, m), 3.64-3.79 (2H, m), 3.88-4.03 (1H, m), 4.91 (1H, dddd, J = 63.6, 6.0, 6.0, 3.6 Hz), 5.05 (1H, d, J = 7.3 Hz). | Reference example 95 | Reference example 115 |

| Example | Structure | Spectral data | Material A | Material B |
|---|---|---|---|---|
| 118 | 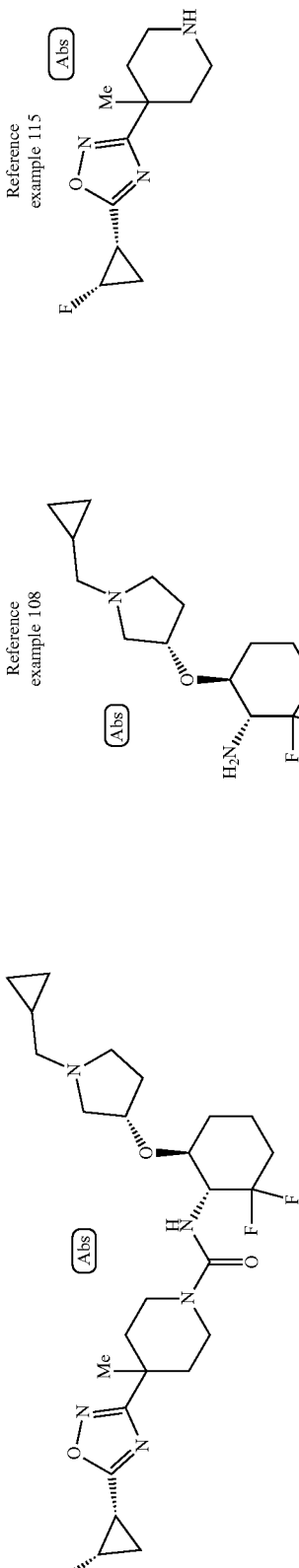 | ¹H-NMR (CDCl₃) δ: 0.13 (2H, d, J = 4.3 Hz), 0.50 (2H, d, J = 7.3 Hz), 0.84-0.95 (1H, m), 1.33 (3H, s), 1.36-1.54 (3H, m), 1.56-1.87 (7H, m), 1.91-2.21 (4H, m), 2.21-2.30 (2H, m), 2.31-2.46 (3H, m), 2.47-2.60 (1H, m), 2.95-3.27 (4H, m), 3.64-3.74 (2H, m), 4.10-4.25 (2H, m), 4.56 (1H, d, J = 8.5 Hz), 4.92 (1H, dddd, J = 63.6, 6.0, 6.0, 3.6 Hz). | Reference example 108 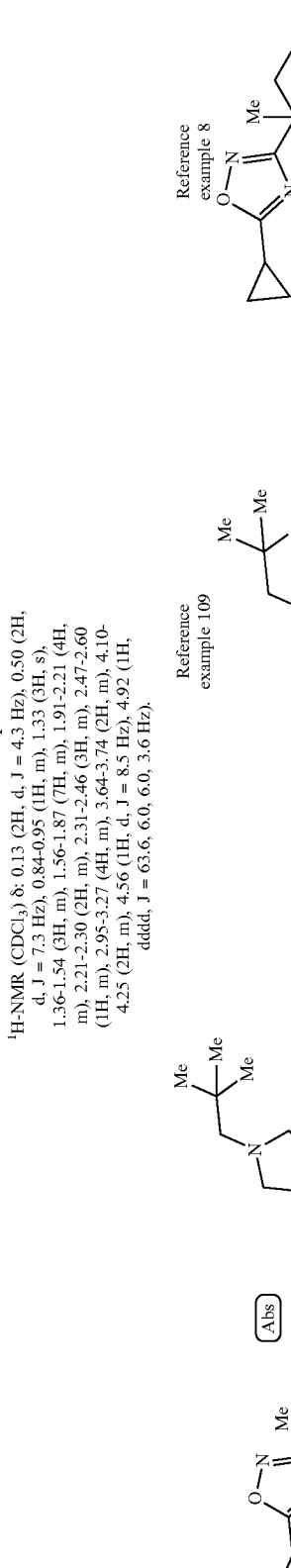 | Reference example 115 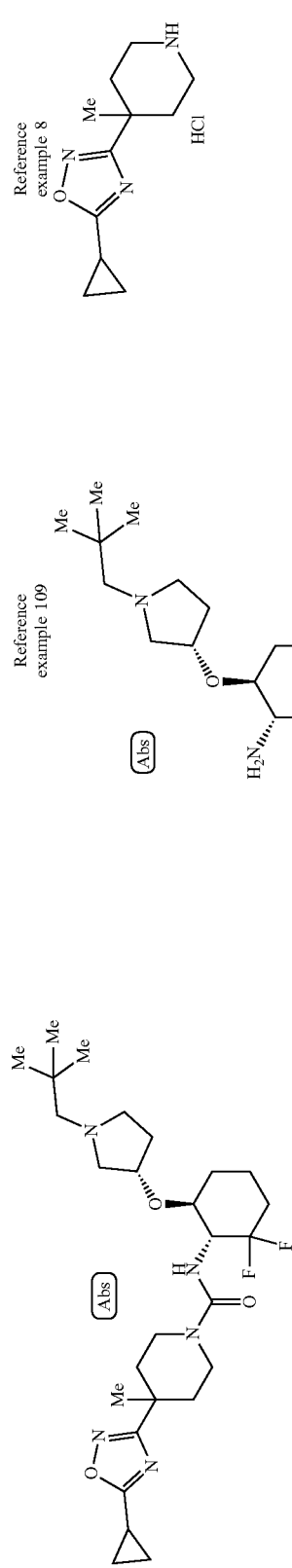 |
| 119 | 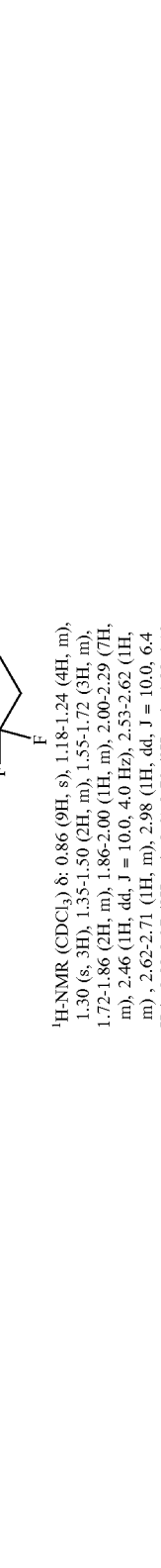 | ¹H-NMR (CDCl₃) δ: 0.86 (9H, s), 1.18-1.24 (4H, m), 1.30 (s, 3H), 1.35-1.50 (2H, m), 1.55-1.72 (3H, m), 1.72-1.86 (2H, m), 1.86-2.00 (1H, m), 2.00-2.29 (7H, m), 2.46 (1H, dd, J = 10.0, 4.0 Hz), 2.53-2.62 (1H, m), 2.62-2.71 (1H, m), 2.98 (1H, dd, J = 10.0, 6.4 Hz), 3.03-3.27 (3H, m), 3.61-3.78 (2H, m), 4.03-4.12 (1H, m), 4.13-4.29 (1H, m), 4.53 (1H, d, J = 9.2 Hz). | Reference example 109 | Reference example 8 |

| Example | Structure | Spectral data | Material A | Material B |
|---|---|---|---|---|
| 120 | 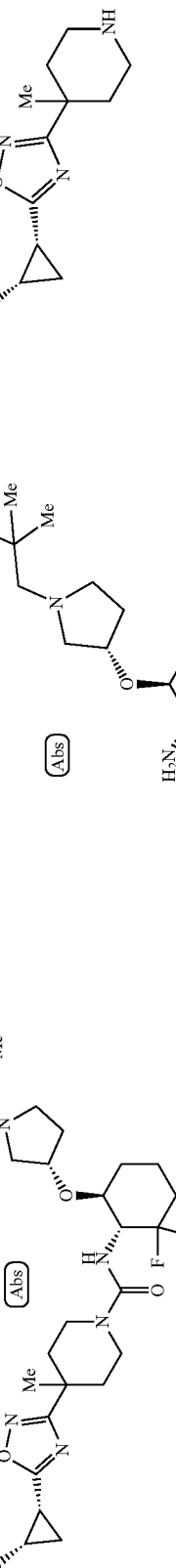 | 1H-NMR (CDCl3) δ: 0.87 (9H, s), 1.33 (3H, s), 1.33-1.54 (3H, m), 1.56-1.85 (6H, m), 1.86-2.31 (7H, m), 2.32-2.42 (1H, m), 2.43-2.52 (1H, m), 2.54-2.75 (2H, m), 2.89-3.26 (4H, m), 3.63-3.80 (2H, m), 4.02-4.12 (1H, m), 4.13-4.29 (1H, m), 4.54 (1H, d, J = 9.2 Hz), 4.92 (1H, dddd, J = 63.6, 6.4, 6.4, 4.0 Hz). | Reference example 109 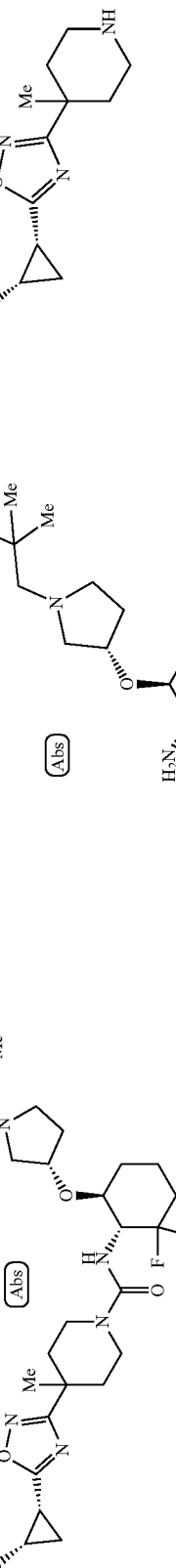 | Reference example 115 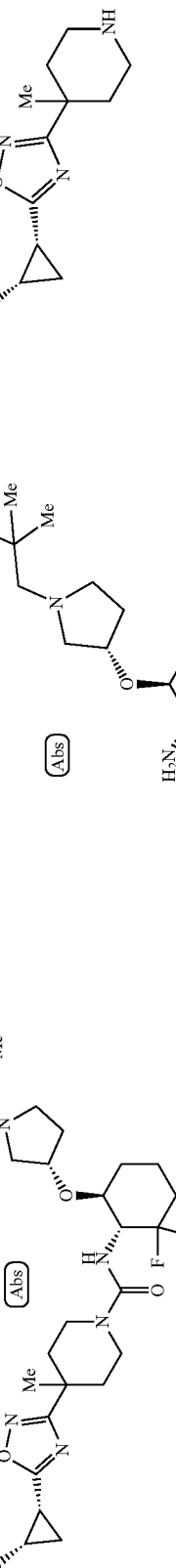 |
| 121 | 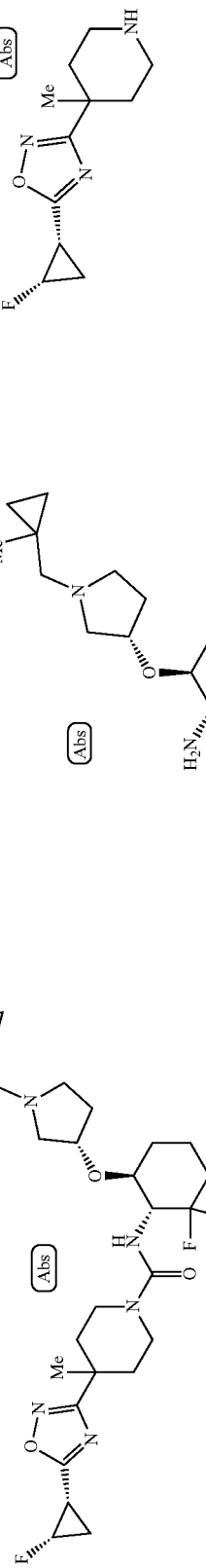 | 1H-NMR (CDCl3) δ: 0.19-0.38 (4H, m), 1.03-1.17 (3H, m), 1.32-1.54 (4H, m), 1.34 (3H, s), 1.56-1.84 (6H, m), 1.90-2.56 (10H, m), 3.01-3.24 (4H, m), 3.63-3.75 (2H, m), 4.10-4.27 (2H, m), 4.57 (1H, d, J = 9.2 Hz), 4.92 (1H, dddd, J = 63.5, 6.0, 6.0, 3.7 Hz). | Reference example 110 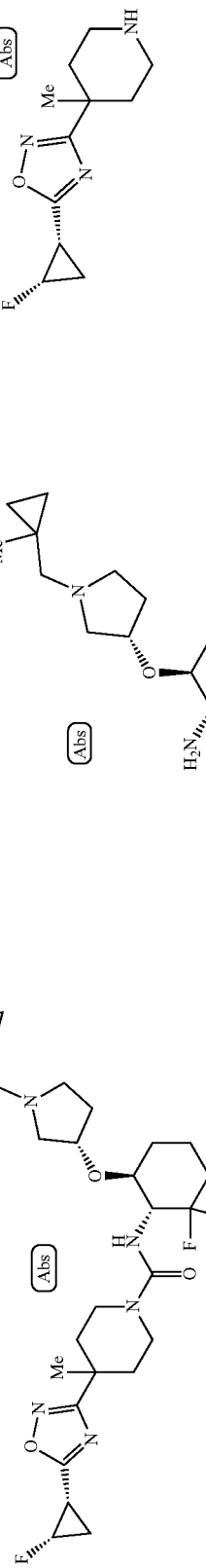 | Reference example 115 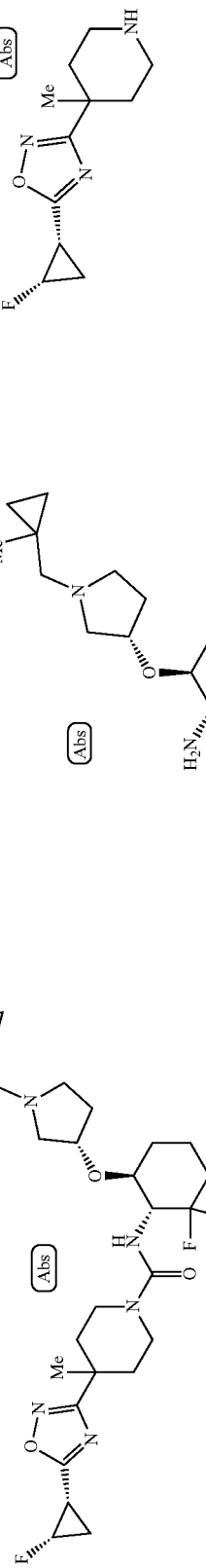 |

| Example | Structure | Spectral data | Material A | Material B |
|---|---|---|---|---|
| 122 | 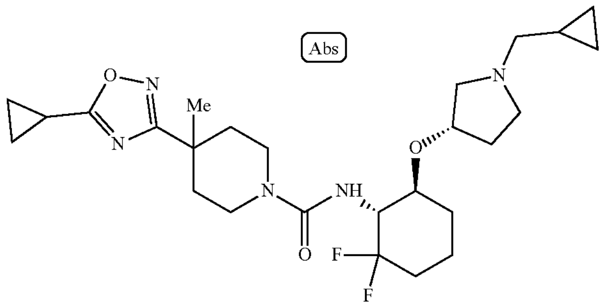 [SMILES: CC1(c2noc(C3CC3)n2)CCN(C(=O)N[C@@H]2[C@@H](O[C@H]3CCN(CC4CC4)C3)CCCC2(F)F)CC1] | ¹H-NMR (CDCl₃) δ: 0.06-0.16 (2H, m), 0.44-0.52 (2H, m), 0.81-0.93 (1H, m), 1.09-1.23 (5H, m), 1.30 (3H, s), 1.34-1.49 (2H, m), 1.54-1.85 (4H, m), 1.94-2.26 (6H, m), 2.26-2.42 (3H, m), 2.46-2.54 (1H, m), 2.70-2.79 (1H, m), 3.02-3.26 (4H, m), 3.61-3.74 (2H, m), 4.09-4.27 (2H, m), 4.56 (1H, d, J = 9.2 Hz). | Reference example 108 | Reference example 8, HCl |
| 123 | 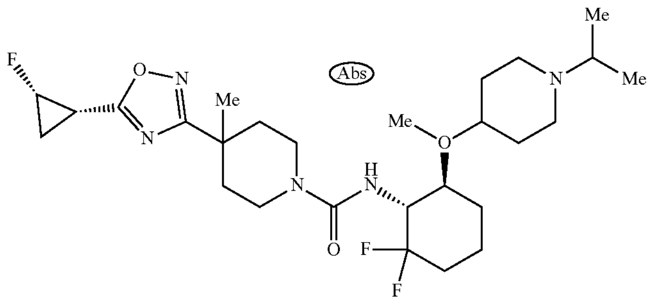 | ¹H-NMR (CDCl₃) δ: 0.97-1.09 (6H, m), 1.32 (3H, s), 1.36-1.53 (4H, m), 1.53-1.69 (3H, m), 1.69-1.87 (4H, m), 1.91-2.04 (2H, m), 2.04-2.20 (3H, m), 2.20-2.28 (5H, m), 2.30-2.42 (2H, m), 2.62-2.77 (2H, m), 2.82-2.95 (2H, m), 3.03-3.15 (2H, m), 3.63- 3.76 (2H, m), 4.03-4.18 (1H, m), 4.52 (1H, d, J = 7.2 Hz), 4.91 (1H, dddd, J = 63.6, 6.0, 6.0, 3.6 Hz). | Reference example 63 | Reference example 115 |

| Example | Structure | Spectral data | Material A | Material B |
|---|---|---|---|---|
| 124 | 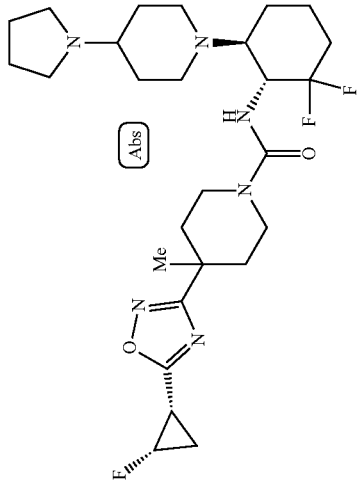 | $^1$H-NMR (CDCl$_3$) δ: 1.18-1.36 (5H, m), 1.36-1.54 (3H, m), 1.60-2.05 (13H, m), 2.06-2.20 (2H, m), 2.21-2.30 (2H, m), 2.34-2.43 (1H, m), 2.45-2.66 (7H, m), 2.74-2.83 (1H, m), 3.01-3.16 (2H, m), 3.72-3.82 (1H, m), 3.72-3.82 (1H, m), 4.09-4.23 (1H, m), 4.57 (1H, d, J = 7.2 Hz), 4.92 (1H, dddd, J = 64.0, 6.0, 6.0, 3.6 Hz). | Reference example 64 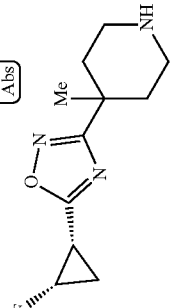 | Reference example 115 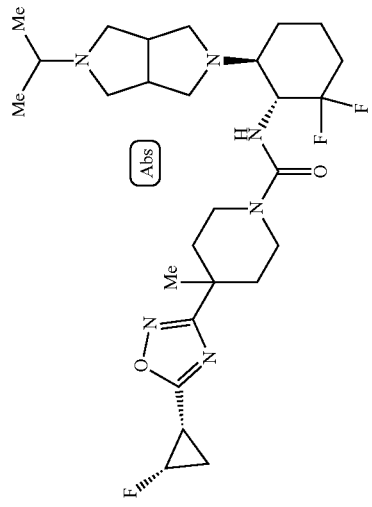 |
| 125 | 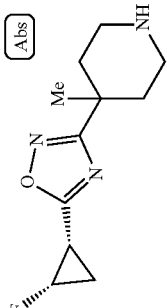 |  | Reference example 65  | Reference example 115 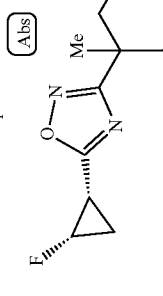 |

| Example | Structure | Spectral data | Material A | Material B |
|---|---|---|---|---|
| 126 | 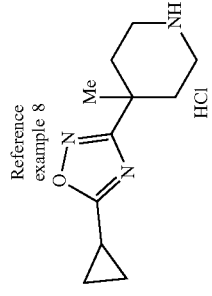 | ¹H-NMR (CDCl₃) δ: 0.97-1.10 (6H, m), 1.21-1.35 (4H, m), 1.35-1.52 (2H, m), 1.62-1.76 (4H, m), 1.76-1.87 (2H, m), 1.87-2.22 (4H, m), 2.22-2.31 (2H, m), 2.31-2.42 (3H, m), 2.48-2.64 (3H, m), 2.64-2.80 (2H, m), 2.98-3.09 (1H, m), 3.09-3.24 (3H, m), 3.58-3.70 (1H, m), 3.76-3.88 (1H, m), 4.07-4.24 (1H, m), 4.52 (1H, d, J = 8.0 Hz), 4.91 (1H, dddd, J = 64.0, 6.0, 6.0, 3.6 Hz). | <br>Reference example 110<br>¹H-NMR (CDCl₃) δ: 0.22-0.34 (4H, m), 1.04-1.24 (8H, m), 1.31 (3H, s), 1.33-1.49 (2H, m), 1.54-1.84 (6H, m), 1.93-2.55 (9H, m), 3.02-3.24 (4H, m), 3.61-3.74 (2H, m), 4.11-4.27 (2H, m), 4.56 (1H, d, J = 9.2 Hz). | 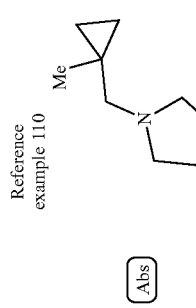<br>Reference example 8 |

| Example | Structure | Spectral data | Material A | Material B |
|---|---|---|---|---|
| 127 | 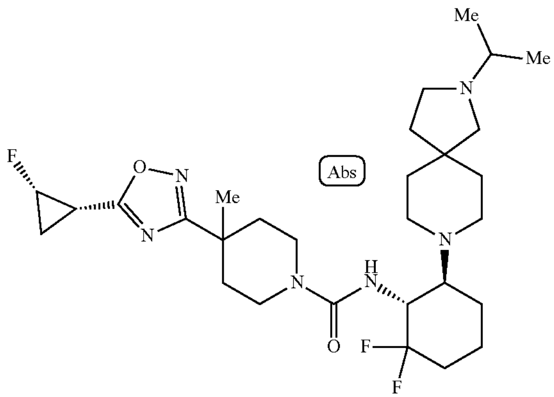 [SMILES: CC(C)N1CCC2(CCN([C@H]3CCCC(F)(F)[C@@H]3NC(=O)N3CCC(C)(c4noc([C@@H]5C[C@@H]5F)n4)CC3)CC2)C1] | $^1$H-NMR (CDCl$_3$) δ: 1.00-1.12 (6H, m), 1.21-1.40 (5H, m), 1.40-1.59 (6H, m), 1.59-1.74 (4H, m), 1.74-1.84 (1H, m), 1.84-2.06 (2H, m), 2.08-2.22 (1H, m), 2.22-2.43 (8H, m), 2.43-2.65 (5H, m), 3.03-3.12 (1H, m), 3.12-3.22 (1H, m), 3.63-3.73 (1H, m), 3.73-3.83 (1H, m), 4.07-4.23 (1H, m), 4.56 (1H, d, J = 8.0 Hz), 4.91 (1H, dddd, J = 63.6, 6.0, 6.0, 3.6 Hz). | Reference example 66 | Reference example 115 |
| 128 | 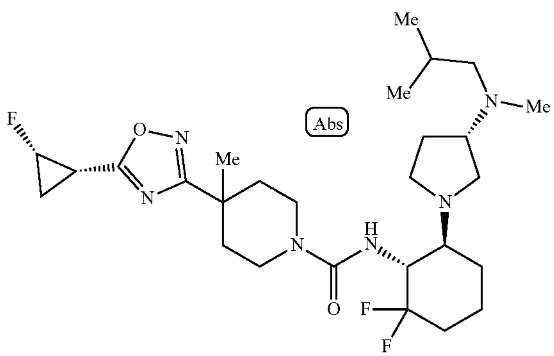 [SMILES: CC(C)CN(C)[C@H]1CCN([C@H]2CCCC(F)(F)[C@@H]2NC(=O)N2CCC(C)(c3noc([C@@H]4C[C@@H]4F)n3)CC2)C1] | | Reference example 86 | Reference example 115 |

| Example | Structure | Spectral data | Material A | Material B |
|---|---|---|---|---|
| 129 | (structure with piperidine-methyloxadiazole-fluorocyclopropyl and fluorocyclohexyl urea) | ¹H-NMR (CDCl₃) δ: 0.86 (6H, d, J = 6.8 Hz), 1.29-1.53 (6H, m), 1.53-1.76 (4H, m), 1.76-2.08 (7H, m), 2.08-2.28 (6H, m), 2.32-2.41 (1H, m), 2.42-2.52 (1H, m), 2.52-2.63 (1H, m), 2.63-2.73 (1H, m), 2.76-2.90 (3H, m), 3.02-3.17 (2H, m), 3.70 (2H, tt, J = 14.8, 4.0 Hz), 4.07-4.22 (1H, m), 4.55 (1H, d, J = 8.0 Hz), 4.91 (1H, dddd, J = 63.6, 6.0, 6.0, 3.6 Hz) | Reference example 67 | Reference example 115 |
| 130 | (structure with methylcyclopropyl-pyrrolidine-oxy-difluorocyclohexyl urea and methylphenyl-methylpiperidine) | ¹H-NMR (CDCl₃) δ: 0.90-1.84 (20H, m), 1.84-2.04 (3H, m), 2.05-2.31 (5H, m), 2.32-2.43 (1H, m), 2.43-2.77 (6H, m), 2.79-2.95 (1H, m), 3.03-3.19 (2H, m), 3.65-3.81 (2H, m), 4.08-4.24 (1H, m), 4.54 (1H, d, J = 7.9 Hz), 4.93 (1H, dddd, J = 63.6, 6.0, 6.0, 3.6 Hz). | Reference example 110 | Commercial product · HCl |

| Example | Structure | Spectral data | Material A | Material B |
|---|---|---|---|---|
| 131 | 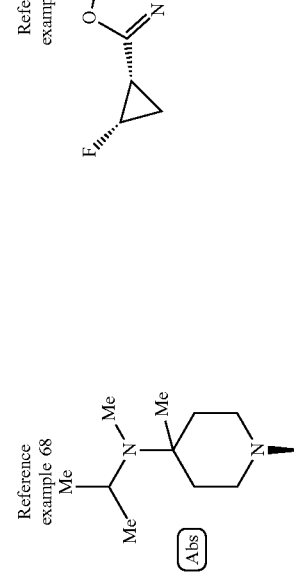 | ¹H-NMR (CDCl₃) δ: 0.16-0.48 (4H, m), 0.98-1.28 (4H, m), 1.25 (3H, s), 1.30-1.50 (2H, m), 1.50-1.89 (7H, m), 1.95-2.21 (5H, m), 2.22-2.65 (2H, m), 2.33 (3H, s), 3.11-3.24 (1H, m), 3.25-3.41 (2H, m), 3.41-3.67 (3H, m), 4.10-4.27 (2H, m), 4.58 (1H, d, J = 7.9 Hz), 7.16 (2H, d, J = 7.9 Hz), 7.21 (2H, d, J = 7.9 Hz). | Reference example 68 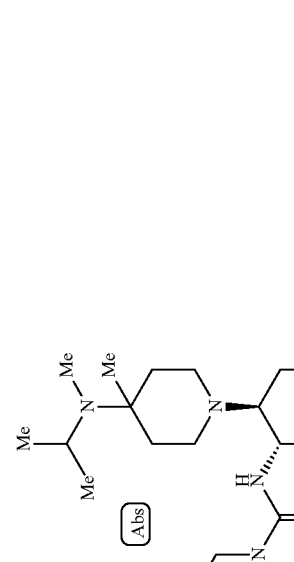 | Reference example 115 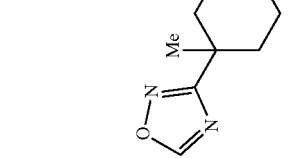 |
| 132 | 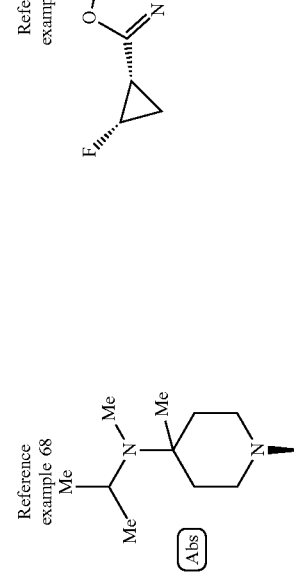 | ¹H-NMR (CDCl₃) δ: 0.88 (3H, s), 0.92-0.98 (6H, m), 1.22-1.52 (8H, m), 1.60-1.84 (6H, m), 1.89-2.03 (2H, m), 2.04 (3H, s), 2.09-2.31 (4H, m), 2.31-2.41 (1H, m), 2.41-2.55 (3H, m), 2.70-2.80 (1H, m), 3.00-3.23 (2H, m), 3.64-3.75 (1H, m), 3.75-3.85 (1H, m), 4.06-4.22 (1H, m), 4.58 (1H, d, J = 7.2 Hz), 4.91 (1H, dddd, J = 63.6, 6.0, 6.0, 3.6 Hz). | Reference example 94 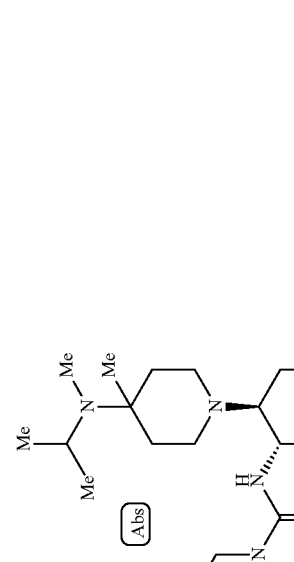 | Reference example 115 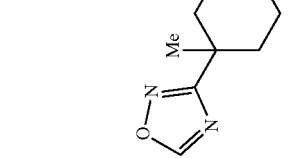 |

| Example | Structure | Spectral data | Material A | Material B |
|---|---|---|---|---|
| 133 | 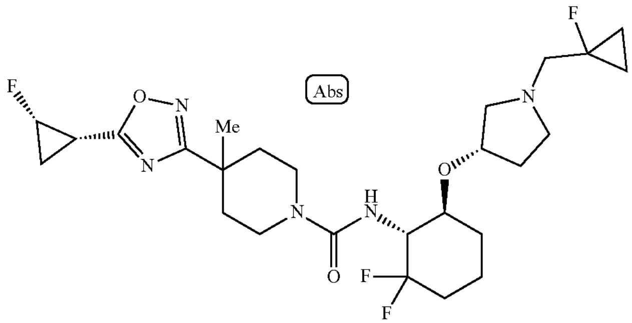 [SMILES: CC1(c2noc([C@@H]3C[C@@H]3F)n2)CCN(C(=O)N[C@@H]2[C@@H](O[C@H]3CCN(CC4(F)CC4)C3)CCCC2(F)F)CC1] | ¹H-NMR (CDCl₃) δ: 1.04 (6H, d, J = 6.7 Hz), 1.31 (3H, s), 1.41-2.05 (9H, m), 2.14-2.27 (3H, m), 2.31-2.59 (5H, m), 2.64-2.77 (1H, m), 2.85-2.96 (1H, m), 2.99-3.10 (2H, m), 3.46-3.74 (6H, m), 4.46-4.53 (1H, m), 4.53-4.68 (1H, m), 4.91 (1H, dddd, J = 63.6, 6.0, 6.0, 3.6 Hz). | Reference example 111 | Reference example 115 |
| 134 | 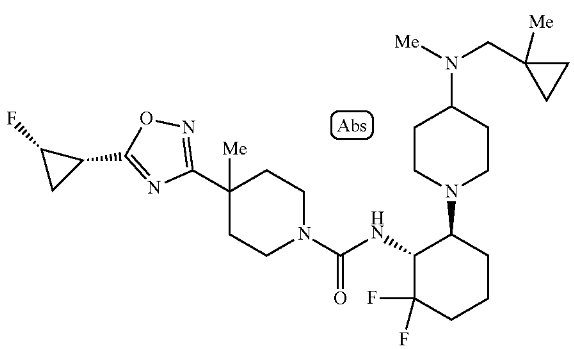 [SMILES: CN(CC1(F)CC1)C1CCN([C@H]2CCCC(F)(F)[C@@H]2NC(=O)N2CCC(C)(c3noc([C@@H]4C[C@@H]4F)n3)CC2)CC1] | ¹H-NMR (CDCl₃) δ: 0.57-0.69 (2H, m), 0.99-1.10 (2H, m), 1.33 (3H, s), 1.35-1.53 (3H, m), 1.58-1.89 (4H, m), 1.91-2.20 (5H, m), 2.20-2.30 (2H, m), 2.32-2.41 (1H, m), 2.41-2.49 (1H, m), 2.51-2.61 (1H, m), 2.75-2.94 (3H, m), 3.04-3.26 (4H, m), 3.65-3.75 (2H, m), 4.13-4.27 (2H, m), 4.58 (1H, d, J = 9.2 Hz), 4.92 (1H, dddd, J = 63.6, 6.0, 6.0, 3.6 Hz). | Reference example 69 | Reference example 115 |

| Example | Structure | Spectral data | Material A | Material B |
|---|---|---|---|---|
| | | -continued | | |
| | | ¹H-NMR (CDCl₃) δ: 0.14-0.34 (4H, m), 0.98-1.10 (3H, m), 1.18-1.37 (6H, m), 1. 37-1.54 (3H, m), 1.54-1.74 (2H, m), 1.74-1.84 (2H, m), 1.84-2.03 (2H, m), 2.03-2.42 (12H, m), 2.46-2.57 (2H, m), 2.62-2.72 (1H, m), 2.79-2.90 (1H, m), 3.01-3.20 (2H, m), 3.65-3.74 (1H, m), 3.74-3.85 (1H, m), 4.07-4.21 (1H, m), 4.55 (1H, d, J = 7.3 Hz), 4.92 (1H, dddd, J = 63.6, 6.0, 6.0, 3.6 Hz). | | |
| 135 | 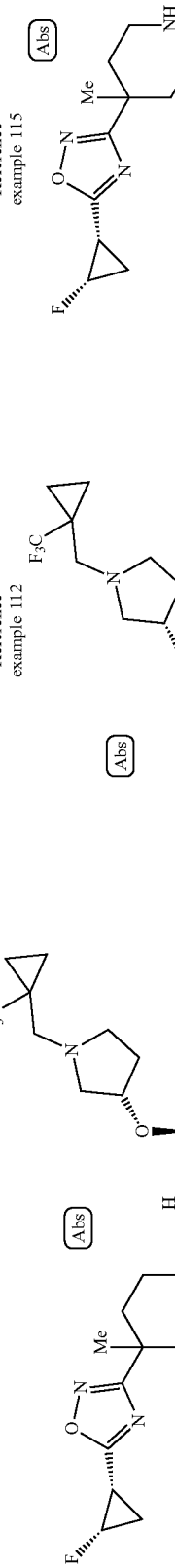 | ¹H-NMR (CDCl₃) δ: 0.58-0.72 (2H, m), 0.93-1.02 (2H, m), 1.29-1.54 (4H, m), 1.33 (3H, s), 1.55-1.84 (4H, m), 1.90-2.03 (2H, m), 2.03-2.21 (2H, m) , 2.21-2.30 (2H, m), 2.30-2.50 (3H, m), 2.55-2.82 (3H, m), 3.00-3.24 (4H, m), 3.65-3.75 (2H, m), 4.08-4.27 (2H, m), 4.56 (1H, d, J = 9.2 Hz), 4.92 (1H, dddd, J = 63.6, 6.0, 6.0, 3.6 Hz). | Reference example 112 | Reference example 115 |
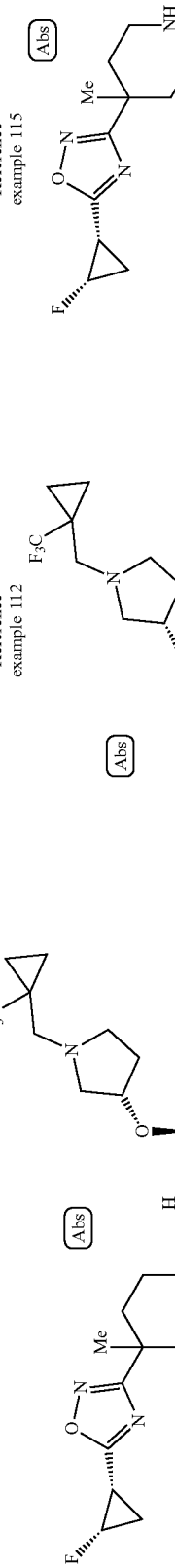

| Example | Structure | Spectral data | Material A | Material B |
|---|---|---|---|---|
| 136 | 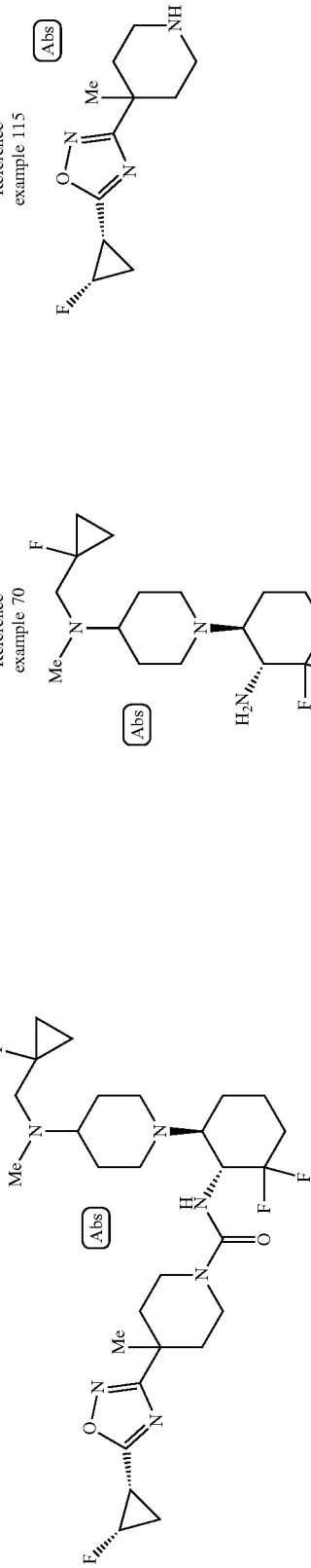 | ¹H-NMR (CDCl₃) δ: 0.52-0.66 (2H, m), 0.99-1.09 (2H, m), 1.16-1.36 (3H, m), 1.33 (3H, s), 1.36-1.53 (3H, m), 1.53-1.84 (5H, m), 1.84-2.03 (2H, m), 2.04-2.20 (2H, m), 2.21-2.31 (2H, m), 2.31-2.47 (5H, m), 2.47-2.60 (2H, m), 2.63-2.92 (4H, m), 3.04-3.19 (2H, m), 3.68-3.79 (2H, m), 4.08-4.23 (1H, m), 4.49-4.62 (1H, m), 4.92 (1H, dddd, J = 63.6, 6.0, 6.0, 3.6 Hz). | Reference example 70 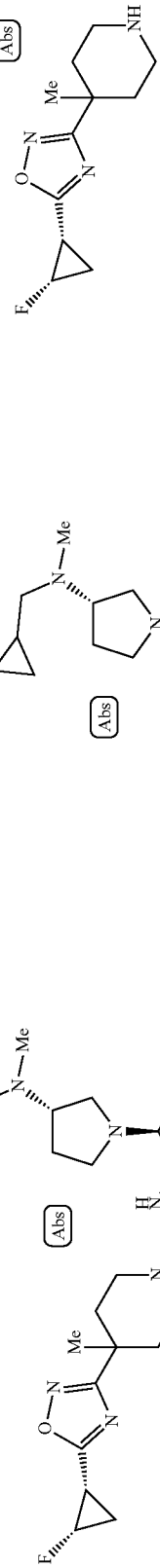 | Reference example 115 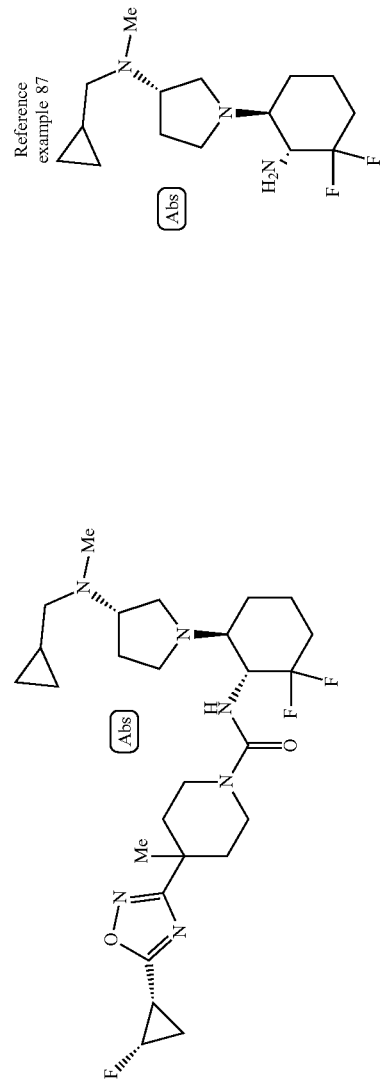 |
| 137 | 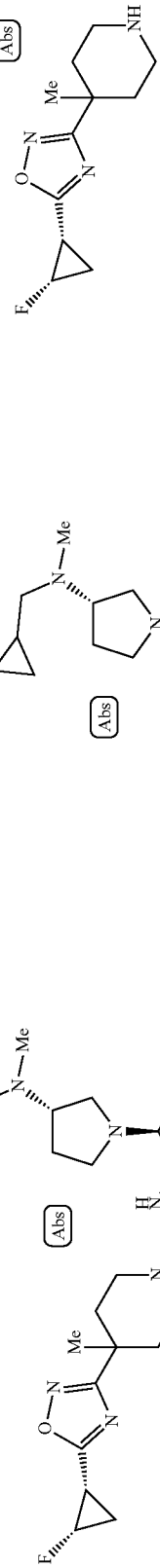 | | Reference example 87 | Reference example 115 |

| Example | Structure | Spectral data | Material A | Material B |
|---|---|---|---|---|
| | | ¹H-NMR (CDCl₃) δ: 0.13-0.33 (2H, m), 0.52-0.74 (2H, m), 0.90-1.14 (1H, m), 1.23-1.38 (5H, m), 1.38-1.55 (2H, m), 1.57-1.69 (2H, m), 1.69-1.87 (2H, m), 1.87-2.05 (4H, m), 2.10-2.27 (4H, m), 2.32-2.41 (2H, m), 2.41-2.62 (4H, m), 2.62-2.73 (2H, m), 2.90-3.04 (2H, m), 3.04-3.17 (2H, m), 3.52-3.75 (2H, m), 4.06-4.23 (1H, m), 4.51-4.64 (1H, m), 4.92 (1H, dddd, J = 64.0, 6.0, 6.0, 3.6 Hz). | | |
| 138 | 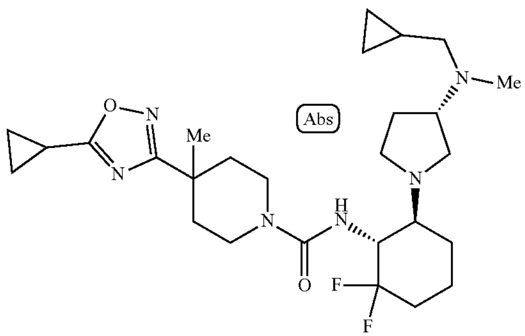 [SMILES: CN(CC1CC1)[C@H]1CCN([C@H]2CCCC(F)(F)[C@@H]2NC(=O)N2CCC(C)(c3noc(C4CC4)n3)CC2)C1] | ¹H-NMR (CDCl₃) δ: 0.05-0.24 (2H, m), 0.44-0.63 (2H, m), 0.80-1.00 (1H, m), 1.13 (4H, d, J = 6.0 Hz), 1.17-1.23 (4H, m), 1.24-1.50 (5H, m), 1.54-1.86 (4H, m), 1.86-1.99 (2H, m), 2.11-2.24 (4H, m), 2.24-2.45 (4H, m), 2.52-2.73 (2H, m), 2.82-2.96 (2H, m), 3.00-3.16 (2H, m), 3.58-3.72 (2H, m), 4.06-4.22 (1H, m), 4.55 (1H, d, J = 8.0 Hz). | Reference example 87 | Reference example 8 |

| Example | Structure | Spectral data | Material A | Material B |
|---|---|---|---|---|
| 139 | (structure shown) | $^1$H-NMR (CDCl$_3$) δ: 1.01 (6H, d, J = 6.4 Hz), 1.16-1.24 (6H, m), 1.30 (3H, s), 1.54-1.70 (3H, m), 1.81-1.88 (2H, m), 2.09-2.31 (5H, m), 2.34-2.53 (6H, m), 2.53-2.63 (1H, m), 2.67-2.76 (2H, m), 3.04-3.18 (2H, m), 3.62-3.72 (1H, m), 3.72-3.88 (2H, m), 4.19 (1H, dddd, J = 63.6, 6.0, 6.0, 3.6 Hz), 4.68 (1H, d, J = 6.1 Hz). | Reference example 123 | Reference example 8, HCl |
| 140 | (structure shown, Abs) | $^1$H-NMR (CDCl$_3$) δ: 0.57-0.64 (2H, m), 0.87-0.93 (2H, m), 1.10-1.53 (9H, m), 1.54-1.73 (4H, m), 1.74-1.84 (1H, m), 1.84-1.91 (1H, m), 1.91-2.11 (2H, m), 2.11-2.30 (7H, m), 2.31-2.40 (1H, m), 2.45-2.55 (2H, m), 2.55-2.69 (3H, m), 2.80-2.87 (1H, m), 3.02-3.19 (2H, m), 3.65-3.83 (2H, m), 4.06-4.21 (1H, m), 4.53 (1H, dddd, J = 63.6, 6.0, 6.0, 3.6 Hz), 4.83-5.00 (1H, m). | Reference example 71 | Reference example 115 |

-continued

| Example | Structure | Spectral data | Material A | Material B |
|---|---|---|---|---|
| 141 | 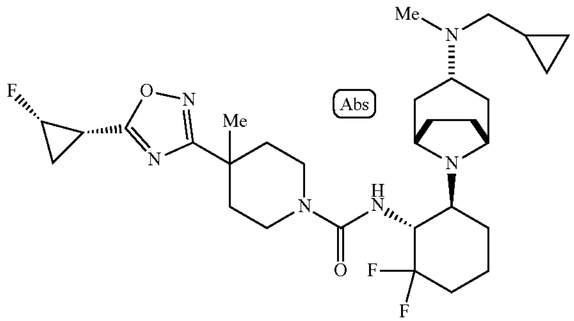 [SMILES: CN(CC1CC1)[C@@H]1C[C@H]2CC[C@@H](C1)N2[C@H]1CCCC(F)(F)[C@@H]1NC(=O)N1CCC(C)(c2noc([C@@H]3C[C@@H]3F)n2)CC1] | ¹H-NMR (CDCl₃) δ: 0.00-0.06 (2H, m), 0.42-0.49 (2H, m), 0.72-0.83 (1H, m), 1.19-1.42 (3H, m), 1.31 (3H, s), 1.42-1.82 (13H, m), 1.89-2.02 (1H, m), 2.05-2.16 (1H, m), 2.16-2.28 (7H, m), 2.30-2.40 (1H, m), 2.51-2.60 (1H, m), 2.72-2.85 (1H, m), 2.99-3.09 (1H, m), 3.09-3.18 (1H, m), 3.20-3.26 (1H, m), 3.36-3.41 (1H, m), 3.65-3.74 (1H, m), 3.77-3.85 (1H, m), 3.97-4.10 (1H, m), 4.67 (1H, d, J = 7.3 Hz), 4.90 (1H, dddd, J = 63.6, 6.0, 6.0, 3.6 Hz). | Reference example 72 | Reference example 115 |
| 142 | 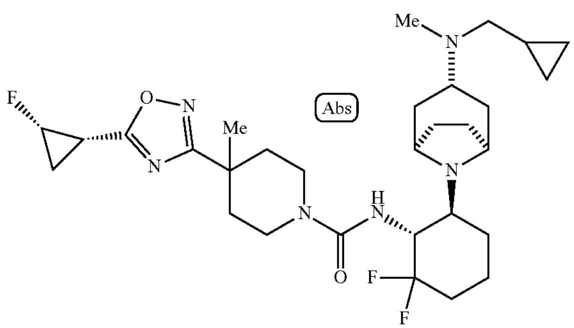 [SMILES: CN(CC1CC1)[C@H]1C[C@H]2CC[C@@H](C1)N2[C@H]1CCCC(F)(F)[C@@H]1NC(=O)N1CCC(C)(c2noc([C@@H]3C[C@@H]3F)n2)CC1] | ¹H-NMR (CDCl₃) δ: 0.01-0.22 (2H, m), 0.39-0.64 (2H, m), 0.77-0.97 (1H, m), 1.13-1.52 (6H, m), 1.52-1.87 (13H, m), 1.89-2.03 (1H, m), 2.03-2.72 (10H, m), 3.01-3.32 (4H, m), 3.33-3.50 (1H, m), 3.60-3.72 (1H, m), 3.74-3.87 (1H, m), 3.95-4.12 (1H, m), 4.65 (1H, d, J = 7.9 Hz), 4.91 (1H, dddd, J = 63.6, 6.0, 6.0, 3.6 Hz). | Reference example 73 | Reference example 115 |

| Example | Structure | Spectral data | Material A | Material B |
|---|---|---|---|---|
| 143 | 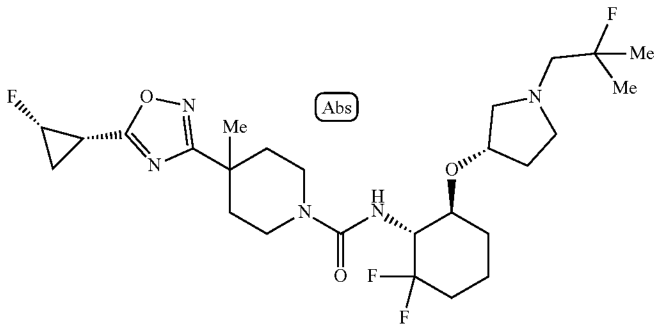 [SMILES: CC(C)(F)CN1CC[C@H](O[C@H]2CCCC(F)(F)[C@@H]2NC(=O)N2CCC(C)(c3noc([C@@H]4C[C@@H]4F)n3)CC2)C1] | $^1$H-NMR (CDCl$_3$) δ: 1.17-1.86 (18H, m), 1.88-2.20 (5H, m), 2.20-2.30 (2H, m), 2.30-2.42 (1H, m), 2.44-3.03 (3H, m), 3.04-3.24 (4H, m), 3.61-3.75 (2H, m), 4.09-4.28 (2H, m), 4.60 (1H, d, J = 9.2 Hz), 4.91 (1H, dddd, J = 63.6, 6.0, 6.0, 3.6 Hz). | Reference example 113 | Reference example 115 |
| 144 | 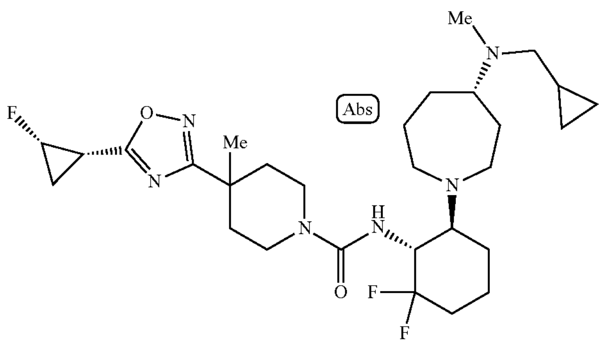 [SMILES: CN(CC1CC1)[C@H]1CCCN([C@H]2CCCC(F)(F)[C@@H]2NC(=O)N2CCC(C)(c3noc([C@@H]4C[C@@H]4F)n3)CC2)CC1] | $^1$H-NMR (CDCl$_3$) δ: 0.02-0.10 (2H, m), 0.44-0.52 (2H, m), 0.76-0.87 (1H, m), 1.24-1.52 (10H, m), 1.58-1.87 (5H, m), 1.89-2.01 (2H, m), 2.06-2.16 (1H, m), 2.16-2.30 (8H, m), 2.30-2.40 (1H, m), 2.46-2.79 (6H, m), 3.03-3.19 (2H, m), 3.65-3.78 (2H, m), 4.02-4.16 (1H, m), 4.61 (1H, d, J = 7.3 Hz), 4.90 (1H, dddd, J = 63.6, 6.0, 6.0, 3.6 Hz). | Reference example 74 | Reference example 115 |

-continued

| Example | Structure | Spectral data | Material A | Material B |
|---|---|---|---|---|
| 145 | 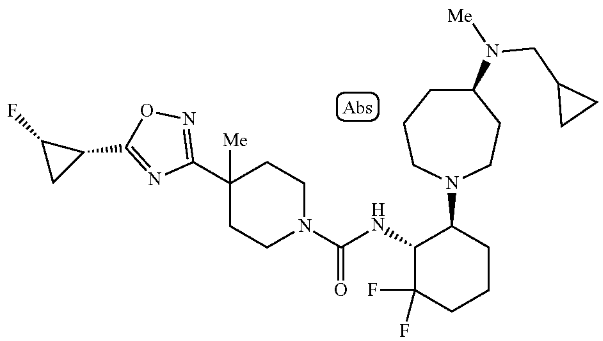 [SMILES: CN(CC1CC1)[C@@H]1CCCN([C@H]2CCCC(F)(F)[C@@H]2NC(=O)N2CCC(C)(c3noc([C@@H]4C[C@@H]4F)n3)CC2)CC1] | ¹H-NMR (CDCl₃) δ: 0.05-0.19 (2H, m), 0.47-0.60 (2H, m), 0.83-0.98 (1H, m), 1.21-1.53 (10H, m), 1.53-2.03 (7H, m), 2.07-2.19 (1H, m), 2.19-2.66 (13H, m), 2.68-2.83 (2H, m), 3.03-3.15 (2H, m), 3.62-3.80 (2H, m), 4.01-4.18 (1H, m), 4.59 (1H, d, J = 7.9 Hz), 4.91 (1H, dddd, J = 63.6, 6.0, 6.0, 3.6 Hz). | Reference example 75 | Reference example 115 |
| 146 | 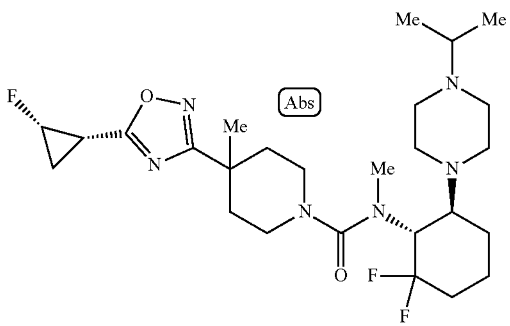 [SMILES: CC(C)N1CCN([C@H]2CCCC(F)(F)[C@@H]2N(C)C(=O)N2CCC(C)(c3noc([C@@H]4C[C@@H]4F)n3)CC2)CC1] | ¹H-NMR (CDCl₃) δ: 1.03 (6H, d, J = 6.7 Hz), 1.27-1.39 (5H, m), 1.39-1.51 (1H, m), 1.52-1.83 (4H, m), 1.89-2.13 (3H, m), 2.17-2.28 (2H, m), 2.29-2.58 (7H, m), 2.58-2.69 (1H, m), 2.75-2.99 (7H, m), 2.99-3.09 (1H, m), 3.34-3.46 (2H, m), 4.35-4.49 (1H, m), 4.89 (1H, dddd, J = 63.6, 6.0, 6.0, 3.6 Hz). | Reference example 120 | Reference example 115 |

| Example | Structure | Spectral data | Material A | Material B |
|---|---|---|---|---|
| 147 | 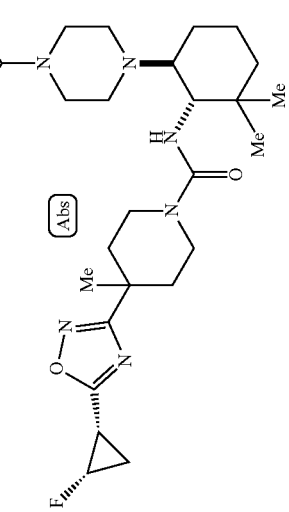 | 1H-NMR (CDCl3) δ: 0.86 (3H, s), 0.90 (3H, s), 1.01 (3H, d, J = 6.8 Hz), 1.02 (3H, d, J = 6.8 Hz), 1.10-1.33 (6H, m), 1.31 (3H, s), 1.35-1.49 (2H, m), 1.55-1.72 (3H, m), 1.84-1.93 (1H, m), 2.13-2.28 (3H, m), 2.30-2.59 (8H, m), 2.66-2.75 (2H, m), 3.09-3.18 (2H, m), 3.28-3.35 (1H, m), 3.53 (1H, d, J = 11.6 Hz), 3.67-3.79 (2H, m). | Reference example 121 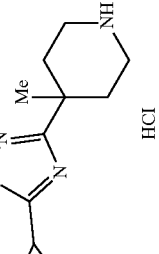 | Reference example 8 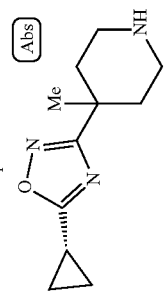 HCl |
| 148 | 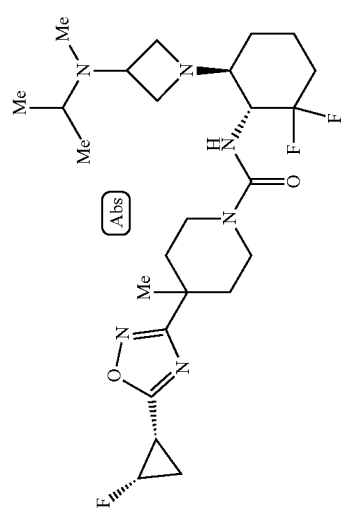 | 1H-NMR (CDCl3) δ: 1.15-1.30 (6H, m), 1.33 (3H, s), 1.37-1.57 (3H, m), 1.57-1.85 (6H, m), 1.85-2.03 (3H, m), 2.11-2.30 (3H, m), 2.30-2.61 (4H, m), 3.10-3.22 (2H, m), 3.22-3.42 (1H, m), 3.47-3.68 (4H, m), 3.68-3.77 (1H, m), 3.77-3.84 (1H, m), 4.04-4.25 (1H, m), 4.91 (1H, dddd, J = 63.6, 6.0, 6.0, 3.6 Hz). | Reference example 76 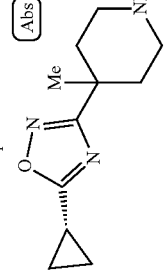 | Reference example 115  |

| Example | Structure | Spectral data | Material A | Material B |
|---|---|---|---|---|
| 149 | 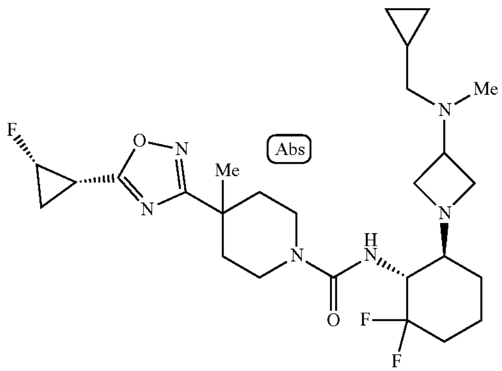 [SMILES: CN(CC1CC1)C1CN([C@H]2CCCC(F)(F)[C@@H]2NC(=O)N2CCC(C)(c3noc([C@@H]4C[C@@H]4F)n3)CC2)C1] | ¹H-NMR (CDCl₃) δ: 0.02-0.19 (2H, m), 0.44-0.59 (2H, m), 0.75-0.90 (1H, m), 1.12-1.28 (1H, m), 1.32 (3H, s), 1.40-1.55 (2H, m), 1.55-1.70 (3H, m), 1.70-1.82 (2H, m), 1.84-2.04 (4H, m), 2.08-2.29 (8H, m), 2.98-3.20 (4H, m), 3.46-3.56 (2H, m), 3.66-3.76 (2H, m), 4.08-4.23 (1H, m), 4.59-4.73 (1H, m) 4.91 (1H, dddd, J = 64.0, 6.0, 6.0, 4.0 Hz). | Reference example 77 | Reference example 115 |
| 150 | 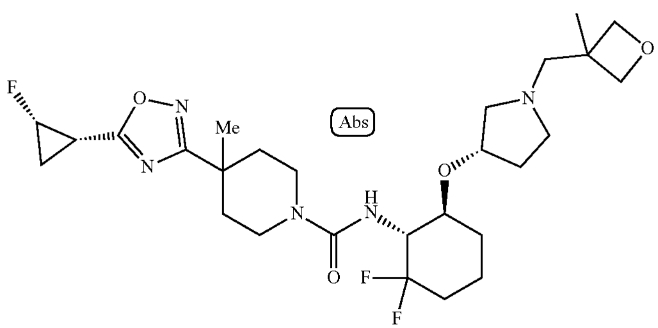 [SMILES: CC1(CN2CC[C@H](O[C@H]3CCCC(F)(F)[C@@H]3NC(=O)N3CCC(C)(c4noc([C@@H]5C[C@@H]5F)n4)CC3)C2)COC1] | ¹H-NMR (CDCl₃) δ: 1.32-1.55 (6H, m), 1.35 (3H, s), 1.58-1.86 (6H, m), 1.91-2.11 (3H, m), 2.11-2.21 (1H, m), 2.22-2.31 (2H, m), 2.32-3.05 (6H, m), 3.06-3.24 (3H, m), 3.64-3.76 (2H, m) , 4.08-4.28 (2H, m), 4.30-4.35 (2H, m), 4.44-4.51 (2H, m), 4.60 (1H, d, J = 8.5 Hz), 4.93 (1H, dddd, J = 63.6, 6.0, 6.0, 3.6 Hz). | Reference example 114 | Reference example 115 |

-continued

| Example | Structure | Spectral data | Material A | Material B |
|---|---|---|---|---|
| 151 | 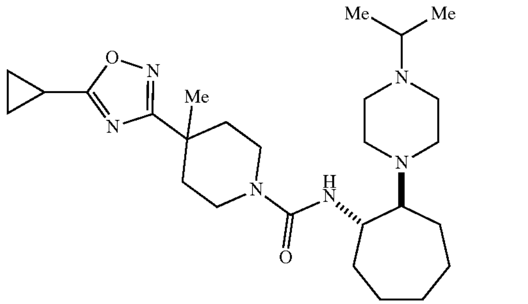 [SMILES: CC(C)N1CCN([C@H]2CCCCC[C@@H]2NC(=O)N2CCC(C)(c3noc(C4CC4)n3)CC2)CC1] | | Reference example 122 | Reference example 115 |
| 152 | 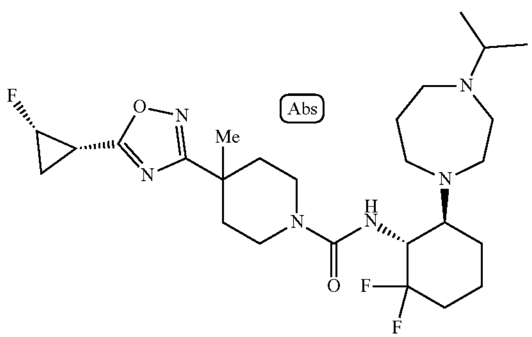 [SMILES: CC(C)N1CCCN([C@H]2CCCC(F)(F)[C@@H]2NC(=O)N2CCC(C)(c3noc([C@@H]4C[C@@H]4F)n3)CC2)CC1] | $^1$H-NMR (CDCl$_3$) δ: 1.07 (6H, d, J = 5.5 Hz), 1.14-1.25 (6H, m), 1.31 (3H, s), 1.31-1.43 (2H, m), 1.43-1.79 (4H, m), 1.83-1.93 (1H, m), 2.13-2.26 (4H, m), 2.26-2.82 (12H, m), 3.01-3.16 (2H, m), 3.29-3.42 (1H, 3.59-3.76 (2H, m), 5.80-6.06 (1H, brs). | Reference example 78 | Reference example 115 |
|  |  | $^1$H-NMR (CDCl$_3$) δ: 0.90-1.12 (6H, m), 1.22-1.53 (7H, m), 1.54-2.05 (7H, m), 2.08-2.20 (1H, m), 2.20-(2H, m), 2.30-2.40 (1H, m), 2.48-3.04 (10H, m), 3.04-3.17 (2H, m), 3.66-3.80 (2H, m), 4.02-4.17 (1H, m), 4.72 (1H, s), 4.90 (1H, dddd, J = 63.6, 6.0, 6.0, 3.6 Hz). |  |  |

| Example | Structure | Spectral data | Material A | Material B |
|---|---|---|---|---|
| 153 |  | $^1$H-NMR (CDCl$_3$) δ: 0.89-1.17 (6H, m), 1.33 (3H, s), 1.42-1.69 (6H, m), 1.69-1.89 (2H, m), 1.91-2.04 (1H, m), 2.04-2.14 (1H, m), 2.14-2.82 (8H, m), 2.99-3.13 (2H, m), 3.28-3.77 (6H, m), 4.20-4.35 (1H, m), 4.68-4.80 (1H, m), 4.92 (1H, dddd, J = 63.6, 6.0, 6.0, 3.6 Hz), 4.94 (1H, d, J = 8.5 Hz). | Reference example 125 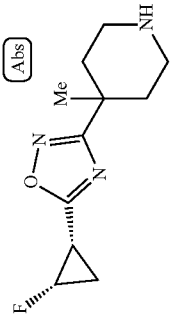 | Reference example 115  |
| 154 | 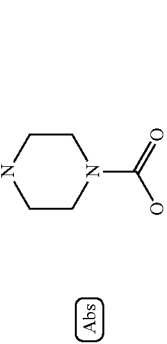 | $^1$H-NMR (CDCl$_3$) δ: 1.03-1.21 (6H, m), 1.35 (3H, s), 1.41-1.90 (8H, m), 1.91-2.61 (11H, m), 2.61-2.71 (1H, m), 2.71-3.04 (4H, m), 3.05-3.21 (2H, m), 3.64-3.79 (2H, m), 4.11-4.27 (1H, m), 4.63 (1H, d, J = 9.8 Hz), 4.93 (1H, dddd, J = 63.6, 6.0, 6.0, 3.6 Hz). | Reference example 88 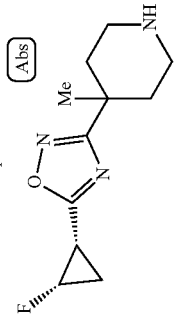 | Reference example 115 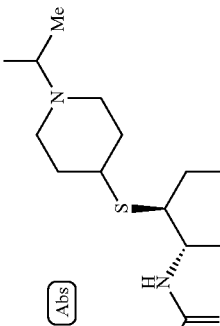 |

| Example | Structure | Spectral data | Material A | Material B |
|---|---|---|---|---|
| 155 | 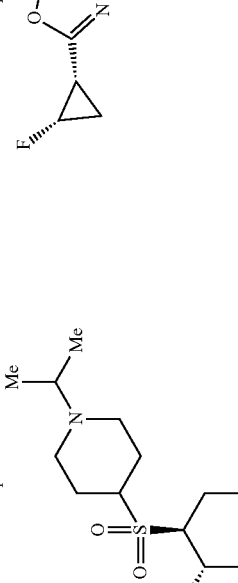 | ¹H-NMR (CDCl₃) δ: 0.93-1.14 (6H, m), 1.33 (3H, s), 1.43-1.54 (1H, m), 1.54-1.81 (5H, m), 1.82-2.32 (11H, m), 2.32-2.45 (2H, m), 2.71-2.85 (1H, m), 2.96-3.24 (6H, m), 3.66-3.82 (2H, m), 4.67-4.80 (1H, m), 4.92 (1H, dddd, J = 63.6, 6.0, 6.0, 3.6 Hz), 4.93 (1H, d, J = 9.2 Hz). | Reference example 126  | Reference example 115  |
| 156 | 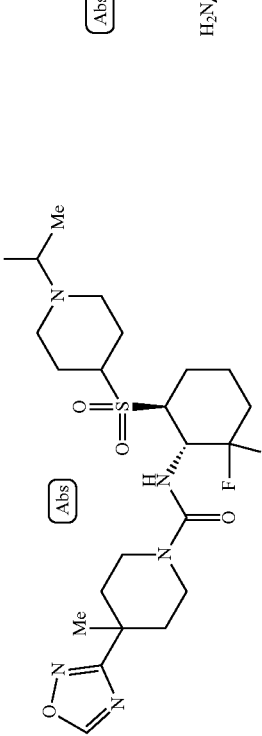 | ¹H-NMR (CDCl₃) δ: 0.98-1.38 (10H, m), 1.40-1.78 (10H, m), 1.89-2.11 (3H, m), 2.16-2.32 (2H, m), 2.32-2.42 (1H, m), 2.43-3.44 (9H, m), 3.54-3.77 (2H, m), 4.89-5.26 (2H, m), 4.93 (1H, dddd, J = 63.6, 6.0, 6.0, 3.6 Hz). | Reference example 124 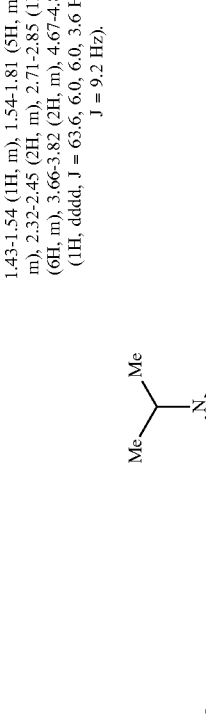 | Reference example 115 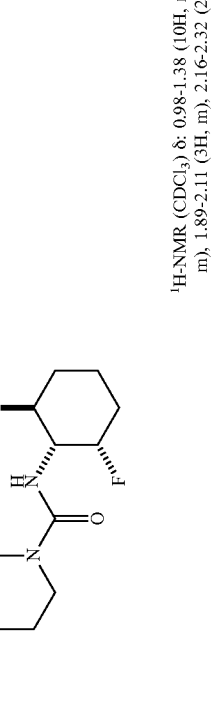 |

The chemical names of Example 82 to Example 155 are listed below.

Example 82: N-{(1S,6R)-2,2-difluoro-6-[4-(propan-2-yl)piperazin-1-yl]cyclohexyl}-4-{5-[(1R,2R)-2-fluorocyclopropyl]-1,2,4-oxadiazol-3-yl}-4-methylpiperidine-1-carboxamide Example 83: N-[(1R,6S)-2,2-difluoro-6-{[1-(propan-2-yl)piperidin-4-yl]oxy}cyclohexyl]-4-{5-[(1S,2S)-2-fluorocyclopropyl]-1,2,4-oxadiazol-3-yl}-4-methylpiperidine-1-carboxamide Example 84: 4-(5-cyclopropyl-1,2,4-oxadiazol-3-yl)-N-[(1R,6S)-2,2-difluoro-6-{[1-(propan-2-yl)piperidin-4-yl]oxy}cyclohexyl]-4-methylpiperidine-1-carboxamide Example 85: 4-(5-cyclopropyl-1,2,4-oxadiazol-3-yl)-N-{(1R,6S)-2,2-difluoro-6-[5-(propan-2-yl)-1,2,4-oxadiazol-3-yl]cyclohexyl}-4-methylpiperidine-1-carboxamide Example 86: N-{(1R,6S)-2,2-difluoro-6-[5-(propan-2-yl)-1,2,4-oxadiazol-3-yl]cyclohexyl}-4-{5-[(1S,2S)-2-fluorocyclopropyl]-1,2,4-oxadiazol-3-yl}-4-methylpiperidine-1-carboxamide Example 87: N-[(1R,6S)-2,2-difluoro-6-{[3-(propan-2-yl)-1,2,4-thiadiazol-5-yl]oxy}cyclohexyl]-4-(5-[(1S,2S)-2-fluorocyclopropyl]-1,2,4-oxadiazol-3-yl}-4-methylpiperidine-1-carboxamide Example 88: N-[(1R,6S)-2,2-difluoro-6-{[1-(propan-2-yl)-1H-pyrazol-4-yl]oxy}cyclohexyl]-4-{5-[(1S,2S)-2-fluorocyclopropyl]-1,2,4-oxadiazol-3-yl}-4-methylpiperidine-1-carboxamide Example 89: N-[(1R,6S)-2,2-difluoro-6-{[1-(propan-2-yl)azetidin-3-yl]oxy}cyclohexyl]-4-{5-[(1S,2S)-2-fluorocyclopropyl]-1,2,4-oxadiazol-3-yl}-4-methylpiperidine-1-carboxamide Example 90: 4-(5-cyclopropyl-1,2,4-oxadiazol-3-yl)-N-[(1R,6S)-2,2-difluoro-6-{[1-(propan-2-yl)-1H-pyrazol-4-yl]oxy}cyclohexyl]-4-methylpiperidine-1-carboxamide Example 91: N-[(1R,6S)-6-{benzyl[(3S)-1-(propan-2-yl)pyrrolidin-3-yl]amino}-2,2-difluorocyclohexyl]-4-{5-[(1S,2S)-2-fluorocyclopropyl]-1,2,4-oxadiazol-3-yl}-4-methylpiperidine-1-carboxamide Example 92: N-[(1R,6S)-2,2-difluoro-6-{[2-(propan-2-yl)pyrimidin-4-yl]oxy}cyclohexyl]-4-{5-[(1S,2S)-2-fluorocyclopropyl]-1,2,4-oxadiazol-3-yl}-4-methylpiperidine-1-carboxamide Example 93: N-{(1R,6S)-2,2-difluoro-6-[4-(propan-2-yl)-1H-1,2,3-triazol-1-yl]cyclohexyl}-4-{5-[(1S,2S)-2-fluorocyclopropyl]-1,2,4-oxadiazol-3-yl}-4-methylpiperidine-1-carboxamide Example 94: N-{(1R,6S)-2,2-difluoro-6-[4-(2-methylpropyl)-1H-1,2,3-triazol-1-yl]cyclohexyl}-4-{5 [(1S,2S)-2-fluorocyclopropyl]-1,2,4-oxadiazol-3-yl}-4-methylpiperidine-1-carboxamide Example 95: N-[(1R,6S)-2,2-difluoro-6-{methyl[(3S)-1-(propan-2-yl)pyrrolidin-3-yl]amino}cyclohexyl]-4-{5-[(1S,2S)-2-fluorocyclopropyl]-1,2,4-oxadiazol-3-yl}-4-methylpiperidine-1-carboxamide Example 96: N-[(1R,6S)-2,2-difluoro-6-{(3S)-3-[methyl(propan-2-yl)amino]pyrrolidin-1-yl}cyclohexyl]-4 {5 [(1S,2S)-2-fluorocyclopropyl]-1,2,4-oxadiazol-3-yl}-4-methylpiperidine-1-carboxamide Example 97: 4-(5-cyclobutyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide Example 98: N-[(1R,6S)-2,2-difluoro-6-{[(1R,3S,5S)-8-(propan-2-yl)-8-azabicyclo[3.2.1]octan-3-yl]oxy}cyclohexyl]-4-{5-[(1S,2S)-2-fluorocyclopropyl]-1,2,4-oxadiazol-3-yl}-4-methylpiperidine-1-carboxamide Example 99: 4-(5-cyclopropyl-1,2,4-oxadiazol-3-yl)-N-[(1R,6S)-2,2-difluoro-6-{(3S)-3-[methyl(propan-2-yl)amino]pyrrolidin-1-yl}cyclohexyl]-4-methylpiperidine-1-carboxamide Example 100: N-[(1R,6S)-2,2-difluoro-6-{[(1R,5S,8R)-3-(propan-2-yl)-3-azabicyclo[3.2.1]octan-8-yl]oxy}cyclohexyl]-4-{5-[(1S,2S)-2-fluorocyclopropyl]-1,2,4-oxadiazol-3-yl}-4-methylpiperidine-1-carboxamide Example 101: N-[(1R,6S)-2,2-difluoro-6-{4-[(propan-2-yl)oxy]piperidin-1-yl}cyclohexyl]-4-{5-[(1S,2S)-2-fluorocyclopropyl]-1,2,4-oxadiazol-3-yl}-4-methylpiperidine-1-carboxamide Example 102: 4-(5-cyclobutyl-1,2,4-oxadiazol-3-yl)-N-[(1R,6S)-2,2-difluoro-6-{[(3S)-1-(propan-2-yl)pyrrolidin-3-yl]oxy}cyclohexyl]-4-methylpiperidine-1-carboxamide Example 103: N-[(1R,6S)-2,2-difluoro-6-{[(3S)-1-(propan-2-yl) pyrrolidin-3-yl]oxy}cyclohexyl]-4-ethyl-4-{5-[(1S,2S)-2-fluorocyclopropyl]-1,2,4-oxadiazol-3-yl}piperidine-1-carboxamide Example 104: N-[(1R,6S)-2,2-difluoro-6-{[(1R,5S,8S)-3-(propan-2-yl)-3-azabicyclo[3.2.1]octan-8-yl]oxy}cyclohexyl]-4-{5-[(1S,2S)-2-fluorocyclopropyl]-1,2,4-oxadiazol-3-yl}-4-methylpiperidine-1-carboxamide Example 105: N-[(1R,6S)-2,2-difluoro-6-{[(1R,3R,5S)-8-(propan-2-yl)-8-azabicyclo[3.2.1]octan-3-yl]oxy}cyclohexyl]-4-{5-[(1S,2S)-2-fluorocyclopropyl]-1,2,4-oxadiazol-3-yl}-4-methylpiperidine-1-carboxamide Example 106: N-[(1R,6S)-2,2-difluoro-6-{[(1R,5S,6S)-3-(propan-2-yl)-3-azabicyclo[3.1.0]hexan-6-yl]oxy}cyclohexyl]-4-{5-[(1S,2S)-2-fluorocyclopropyl]-1,2,4-oxadiazol-3-yl}-4-methylpiperidine-1-carboxamide Example 107: N-[(1R,6S)-2,2-difluoro-6-{[(3S)-1-(2-methylpropyl) pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide Example 108: N-[(1R,6S)-2,2-difluoro-6-{[(3R,4R)-4-methoxy-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide Example 109: N-[(1R,6S)-2,2-difluoro-6-{[4-methyl-1-(propan-2-yl) piperidin-4-yl]oxy}cyclohexyl]-4-{5-[(1S,2S)-2-fluorocyclopropyl]-1,2,4-oxadiazol-3-yl}-4-methylpiperidine-1-carboxamide Example 110: N-{(1R,6S)-2,2-difluoro-6-[(2S)-2-methyl-4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide Example 111: N-{(1R,6S)-2,2-difluoro-6-[(2R)-2-methyl-4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide Example 112: N-[(1R,6S)-2,2-difluoro-6-{(3R)-3-[methyl(propan-2-yl)amino]pyrrolidin-1-yl}cyclohexyl]-4-{5-[(1S,2S)-2-fluorocyclopropyl]-1,2,4-oxadiazol-3-yl}-4-methylpiperidine-1-carboxamide Example 113: N-[(1R,6S)-2,2-difluoro-6-{methyl[(3R)-1-(propan-2-yl)pyrrolidin-3-yl]amino}cyclohexyl]-4-{5-[(1S,2S)-2-fluorocyclopropyl]-1,2,4-oxadiazol-3-yl}-4-methylpiperidine-1-carboxamide Example 114: N-[(1R,6S)-2,2-difluoro-6-{4-[methyl(propan-2-yl)amino]piperidin-1-yl}cyclohexyl]-4-{5-[(1S,2S)-2-fluorocyclopropyl]-1,2,4-oxadiazol-3-yl}-4-methylpiperidine-1-carboxamide Example 115: N-[(1R,6S)-6-{(3S)-3-[cyclopropyl(methyl)amino]pyrrolidin-1-yl}-2,2-difluorocyclohexyl]-4-{5-[(1S,2S)-2-fluorocyclopropyl]-1,2,4-oxadiazol-3-yl}-4-methylpiperidine-1-carboxamide Example 116: 4-(5-cyclopropyl-1,2,4-oxadiazol-3-yl)-N-[(1R,6S)-2,2-difluoro-6-{[(3S)-1-(2-methylpropyl)pyrrolidin-3-yl]oxy}cyclohexyl]-4-methylpiperidine-1-carboxamide Example 117: N-[(1R,6R)-2,2-difluoro-6-{[4-(propan-2-yl)piperazin-1-yl]methyl}cyclohexyl]-4-{5-[(1S,2S)-2-fluorocyclopropyl]-1,2,4-oxadiazol-3-yl}-4-methylpiperidine-1-carboxamide Example 118: N-[(1R,6S)-6-{[(3S)-1-(cyclopropylmethyl)pyrrolidin-3-yl]oxy}-2,2-difluorocyclohexyl]-4-{5-[(1S,2S)-2-fluorocyclopropyl]-1,2,4-oxadiazol-3-yl}-4-methylpiperidine-1-carboxamide Example 119: 4-(5-cyclopropyl-1,2,4-oxadiazol-3-yl)-N-[(1R,6S)-6-{[(3S)-1-(2,2-dimethylpropyl)pyrrolidin-3-yl]oxy}-2,2-difluorocyclohexyl]-4-methylpiperidine-1-carboxamide Example 120: N-[(1R,6S)-6-{[(3S)-1-(2,2-dimethylpropyl)pyrrolidin-3-yl]oxy}-2,2-difluorocyclohexyl]-4-{5-[(1S,2S)-2-fluorocyclopropyl]-1,2,4-oxadiazol-3-yl}-4-methylpiperidine-1-carboxamide Example 121: N-[(1R,6S)-2,2-difluoro-6-({(3S)-1-[(1-methylcyclopropyl)methyl]pyrrolidin-3-yl}oxy)cyclohexyl]-4-{5-[(1S,2S)-2-fluorocyclopropyl]-1,2,4-oxadiazol-3-yl}-4-methylpiperidine-1-carboxamide Example 122: N-[(1R,6S)-6-{[(3S)-1-(cyclopropylmethyl)pyrrolidin-3-yl]oxy}-2,2-difluorocyclohexyl]-4-(5-cyclopropyl-1,2,4-oxadiazol-3-yl)-4-methylpiperidine-1-carboxamide Example 123: N-[(1R,6S)-2,2-difluoro-6-{methyl[1-(propan-2-yl) piperidin-4-yl]amino}cyclohexyl]-4-{5-[(1S,2S)-2-fluorocyclopropyl]-1,2,4-oxadiazol-3-yl}-4-methylpiperidine-1-carboxamide Example 124: N-{(1R,6S)-2,2-difluoro-6-[4-(pyrrolidin-1-yl)piperidin-1-yl]cyclohexyl}-4-{5-[(1S,2S)-2-fluorocyclopropyl]-1,2,4-oxadiazol-3-yl}-4-methylpiperidine-1-carboxamide Example 125: N-{(1R,6S)-2,2-difluoro-6-[5-(propan-2-yl)hexahydropyrrolo[3,4-c]pyrrol-2(1H)-yl]cyclohexyl}-4-{5 [(1S,2S)-2-fluorocyclopropyl]-1,2,4-oxadiazol-3-yl}-4-methylpiperidine-1-carboxamide Example 126: 4-(5-cyclopropyl-1,2,4-oxadiazol-3-yl)-N-[(1R,6S)-2,2-difluoro-6-({(3S)-1-[ti-methylcyclopropyl)methyl]pyrrolidin-3-yl}oxy)cyclohexyl]-4-methylpiperidine-1-carboxamide Example 127: N-{(1R,6S)-2,2-difluoro-6-[2-(propan-2-yl)-2,8-diazaspiro[4.5]decan-8-yl]cyclohexyl}-4-{5-[(1S,2S)-2-fluorocyclopropyl]-1,2,4-oxadiazol-3-yl}-4-methylpiperidine-1-carboxamide Example 128: N-[(1R,6S)-2,2-difluoro-6-{(3S)-3-[methyl(2-methylpropyl)amino]pyrrolidin-1-yl}cyclohexyl]-4-{5-[(1S,2S)-2-fluorocyclopropyl]-1,2,4-oxadiazol-3-yl}-4-methylpiperidine-1-carboxamide Example 129: N-{(1R,6S)-6-[4-(diethylamino)piperidin-1-yl]-2,2-difluorocyclohexyl}-4-{5-[(1S,2S)-2-fluorocyclopropyl]-1,2,4-oxadiazol-3-yl}-4-methylpiperidine-1-carboxamide Example 130: N-[(1R,6S)-2,2-difluoro-6-({(3S)-1-[(1-methylcyclopropyl)methyl]pyrrolidin-3-yl}oxy)cyclohexyl]-4-methyl-4-(4-methylphenyl)piperidine-1-carboxamide Example 131: N-[(1R,6S)-2,2-difluoro-6-{4-methyl-4-[methyl(propan-2-yl)amino]piperidin-1-yl}cyclohexyl]-4-{5-[(1S,2S)-2-fluorocyclopropyl]-1,2,4-oxadiazol-3-yl}-4-methylpiperidine-1-carboxamide Example 132: N-{(1R,6S)-2,2-difluoro-6-[4-(propan-2-yl)piperazine-1-carbonyl]cyclohexyl}-4-{5-[(1S,2S)-2-fluorocyclopropyl]-1,2,4-oxadiazol-3-yl}-4-methylpiperidine-1-carboxamide Example 133: N-[(1R,6S)-2,2-difluoro-6-({(3S)-1-[(1-fluorocyclopropyl)methyl]pyrrolidin-3-yl}oxy)cyclohexyl] 4 {5-[(1S,2S)-2-fluorocyclopropyl]-1,2,4-oxadiazol-3-yl}-4-methylpiperidine-1-carboxamide Example 134: N-[(1R,6S)-2,2-difluoro-6-(4-{methyl[timethy 1 cyclopropyl)methyl]amino}piperidin-1-yl)cyclohexyl]-4-{5-[(1S,2S)-2-fluorocyclopropyl]-1,2,4-oxadiazol-3-yl}-4-methylpiperidine-1-carboxamide Example 135: N-[(1R,6S)-2,2-difluoro-6-{[(3S)-1-{[1-(trifluoromethyl)cyclopropyl]methyl}pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide Example 136: N-[(1R,6S)-2,2-difluoro-6-(4-{[(1-fluorocyclopropyl)methyl](methyl)amino}piperidin-1-yl)cyclohexyl]-4-{5-[(1S,2S)-2-fluorocyclopropyl]-1,2,4-oxadiazol-3-yl}-4-methylpiperidine-1-carboxamide Example 137: N-[(1R,6S)-6-{(3S)-3-[(cyclopropylmethyl)(methyl)amino]pyrrolidin-1-yl}-2,2 difluorocyclohexyl]-4-{5-[(1S,2S)-2-fluorocyclopropyl]-1,2,4-oxadiazol-3-yl}-4-methylpiperidine-1-carboxamide Example 138: N-[(1R,6S)-6-{(3S)-3-[(cyclopropylmethyl)(methyl)amino]pyrrolidin-1-yl}-2,2-difluorocyclohexyl]-4-(5-cyclopropyl-1,2,4-oxadiazol-3-yl)-4-methylpiperidine-1-carboxamide Example 139: rac-4-(5-cyclopropyl-1,2,4-oxadiazol-3-yl)-N-{(1R,2R,6S)-2-fluoro-6-[4-(propan-2-yl)piperazin-1-yl]cyclohexyl}-4-methylpiperidine-1-carboxamide Example 140: N-{(1R,6S)-2,2-difluoro-6-[4-(methyl{[1-(trifluoromethyl)cyclopropyl]methyl}amino)piperidin-1-yl]cyclohexyl}-4-{5-[(1S,2S)-2-fluorocyclopropyl]-1,2,4-oxadiazol-3-yl}-4-methylpiperidine-1-carboxamide Example 141: N-[(1R,6S)-6-{(1R,3R,5S)-3-[(cyclopropylmethyl)(methyl)amino]-8-azabicyclo[3.2.1]octan-8-yl}-2,2-difluorocyclohexyl]-4-{5-[(1S,2S)-2-fluorocyclopropyl]-1,2,4-oxadiazol-3-yl}-4-methylpiperidine-1-carboxamide Example 142: N-[(1R,6S)-6-{(1R,3S,5S)-3-[(cyclopropylmethyl)(methyl)amino]-8-azabicyclo[3.2.1]octan-8-yl}-2,2-difluorocyclohexyl]-4-{5-[(1S,2S)-2-fluorocyclopropyl]-1,2,4-oxadiazol-3-yl}-4-methylpiperidine-1-carboxamide Example 143: N-[(1R,6S)-2,2-difluoro-6-{[(3S)-1-(2-fluoro-2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide Example 144: N-[(1R,6S)-6-{(4S)-4-[(cyclopropylmethyl) (methyl)amino]azepan-1-yl}-2,2-difluorocyclohexyl]-4-{5-[(1S,2S)-2-fluorocyclopropyl]-1,2,4-oxadiazol-3-yl}-4-methylpiperidine-1-carboxamide Example 145: N-[(1R,6S)-6-{(4R)-4-[(cyclopropylmethyl) (methyl)amino]azepan-1-yl}-2,2-difluorocyclohexyl]-4-{5-[(1S,2S)-2-fluorocyclopropyl]1,2,4-oxadiazol-3-yl}-4-methylpiperidine-1-carboxamide Example 146: N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-N,4-dimethylpiperidine-1-carboxamide Example 147: 4-(5-cyclopropyl-1,2,4-oxadiazol-3-yl)-N-{(1S,6S)-2,2-dimethyl-6-[4-(propan-2-yl)piperazin-1-yl]cyclohexyl}-4-methylpiperidine-1-carboxamide Example 148: N-[(1R,6S)-2,2-difluoro-6-{3-[methyl(propan-2-yl)amino]azetidin-1-yl}cyclohexyl]-4-{5-[(1S,2S)-2-fluorocyclopropyl]-1,2,4-oxadiazol-3-yl}-4-methylpiperidine-1-carboxamide Example 149: N-[(1R,6S)-6-{3-[(cyclopropylmethyl)(methyl)amino]azetidin-1-yl}-2,2-difluorocyclohexyl]-4-{5-[(1S,2S)-2-fluorocyclopropyl]-1,2,4-oxadiazol-3-yl}-4-methylpiperidine-1-carboxamide Example 150: N-[(1R,6S)-2,2-difluoro-6-({(3S)-1-[(3-methyloxetan-3-yl)methyl]pyrrolidin-3-yl}oxy)cyclohexyl]-4-{5-[(1S,2S)-2-fluorocyclopropyl]-1,2,4-oxadiazol-3-yl}-4-methylpiperidine-1-carboxamide Example 151: rac-4-(5-cyclopropyl-1,2,4-oxadiazol-3-yl)-4-methyl-N-{(1S,2S)-2-[4-(propan-2-yl)piperazin-1-yl]cycloheptyl}piperidine-1-carboxamide Example 152: N-{(1R,6S)-2,2-difluoro-6-[4-(propan-2-yl)-1,4-diazepan-1-yl]cyclohexyl}-4-{5-[(1S,2S)-2-fluorocyclopropyl]-1,2,4-oxadiazol-3-yl}-4-methylpiperidine-1-carboxamide Example 153: (1S,2R)-3,3-difluoro-2-[(4-{5-[(1S,2S)-2-fluorocyclopropyl]-1,2,4-oxadiazol-3-yl}-4-methylpiperidine-1-carbonyl)amino]cyclohexyl 4-(propan-2-yl)piperazine-1-carboxylate The compound of the above Reference example 124 which is a diastereomixture and its intermediates for preparing the compound can be obtained as a sole enantiomer by optical resolution with chiral column chromatography or by crystallization with an acid having a chiral center. In addition, the compound of Reference example 124 can be also prepared as a sole enantiomer by using optically-active epoxide as a starting material. Thus, when Reference example 124 as a starting Material A is further determined through separation or asymmetric synthesis, the diastereomixture of Example 156 can be prepared as each diastereomer.

In addition, the compound of Example 156 which is a diastereomixture can be obtained as a sole enantiomer by optical resolution with chiral column chromatography or by crystallization with an acid having a chiral center. Thus, the two diastereomers of Example 156 can be separated as each diastereomer.

The compound of Example 156 is a diastereomixture comprising two different diastereomers. These diastereomers can be separated through its process or by optical resolution with chiral column chromatography. It means that the two different diastereomers were substantially prepared.

| No. | Chemical structure of diastereomer | Chemical name |
|---|---|---|
| 156-A | 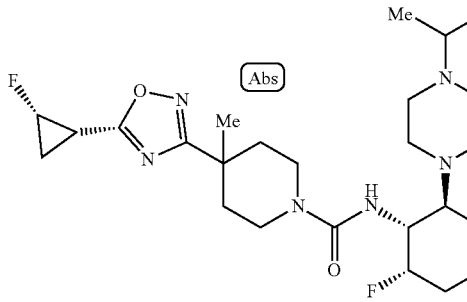 | 4-{5-[(1S,2S)-2-fluorocyclopropyl]-1,2,4-oxadizaol-3-yl}-N-{(1R,2S,6S)-2-fluoro-6-[4-(propan-2-yl)piperazin-1-yl]cyclohexyl}-4-methylpiperidine-1-carboxamide |
| 156-B | 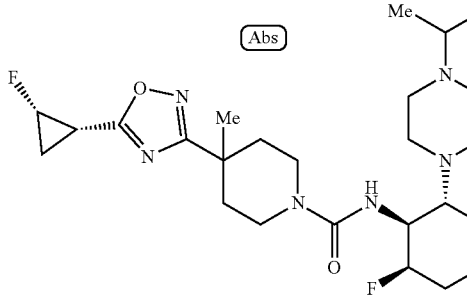 | 4{5-[(1S,2S)-2-fluorocyclopropyl]-1,2,4-oxadiazol-3-yl}-N-{(1S,2R,6R)-2-fluoro-6-{4-(propan-2-yl)piperazin-1-yl]cyclohexyl}-4-methylpiperidine-1-carboxamide |

Example 154: N-[(1S,6S)-2,2-difluoro-6-{[1-(propan-2-yl)piperidin-4-yl]sulfanyl}cyclohexyl]-4-{5-[(1S,2S)-2-fluorocyclopropyl]-1,2,4-oxadiazol-3-yl}-4-methylpiperidine-1-carboxamide Example 155: N-{(1S,6S)-2,2-difluoro-6-[1-(propan-2-yl)piperidine-4-sulfonyl]cyclohexyl}-4-{5-[(1S,2S)-2-fluorocyclopropyl]-1,2,4-oxadiazol-3-yl}-4-methylpiperidine-1-carboxamide.

Examples 157-160

The compounds of Examples 157-160 shown in the table below were prepared according to the process in Example 17 by using the compound of Reference example 80 and each appropriate commercial aldehyde or ketone compound.

| Example | Chemical structure | Spectral data |
|---|---|---|
| 157 | 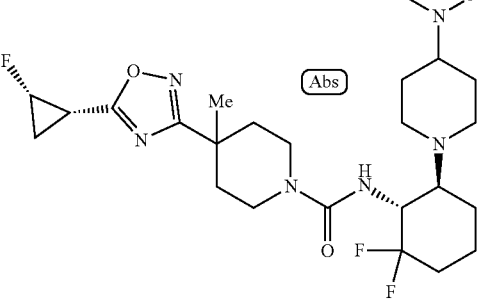 | ¹H-NMR (CDCl₃) δ: 0.84 (6H, d, J = 6.0 Hz), 1.18-1.35 (4H, m), 1.35-1.54 (3H, m), 1.60-1.84 (8H, m), 1.83-2.04 (2H, m), 2.04-2.31 (11H, m), 2.31-2.41 (1H, m), 2.45-2.56 (1H, m), 2.61-2.71 (1H, m), 2.77-2.87 (1H, m), 3.01-3.20 (2H, m), 3.65-3.75 (1H, m), 3.75-3.86 (1H, m), 4.06-4.22 (1H, m), 4.55 (1H, d, J = 8.0 Hz), 4.91 (1H, ddd, J = 63.6, 6.0, 6.0, 3.6 Hz). |
| 158 | 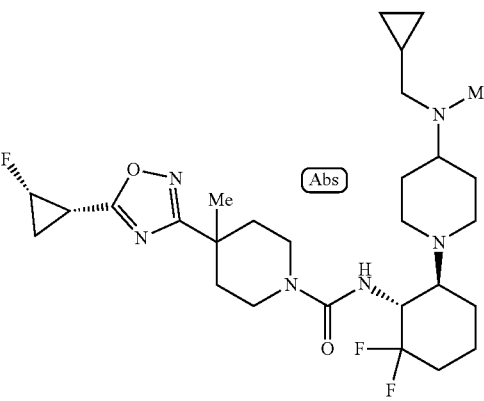 | ¹H-NMR (CDCl₃) δ: 0.06-0.13 (2H, m), 0.47-0.55 (2H, m), 0.80-0.91 (1H, m), 1.19-1.36 (6H, m), 1.36-1.53 (4H, m), 1.53-1.84 (3H, m), 1.84-2.03 (2H, m), 2.04-2.21 (2H, m), 2.21-2.45 (10H, m), 2.46-2.58 (2H, m), 2.64-2.71 (1H, m), 2.81-2.89 (1H, m), 3.04-3.19 (2H, m), 3.67-3.79 (2H, m), 4.07-4.22 (1H, m), 4.55 (1H, d, J = 7.9 Hz), 4.92 (1H, dddd, J = 63.6, 6.0, 6.0, 3.6 Hz). |
| 159 | 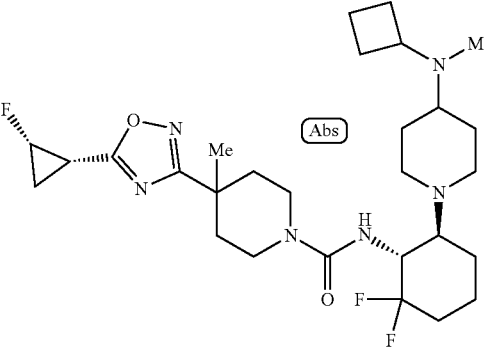 | ¹H-NMR (CDCl₃) δ: 1.15-1.35 (5H, m), 1.35-1.53 (3H, m), 1.53-1.74 (4H, m), 1.74-2.21 (14H, m), 2.21-2.30 (2H, m), 2.30-2.43 (2H, m), 2.44-2.57 (2H, m), 2.61-2.72 (1H, m), 2.74-2.88 (1H, m), 3.00-3.20 (3H, m), 3.65-3.82 (2H, m), 4.05-4.21 (1H, m), 4.54 (1H, d, J = 8.0 Hz), 4.91 (1H, dddd, J = 64.0, 6.0, 6.0, 3.6 Hz). |
| 160 | 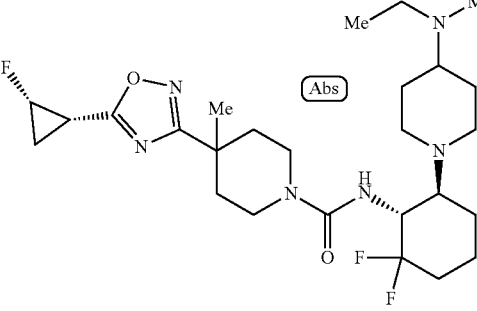 | ¹H-NMR (CDCl₃) δ: 1.08-1.83 (16H, m), 1.84-2.03 (3H, m), 2.07-2.43 (9H, m), 2.45-2.76 (5H, m), 2.86-2.98 (1H, m), 3.06-3.20 (2H, m), 3.62-3.77 (2H, m), 4.08-4.23 (1H, m), 4.53 (1H, d, J = 7.9 Hz), 4.93 (1H, dddd, J = 63.6, 6.0, 6.0, 3.6 Hz). |

The chemical names of Example 157 to Example 160 are listed below.

Example 157: N-[(1R,6S)-2,2-difluoro-6-{4-[methyl(2-methylpropyl)amino]piperidin-1-yl}cyclohexyl]-4-{5-[(1S,2S)-2-fluorocyclopropyl]-1,2,4-oxadiazol-3-yl}-4-methylpiperidine-1-carboxamide Example 158: N-[(1R,6S)-6-{4-[(cyclopropylmethyl)(methyl)amino]piperidin-1-yl}-2,2-difluorocyclohexyl]-4-{5-[(1S,2S)-2-fluorocyclopropyl]-1,2,4-oxadiazol-3-yl}-4-methylpiperidine-1-carboxamide Example 159: N-[(1R,6S)-6-{4-[cyclobutyl(methyl)amino]piperidin-1-yl}-2,2-difluorocyclohexyl]-4-{5-[(1S,2S)-2-fluorocyclopropyl]-1,2,4-oxadiazol-3-yl}-4-methylpiperidine-1-carboxamide Example 160: N-[(1R,6S)-6-{4-[ethyl(methyl)amino]piperidin-1-yl}-2,2-difluorocyclohexyl]-4-{5-[(1S,2S)-2-fluorocyclopropyl]-1,2,4-oxadiazol-3-yl}-4-methylpiperidine-1-carboxamide Example 161

N-[(1R,6S)-2,2-Difluoro-6-{[(3S)-1-(propan-2-yl)pyrrolidin-3-yl]amino}cyclohexyl]-4-{5-[(1S,2S)-2-fluorocyclopropyl]-1,2,4-oxadiazol-3-yl}-4-methylpiperidine-1-carboxamide

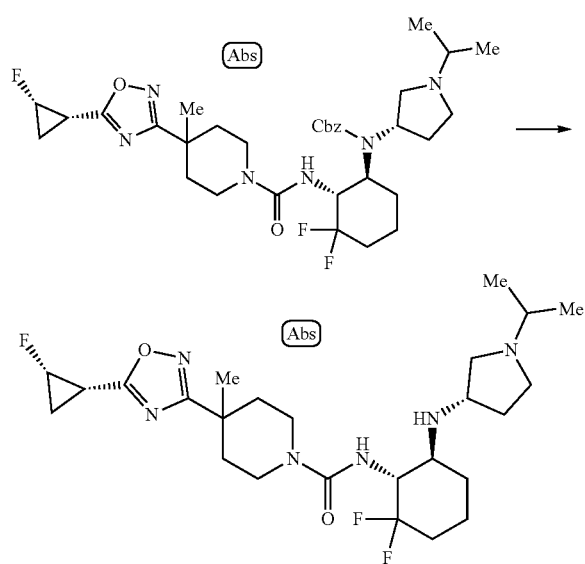

To a mixture of Reference example 90 (175 mg) and ethanol (1.3 mL) was added palladium carbon (6.4 mg) at room temperature, and the mixture was stirred under hydrogen atmosphere. After the reaction was terminated as judged by LC-MS, the reaction mixture was filtrated with Celite, and concentrated in vacuo. Then, the obtained residue was purified by HPLC (eluate: acetonitrile/water/TFA) to give the title compound (44.1 mg).

$^1$H-NMR (CDCl$_3$) δ: 1.03-1.31 (2H, m), 1.13 (6H, d, J=6.0 Hz), 1.34 (3H, s), 1.38-1.88 (13H, m), 1.91-2.23 (3H, m), 2.27 (2H, d, J=13.2 Hz), 2.33-2.42 (1H, m), 2.42-2.54 (1H, m), 2.95-3.21 (2H, m), 3.32-3.54 (1H, brs), 3.58-3.80 (2H, m), 3.91-4.08 (1H, m), 4.65 (1H, d, J=9.2 Hz), 4.93 (1H, dddd, J=63.6, 6.4, 6.4, 4.0 Hz).

Reference Example 1 rac-(1S,2S)-2-[4-(Propan-2-yl)piperazin-1-yl]cyclohexan-1-amine

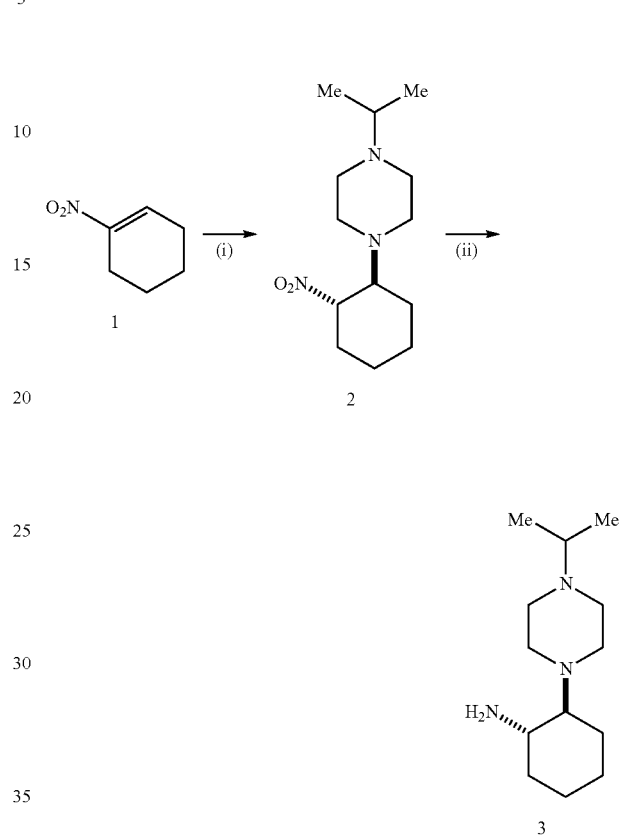

Step (i):

To a mixture of Compound 1 (1.13 g) and dichloromethane (2 mL) was added 1-isopropylpiperazine (1.14 g) at room temperature, and the mixture was stirred for 17 hours. After the reaction was terminated as judged by the consumption of the starting material, diethyl ether was added to the reaction mixture. The precipitate was removed by filtration, and the filtrate was concentrated in vacuo to give a crude product. The obtained crude product was purified by amino silica gel column chromatography (eluate: hexane/ethyl acetate) to give the title compound 2 (1.82 g).

LCMS: [M+H]$^+$/Rt (min): 256/0.48

Step (ii):

To a mixture of Compound 2 (1.14 g), acetic acid (2.04 mL), and ethanol (15 mL) was added palladium/carbon (0.95 g) at room temperature, and the mixture was stirred under hydrogen atmosphere for 18 hours. After the reaction was terminated as judged by LC-MS, the reaction mixture was filtrated with Celite, and concentrated in vacuo. Then, the obtained residue was purified by amino silica gel column chromatography (eluate: chloroform) to give the title compound 3 (0.370 g).

LCMS: [M+H]$^+$/Rt (min): 226/0.31

Reference Example 2 rac-4-(4-Methylphenyl)-N-[(1S,2S)-2-(piperazin-1-yl)cyclohexyl]piperidine-1-carboxamide dihydrochloride

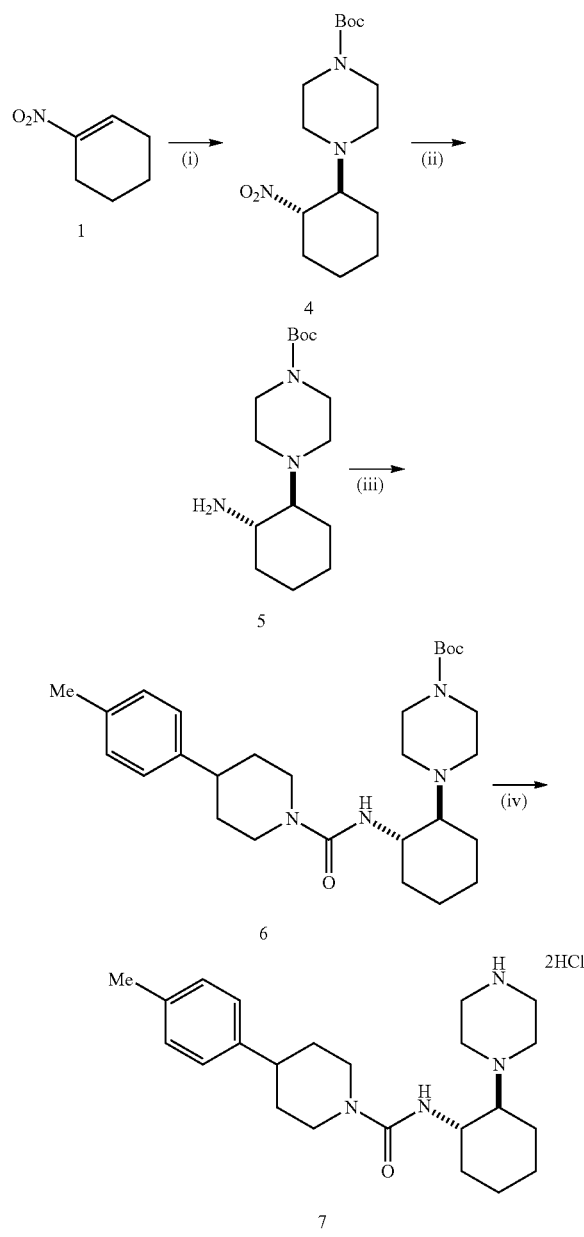

Step (i):
The title compound 4 (1.28 g) was prepared in the same manner as Step (i) in Reference example 1 by using Compound 1 (1.17 g) and 1-Boc-piperazine (1.72 g).

Step (ii):
To a solution of Compound 4 (593 mg) in ethanol (9 mL) was added palladium hydroxide (266 mg) at room temperature, and the mixture was stirred under hydrogen atmosphere. After the reaction was terminated as judged by LC-MS, the reaction mixture was filtrated with Celite, and the filtrate was concentrated in vacuo to give the title compound 5 (560 mg).

Step (iii):
To a mixture of Compound 5 (370 mg), triethylamine (0.91 mL), and dichloromethane (5 mL) was added 4-nitrophenyl chloroformate (316 mg) at 0° C., and the mixture was stirred for 2 hours. Then, 4-(4-methylphenyl)piperidine (297 mg) was added to the reaction mixture at 0° C., and the stirring was continued at room temperature. After the reaction was terminated as judged by the consumption of the reaction intermediate, water was added to the reaction mixture, and the mixture was extracted with chloroform. The organic layer was dried over anhydrous sodium sulfate and concentrated in vacuo, and then the obtained residue was purified by amino silica gel column chromatography (eluate: hexane/ethyl acetate) to give the title compound 6 (435 mg).

Step (iv):
To a mixture of Compound 6 (430 mg) and chloroform (3 mL) was added hydrogen chloride/dioxane solution (4 M, 2.22 mL) at 0° C., and the mixture was stirred for 16 hours. Then, the reaction mixture was concentrated in vacuo to give the title compound 7 (310 mg).
LCMS: [M+H]$^+$/Rt (min): 385/0.71

Reference Example 3 rac-(1R,2S)-2-(4-Ethylpiperazin-1-yl)cyclohexan-1-amine

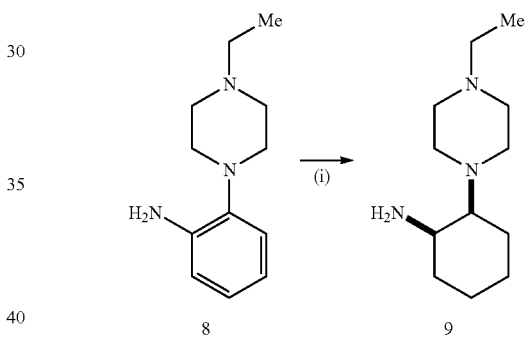

Step (i):
To a mixture of Compound 8 (312 mg) and acetic acid (5 mL) was added platinum(IV) oxide (86 mg), and mixture was stirred at 70° C. under hydrogen atmosphere for 6 hour. Then, the reaction mixture was filtrated with Celite, and the filtrate was concentrated in vacuo to give a crude product. The obtained crude product was purified by amino silica gel column chromatography (eluate: hexane/ethyl acetate) to give the title compound 9 (9 mg).
LCMS: [M+H]$^+$/Rt (min): 212/0.15

Reference Example 4 rac-(1R,2S,6S)-2-Methoxy-6-[4-(propan-2-yl)piperazin-1-yl]cyclohexan-1-amine trihydrochloride

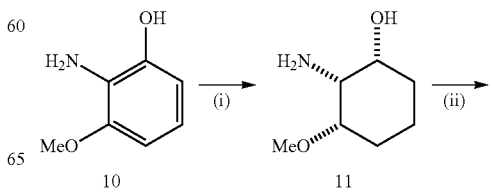

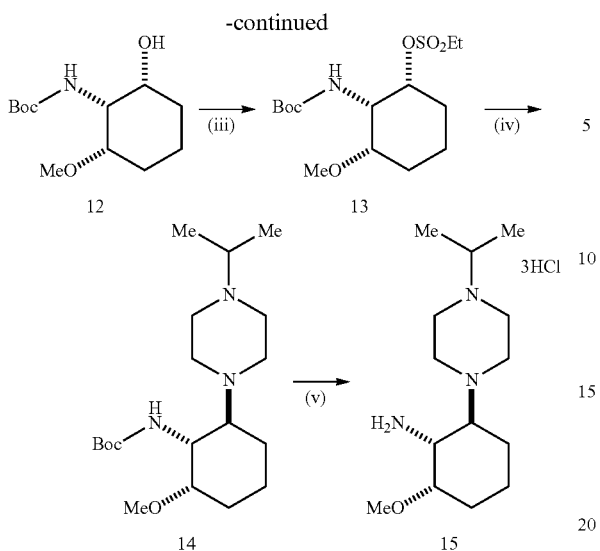

Step (i):
The title compound 11 (424 mg) was prepared in the same manner as Step (i) in Reference example 3 by using Compound (407 mg).
LCMS: [M+H]$^+$/Rt (min): 146/0.15

Step (ii):
To a mixture of Compound 11 (424 mg), triethylamine (1.22 mL), and acetonitrile (10 mL) was added Boc$_2$O (765 mg) at room temperature, and the mixture was stirred at room temperature. After the reaction was terminated as judged by LC-MS, water was added to the reaction mixture and the mixture was extracted with ethyl acetate. The organic layer was dried over anhydrous sodium sulfate and concentrated in vacuo, and then the obtained residue was purified by silica gel column chromatography (eluate: hexane/ethyl acetate) to give the title compound 12 (310 mg).
LCMS: [M+H]$^+$/Rt (min): 246/0.78

Step (iii):
To a mixture of Compound 12 (141 mg), triethylamine (0.160 mL), and THF (3 mL) was added ethanesulfonyl chloride (0.160 mL) under ice temperature, and the mixture was warmed to room temperature and the stirring was continued. After the reaction was terminated as judged by LC-MS, water was added to the reaction mixture, and the mixture was extracted with chloroform. The organic layer was dried over anhydrous sodium sulfate and concentrated in vacuo, and then the obtained residue was purified by silica gel column chromatography (eluate: hexane/ethyl acetate) to give the title compound 13 (180 mg).
LCMS: [M+H]$^+$/Rt (min): 338/0.86

Step (iv):
To a mixture of Compound 13 (155 mg), 1-isopropylpiperazine (236 mg), and 1,4-dioxane (4 mL) was added potassium carbonate (76 mg) at room temperature, and the mixture was stirred for 13 hours heating at 150° C. with a microwave device. Then, water was added to the reaction mixture, and the mixture was extracted with chloroform. The organic layer was dried over anhydrous sodium sulfate and concentrated in vacuo, and then the obtained residue was purified by amino silica gel column chromatography (eluate: hexane/ethyl acetate) to give the title compound 14 (17 mg).
LCMS: [M+H]$^+$/Rt (min): 356/0.81

Step (v):
The title compound 15 (16.8 mg) was prepared in the same manner as Step (iv) in Reference example 2 by using Compound 14 (16.3 mg).
LCMS: [M+H]$^+$/Rt (min): 256/0.32

Reference Example 5 rac-(1S,2S)-2-[4-(Propan-2-yl)piperazin-1-yl]cyclopentane-1-amine

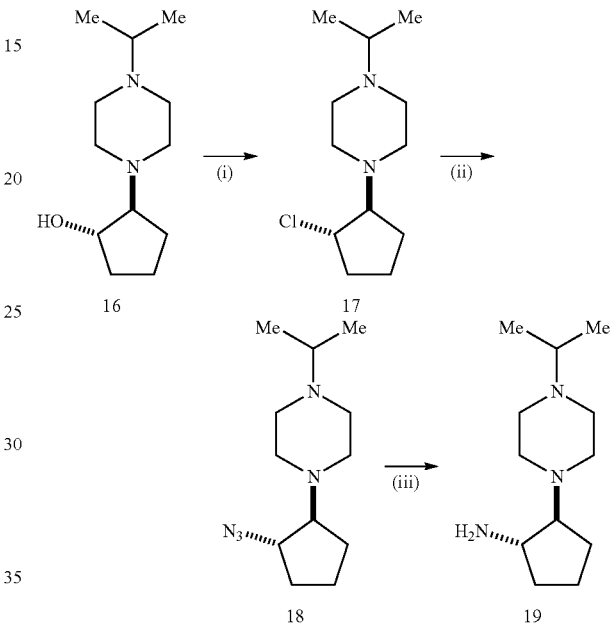

Step (i):
To a mixture of Compound 16 (315 mg), triethylamine (0.289 mL), and THF (5 mL) was added ethanesulfonyl chloride (0.15 mL), and the mixture was stirred at room temperature for 15 hours. After the reaction was terminated as judged by the consumption of the starting material, water was added to the reaction mixture, and the mixture was extracted with chloroform. The organic layer was dried over anhydrous sodium sulfate and concentrated in vacuo, and then the obtained residue was purified by amino silica gel column chromatography (eluate: ethyl acetate/hexane) to give the title compound 17 (140 mg).
LCMS: [M+H]$^+$/Rt (min): 231/0.44

Step (ii):
To a mixture of Compound 17 (136 mg) and DMF (4 mL) was added sodium azide (77 mg), and the mixture was stirred at 80° C. for 3.5 hours. After the reaction was terminated as judged by the consumption of the starting material, water was added to the reaction mixture, and the mixture was extracted with chloroform. The organic layer was dried over anhydrous sodium sulfate, and concentrated in vacuo to give the title compound 18 (137 mg).
LCMS: [M+H]$^+$/Rt (min): 238/0.42

Step (iii):
To a mixture of Compound 18 (42.4 mg), hydrogen chloride/ethyl acetate solution (4.0 M, 0.711 mL), and ethanol (2.8 mL) was added palladium/carbon (202 mg), and the mixture was stirred under hydrogen atmosphere for 8 hours. After the reaction was terminated as judged by LC-MS, methanol and aqueous sodium bicarbonate were added to the reaction mixture, and the mixture was filtrated with Celite and extracted with chloroform/methanol (6/1). The organic layer was dried over anhydrous sodium sulfate and concentrated in vacuo, and then the obtained residue was purified by amino silica gel column chromatography (eluate: chloroform/methanol) to give the title compound 19 (98.7 mg).

LCMS: [M+H]$^+$/Rt (min): 212/0.15

Reference Example 6 rac-(1R,6S)-2,2-Difluoro-6-[4-(propan-2-yl)piper-azin-1-yl]cyclohexan-1-ol

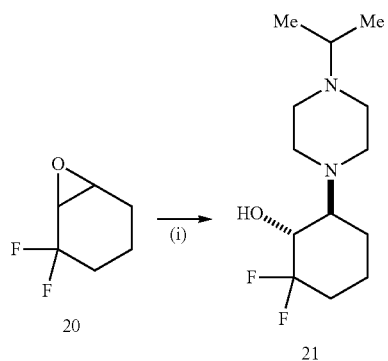 [SMILES: FC1(F)CCCC2OC21 ; CC(C)N1CCN([C@H]2CCCC(F)(F)[C@@H]2O)CC1]

Step (i):

To a mixture of Compound 20 (688 mg) and ethanol (20 mL) was added 1-isopropylpiperazine (723 mg) at room temperature, and the mixture was stirred for 9 hours heating at 80° C. The reaction mixture was cooled to room temperature, and then concentrated in vacuo. And, the obtained residue was purified by amino silica gel column chromatography (eluate: hexane/ethyl acetate) to give the title compound 21 (830 mg).

LCMS: [M+H]$^+$/Rt (min): 263/0.35

Reference Example 7 rac-(1R,2S)-3,3-Difluoro-2-[4-(propan-2-yl)piper-azin-1-yl]cyclohexan-1-amine

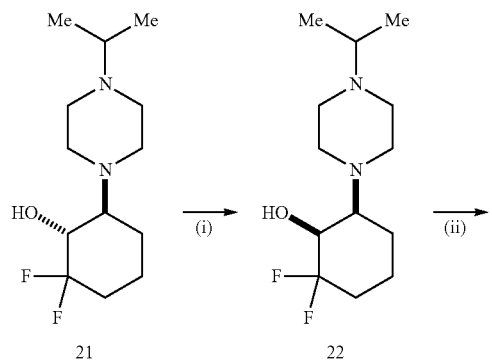

-continued

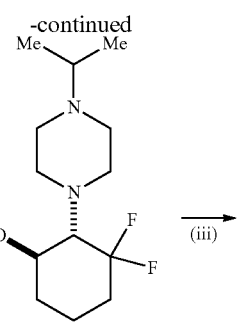

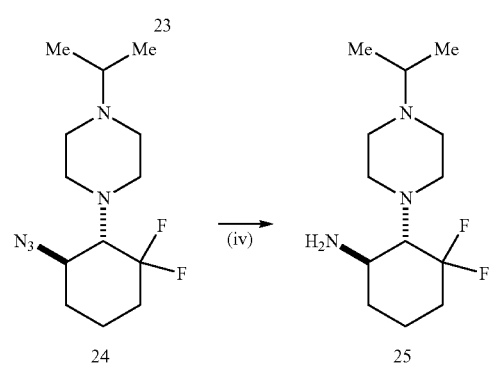

Step (i):

To a mixture of DMSO (0.081 mL) and dichloromethane (2 mL) was added oxalyl chloride (0.075 mL) at −78° C., and the mixture was stirred for 20 minutes. Then, a solution of Compound 21 (150 mL) in dichloromethane (2 mL) was added to the reaction mixture, and the mixture was stirred at −78° C. further for 30 minutes. Triethylamine (0.398 mL) was added to the reaction mixture, and the the mixture was warmed to 0° C. Then, the mixture was stirred for 30 minutes, and sodium borohydride was added thereto. The mixture was stirred for 30 minutes. And, water was added to the reaction mixture, and the mixture was extracted with chloroform. The organic layer was dried over anhydrous sodium sulfate, concentrated in vacuo, and then the obtained residue was purified by silica gel column chromatography (eluate: chloroform/methanol) to give the title compound 22 (27 mg).

LCMS: [M+H]$^+$/Rt (min): 263/0.38

Step (ii):

To a mixture of Compound 22 (27 mg), triethylamine (0.029 mL), and THF (2 mL) was added ethanesulfonyl chloride (0.015 mL), and the mixture was stirred at room temperature. After the reaction was terminated as judged by the consumption of the starting material, water was added to the reaction mixture, and the mixture was extracted with chloroform. The organic layer was dried over anhydrous sodium sulfate and concentrated in vacuo, and then the obtained residue was purified by amino silica gel column chromatography (eluate: chloroform/methanol) to give the title compound 23 (23 mg).

LCMS: [M+H]$^+$/Rt (min): 354/0.65

Step (iii):

The title compound 24 (16.0 mg) was prepared in the same manner as Step (ii) in Reference example 5 by using Compound 23 (23.4 mg).

LCMS: [M+H]$^+$/Rt (min): 288/0.60

Step (iv):

To a mixture of Compound 24 (14 mg), THF (1 mL), and water (1 mL) was added triphenylphosphine (25.6 mg) at room temperature, and the mixture was stirred for 4.5 hours heating at 50° C. Then, the reaction mixture was cooled to room temperature, and aqueous hydrochloric acid was added thereto. The mixture was washed with ethyl acetate, and aqueous sodium bicarbonate was added to the aqueous layer. The obtained mixture was extracted with chloroform/methanol (3/1). The organic layer was dried over anhydrous sodium sulfate, and concentrated in vacuo to give the title compound (7.8 mg).

LCMS: [M+H]$^+$/Rt (min): 262/0.31

Reference Example 8

4-(5-Cyclopropyl-1,2,4-oxadiazol-3-yl)-4-methylpiperidine monohydrochloride

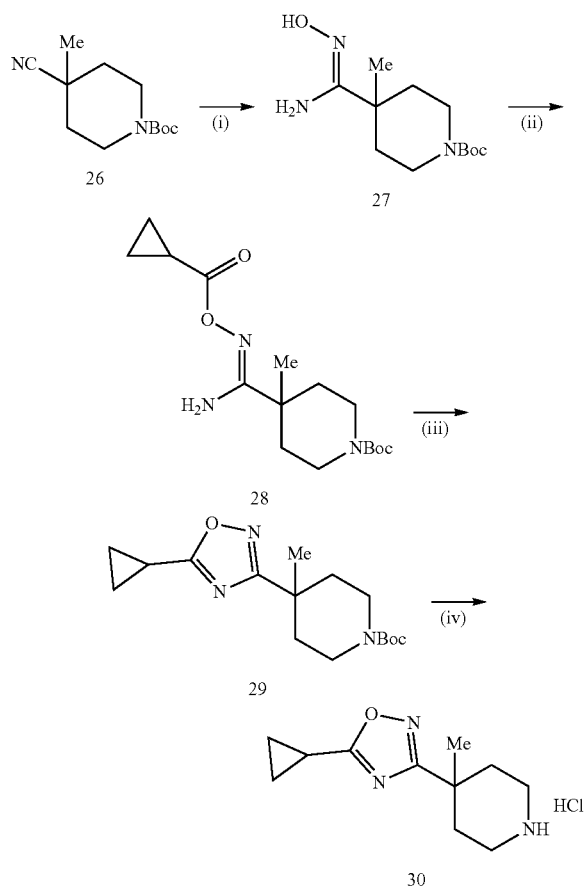

Step (i):

To a solution of Compound 26 (50.0 g) in ethanol (446 mL) was added 50% aqueous hydroxylamine (132 mL), and the mixture was stirred at 70° C. for 8 hours. The reaction mixture was cooled to room temperature, and water (892 mL) was added to the reaction mixture. The mixture was stirred at room temperature for 30 minutes. The precipitated white crystal was collected on a filter, the obtained crystal was suspended in water (344 mL) again, and the suspension was stirred at room temperature for 30 minutes. The precipitated white solid was collected on a filter and dried to give the title compound 27 (52.3 g).

LCMS: [M+H]$^+$/Rt (min): 258/0.52 (Method C)

Step (ii):

To a mixture of Compound 27 (52.3 g), cyclopropanecarboxylic acid (18.4 g), HATU (85 g), and THF (406 mL) in ice bath was added slowly dropwise triethylamine (142 mL), and the mixture was stirred at room temperature for 12 hours. To the reaction mixture was added ethyl acetate (406 mL), and the mixture was washed with water (406 mL) and brine (406 mL). The organic layer was dried over anhydrous sodium sulfate, concentrated in vacuo, and then the obtained residue was purified by silica gel column chromatography (eluate: hexane/ethyl acetate) to give the title compound 28 (59.1 g).

LCMS: [M+H]$^+$/Rt (min): 326/0.77 (Method C)

Step (iii):

A mixture of Compound 28 (59.1 g), DBU (54.2 mL), and toluene (727 mL) was stirred under reflux for one hour. The reaction mixture was cooled to room temperature, and washed with water (727 mL). The organic layer was concentrated in vacuo, and then the obtained residue was purified by silica gel column chromatography (eluate: hexane/ethyl acetate) to give the title compound 29 (54.5 g).

LCMS: [M+H]$^+$/Rt (min): 308/1.11

Step (iv):

The title compound 30 (35.3 g) was prepared in the same manner as Step (iv) in Reference example 2 by using Compound 29 (54.5 g).

LCMS: [M+H]$^+$/Rt (min): 208/0.30 (Method C)

Reference Examples 9 to 12'

The compounds of Reference examples 9 to 12' shown in the table below were prepared according to the process in the above Reference example 8, by using each appropriate starting compound instead of cyclopropanecarboxylic acid at Step (ii) in Reference example 8.

| Reference example | Starting compound | Chemical structure | Instrumental analytical data |
|---|---|---|---|
| 9 | ![propionic acid] | ![structure] | LCMS: [M + H]$^+$/Rt (min): 196/0.32 (Method C) |

| Reference example | Starting compound | Chemical structure | Instrumental analytical data |
|---|---|---|---|
| 10 | difluoroacetic acid | 5-(difluoromethyl)-3-(4-methylpiperidin-4-yl)-1,2,4-oxadiazole · HCl | LCMS: [M + H]⁺/Rt (min): 218/0.44 |
| 11 | (1S,2S)-2-fluorocyclopropanecarboxylic acid [Abs] | 5-[(1S,2S)-2-fluorocyclopropyl]-3-(4-methylpiperidin-4-yl)-1,2,4-oxadiazole · HCl [Abs] | LCMS: [M + H]⁺/Rt (min): 226/0.29 (Method C) |
| 12 | (1R,2S)-2-methylcyclopropanecarboxylic acid [Abs] | 5-[(1R,2S)-2-methylcyclopropyl]-3-(4-methylpiperidin-4-yl)-1,2,4-oxadiazole · HCl [Abs] | LCMS: [M + H]⁺/Rt (min): 222/0.46 (Method C) |
| 12' | (1S,2R)-2-methylcyclopropanecarboxylic acid [Abs] | 5-[(1S,2R)-2-methylcyclopropyl]-3-(4-methylpiperidin-4-yl)-1,2,4-oxadiazole · HCl [Abs] | LCMS: [M + H]⁺/Rt (min): 222/0.46 (Method C) |

Reference example 9: 4-(5-ethyl-1,2,4-oxadiazol-3-yl)-4-methylpiperidine monohydrochloride Reference example 10: 4-[5-(difluoromethyl)-1,2,4-oxadiazol-3-yl]-4-methylpiperidine monohydrochloride Reference example 11: 4-{5-[(1S,2S)-2-fluorocyclopropyl]-1,2,4-oxadiazol-3-yl}-4-methylpiperidine monohydrochloride Reference example 12: 4-methyl-4-{5-[(1R,2S)-2-methylcyclopropyl]-1,2,4-oxadiazol-3-yl}piperidine monohydrochloride Reference example 12': 4-methyl-4-{5-[(1S,2R)-2-methylcyclopropyl]-1,2,4-oxadiazol-3-yl}piperidine monohydrochloride

Reference Example 13 rac-tert-Butyl 4-(6-{[4-(5-cyclopropyl-1,2,4-oxadiazol-3-yl)-4-methylpiperidine-1-carbonyl]amino}cyclohex-1-en-1-yl)-3,6-dihydropyridine-1(2H)-carboxylate

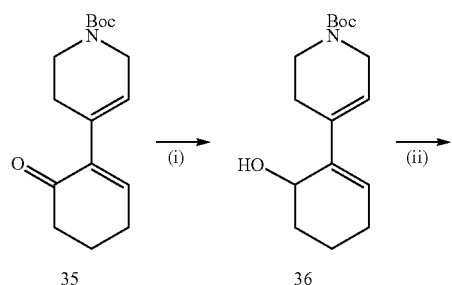

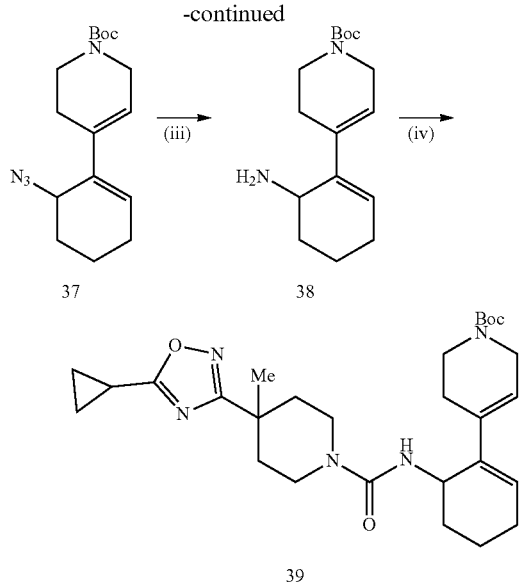

Step (i):

To a mixture of Compound 35 (192 mg), cerium(III) chloride heptahydrate (309 mg), and methanol (3 mL) was added sodium borohydride (51.4 mg) under ice temperature, and the mixture was stirred at the same temperature for 3 hours. To the reaction mixture was added aqueous sodium bicarbonate, and the mixture was extracted with chloroform/ methanol (6/1). The organic layer was dried over anhydrous sodium sulfate and concentrated in vacuo, and then the obtained residue was purified by silica gel column chromatography (eluate: hexane/ethyl acetate) to give the title compound 36 (120 mg).

LCMS: [M+H]⁺/Rt (min): 280/0.97

Step (ii):

To a mixture of Compound 36 (115 mg), triethylamine (0.143 mL), and THF (2 mL) was added ethanesulfonyl chloride (0.058 mL) under ice temperature, and the mixture was stirred for 30 minutes. Then, sodium azide (107 mg) was added to the reaction solution. The mixture was warmed to room temperature, and then the mixture was stirred. After the reaction was terminated as judged by the consumption of the reaction intermediate, water was added to the reaction mixture, and the mixture was extracted with chloroform. The organic layer was dried over anhydrous sodium sulfate and concentrated in vacuo, and then the obtained residue was purified by silica gel column chromatography (eluate: hexane/ethyl acetate) to give the title compound 37 (80 mg).

LCMS: [M+H]⁺/Rt (min): 305/1.25

Step (iii)

The title compound 38 (35 mg) was prepared in the same manner as Step (iv) in Reference example 7 by using Compound 37 (73 mg).

LCMS: [M+H]⁺/Rt (min): 279/0.74

Step (iv)

The title compound 39 (14.0 mg) was prepared in the same manner as Step (iii) in Reference example 2 by using Compound 38 (14.4 mg).

LCMS: [M+H]⁺/Rt (min): 512/1.14

Reference Example 14 rac-(1R,6S)-2,2-Difluoro-6-[4-(propan-2-yl)piperazin-1-yl]cyclohexan-1-amine trihydrochloride

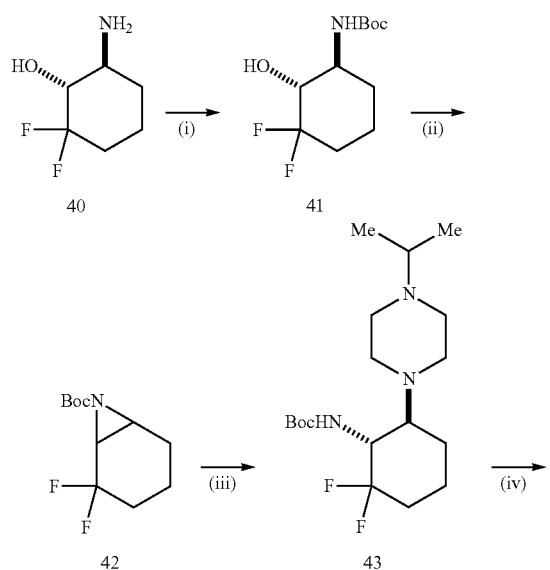

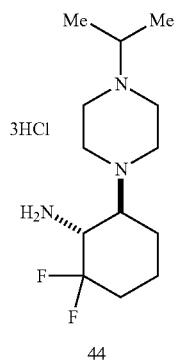

Step (i):

The title compound 41 (1.59 g) was prepared in the same manner as Step (ii) in Reference example 4 by using Compound (1.69 g).

LCMS: [M+H]⁺/Rt (min): 252/0.73

Step (ii):

To a mixture of Compound 41 (1.5 g) and THF (30 mL) was added potassium tert-butoxide (1.01 g) under ice temperature, and the mixture was stirred at the same temperature for 20 minutes. Then, tosyl chloride (1.37 g) was added to the reaction mixture under ice temperature, and the reaction mixture was stirred further for 2.5 hours. Water was added to the reaction mixture under ice temperature, and the mixture was extracted with chloroform. The organic layer was dried over anhydrous sodium sulfate, and concentrated in vacuo. The obtained residue was dissolved in 1,4-dioxane (30 mL), and tosyl chloride (1.37 g) was added to the solution under ice temperature. The solution was heated to 100° C. and stirred for 30 minutes. The reaction solution was cooled to room temperature, and aqueous ammonium chloride was added to the reaction solution. The mixture was extracted with chloroform/ethanol (3/1). The organic layer was dried over anhydrous sodium sulfate and concentrated in vacuo, and then the obtained residue was purified by silica gel column chromatography (eluate: hexane/ethyl acetate) to give the title compound 42 (1.09 g).

LCMS: [M+H]⁺/Rt (min): 234/1.01

Step (iii):

A mixture of Compound 42 (1.09 g), 1-isopropylpiperazine (0.899 g), and ethanol (10 mL) was stirred for 8 hours heating at 120° C. with a microwave device. Then, the reaction solution was concentrated in vacuo, and then the obtained residue was purified by amino silica gel column chromatography (eluate: ethyl acetate/hexane) to give the title compound 43 (1.32 g).

LCMS: [M+H]⁺/Rt (min): 362/0.74

Step (iv):

The title compound 44 (1.40 g) was prepared in the same manner as Step (iv) in Reference example 2 by using Compound 43 (1.31 g).

LCMS: [M+H]⁺/Rt (min): 262/0.19

Reference Examples 15 to 17

The compounds of Reference examples 15 to 17 shown in the table below were prepared according to the process in the above Reference example 14, by using an optically active isomer of Compound 40 (as Material A) instead of Compound 40 at Step (i) in Reference example 14 and each appropriate starting compound (as Material B) instead of 1-isopropylpiperazine at Step (iii) in Reference example 14.

| Reference example | Material A | Material B | Chemical structure | Instrumental analytical data |
|---|---|---|---|---|
| 15 | (1R,6S) 2,2-difluoro-6-amino-cyclohexan-1-ol [Abs] | 1-(propan-2-yl)piperazine | Structure 3HCl | LCMS: [M + H]⁺/Rt (min): 262/0.19 |
| 15' | (1S,6R) 2,2-difluoro-6-amino-cyclohexan-1-ol [Abs] | 1-(propan-2-yl)piperazine | Structure 3HCl | LCMS: [M + H]⁺/Rt (min): 262/0.19 (Method C) |
| 16 | (1R,6S) 2,2-difluoro-6-amino-cyclohexan-1-ol [Abs] | 6-(propan-2-yl)-3,6-diazabicyclo[3.1.1]heptane | Structure 46, 3HCl | LCMS: [M + H]⁺/Rt (min): 274/0.242 |
| 17 | (1R,6S) 2,2-difluoro-6-amino-cyclohexan-1-ol [Abs] | 3-(propan-2-yl)-3,8-diazabicyclo[3.2.1]octane | Structure 47, 3HCl | LCMS: [M + H]⁺/Rt (min): 288/0.239 |

Reference example 15: (1R,6S)-2,2-difluoro-6-[4-(propan-2-yl)piperazin-1-yl]cyclohexan-1-amine trihydrochloride Reference example 15': (1S,6R)-2,2-difluoro-6-[4-(propan-2-yl)piperazin-1-yl]cyclohexan-1-amine Reference example 16: (1R,6S)-2,2-difluoro-6-[6-(propan-2-yl)-3,6-diazabicyclo[3.1.1]heptan-3-yl]cyclohexan-1-amine Reference example 17: (1R,6S)-2,2-difluoro-6-[3-(propan-2-yl)-3,8-diazabicyclo[3.2.1]octan-8-yl]cyclohexan-1-amine

Reference Example 18

(1R,6S)-2,2-Difluoro-6-[4-(propan-2-yl)piperazin-1-yl]cyclohexan-1-amine

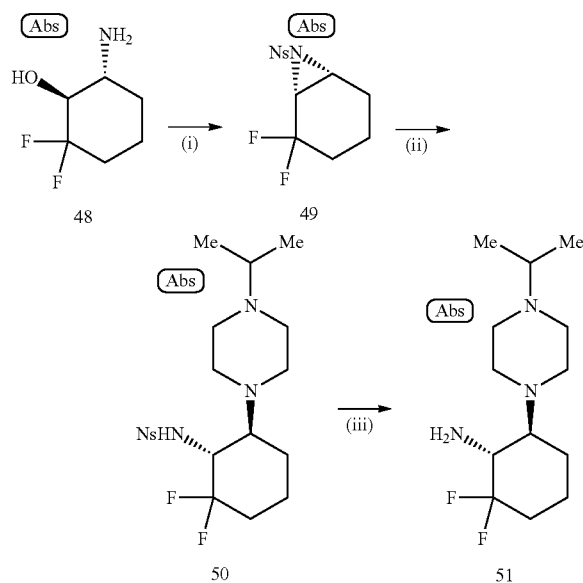

Step (i):

To a mixture of Compound 48 (5.94 g), sodium bicarbonate (13.2 g), and THF (131 mL) was added 2-nitrobenzenesulfonyl chloride (10.5 g) at room temperature, and the mixture was stirred at the same temperature for 16 hours. To the reaction mixture was added aqueous sodium bicarbonate, and the mixture was extracted with chloroform. The organic layer was dried over anhydrous sodium sulfate and concentrated in vacuo. The obtained residue was dissolved in THF (131 mL), and triethylamine (11 mL) and methanesulfonyl chloride (3.67 mL) were added to the solution under ice temperature. The mixture was stirred. After the reaction was terminated as judged by the consumption of the starting material, water was added to the reaction mixture, and the mixture was extracted with chloroform. The organic layer was dried over anhydrous sodium sulfate, and concentrated in vacuo. The obtained residue was dissolved in acetonitrile (393 mL), and potassium carbonate (16.3 mg) was added to the solution. The mixture was stirred for one hour heating at 80° C. To the reaction mixture was added water, and the mixture was extracted with chloroform. The organic layer was dried over anhydrous sodium sulfate and concentrated in vacuo, and then the obtained residue was purified by silica gel column chromatography (eluate: hexane/ethyl acetate) to give the title compound 49 (9.25 g).

LCMS: [M+H]$^+$/Rt (min): 319/0.94

Step (ii):

A mixture of Compound 49 (7.1 g), 1-isopropylpiperazine (3.56 mL), and toluene (22.3 mL) was stirred for one hour heating at 110° C. After the reaction was terminated as judged by the consumption of the starting material, the reaction mixture was concentrated in vacuo, and the obtained residue was purified by amino silica gel column chromatography (eluate: hexane/ethyl acetate) to give the title compound 50 (9.79 g).

LCMS: [M+H]$^+$/Rt (min): 447/0.68

Step (iii):

To a mixture of benzenethiol (0.530 mL) and toluene (11.2 mL) was added sodium hydride (55%, 0.215 g) under ice temperature, and the mixture was warmed to room temperature and stirred for 10 minutes. Then, to the reaction mixture was added a solution of Compound 50 (1 g) in toluene (9 mL), and the mixture was stirred heating at 60° C. After the reaction was terminated as judged by the consumption of the starting material, the reaction solution was cooled to 0° C., and 40% aqueous sodium hydroxide was added to the reaction mixture. The mixture was extracted with toluene. To the organic layer was added 5 M hydrochloric acid under ice temperature, and the aqueous layer was extracted from the mixture. To the obtained aqueous layer was added 40% aqueous sodium hydroxide, and the obtained mixture was again extracted with toluene. The organic layer was dried over anhydrous sodium sulfate and concentrated in vacuo, and then the obtained residue was purified by amino silica gel column chromatography (eluate: hexane/ethyl acetate) to give the title compound 51 (0.47 g).

LCMS: [M+H]$^+$/Rt (min): 262/0.17

Reference Example 19

2-(4-Methylpiperidin-4-yl)-4,5,6,7-tetrahydro-1,3-benzoxazole

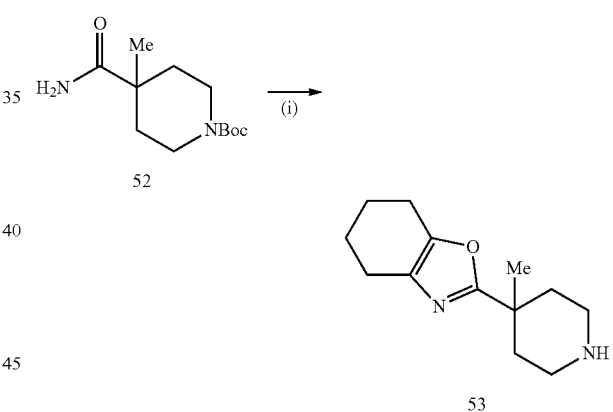

Step (i):

A mixture of Compound 52 (120 mg), 2-chlorocyclohexanone (68.9 mg), and DMF (1.5 mL) was stirred for 11 hours heating at 130° C. with a microwave device. Then, to the reaction solution was added hydrogen chloride/1,4-dioxane solution (0.25 mL), and the mixture was stirred for 6 hours heating at 130° C. with a microwave device. The reaction solution was concentrated in vacuo, and the obtained residue was dissolved in ethanol. 15% Aqueous sodium hydroxide (2 mL) was added to the solution, and the mixture was stirred for 3 hours heating at 150° C. with a microwave device. To the reaction mixture was added water, and the mixture was extracted with chloroform. The organic layer was dried over anhydrous sodium sulfate and concentrated in vacuo, and then the obtained residue was purified by amino silica gel column chromatography (eluate: hexane/ethyl acetate) to give the title compound 53 (14 mg).

LCMS: [M+H]$^+$/Rt (min): 221/0.57

Reference Example 20

4-(5-Cyclopropyl-1,2-oxazol-3-yl)-4-methylpiperidine monohydrochloride

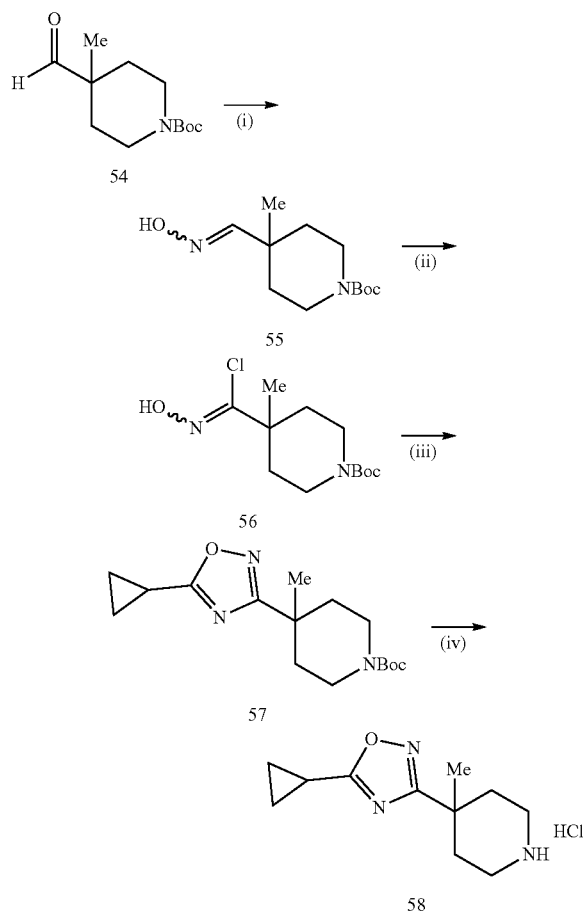

Step (i):

To a mixture of Compound 54 (900 mg), sodium acetate (650 mg), and methanol (5 mL) was added hydroxylamine hydrochloride (550 mg), and the mixture was stirred at room temperature for 24 hours. The reaction solution was cooled to 0° C., and water was added thereto. The mixture was extracted with chloroform, and the organic layer was dried over anhydrous sodium sulfate and concentrated in vacuo to give the title compound 55 (1.23 g).

Step (ii):

To a mixture of Compound 55 (416 mg) and DMF (4 mL) was added N-chlorosuccinimide (252 mg), and the mixture was stirred for 3 hours. The reaction solution was cooled to 0° C., and water (6 mL) was added thereto. The precipitated solid was collected on a filter, and dried to give the title compound 56 (326 mg).

Step (iii):

To a mixture of ethynylcyclopropane (117 mg) and toluene (5 mL) were added Compound 56 (326 mg) and sodium bicarbonate (198 mg), and the mixture was stirred at room temperature. After the reaction was terminated as judged by the consumption of the starting material, water was added to the reaction mixture and the mixture was extracted with ethyl acetate. The organic layer was dried over anhydrous sodium sulfate, and concentrated in vacuo. Then, the obtained residue was purified by silica gel column chromatography (eluate: hexane/ethyl acetate) to give the title compound 57 (348 mg).

LCMS: [M+H]$^+$/Rt (min): 307/1.13

Step (iv):

The title compound 58 (307 mg) was prepared in the same manner as Step (iv) in Reference example 2 by using Compound 57 (337 mg).

LCMS: [M+H]$^+$/Rt (min): 207/0.49

Reference Example 21

2-(4-Methylpiperidin-4-yl)-1,3-benzoxazole

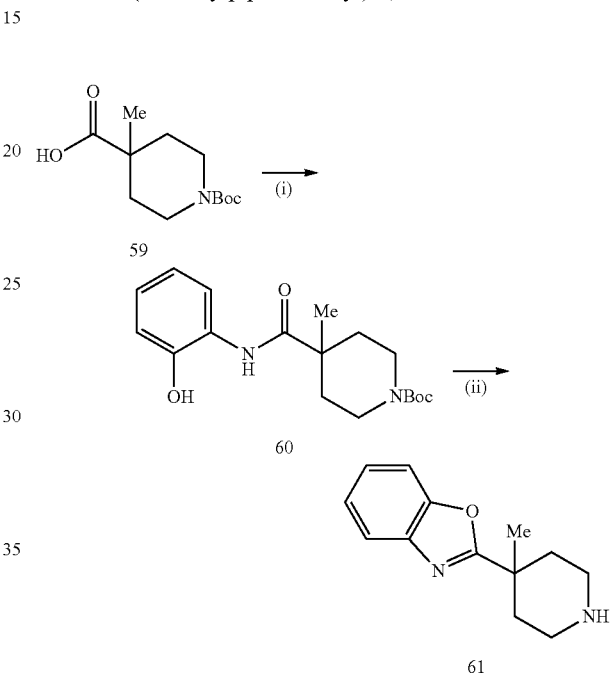

Step (i):

To a solution of Compound 59 (1.46 g) in THF (30 mL) were added isobutyl chloroformate (819 mg) and diisopropylethylamine (3.88 g) under ice temperature, and the mixture was stirred for one hour. 2-Aminophenol (655 mg) was added to the reaction mixture under ice temperature, and the mixture was stirred for 6 hours heating at 70° C. The reaction solution was directly purified by amino silica gel column chromatography (eluate: ethyl acetate/hexane) to give the title compound 60 (710 mg).

LCMS: [M+H]$^+$/Rt (min): 335/2.28 (Method B)

Step (ii):

A mixture of Compound 60 (204 mg) and acetic acid (1.10 mL) was stirred for 2 hours heating at 90° C., and concentrated in vacuo. The obtained residue was dissolved in chloroform (2 mL), and trifluoromethanesulfonic acid (2.1 mL) was added to the solution. The mixture was stirred at room temperature for one hour. The reaction solution was concentrated in vacuo, ethyl acetate and aqueous sodium bicarbonate were added to the residue. The mixture was extracted with ethyl acetate. The organic layer was dried over anhydrous sodium sulfate and concentrated in vacuo, and then the obtained residue was purified by amino silica gel column chromatography (eluate: ethyl acetate/hexane) to give the title compound 61 (99 mg).

LCMS: [M+H]$^+$/Rt (min): 217/1.36 (Method B)

Reference Example 22

4-Cyclopentyl-4-methylpiperidine monohydrochloride

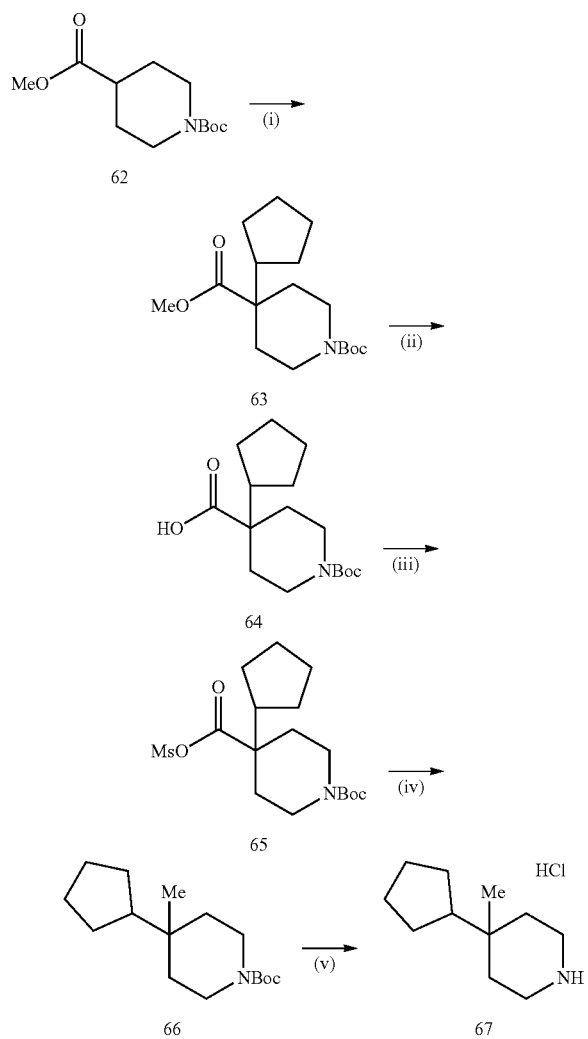

Step (i):

To a mixture of Compound 62 (700 mg) and THF (14 mL) was added lithium diisopropylamide (2 M, 5.18 mL) at −78° C., and the mixture was stirred at the same temperature for 2 hours. To the reaction mixture were added bromocyclopentane (1.23 mL) and potassium iodide (478 mg), and the mixture was warmed to room temperature. The mixture was stirred overnight, and then water was added to the mixture. The mixture was extracted with ethyl acetate. The organic layer was dried over anhydrous sodium sulfate and concentrated in vacuo, and then the obtained residue was purified by silica gel column chromatography (eluate: ethyl acetate/hexane) to give the title compound 63 (468 mg).

LCMS: $[M+H]^+$/Rt (min): 312/1.26

Step (ii):

To a mixture of lithium aluminium hydride (104 mg) and THF (3 mL) were added Compound 63 (371 mg) and THF (6 mL) under ice temperature, and the mixture was stirred for 4 hours. After the reaction was terminated as judged by the consumption of the starting material, water (0.104 mL), 15% aqueous sodium hydroxide (0.104 mL), and then water (0.312 mL) were added to the reaction mixture at 0° C., and the mixture was stirred. The reaction mixture was filtrated. The filtrate was concentrated in vacuo, and then the obtained residue was purified by silica gel column chromatography (eluate: ethyl acetate/hexane) to give the title compound 64 (320 mg).

LCMS: $[M+H]^+$/Rt (min): 284/1.06

Step (iii):

To a mixture of Compound 64 (314 mg), triethylamine (0.309 mL), and THF (5 mL) was added methanesulfonyl chloride (0.104 mL), and the mixture was stirred at room temperature. After the reaction was terminated as judged by the consumption of the starting material, water was added to the reaction mixture, and the mixture was extracted with chloroform. The organic layer was dried over anhydrous sodium sulfate and concentrated in vacuo, and then the obtained residue was purified by silica gel column chromatography (eluate: ethyl acetate/hexane) to give the title compound 65 (290 mg).

LCMS: $[M+H]^+$/Rt (min): 362/1.15

Step (iv):

To a mixture of Compound 65 (278 mg) and THF (3 mL) was added lithium triethylborohydride (0.99 M, 1.55 mL), and the mixture was stirred at room temperature. Then, the reaction solution was heated to 70° C. After the reaction was terminated as judged by the consumption of the starting material, the reaction solution was cooled to 0° C., and aqueous ammonium chloride was added to the reaction solution. The mixture was extracted with chloroform, and the organic layer was dried over anhydrous sodium sulfate and concentrated in vacuo. Then, the obtained residue was purified by silica gel column chromatography (eluate: hexane/ethyl acetate) to give the title compound 66 (100 mg).

LCMS: $[M+H]^+$/Rt (min): 268/1.42

Step (v):

The title compound 67 (58.5 mg) was prepared in the same manner as Step (iv) in Reference example 2 by using Compound 66 (90 mg).

LCMS: $[M+H]^+$/Rt (min): 168/0.62

Reference Example 23

4-(4,4-Difluorocyclohexyl)-4-methylpiperidine monohydrochloride

The compound of Reference example 23 shown in the table below was prepared according to the process in the above Reference example 22, by using 1,1-difluoro-4-iodo-cyclohexane instead of bromocyclopentane at Step (i) in Reference example 22.

| Reference example | Chemical structure | Instrumental analytical data |
|---|---|---|
| 23 | ![structure] | LCMS: $[M + H]^+$/Rt (min): 218/0.57 |

Reference Example 24

4-(5-Cyclopropyl-1,3,4-thiadiazol-2-yl)-4-methylpiperidine monohydrochloride

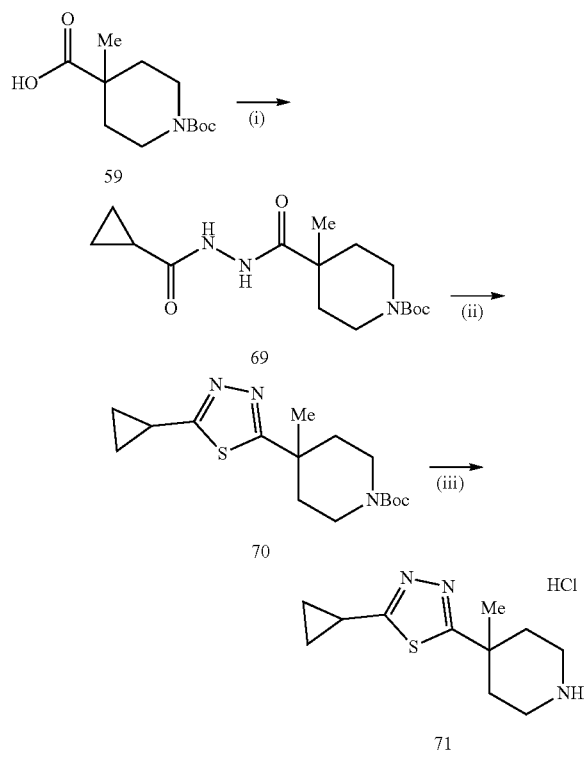

Step (i):

To a mixture of Compound 59 (399 mg), cyclopropanecarbohydrazide hydrochloride (269 mg), and DMF (5 mL) were added HATU (686 mg) and diisopropylethylamine (1.15 mL), and the mixture was stirred at room temperature for 3 hours. Water was added to the reaction solution, and the mixture was extracted with ethyl acetate. The organic layer was dried over anhydrous sodium sulfate and concentrated in vacuo, and then the obtained residue was purified by silica gel column chromatography (eluate: hexane/ethyl acetate) to give the title compound 69 (520 mg).

LCMS: [M+H]$^+$/Rt (min): 326/0.74

Step (ii):

To a mixture of Compound 69 (255 mg) and toluene (6 mL) was added Lawesson's reagent (349 mg), and the mixture was stirred under reflux for one hour. The reaction solution was cooled to 0° C., and aqueous sodium bicarbonate was added to the reaction solution. The mixture was extracted with ethyl acetate. The organic layer was dried over anhydrous sodium sulfate and concentrated in vacuo, and then the obtained residue was purified by silica gel column chromatography (eluate: hexane/ethyl acetate) and then by amino silica gel column chromatography (eluate: hexane/ethyl acetate) to give the title compound 70 (102 mg).

LCMS: [M+H]$^+$/Rt (min): 324/1.08

Step (iii):

The title compound 71 (78 mg) was prepared in the same manner as Step (iv) in Reference example 2 by using Compound 70 (92 mg).

LCMS: [M+H]$^+$/Rt (min): 224/0.45

Reference Example 25

4-(5-Cyclopropyl-1,3-thiazol-2-yl)-4-methylpiperidine monohydrochloride

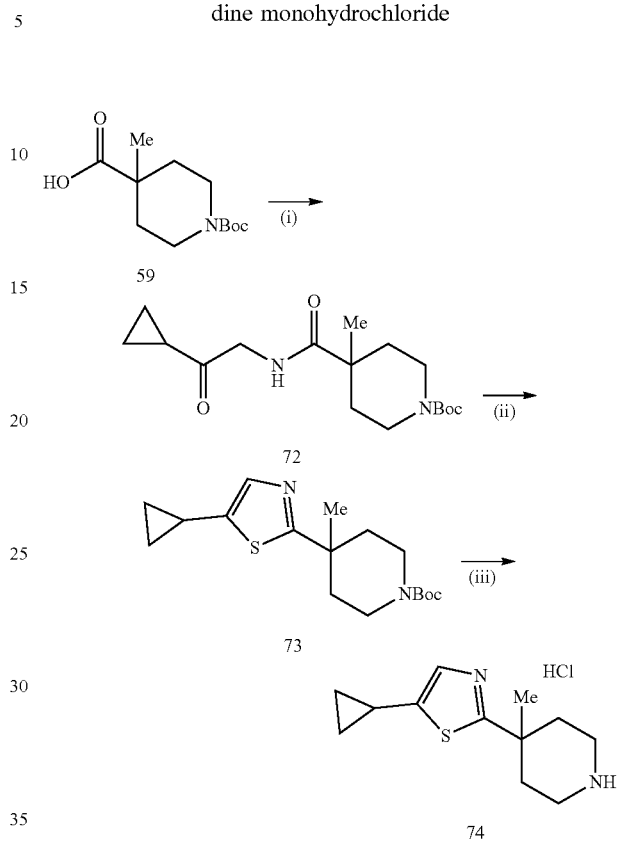

Step (i):

The title compound 72 (796 mg) was prepared in the same manner as Step (i) in Reference example 24 by using Compound 59 (718 mg) and 2-amino-1-cyclopropylethan-1-one hydrochloride (400 mg).

LCMS: [M+H]$^+$/Rt (min): 325/0.83

Step (ii):

To a mixture of Compound 72 (127 mg), pyridine (0.063 mL), and toluene (3 mL) was added Lawesson's reagent (205 mg), and the mixture was stirred under reflux for 14 hours. The reaction solution was cooled to room temperature, and then aqueous sodium bicarbonate was added to the reaction solution. The mixture was extracted with ethyl acetate. The organic layer was dried over anhydrous sodium sulfate and concentrated in vacuo, and then the obtained residue was purified by amino silica gel column chromatography (eluate: hexane/ethyl acetate) to give the title compound 73 (76.3 mg).

LCMS: [M+H]$^+$/Rt (min): 323/1.43

Step (iii):

The title compound 74 (66.5 mg) was prepared in the same manner as Step (iv) in Reference example 2 by using Compound 73 (77 mg).

LCMS: [M+H]$^+$/Rt (min): 223/0.67

Reference Example 26

4-(2-Cyclopropyl-1,3-thiazol-4-yl)-4-methylpiperidine monohydrochloride

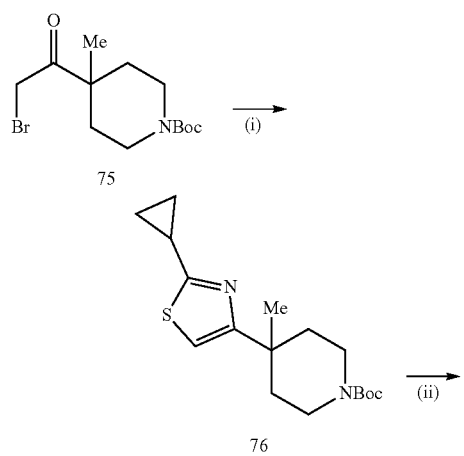

Step (i):

A solution of Compound 75 (532 mg) and cyclopropanecarbothioamide (168 mg) in methanol (6 mL) was stirred under reflux for 2.5 hours. The reaction mixture was allowed to cool to room temperature, and then saturated aqueous sodium bicarbonate was added to the reaction mixture. The mixture was extracted with chloroform. The organic layer was dried over anhydrous sodium sulfate and concentrated in vacuo, and then the obtained residue was purified by silica gel column chromatography (eluate: hexane/ethyl acetate) to give the title compound 76 (119 mg).

Step (ii):

The title compound 77 (137 mg) was prepared in the same manner as Step (iv) in Reference example 2 by using Compound 76 (119 mg).

LCMS: [M+H]$^+$/Rt (min): 223/0.572

Reference Example 27

4-(1-Cyclopropyl-1H-1,2,4-triazol-3-yl)-4-methylpiperidine dihydrochloride

Step (i):

The title compound 78 (648 mg) was prepared in the same manner as Step (i) in Reference example 24 by using Compound 59 (611 mg) and cyclopropylhydrazine hydrochloride (300 mg).

LCMS: [M+H]$^+$/Rt (min): 298/0.80

Step (ii):

A mixture of Compound 78 (374 mg), ammonium formate (1.43 g), and trimethyl orthoformate (2.78 mL) was stirred heating at 100° C. After the reaction was completed, the reaction solution was concentrated. To the obtained residue was added water, and the mixture was extracted with chloroform. The organic layer was dried over anhydrous sodium sulfate and concentrated in vacuo, and then the obtained residue was purified by silica gel column chromatography (eluate: hexane/ethyl acetate) to give the title compound 79 (163 mg).

LCMS: [M+H]$^+$/Rt (min): 307/0.89

Step (iii):

The title compound 80 (142 mg) was prepared in the same manner as Step (iv) in Reference example 2 by using Compound 79 (144 mg).

LCMS: [M+H]$^+$/Rt (min): 207/0.39

Reference Example 28

4-(5-Cyclopropyl-1,2,4-thiadiazol-3-yl)-4-methylpiperidine

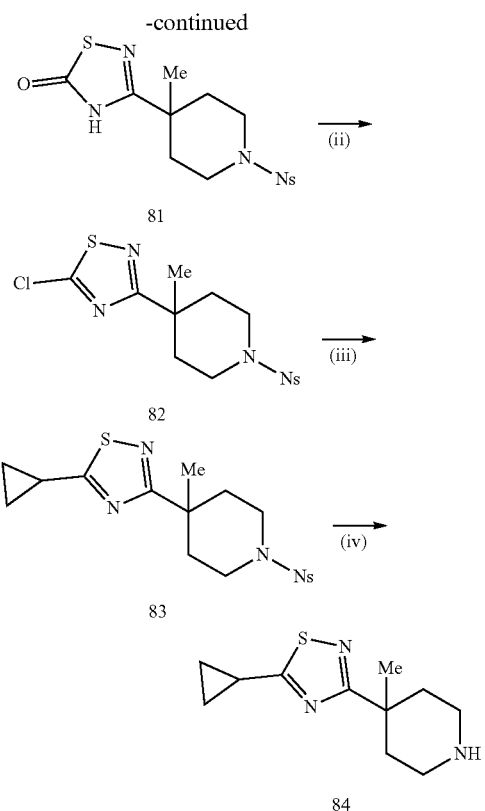

Step (i):

To a solution of Compound 27 (1.04 g) in THF (15 mL) was added thiocarbonylimidazole (0.864 mg) under ice temperature, and the mixture was stirred at room temperature. After the reaction was terminated as judged by the consumption of the starting material, the reaction solution was cooled to 0° C., and water was added to the reaction solution. The mixture was extracted with ethyl acetate. The organic layer was dried over sodium sulfate, and concentrated in vacuo.

The obtained residue was dissolved in THF (15 mL), and boron trifluoride-diethyl ether complex (1.52 mL) was added to the solution at 0° C. The mixture was warmed to room temperature under stirring. After the reaction was completed, aqueous sodium bicarbonate was added to the reaction solution, and the mixture was extracted with chloroform. The organic layer was dried over sodium sulfate and concentrated in vacuo, and then the obtained residue was purified by amino silica gel column chromatography (eluate: hexane/ethyl acetate).

To a solution of the purified compound in THF (15 mL) was added hydrogen chloride/dioxane solution (4 M, 5.05 mL) at 0° C., and the mixture was warmed to room temperature and stirred. After the reaction was completed, the reaction solution was concentrated in vacuo, and the obtained residue was dissolved in THF (15 mL). To the solution were added triethylamine (3.38 ml) and 2-nitrobenzenesulfonyl chloride (0.985 g), and the mixture was stirred at room temperature. After the reaction was completed, water was added to the reaction solution, and the mixture was extracted with chloroform. The organic layer was dried over anhydrous sodium sulfate and concentrated in vacuo, and then the obtained residue was purified by silica gel column chromatography (eluate: chloroform/methanol) to give the title compound 81 (627 mg).

LCMS: [M+H]$^+$/Rt (min): 385/0.93

Step (ii):

To a mixture of Compound 81 (590 mg), pyridine (0.248 mL), and toluene (7 mL) was added phosphoryl chloride (0.572 mL), and the mixture was stirred under reflux. After the reaction was completed, the reaction solution was added to aqueous sodium bicarbonate at 0° C., and the mixture was filtrated. The filtrate was extracted with ethyl acetate. The organic layer was dried over sodium sulfate and concentrated in vacuo, and then the obtained residue was purified by amino silica gel column chromatography (eluate: hexane/ethyl acetate) to give the title compound 82 (432 mg).

LCMS: [M+H]$^+$/Rt (min): 403/1.21

Step (iii):

To a mixture of Compound 82 (210 mg), cyclopropylzinc (II) bromide (0.5 M, 3.13 mL), and THF (2 mL) was added tetrakis(triphenylphosphine)palladium(0) (30.1 mg), and the mixture was stirred at 60° C. for 1.5 hours. After the reaction was completed, aqueous sodium bicarbonate was added to the reaction solution, and the mixture was extracted with ethyl acetate. The organic layer was dried over sodium sulfate and concentrated in vacuo, and then the obtained residue was purified by amino silica gel column chromatography (eluate: hexane/ethyl acetate) to give the title compound 83 (84 mg).

LCMS: [M+H]$^+$/Rt (min): 409/1.24

Step (iv):

To a mixture of Compound 83 (71.4 mg), 1-dodecanethiol (0.251 mL), and acetonitrile (3 mL) was added potassium carbonate (145 mg), and the mixture was stirred at 80° C. After the reaction was completed, water was added to the reaction solution, and the mixture was extracted with chloroform/methanol (6/1). The organic layer was dried over sodium sulfate and concentrated in vacuo, and then the obtained residue was purified by amino silica gel column chromatography (eluate: hexane/ethyl acetate=>chloroform/methanol) to give the title compound 84 (38 mg).

LCMS: [M+H]$^+$/Rt (min): 224/0.52

Reference Example 29

4-(5-Methoxy-1,2,4-thiadiazol-3-yl)-4-methylpiperidine

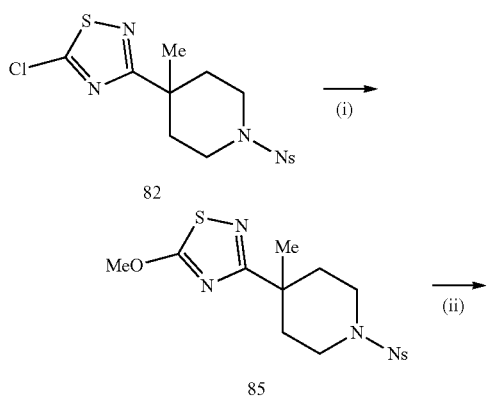

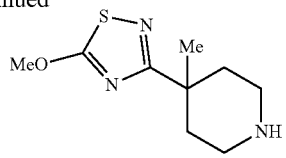

86

Step (i):

To a solution of Compound 82 (119 mg) in methanol (2 mL) was added sodium methoxide (28%, 285 mg), and the mixture was stirred at room temperature. After the reaction was completed, water was added to the reaction solution, and the mixture was extracted with chloroform. The organic layer was concentrated in vacuo to give the title compound 85 (97.1 mg).

LCMS: [M+H]$^+$/Rt (min): 399/1.18

Step (ii):

The title compound 86 (14.9 mg) was prepared in the same manner as Step (iv) in Reference example 28 by using Compound 85 (91.6 mg).

LCMS: [M+H]$^+$/Rt (min): 214/0.48

Reference Example 30

4-[5-(Cyclopropyloxy)-1,2,4-thiadiazol-3-yl]-4-methylpiperidine

The compound of Reference example 30 shown in the table below was prepared according to the process in the above Reference example 29, by using cyclopropyl alcohol and sodium hydride instead of sodium methoxide at Step (i) in Reference example 29.

| Reference example | Chemical structure | Instrumental analytical data |
|---|---|---|
| 30 | 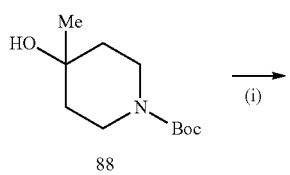 | LCMS: [M + H]$^+$/Rt (min): 240/0.56 |

Reference Example 31

2-[(4-Methylpiperidin-4-yl)oxy]pyridine monohydrochloride

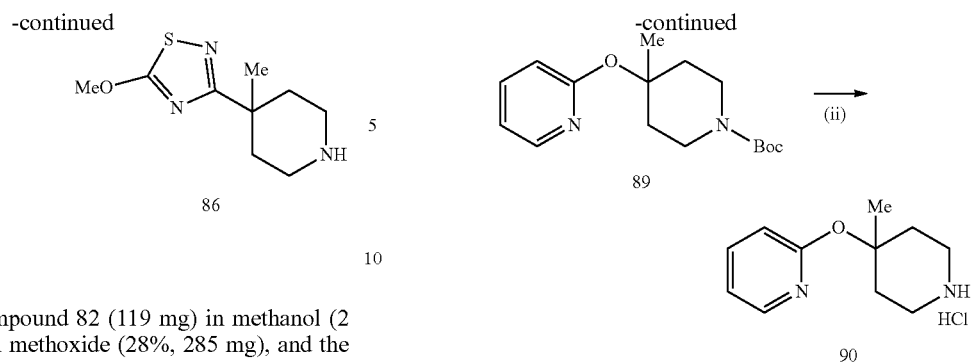

Step (i):

To a solution of Compound 88 (183 mg) in DMF (2 mL) was added sodium hydride (55%, 48.2 mg) under ice temperature, and the mixture was stirred for 20 minutes. To the reaction mixture was added 2-fluoropyridine (0.109 mL), and the mixture was stirred at room temperature. After the reaction was completed, the reaction mixture was cooled to 0° C. To the reaction mixture was added water, and the mixture was extracted with chloroform. The organic layer was dried over sodium sulfate and concentrated in vacuo, and then the obtained residue was purified by silica gel column chromatography (eluate: hexane/ethyl acetate) to give the title compound 89 (18 mg).

LCMS: [M+H]$^+$/Rt (min): 293/1.29

Step (ii):

The title compound 90 (13.2 mg) was prepared in the same manner as Step (iv) in Reference example 2 by using Compound 89 (14.7 mg).

LCMS: [M+H]$^+$/Rt (min): 193/0.48

Reference Example 32

4-(2-Fluoro-4-methylphenyl)-4-methylpiperidine

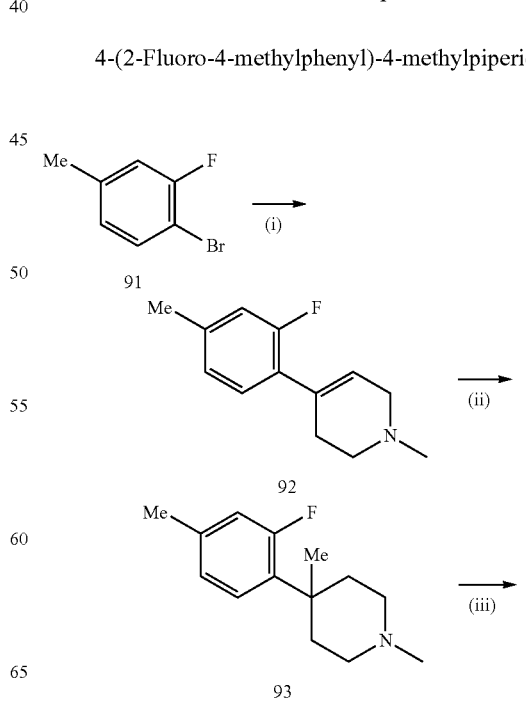

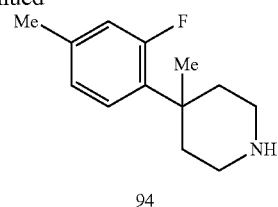

Step (i):

To a mixture of Compound 91 (211 mg), 1-methyl-1,2,3,6-tetrahydropyridine-4-boronic acid pinacol ester (274 mg), potassium carbonate (386 mg), 1,2-dimethoxymethane (4 mL), and water (1 mL) was added dichloro(1,1'-bis(diphenylphosphino)ferrocene)palladium (45.6 mg) at room temperature, and then the mixture was heated under reflux. After the reaction was completed, water was added to the reaction solution, and the mixture was extracted with chloroform. The organic layer was dried over sodium sulfate and concentrated in vacuo, and then the obtained residue was purified by amino silica gel column chromatography (eluate: hexane/ethyl acetate) to give the title compound 92 (32 mg).

LCMS: [M+H]$^+$/Rt (min): 206/0.51

Step (ii):

To a solution of Compound 92 (137 mg) in THF (3 mL) was added n-butyllithium solution (1.57 M, 0.68 mL) at −18° C., and the mixture was further cooled to −50° C. Dimethyl sulfate was added dropwise to the reaction solution, and the mixture was stirred at −50° C. for one hour. To the reaction solution was added aqueous ammonia, and the mixture was extracted with ethyl acetate. The organic layer was dried over sodium sulfate, and concentrated in vacuo to give a residue.

The obtained residue was dissolved in methanol (3 mL), and sodium borohydride (80 mg) was added to the solution under ice temperature. After the reaction was completed, aqueous sodium bicarbonate was added to the reaction solution, and the mixture was extracted with chloroform. The organic layer was dried over sodium sulfate and concentrated in vacuo, and then the obtained residue was purified by amino silica gel column chromatography (eluate: hexane/ethyl acetate) to give the title compound 93 (32 mg).

LCMS: [M+H]$^+$/Rt (min): 222/0.63

Step (iii):

To a solution of Compound 93 (30.4 mg) in 1,2-dichloroethane (3 mL) was added 1-chloroethyl chloroformate (0.045 mL) at room temperature, and the mixture was heated under reflux. The reaction solution was concentrated in vacuo, and chloroform and aqueous sodium hydroxide were added to the obtained residue. The mixture was stirred at room temperature, and then extracted with chloroform. The organic layer was dried over sodium sulfate and concentrated in vacuo, and then the obtained residue was purified by amino silica gel column chromatography (eluate: chloroform/methanol) to give the title compound 94 (22 mg).

LCMS: [M+H]$^+$/Rt (min): 208/0.66

Reference Example 33

4-[4-(Difluoromethyl)phenyl]-4-methylpiperidine monohydrochloride

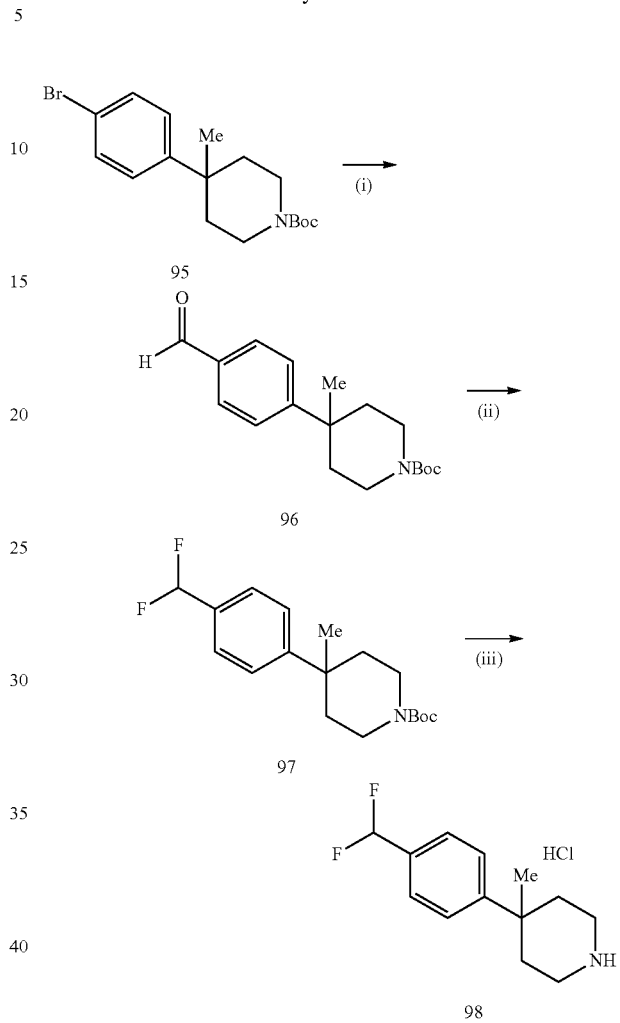

Step (i):

To a solution of Compound 95 (490 mg) in THF (6 mL) was added n-butyllithium solution (1.57 M, 1.15 mL) at −78° C., and the mixture was stirred for 30 minutes. To the reaction solution was added DMF (0.535 mL), and the mixture was warmed to 0° C. After the reaction was completed, water was added to the reaction solution, and the mixture was extracted with chloroform. The organic layer was dried over sodium sulfate and concentrated in vacuo, and then the obtained residue was purified by silica gel column chromatography (eluate: hexane/ethyl acetate) to give the title compound 96 (256 mg).

LCMS: [M+H]$^+$/Rt (min): 304/1.10

Step (ii):

To a solution of Compound 96 (157 mg) in dichloromethane (2 mL) was added Deoxo-Fluor(R) (0.285 mL) under ice temperature, and then the mixture was stirred at room temperature. After the reaction was completed, the reaction solution was added to aqueous sodium bicarbonate in ice bath, and the mixture was extracted with chloroform. The organic layer was dried over sodium sulfate and concentrated in vacuo, and then the obtained residue was purified by amino silica gel column chromatography (eluate: hexane/ethyl acetate) to give the title compound 97 (110 mg).
LCMS: [M+H]$^+$/Rt (min): 326/1.20
Step (iii):
The title compound 98 (84.5 mg) was prepared in the same manner as Step (iv) in Reference example 2 by using Compound 97 (104.8 mg).
LCMS: [M+H]$^+$/Rt (min): 226/0.60

Reference Example 34

5-Methyl-2-(4-methylpiperidin-4-yl)benzonitrile

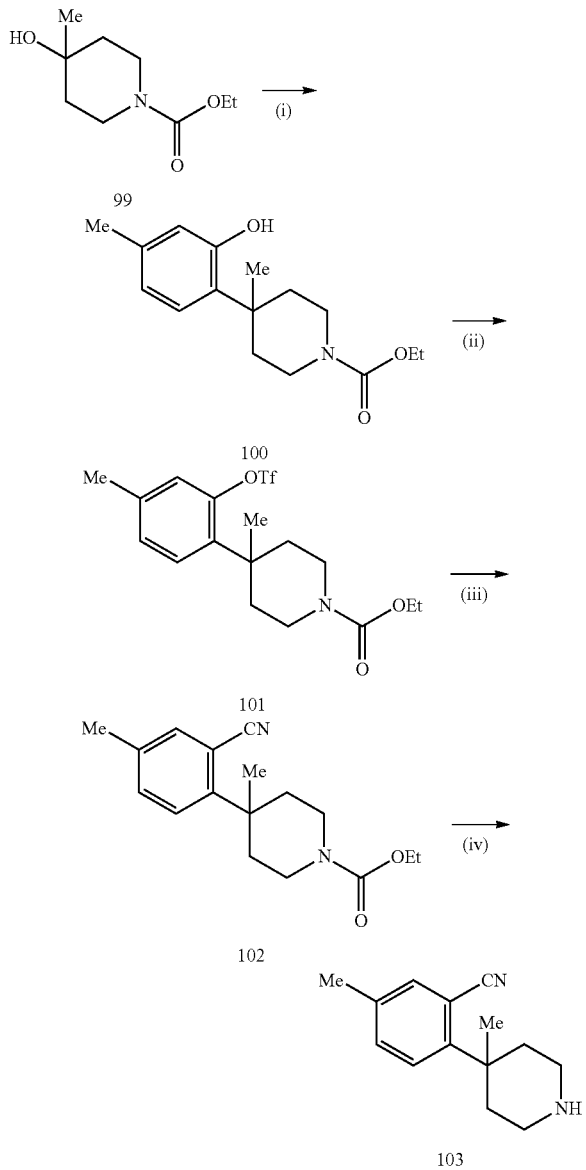

Step (i):
To a mixture of Compound 99 (267 mg) and m-cresol (1.20 mL) was added trifluoromethanesulfonic acid (1.01 mL), and the mixture was stirred at room temperature. After the reaction was completed, the reaction solution was added to aqueous sodium bicarbonate at 0° C., and the mixture was extracted with chloroform. The organic layer was dried over sodium sulfate, concentrated in vacuo, and then the obtained residue was purified by silica gel column chromatography (eluate: hexane/ethyl acetate) to give the title compound 100 (388 mg).
LCMS: [M+H]$^+$/Rt (min): 278/1.01
Step (ii):
To a mixture of Compound 100 (113 mg), potassium carbonate (169 mg), and THF (4 mL) was added N-phenyl-bis(trifluoromethanesulfonimide) (175 mg), and the mixture was stirred heating at 120° C. with a microwave device. After the reaction was completed, water was added to the reaction solution, and the mixture was extracted with chloroform. The organic layer was dried over sodium sulfate and concentrated in vacuo, and then the obtained residue was purified by silica gel column chromatography (eluate: hexane/ethyl acetate) to give the title compound 101 (138 mg).
LCMS: [M+H]$^+$/Rt (min): 410/1.26
Step (iii):
The title compound 102 (40.8 mg) was prepared in the same manner as Step (iii) in Reference example 28 by using Compound 101 (130 mg) and zinc cyanide (55.8 mg).
LCMS: [M+H]$^+$/Rt (min): 287/1.07
Step (iv):
To a solution of Compound 102 (40 mg) in 2-propanol (3 ml) was added potassium hydroxide (78 mg) at room temperature, and then the mixture was stirred heating at 110° C. with a microwave device. After the reaction was completed, water was added to the reaction solution. The mixture was extracted with chloroform/ethanol (4/1). The organic layer was dried over sodium sulfate and concentrated in vacuo, and then the obtained residue was purified by amino silica gel column chromatography (eluate: chloroform/methanol) to give the title compound 103 (20.6 mg).
LCMS: [M+H]$^+$/Rt (min): 215/0.57

Reference Example 35

(3S,4S)-4-Fluoro-1-(propan-2-yl)pyrrolidin-3-ol

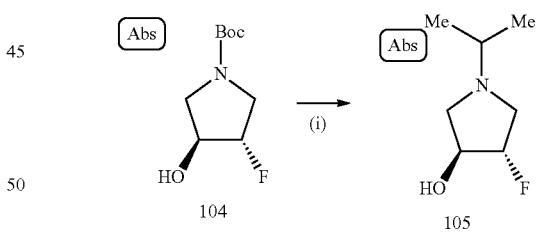

Step (i):
To a solution of Compound 104 (500 mg) in chloroform (2 mL) was added hydrogen chloride/1,4-dioxane (4 M, 6 mL) at 0° C., and the mixture was warmed to room temperature and stirred. After the reaction was terminated as judged by the consumption of the starting material, the reaction solution was concentrated in vacuo. The obtained residue was dissolved in chloroform (2 mL). To the solution were added acetone (1.79 mL), sodium acetate (200 mg), and sodium triacetoxyborohydride (1.03 g) at 0° C., and the mixture was warmed to room temperature and stirred. After the reaction was completed, aqueous sodium bicarbonate was added to the reaction mixture at 0° C., and the mixture was extracted with chloroform/methanol (5/1). The organic layer was dried over anhydrous sodium sulfate and concentrated in vacuo, and then the obtained residue was purified by amino silica gel column chromatography (eluate: hexane/ethyl acetate) to give the title compound 105 (348 mg).

LCMS: [M+H]⁺/Rt (min): 148/0.17

Reference Example 36

(3R)-4,4-Difluoro-1-(propan-2-yl)pyrrolidin-3-ol

The compound of Reference example 36 shown in the table below was prepared according to the process in the above Reference example 35, by using the appropriate starting compound instead of Compound 104 at Step (i) in Reference example 35.

| Reference example | Chemical structure | Instrumental analytical data |
|---|---|---|
| 36 | 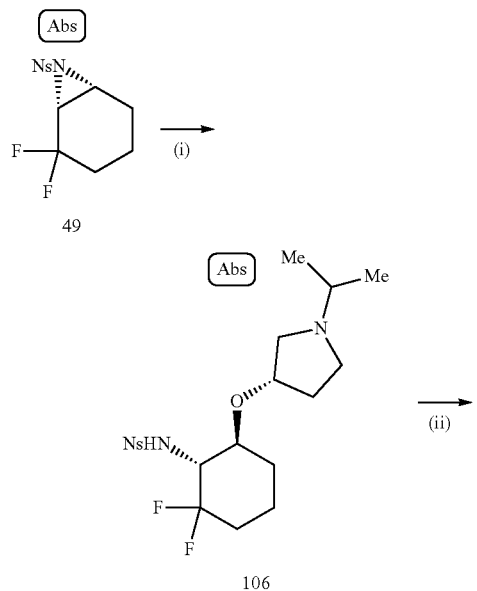 | LCMS: [M + H]⁺/Rt (min): 166/0.19 |

Reference Example 37

(1R,6S)-2,2-Difluoro-6-{[(3S)-1-(propan-2-yl)pyrrolidin-3-yl]oxy}cyclohexan-1-amine

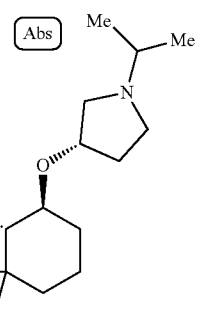

107

Step (i):

A mixture of Compound 49 (1.5 g), (S)-1-isopropylpyrrolidin-3-ol (0.792 mg), and NMP (1 mL) was stirred heating at 150° C. After the reaction was terminated as judged by the consumption of the starting material, the reaction solution was directly purified by silica gel column chromatography (eluate: chloroform/methanol/triethylamine) and then by amino silica gel column chromatography (eluate: hexane/ethyl acetate) to give the title compound 106 (1.03 g).

LCMS: [M+H]⁺/Rt (min): 448/0.78

Step (ii):

The title compound 107 (43 mg) was prepared in the same manner as Step (iii) in Reference example 18 by using Compound 106 (100 mg).

LCMS: [M+H]⁺/Rt (min): 263/0.22

Reference Examples 38 to 40

The compounds of Reference examples 38 to 40 shown in the table below were prepared according to the process in the above Reference example 37, by using each appropriate starting compound instead of (S)-1-isopropylpyrrolidin-3-ol at Step (i) in Reference example 37.

| Reference example | Chemical structure | Instrumental analytical data |
|---|---|---|
| 38 | 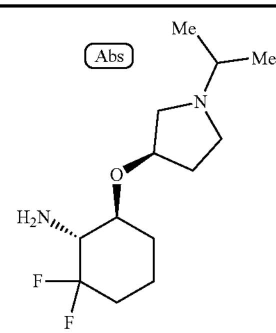 | LCMS: [M + H]⁺/Rt (min): 263/0.151 |

-continued

| Reference example | Chemical structure | Instrumental analytical data |
|---|---|---|
| 39 | (structure with Abs label) | LCMS: [M + H]⁺/Rt (min): 281/0.18 |
| 40 | (structure with Abs label) | LCMS: [M + H]⁺/Rt (min): 299/0.35 |

Reference example 38: (1R,6S)-2,2-difluoro-6-{[(3R)-1-(propan-2-yl)pyrrolidin-3-yl]oxy}cyclohexan-1-amine Reference example 39: (1R,6S)-2,2-difluoro-6-{[(3S,4S)-4-fluoro-1-(propan-2-yl)pyrrolidin-3-yl]oxy}cyclohexan-1-amine Reference example 40: (1R,6S)-6-{[(3R)-4,4-difluoro-1-(propan-2-yl)pyrrolidin-3-yl]oxy}-2,2-difluorocyclohexan-1-amine Reference Example 41

3-Fluoro-5-methyl-2-(piperidin-4-yl)pyridine

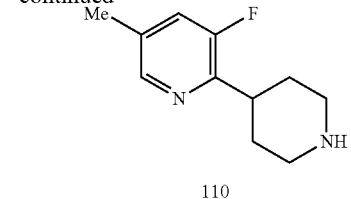

Step (i):
The title compound 109 (90.5 mg) was prepared in the same manner as Step (i) in Reference example 32 by using Compound 108 (72.4 mg) and 1-carbobenzoxy-1,2,3,6-tetrahydro-4-(4,4,5,5-tetramethyl-1,3,2-dioxaboran-2-yl)pyridine.
LCMS: [M+H]⁺/Rt (min): 327/1.04 (Method C)

Step (ii):
To a solution of Compound 109 (88.0 mg) in ethyl acetate (1.5 mL) was added palladium/carbon (88.0 mg), and the mixture was stirred under hydrogen atmosphere for 8 hours. The reaction solution was filtrated with Celite, and the filtrate was concentrated in vacuo to give the title compound 110 (22.2 mg).
LCMS: [M+H]⁺/Rt (min): 195/0.35 (Method C)

Reference Example 42

(1R,6S)-2,2-Difluoro-6-[4-(propan-2-yl)piperazin-1-yl]cyclohexan-1-ol

Step (i):
To a solution of Compound 111 (300 mg) and sodium bicarbonate (634 mg) in ethanol (10 mL) was added N-benzyl-N,N-bis(2-chloroethyl)amine hydrochloride (586 mg), and the mixture was stirred heating at 120° C. with a microwave device. After the reaction was completed, water was added to the reaction solution, and the mixture was extracted with chloroform. The organic layer was dried over sodium sulfate and concentrated in vacuo, and then the obtained residue was purified by amino silica gel column chromatography (eluate: hexane/ethyl acetate) to give the title compound 112 (398 mg).

LCMS: [M+H]⁺/Rt (min): 311/0.46

Step (ii):

The title compound 113 (289 mg) was prepared in the same manner as Step (ii) in Reference example 2 by using Compound 112 (389 mg).

LCMS: [M+H]⁺/Rt (min): 221/0.16

Step (iii):

To a mixture of Compound 113 (389 mg), acetone (1.73 mL), and dichloromethane (6 mL) was added sodium triacetoxyborohydride (1.5 g) at 0° C., and the mixture was warmed to room temperature and the stirring was continued for 1.5 hours. To the reaction mixture was added water at 0° C., and the mixture was extracted with chloroform. The organic layer was dried over anhydrous sodium sulfate and concentrated in vacuo, and then the obtained residue was purified by amino silica gel column chromatography (eluate: hexane/ethyl acetate) to give the title compound 114 (255 mg).

LCMS: [M+H]⁺/Rt (min): 263/0.36

Reference Example 43 tert-Butyl [(1S,4R)-3-{[4-(propan-2-yl)piperazin-1-yl]methyl}bicyclo[2.2.1]heptan-2-yl]carbamate

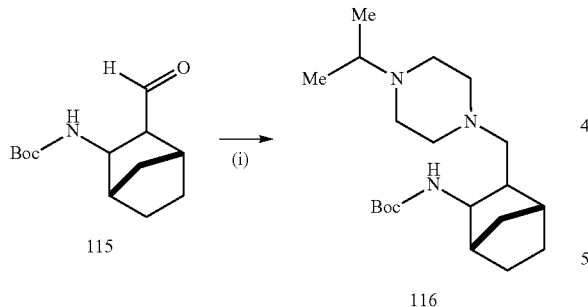

Step (i):

To a mixture of Compound 115 (239 mg), 1-isopropylaziridine (128 mg), acetic acid (0.086 mL), and THF (2.5 mL) was added sodium triacetoxyborohydride (635 mg) at room temperature, and the mixture was stirred at the same temperature for 3 hours. To the reaction mixture was added aqueous sodium bicarbonate at 0° C., and the mixture was extracted with ethyl acetate. The organic layer was dried over anhydrous sodium sulfate and concentrated in vacuo, and then the obtained residue was purified by amino silica gel column chromatography (eluate: hexane/ethyl acetate) to give the title compound 116 (310 mg).

LCMS: [M+H]⁺/Rt (min): 352/1.35 (Method B)

Reference Example 44 rac-2-[6-(Propan-2-yl)pyridin-3-yl]cyclohex-2-en-1-amine

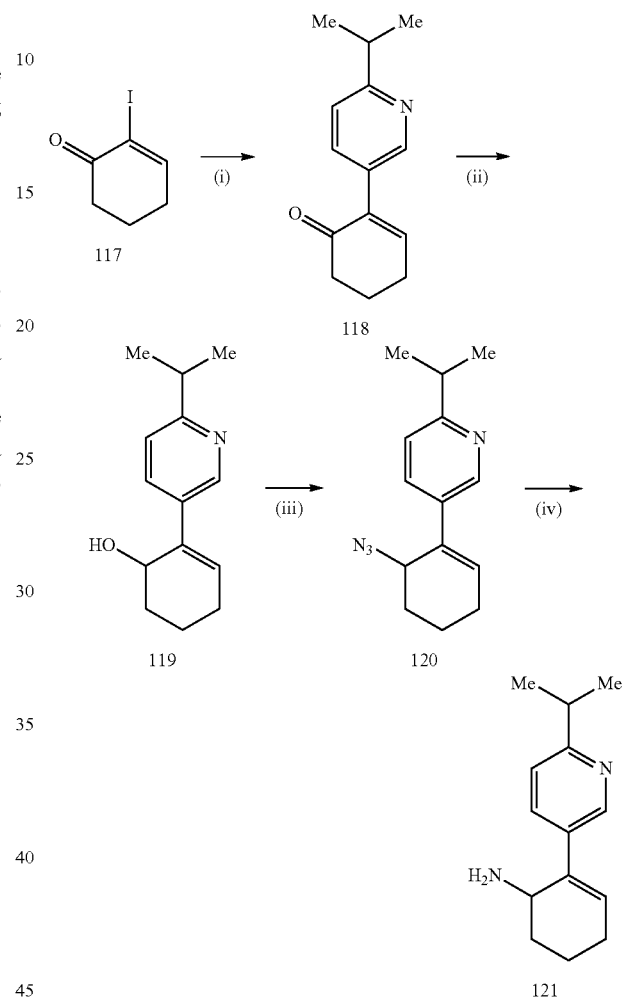

Step (i):

To a mixture of Compound 117 (350 mg), 6-isopropylpyridin-3-yl boronate (273 mg), cesium carbonate (1.28 g), 1,4-dioxane (5 mL), and water (1 mL) was added [1,1'-bis(diphenylphosphino)ferrocene]palladium(II) dichloride dichloromethane adduct (129 mg) at room temperature, and the mixture was stirred at 90° C. for 3 hours. To the reaction mixture was added water at 0° C., and the mixture was extracted with chloroform. The organic layer was dried over anhydrous sodium sulfate and concentrated in vacuo, and then the obtained residue was purified by silica gel column chromatography (eluate: hexane/ethyl acetate) to give the title compound 118 (168 mg).

Step (ii) to Step (iv):

The title compound 121 (29.7 mg) was prepared in the same manner as Steps (i) to (iii) in Reference example 13 by using Compound 118 (68.2 mg).

LCMS: [M+H]⁺/Rt (min): 217/0.39

Reference Example 45

N-Methyl-N-[(1-methylcyclopropyl)methyl]piperidin-4-amine

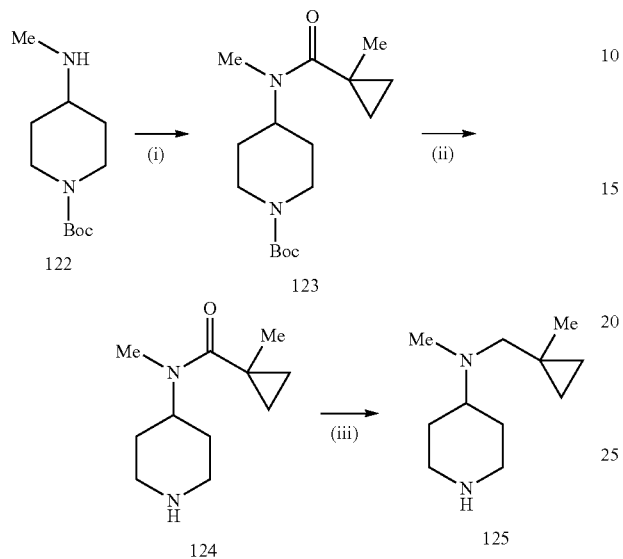

Step (i):

To a solution of tert-butyl 4-(methylamino) piperidine-1-carboxylate (584 mg), 1-methylcyclopropane-1-carboxylic acid (300 mg), and triethylamine (0.76 mL) in DMF (4 mL) was added HATU (1.24 g), and the mixture was stirred at room temperature. After the reaction was completed, water was added to the reaction mixture, and the mixture was extracted with ethyl acetate. The organic layer was dried over anhydrous sodium sulfate, concentrated in vacuo, and then the obtained residue was purified by silica gel column chromatography (eluate: hexane/ethyl acetate) to give the title compound 123 (926 mg).

Step (ii):

To a solution of Compound 123 (806 mg) in chloroform (4.5 mL) was added hydrochloric acid (in CPME, 5 M, 2.7 mL) at 0° C., and the reaction solution was warmed to room temperature and stirred. After the reaction was completed, the reaction mixture was concentrated in vacuo, and then the obtained residue was purified by amino silica gel column chromatography (eluate: chloroform/methanol) to give the title compound 124 (477 mg).

Step (iii):

The title compound 125 (203 mg) was prepared in the same manner as Step (ii) in Reference example 22 by using Compound 124 (413 mg).

LCMS: [M+H]⁺/Rt (min):183/0.15

Reference Examples 46-47

The compounds of Reference examples 46-47 shown in the table below was prepared according to the process in the above Reference example 45, by using each appropriate starting compound instead of 1-methylcyclopropane-1-carboxylic acid at Step (i) in Reference example 45.

| Reference example | Chemical structure | Instrumental analytical data |
|---|---|---|
| 46 | Me-N-CH₂-(1-fluorocyclopropyl), piperidin-4-yl | LCMS: [M + H]⁺/Rt (min): 187/0.14 |
| 47 | Me-N-CH₂-(1-trifluoromethylcyclopropyl), piperidin-4-yl | LCMS: [M + H]+/Rt (min): 237/0.19 |

Reference example 46: N-[(1-fluorocyclopropyl)methyl]-N-methylpiperidin-4-amine

Reference example 47: N-methyl-N-{[1-(trifluoromethyl)cyclopropyl]methyl}piperidin-4-amine Reference example 48: (3S)-1-{[1-(trifluoromethyl)cyclopropyl]methyl}pyrrolidin-3-ol

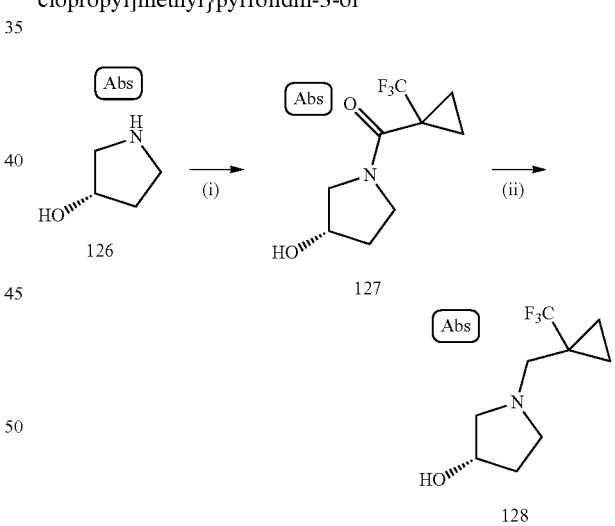

Step (i):

The title compound 127 (196 mg) was prepared in the same manner as Step (i) in Reference example 45 by using (S)-3-pyrrolidinol (103 mg) and 1-(trifluoromethyl)cyclopropane-1-carboxylic acid (200 mg).

Step (ii):

The title compound 128 (87.2 mg) was prepared in the same manner as Step (iii) in Reference example 45 by using Compound 127 (184 mg).

LCMS: [M+H]⁺/Rt (min):210/0.30

Reference Example 49

(1R,3S,5S)—N-(Cyclopropylmethyl)-N-methyl-8-azabicyclo[3.2.1]oxtan-3-amine

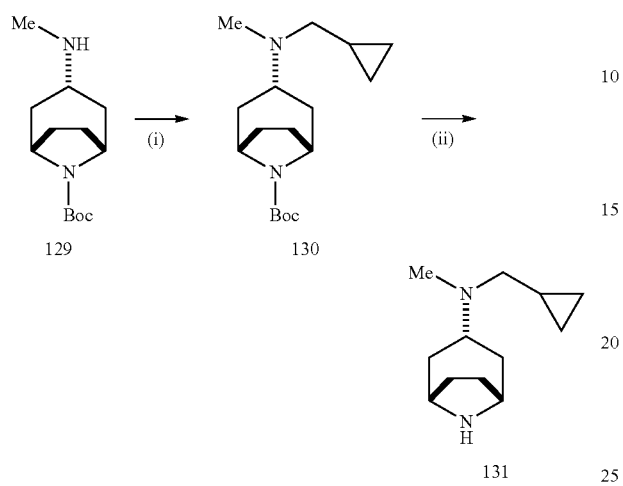

Step (i):
The title compound 130 (178 mg) was prepared in the same manner as Step (iii) in Reference example 42 by using Compound 129 (146 mg) and cyclopropane-carbaldehyde (170 mg).

Step (ii):
The title compound 131 (106 mg) was prepared in the same manner as Step (ii) in Reference example 45 by using Compound 130 (166 mg).

LCMS: [M+H]$^+$/Rt (min): 195/0.14

Reference Examples 50-52

The compounds of Reference examples 50-52 shown in the table below were prepared according to the process in the above Reference example 49, by using each appropriate starting compound instead of Compound 129 at Step (i) in Reference example 49.

| Reference example | Chemical structure | Instrumental analytical data |
|---|---|---|
| 50 | 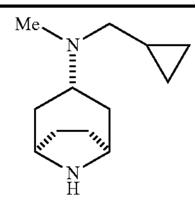 | LCMS: [M + H]$^+$/Rt (min): 195/0.14 |
| 51 | 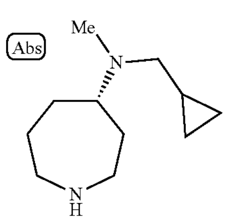 [SMILES: CN(CC1CC1)[C@H]1CCCNCC1] | LCMS: [M + H]$^+$/Rt (min): 183/0.14 |
| 52 | | LCMS: [M + H]$^+$/Rt (min): 183/0.14 |

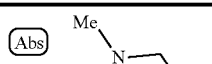

Reference example 50: (1R,3R,5S)—N-(cyclopropylmethyl)-N-methyl-8-azabicyclo[3.2.1]octan-3-amine
Reference example 51: (4S)—N-(cyclopropylmethyl)-N-methylazepan-4-amine
Reference example 52: (4R)—N-(cyclopropylmethyl)-N-methylazepan-4-amine

Reference Example 53

(1R,3S,5S)-8-(Propan-2-yl)-8-azabicyclo[3.2.1]octan-3-ol

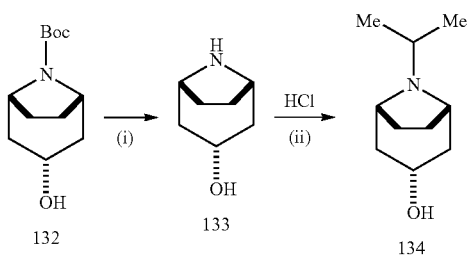 [SMILES: CC(C)(C)OC(=O)N1[C@@H]2CC[C@H]1C[C@H](O)C2 ; O[C@@H]1C[C@H]2CC[C@@H](C1)N2 ; Cl ; CC(C)N1[C@@H]2CC[C@H]1C[C@H](O)C2]

Step (i):
The title compound was prepared in the same manner as Step (iv) in Reference example 2 by using Compound 132 (3 g).

Step (ii):
The title compound 134 (1.98 g) was prepared in the same manner as Step (iii) in Reference example 42 by using Compound 133 and acetone (1.3 g).

LCMS: [M+H]$^+$/Rt (min): 170/0.15

Reference Examples 54-57

The compounds of Reference examples 54-57 shown in the table below were prepared according to the process in the above Reference example 53, by using each appropriate starting compound instead of Compound 132 at Step (i) in Reference example 53.

| Reference example | Chemical structure | Instrumental analytical data |
|---|---|---|
| 54 | 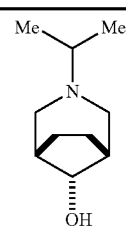 | LCMS: [M + H]$^+$/Rt (min): 170/0.25 |

| Reference example | Chemical structure | Instrumental analytical data |
|---|---|---|
| 55 | [structure with Me, Me, N, OH - azabicyclo[3.2.1]octan-8-ol] | LCMS: [M + H]+/Rt (min): 170/0.15 |
| 56 | [structure with Me, Me, N, OH - azabicyclo[3.2.1]octan-8-ol] | LCMS: [M + H]+/Rt (min): 170/0.24 |
| 57 | [structure with Me, Me, N, H, H, OH - azabicyclo[3.1.0]hexan-6-ol] | LCMS: [M + H]+/Rt (min): 142/0.15 |

Reference example 54: (1R,5S,8R)-3-(propan-2-yl)-3-azabicyclo[3.2.1]octan-8-ol
Reference example 55: (1R,5S,8S)-3-(propan-2-yl)-3-azabicyclo[3.2.1]octan-8-ol
Reference example 56: (1R,3R,5S)-8-(propan-2-yl)-8-azabicyclo[3.2.1]octan-3-ol
Reference example 57: (1R,5S,6S)-3-(propan-2-yl)-3-azabicyclo[3.1.0]hexan-6-ol Reference Examples 58-79

The compounds of Reference examples 58-79 shown in the table below were prepared according to the process in the above Reference example 18, by using each appropriate starting compound instead of 1-isopropylpiperazine at Step (ii) in Reference example 18.

| Reference example | Chemical structure | Instrumental analytical data |
|---|---|---|
| 58 | [piperazine-cyclohexane structure with Me, Me, H2N, H, F, Abs] | LCMS: [M + H]+/Rt (min): 262/0.17 |
| 59 | [pyrrolidine-cyclohexane structure with Me, Me, N-Me, H2N, F, F, Abs] | LCMS: [M + H]+/Rt (min): 276/0.28 |
| 60 | [piperidine-cyclohexane structure with Me, O, Me, H2N, F, F, Abs] | LCMS: [M + H]+/Rt (min): 277/0.55 |
| 61 | [piperazine-cyclohexane structure with Me, Me, Me, H2N, F, F, Abs] | LCMS: [M + H]+/Rt (min): 276/0.20 |
| 62 | [piperidine-cyclohexane structure with Me, Me, Me, H2N, F, F, Abs] | LCMS: [M + H]+/Rt (min): 276/0.20 |

-continued
| Reference example | Chemical structure | Instrumental analytical data |
|---|---|---|
| 63 | 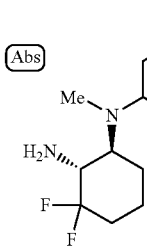 | LCMS: [M + H]⁺/Rt (min): 290/0.24 |
| 64 | 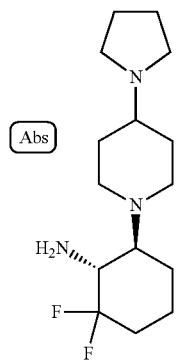 [SMILES: N[C@@H]1[C@@H](N2CCC(N3CCCC3)CC2)CCCC1(F)F] | LCMS: [M + H]⁺/Rt (min): 288/0.31 |
| 65 | 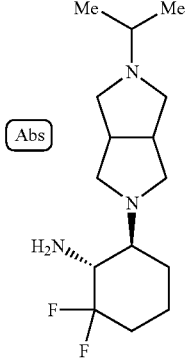 [SMILES: CC(C)N1CC2CN([C@H]3CCCC(F)(F)[C@@H]3N)CC2C1] | LCMS: [M + H]⁺/Rt (min): 288/0.32 |
| 66 | 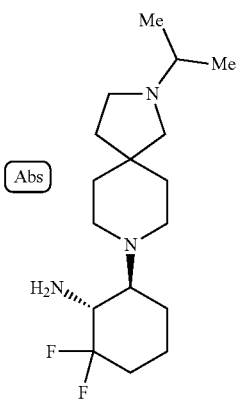 [SMILES: CC(C)N1CCC2(CCN([C@H]3CCCC(F)(F)[C@@H]3N)CC2)C1] | LCMS: [M + H]⁺/Rt (min): 316/0.35 |
-continued
| Reference example | Chemical structure | Instrumental analytical data |
|---|---|---|
| 67 | 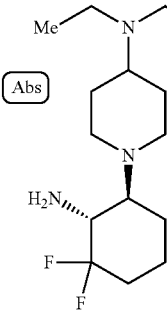 | LCMS: [M + H]⁺/Rt (min): 290/0.38 |
| 68 | 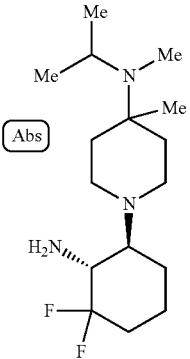 [SMILES: CC(C)N(C)C1(C)CCN([C@H]2CCCC(F)(F)[C@@H]2N)CC1] | LCMS: [M + H]⁺/Rt (min): 304/0.32 |
| 69 | 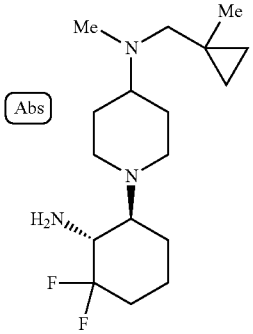 [SMILES: CN(CC1(C)CC1)C1CCN([C@H]2CCCC(F)(F)[C@@H]2N)CC1] | LCMS: [M + H]⁺Rt (min): 316/0.36 |
| 70 | 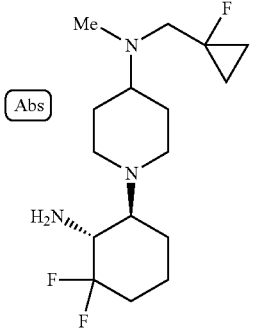 [SMILES: CN(CC1(F)CC1)C1CCN([C@H]2CCCC(F)(F)[C@@H]2N)CC1] | LCMS: [M + H]⁺/Rt (min): 320/0.36 |

| Reference example | Chemical structure | Instrumental analytical data |
|---|---|---|
| 71 | 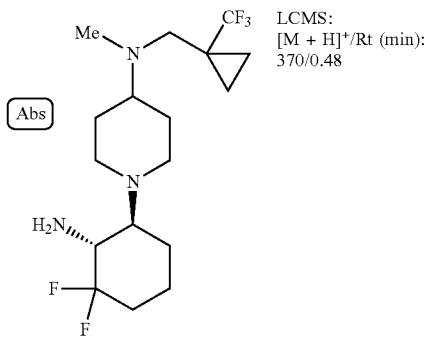 | LCMS: [M + H]⁺/Rt (min): 370/0.48 |
| 72 | 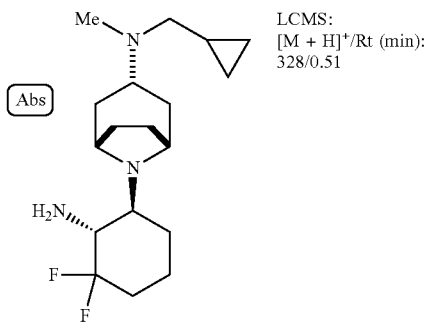 | LCMS: [M + H]⁺/Rt (min): 328/0.51 |
| 73 | 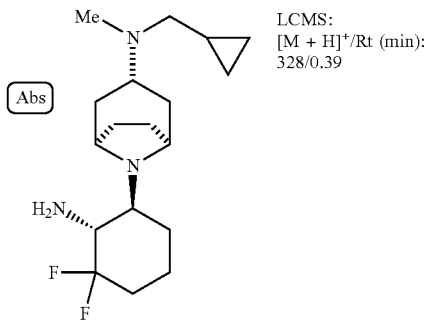 | LCMS: [M + H]⁺/Rt (min): 328/0.39 |
| 74 | 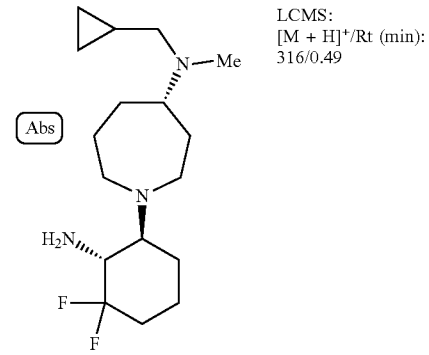 | LCMS: [M + H]⁺/Rt (min): 316/0.49 |
| Reference example | Chemical structure | Instrumental analytical data |
|---|---|---|
| 75 | 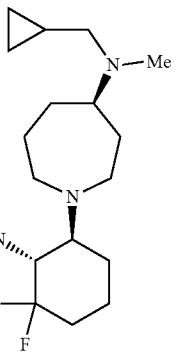 | LCMS: [M + H]⁺/Rt (min): 316/0.46 |
| 76 | 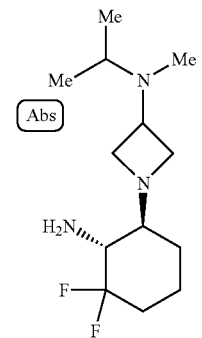 [SMILES: CC(C)N(C)C1CN([C@H]2CCCC(F)(F)[C@@H]2N)C1] | LCMS: [M + H]⁺/Rt (min): 262/0.15 |
| 77 | 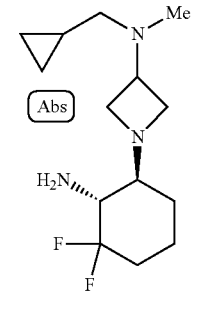 [SMILES: CN(CC1CC1)C1CN([C@H]2CCCC(F)(F)[C@@H]2N)C1] | LCMS: [M + H]⁺/Rt (min): 274/0.15 |
| 78 | 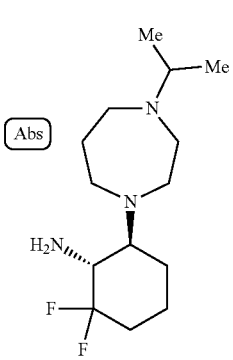 [SMILES: CC(C)N1CCCN([C@H]2CCCC(F)(F)[C@@H]2N)CC1] | LCMS: [M + H]⁺/Rt (min): 276/0.24 |

| Reference example | Chemical structure | Instrumental analytical data |
|---|---|---|
| 79 | (structure) | LCMS: [M + H]⁺/Rt (min): 348/0.66 |

Reference example 58: (1S,6R)-2,2-difluoro-6-[4-(propan-2-yl)piperazin-1-yl]cyclohexan-1-amine Reference example 59: (3S)-1-[(1S,2R)-2-amino-3,3-difluorocyclohexyl]-N-methyl-N-(propan-2-yl)pyrrolidin-1-amine Reference example 60: (1R,6S)-2,2-difluoro-6-{4-[(propan-2-yl)oxy]piperidin-1-yl}cyclohexan-1-amine Reference example 61: (1R,6S)-2,2-difluoro-6-[(2S)-2-methyl-4-(propan-2-yl)piperazin-1-yl]cyclohexan-1-amine Reference example 62: (1R,6S)-2,2-difluoro-6-[(2R)-2-methyl-4-(propan-2-yl)piperazin-1-yl]cyclohexan-1-amine Reference example 63: (1S,2R)-3,3-difluoro-N¹-methyl-N¹-[1-(propan-2-yl)piperidin-4-yl]cyclohexan-1,2-diamine Reference example 64: (1R,6S)-2,2-difluoro-6-[4-(pyrrolidin-1-yl)piperidin-1-yl]cyclohexan-1-amine Reference example 65: (1R,6S)-2,2-difluoro-6-[5-(propan-2-yl)hexahydropyrrolo[3,4-c]pyrrol-2(1H)-yl]cyclohexan-1-amine Reference example 66: (1R,6S)-2,2-difluoro-6-[2-(propan-2-yl)-2,8-diazaspiro[4.5]decan-8-yl]cyclohexan-1-amine Reference example 67: 1-[(1S,2R)-2-amino-3,3-difluorocyclohexyl]-N,N-diethylpiperidin-4-amine Reference example 68: 1-[(1S,2R)-2-amino-3,3-difluorocyclohexyl]-N,4-dimethyl-N-(propan-2-yl)piperidin 4-amine Reference example 69: 1-[(1S,2R)-2-amino-3,3-difluorocyclohexyl]-N-methyl-N-[(1-methylcyclopropyl)methyl]piperidin-4-amine Reference example 70: 1-[(1S,2R)-2-amino-3,3-difluorocyclohexyl]-N-[(1-fluorocyclopropyl)methyl]-N-methylpiperidin-4-amine Reference example 71: 1-[(1S,2R)-2-amino-3,3-difluorocyclohexyl]-N-methyl-N-{[1-(trifluoromethyl)cyclopropyl]methyl}piperidin-4-amine Reference example 72: (1R,3R,5S)-8-[(1S,2R)-2-amino-3,3-difluorocyclohexyl]-N-(cyclopropylmethyl)-N-methyl-8-azabicyclo[3.2.1]octan-3-amine Reference example 73: (1R,3S,5S)-8-[(1S,2R)-2-amino-3,3-difluorocyclohexyl]-N-(cyclopropylmethyl)-N-methyl-8-azabicyclo[3.2.1]octan-3-amine Reference example 74: (4S)-1-[(1S,2R)-2-amino-3,3-difluorocyclohexyl]-N-(cyclopropylmethyl)-N-methylazepan-4-amine Reference example 75: (4R)-1-[(1S,2R)-2-amino-3,3-difluorocyclohexyl]-N-(cyclopropylmethyl)-N-methylazepan-4-amine Reference example 76: 1-[(1S,2R)-2-amino-3,3-difluorocyclohexyl]-N-methyl-N-(propan-2-yl)azetidin-3-amine Reference example 77: 1-[(1S,2R)-2-amino-3,3-difluorocyclohexyl]-N-(cyclopropylmethyl)-N-methylazetidin-3-amine Reference example 78: (1R,6S)-2,2-difluoro-6-[4-(propan-2-yl)-1,4-diazepan-1-yl]cyclohexan-1-amine Reference example 79: tert-butyl {1-[(1S,2R)-2-amino-3,3-difluorocyclohexyl]piperidin-4-yl}methylcarbamate Reference Example 80

N-{(1R,6S)-2,2-Difluoro-6-[4-(methylamino)piperidin-1-yl]cyclohexyl}-4-{5-[(1S,2S)-2-fluorocyclopropyl]-1,2,4-oxadiazol-3-yl}-4-methylpiperidine-1-carboxamide

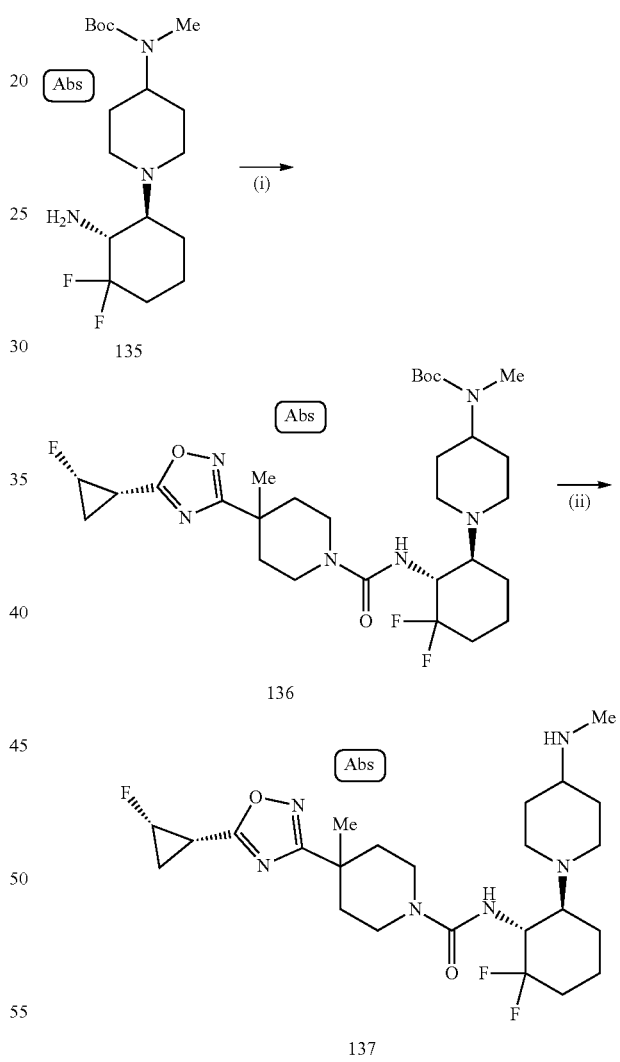

Step (i):
The title compound 136 (2.92 g) was prepared in the same manner as Example 19 by using the compound of Reference example 79 (2.61 g).

Step (ii):
To a solution of Compound 136 (2.92 g) in toluene (24 ml) was added TFA (5.56 g), and the mixture was stirred at room temperature for 3.5 hours. The reaction solution was concentrated in vacuo, the obtained residue was dissolved in water, and aqueous sodium bicarbonate was added to the solution. The mixture was extracted with chloroform, and the organic layer was concentrated in vacuo to give the title compound 137 (2.38 g).

LCMS: [M+H]⁺/Rt (min):499/0.49 (Method C)

Reference Example 81

(1S,2R)-3,3-Difluoro-N¹-methyl-N¹-[(3S)-1-(propan-2-yl)pyrrolidin-3-yl]cyclohexan-1,2-diamine

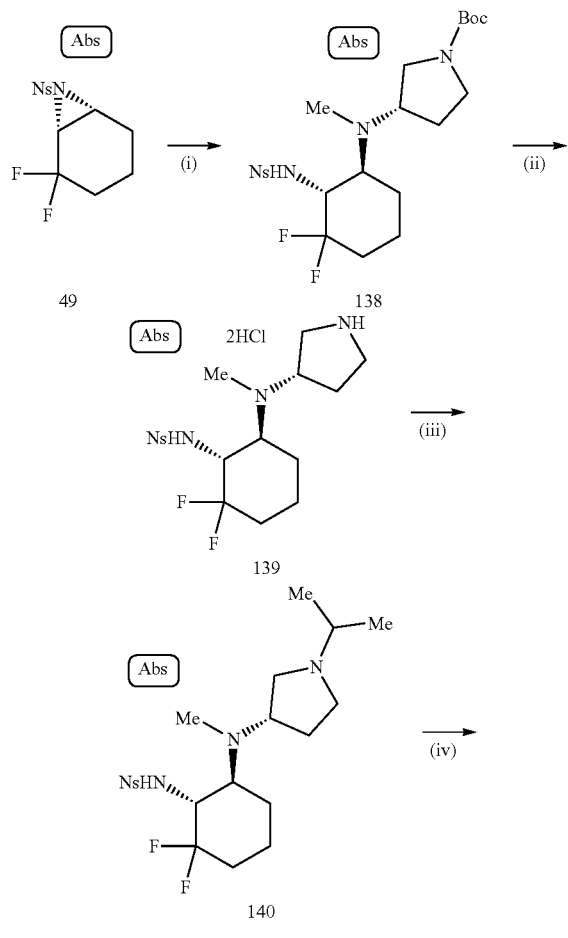

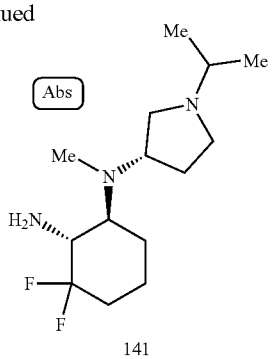

Step (i):

Compound 138 (2.61 g) was prepared in the same manner as Step (ii) in Reference example 18, by using tert-butyl (3S)-3-(methylamino)pyrrolidine-1-carboxylate instead of 1-isopropylpiperazine at Step (ii) in Reference example 18.

Step (ii):

The title compound 139 (2.59 g) was prepared in the same manner as Step (iv) in Reference example 2 by using Compound 138 (2.61 g).

Step (iii):

The title compound 140 (1.97 g) was prepared in the same manner as Step (iii) in Reference example 42 by using Compound 139 (2.59 g) and acetone (3.87 mL).

Step (iv):

The title compound 141 (925 mg) was prepared in the same manner as Step (iii) in Reference example 18 by using Compound 140 (1.97 g).

LCMS: [M+H]⁺/Rt (min): 276/0.15

Reference Examples 82-88

The compounds of Reference examples 82-88 shown in the table below were prepared in the same manner as Reference example 81, by using the appropriate starting compound (Material A) instead of tert-butyl (3S)-3-(methylamino)pyrrolidine-1-carboxylate at Step (i) in Reference example 81, and each appropriate starting compound (Material B) instead of acetone at Step (iii) in Reference example 81.

| Reference example | Material A | Material B | Chemical structure | Instrumental analytical data |
|---|---|---|---|---|
| 82 | Boc-N(Me)-[(3S)-pyrrolidin-3-yl] (Abs) | Me-C(=O)-Me | (Abs) structure with Me, N-Me, pyrrolidine, H₂N, cyclohexyl-F,F | LCMS: [M + H]⁺/Rt (min): 276/0.28 |

-continued

| Reference example | Material A | Material B | Chemical structure | Instrumental analytical data |
|---|---|---|---|---|
| 83 | (Abs) pyrrolidine with Boc and MeNH | Me-C(=O)-Me (acetone) | (Abs) structure | LCMS: [M + H]+/Rt (min): 276/0.16 |
| 84 | Boc-N(Me)-piperidine (NH) | Me-C(=O)-Me (acetone) | (Abs) structure | LCMS: [M + H]+/Rt (min): 290/0.34 |
| 85 | (Abs) Boc-N(Me)-pyrrolidine | cyclopropyl silyl ketene acetal with OEt, OSi(Me)3 | (Abs) structure | LCMS: [M + H]+/Rt (min): 274/0.30 |
| 86 | (Abs) Boc-N(Me)-pyrrolidine | Me2CH-CHO (isobutyraldehyde) | (Abs) structure | LCMS: [M + H]+/Rt (min): 290/0.37 |

-continued

| Reference example | Material A | Material B | Chemical structure | Instrumental analytical data |
|---|---|---|---|---|
| 87 | 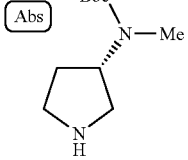 | 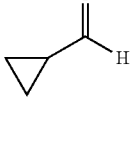 | 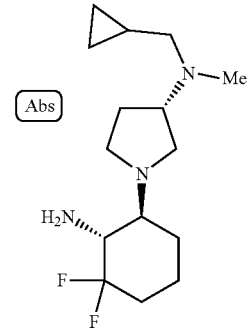 [SMILES: CN(CC1CC1)[C@H]1CCN([C@H]2CCCC(F)(F)[C@@H]2N)C1] | LCMS: [M + H]+/Rt (min): 288/0.36 |
| 88 | 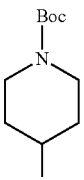 | 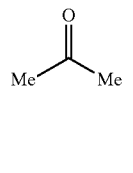 | 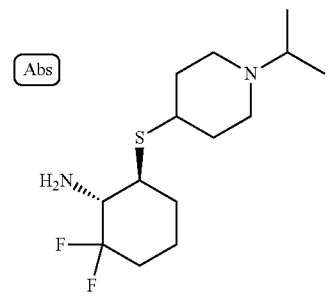 [SMILES: CC(C)N1CCC(S[C@H]2CCCC(F)(F)[C@@H]2N)CC1] | LCMS: [M + H]+/Rt (min): 293/0.33 |

Reference example 82: (3R)-1-[(1S,2R)-2-amino-3,3 difluorocyclohexyl]-N-methyl-N-(propan-2-yl)pyrrolidin-1-amine Reference example 83: (1S,2R)-3,3-difluoro-N¹-methyl-N¹-[(3R)-1-(propan-2-yl)pyrrolidin-3-yl]cyclohexan-1,2-diamine Reference example 84: 1-[(1S,2R)-2-amino-3,3-difluorocyclohexyl]-N-methyl-N-(propan-2-yl)piperidin-4-amine Reference example 85: (3S)-1-[(1S,2R)-2-amino-3,3-difluorocyclohexyl]-N-cyclopropyl-N-methylpyrrolidin-1-amine Reference example 86: (3S)-1-[(1S,2R)-2-amino-3,3-difluorocyclohexyl]-N-methyl-N-(2-methylpropyl)pyrrolidin-1-amine Reference example 87: (3S)-1-[(1S,2R)-2-amino-3,3-difluorocyclohexyl]-N-(cyclopropylmethyl)-N-methylpyrrolidin-1-amine Reference example 88: (1S,6S)-2,2-difluoro-6-{[1-(propan-2-yl) piperidin-4-yl]sulfanyl}cyclohexan-1-amine Reference Example 89

(1S,2R)—N¹-Benzyl-3,3-difluoro-N¹-[(3S)-1-(propan-2-yl) pyrrolidin-3-yl]cyclohexan-1,2-diamine

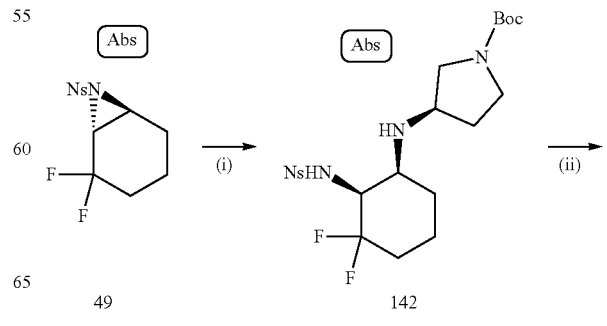

309

-continued

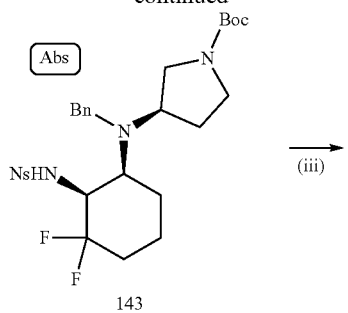
143

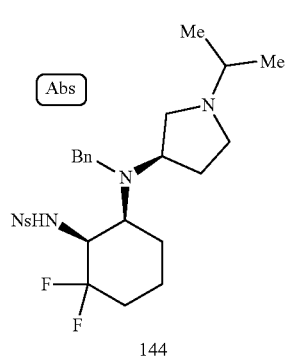
144

145

Step (i):
Compound 142 (2.19 g) was prepared in the same manner as Step (ii) in Reference example 18, by using tert-butyl (3S)-3-aminopyrrolidine-1-carboxylate instead of 1-isopropylpiperazine at Step (ii) in Reference example 18.

Step (ii):
The title compound 143 (240 mg) was prepared in the same manner as Step (iii) in Reference example 42 by using Compound 142 (990 mg) and benzaldehyde (312 mg).

Step (iii):
The title compound 144 (161 mg) was prepared in the same manner as Step (ii) and Step (iii) in Reference example 81 by using Compound 143 (235 mg).

Step (iv):
The title compound 145 (87.4 mg) was prepared in the same manner as Step (iii) in Reference example 18 by using Compound 144 (158 mg).

LCMS: [M+H]⁺/Rt (min): 352/0.42 (Method C)

310

Reference Example 90

Benzyl {(1S,2R)-3,3-difluoro-2-[(4-{5-[(1S,2S)-2-fluorocyclopropyl]-1,2,4-oxadiazol-3-yl}-4-methylpiperidine-1-carbonyl)amino]cyclohexyl}[(3S)-1-(propan-2-yl) pyrrolidin-3-yl]carbamate

142

146

147

148

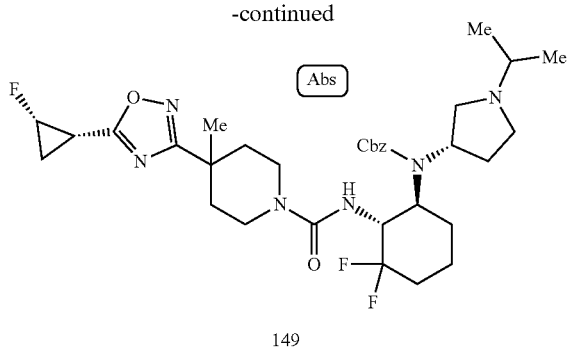

149

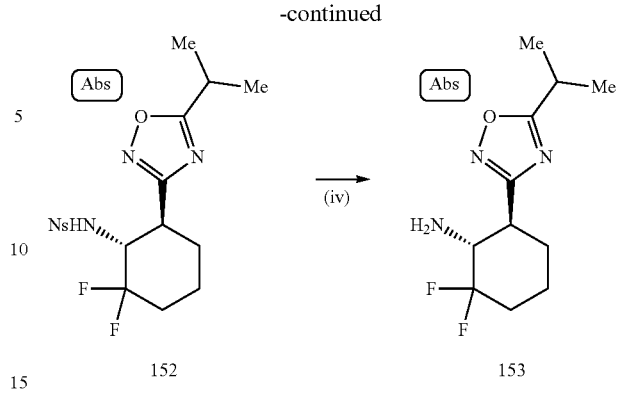

Step (i):

To a solution of Compound 142 (680 mg) in a mixture of dioxane and water (10 mL/3.3 mL) were added benzyl chloroformate (345 mg) and sodium acetate (116 mg) at 0° C., and the reaction solution was refluxed for 2 hours. After the reaction was completed, the reaction solution was extracted with chloroform. The organic layer was concentrated in vacuo to give the title compound 146 (530 mg).

Step (ii):

The title compound 147 (256 mg) was prepared in the same manner as Step (ii) and Step (iii) in Reference example 81 by using Compound 146 (530 mg).

Step (iii):

The title compound 148 (137 mg) was prepared in the same manner as Step (iii) in Reference example 18 by using Compound 147 (254 mg).

Step (iv):

The title compound 149 (175 mg) was prepared in the same manner as Example 19 by using Compound 148 (135 mg).

LCMS: [M+H]$^+$/Rt (min): 647/0.79 (Method C)

Reference Example 91

(1R,6S)-2,2-Difluoro-6-[5-(propan-2-yl)-1,2,4-oxadiazol-3-yl]cyclohexan-1-amine

Step (i):

To a solution of Compound 49 (2.01 g) in acetonitrile (12.6 ml) were added sodium cyanide (495 mg) and lithium perchlorate (67 mg), and the reaction solution was refluxed for 3 hours. After the reaction was completed, water was added to the reaction mixture, and the mixture was extracted with ethyl acetate. The organic layer was dried over anhydrous sodium sulfate, concentrated in vacuo, and then the obtained residue was purified by silica gel column chromatography (eluate: hexane/ethyl acetate) to give the title compound 150 (2.05 g).

Step (ii):

The title compound 151 (1.88 g) was prepared in the same manner as Step (i) in Reference example 8 by using Compound 150 (2.04 g).

Step (iii):

The title compound 152 (89.7 mg) was prepared in the same manner as Step (ii) and Step (iii) in Reference example 8 by using Compound 151 (200 mg) and isobutyric acid (53.6 mg).

Step (iv):

The title compound 153 (41.5 mg) was prepared in the same manner as Step (iii) in Reference example 18 by using Compound 152 (87.7 mg).

LCMS: [M+H]$^+$/Rt (min): 246/0.37 (Method C)

Reference Example 92

(1R,6S)-2,2-Difluoro-6-[4-(propan-2-yl)-1H-1,2,3-triazol-1-yl]cyclohexan-1-amine

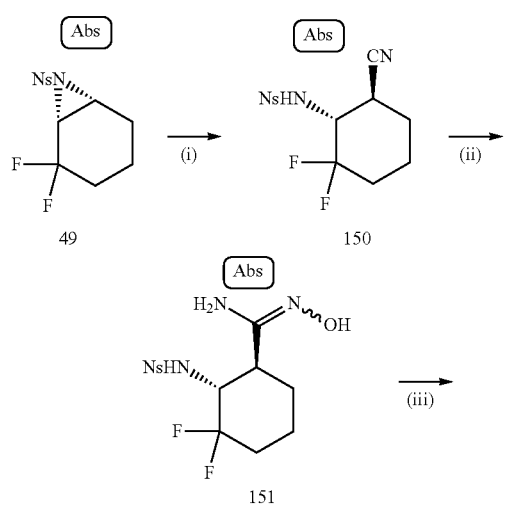

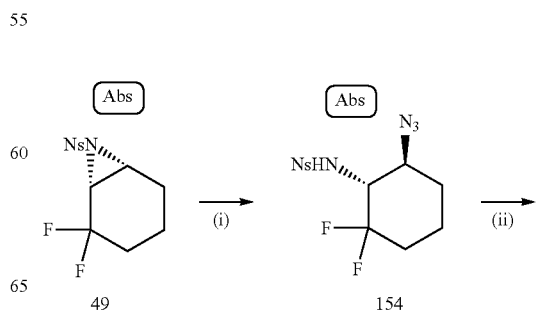

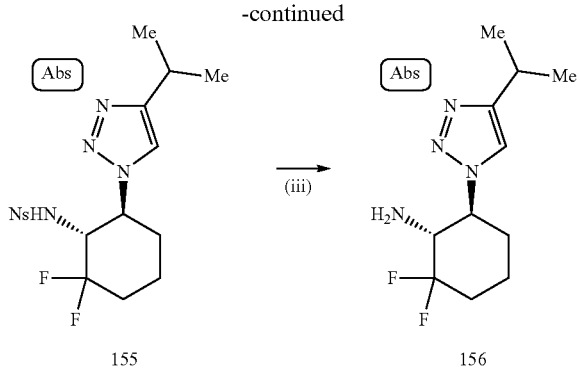

Step (i):

To a solution of Compound 49 (1.6 g) in a mixture of acetonitrile and water (23 mL/2.5 mL) was added sodium azide (490 mg), and the reaction solution was heated at 70° C. for 1.5 hours. After the reaction was completed, saturated aqueous sodium bicarbonate was added to the reaction mixture, and the mixture was extracted with ethyl acetate. The organic layer was dried over anhydrous sodium sulfate, concentrated in vacuo, and then the obtained residue was purified by silica gel column chromatography (eluate: hexane/ethyl acetate) to give the title compound 154 (1.78 g).

Step (ii):

To a solution of Compound 154 (550 mg) in a mixture of methanol and THF (11.4 mL/2.3 mL/4 mL) were added sodium ascorbate (30.2 mg), tris(2-benzimidazolylmethyl)amine (46.5 mg), and 3-methylbut-1-yne (156 mg). A solution of copper sulfate (18.2 mg) in water (3.8 mL) was added to the reaction solution, and the reaction mixture was stirred at room temperature. After the reaction was completed, the reaction mixture was filtrated with Celite, and concentrated in vacuo. Then, the obtained residue was purified by silica gel column chromatography (eluate: hexane/ethyl acetate) to give the title compound 155 (353 mg).

Step (iii):

The title compound 156 (168 mg) was prepared in the same manner as Step (iii) in Reference example 18 by using Compound 155 (353 mg).

LCMS: [M+H]⁺/Rt (min): 245/0.42

Reference Example 93

(1R,6S)-2,2-Difluoro-6-[4-(2-methylpropyl)-1H-1,2,3-triazol-1-yl]cyclohexan-1-amine The compound of Reference example 93 shown in the table below was prepared according to the process in the above Reference example 92 by using 4-methylpent-1-yne instead of 3-methylbut-1-yne at Step (ii) in Reference example 92.

| Reference example | Chemical structure | Instrumental analytical data |
|---|---|---|
| 93 | 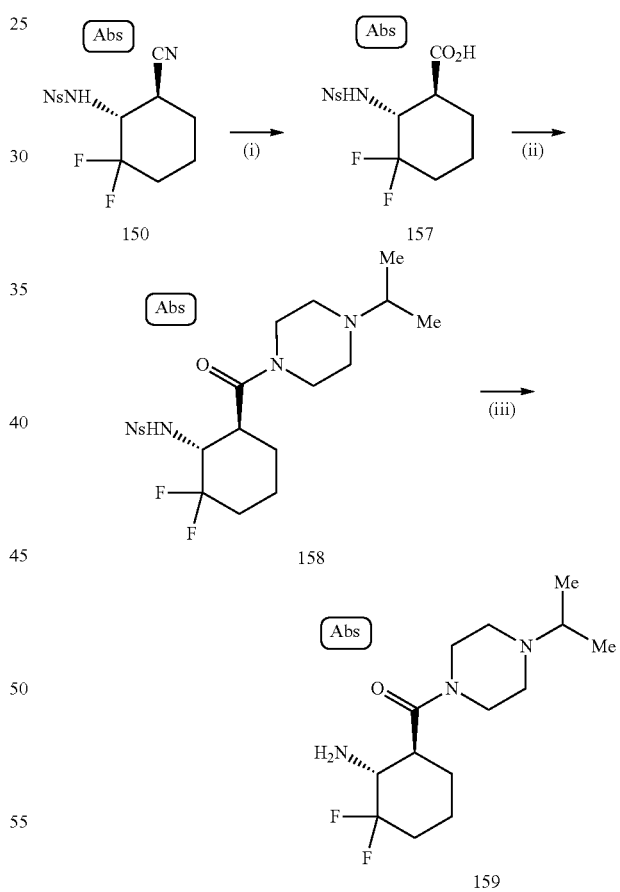 | LCMS: [M + H]⁺/Rt (min): 259/0.51 |

Reference Example 94

[(1S,2R)-2-Amino-3,3-difluorocyclohexyl][4-(propan-2-yl)piperazin-1-yl]methanone

Step (i):

To a solution of Compound 150 (555 mg) in DMSO (6 mL) was added aqueous hydrochloric acid (9 mL), and the reaction solution was heated at 120° C. After the reaction was completed, water was added to the reaction mixture, and the mixture was extracted with ethyl acetate. The organic layer was dried over anhydrous sodium sulfate, and concentrated in vacuo to give the title compound 157 (600 mg).

Step (ii):

To a solution of Compound 157 (476 mg) in DMF (1.5 mL) were added 1-isopropylpiperazine (234 mg), triethylamine (308 mg), and HATU (753 mg), and the reaction solution was stirred at room temperature. After the reaction was completed, water was added to the reaction mixture, and the mixture was extracted with ethyl acetate. The organic layer was dried over anhydrous sodium sulfate, concentrated in vacuo, and then the obtained residue was purified by amino silica gel column chromatography (eluate: chloroform/methanol) to give the title compound 158 (610 mg).

LCMS: [M+H]$^+$/Rt (min): 475/0.59

Step (iii):

The title compound 159 (180 mg) was prepared in the same manner as Step (iii) in Reference example 18 by using Compound 158 (605 mg).

LCMS: [M+H]$^+$/Rt (min): 290/0.16

Reference Example 95

(1R,6R)-2,2-Difluoro-6-{[4-(propan-2-yl)piperazin-1-yl]methyl}cyclohexan-1-amine

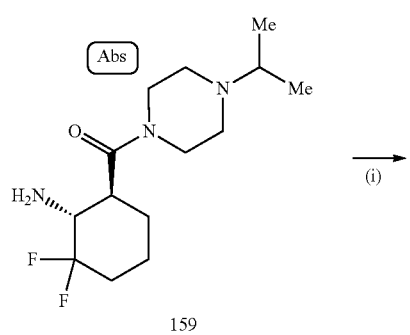

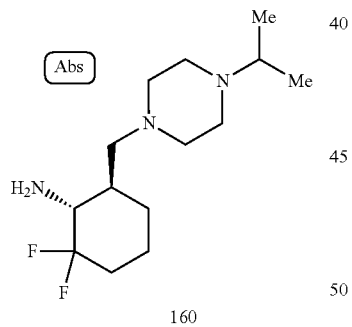

Step (i):

The title compound 160 (112 mg) was prepared in the same manner as Step (ii) in Reference example 22 by using Compound 159 (171 mg).

LCMS: [M+H]$^+$/Rt (min): 276/0.24

Reference Examples 96-114

The compounds of Reference examples shown in the table below were prepared according to the process in the above Reference example 37, by using each appropriate starting compound instead of (S)-1-isopropylpyrrolidin-3-ol at Step (i) in Reference example 37.

| Reference example | Chemical structure | Instrumental analytical data |
|---|---|---|
| 96 | ![structure] | LCMS: [M + H]$^+$/Rt (min): 277/0.30 |
| 97 | ![structure] | LCMS: [M + H]$^+$/Rt (min): 278/0.57 |
| 98 | ![structure] | LCMS: [M + H]$^+$/Rt (min): 260/0.45 |
| 99 | ![structure] | LCMS: [M + H]$^+$/Rt (min): 249/0.16 |
| 100 | ![structure] | LCMS: [M + H]$^+$/Rt (min): 303/0.32 |

| Reference example | Chemical structure | Instrumental analytical data |
|---|---|---|
| 101 | 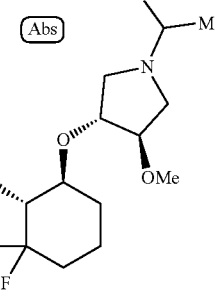 | LCMS: [M + H]⁺/Rt (min): 303/0.33 |
| 102 | 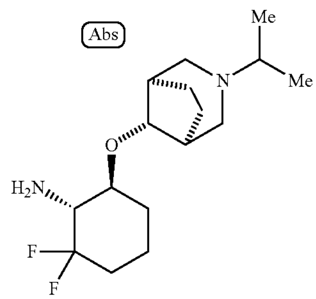 | LCMS: [M + H]⁺/Rt (min): 303/0.31 |
| 103 | 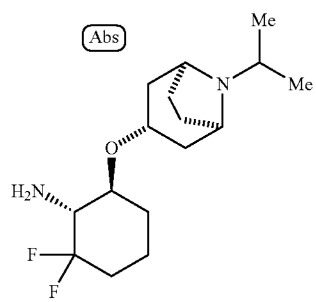 | LCMS: [M + H]⁺/Rt (min): 303/0.32 |
| 104 | 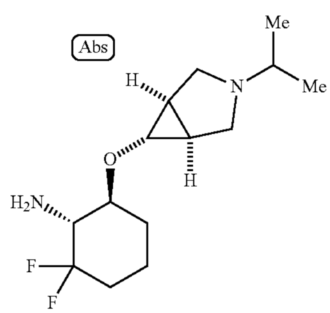 | LCMS: [M + H]⁺/Rt (min): 275/0.43 |
| 105 | 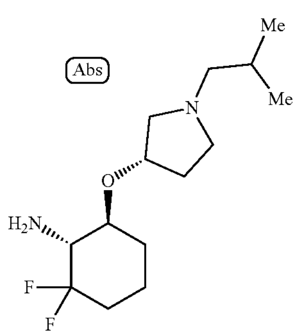 [SMILES: CC(C)CN1CC[C@H](O[C@H]2CCCC(F)(F)[C@@H]2N)C1] | LCMS: [M + H]⁺/Rt (min): 277/0.38 |
| 106 | 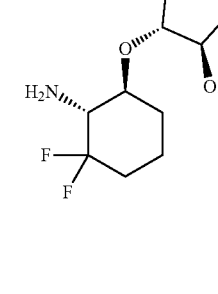 | LCMS: [M + H]⁺/Rt (min): 293/0.36 |
| 107 | 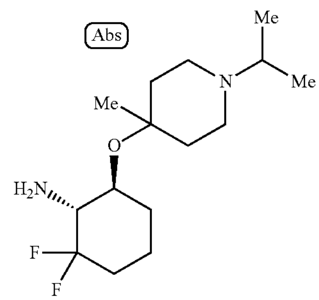 [SMILES: CC(C)N1CCC(C)(O[C@H]2CCCC(F)(F)[C@@H]2N)CC1] | LCMS: [M + H]⁺/Rt (min): 291/0.16 (Method C) |
| 108 | 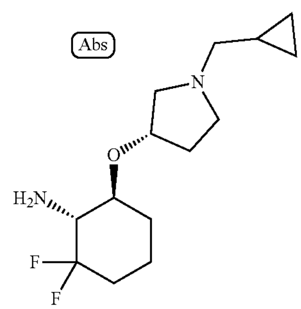 [SMILES: N[C@@H]1[C@@H](O[C@H]2CCN(CC3CC3)C2)CCCC1(F)F] | LCMS: [M + H]⁺/Rt (min): 275/0.49 |
| 109 | 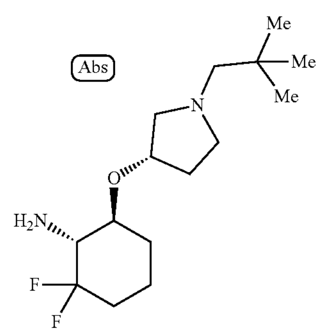 [SMILES: CC(C)(C)CN1CC[C@H](O[C@H]2CCCC(F)(F)[C@@H]2N)C1] | LCMS: [M + H]⁺/Rt (min): 291/0.20 (Method C) |

-continued

| Reference example | Chemical structure | Instrumental analytical data |
|---|---|---|
| 110 | (structure) | LCMS: [M + H]⁺/Rt (min): 289/0.32 |
| 111 | (structure) | LCMS: [M + H]⁺/Rt (min): 293/0.26 |
| 112 | (structure) | LCMS: [M + H]⁺/Rt (min): 343/0.37 |
| 113 | (structure) | LCMS: [M + H]⁺/Rt (min): 295/0.37 |
| 114 | (structure) | LCMS: [M + H]⁺/Rt (min): 305/0.15 |

Reference example 96: (1R,6S)-2,2-difluoro-6-{[1-(propan-2-yl)piperidin-4-yl]oxy}cyclohexan-1-amine Reference example 97: (1R,6S)-2,2-difluoro-6-{[3-(propan-2-yl)-1,2,4-thiadiazol-5-yl]oxy}cyclohexan-1-amine Reference example 98: (1R,6S)-2,2-difluoro-6-{[1-(propan-2-yl)-1H-pyrazol-4-yl]oxy}cyclohexan-1-amine Reference example 99: (1R,6S)-2,2-difluoro-6-{[1-(propan-2-yl)azetidin-3-yl]oxy}cyclohexan-1-amine Reference example 100: (1R,6S)-2,2-difluoro-6-{[(1R,3S,5S)-8-(propan-2-yl)-8-azabicyclo[3.2.1]octan-3-yl]oxy}cyclohexan-1-amine Reference example 101: (1R,6S)-2,2-difluoro-6-{[(1R,5S,8R)-3-(propan-2-yl)-3-azabicyclo[3.2.1]octan-8-yl]oxy}cyclohexan-1-amine Reference example 102: (1R,6S)-2,2-difluoro-6-{[(1R,5S,8S)-3-(propan-2-yl)-3-azabicyclo[3.2.1]octan-8-yl]oxy}cyclohexan-1-amine Reference example 103: (1R,6S)-2,2-difluoro-6-{[(1R,3R,5S)-8-(propan-2-yl)-8-azabicyclo[3.2.1]octan-3-yl]oxy}cyclohexan-1-amine Reference example 104: (1R,6S)-2,2-difluoro-6-{[(1R,5S,6S)-3-(propan-2-yl)-3-azabicyclo[3.1.0]hexan-6-yl]oxy}cyclohexan-1-amine Reference example 105: (1R,6S)-2,2-difluoro-6-{[(3S)-1-(2-methylpropyl)pyrrolidin-3-yl]oxy}cyclohexan-1-amine Reference example 106: (1R,6S)-2,2-difluoro-6-{[(3R,4R)-4-methoxy-1-(propan-2-yl)pyrrolidin-3-yl]oxy}cyclohexan-1-amine Reference example 107: (1R,6S)-2,2-difluoro-6-{[4-methyl-1-(propan-2-yl)piperidin-4-yl]oxy}cyclohexan-1-amine Reference example 108: (1R,6S)-6-{[(3S)-1-(cyclopropylmethyl)pyrrolidin-3-yl]oxy}-2,2-difluorocyclohexan-1-amine Reference example 109: (1R,6S)-6-{[(3S)-1-(2,2-dimethylpropyl)pyrrolidin-3-yl]oxy}-2,2-difluorocyclohexan-1-amine Reference example 110: (1R,6S)-2,2-difluoro-6-({(3S)-1-[(1-methylcyclopropyl)methyl]pyrrolidin-3-yl}oxy)cyclohexan-1-amine Reference example 111: (1R,6S)-2,2-difluoro-6-({(3S)-1-[(1-fluorocyclopropyl)methyl]pyrrolidin-3-yl}oxy)cyclohexan-1-amine Reference example 112: (1R,6S)-2,2-difluoro-6-{[(3S)-1-{[1-(trifluoromethyl)cyclopropyl]methyl}pyrrolidin-3-yl]oxy}cyclohexan-1-amine Reference example 113: (1R,6S)-2,2-difluoro-6-{[(3S)-1-(2-fluoro-2-methylpropyl)pyrrolidin-3-yl]oxy}cyclohexan-1-amine Reference example 114: (1R,6S)-2,2-difluoro-6-({(3S)-1-[(3-methyloxetan-3-yl)methyl]pyrrolidin-3-yl}oxy)cyclohexan-1-amine

Reference Examples 115-118

The compounds of Reference examples 115-118 shown in the table below were prepared in the same manner as Reference example 8, by using the appropriate starting compound (Material A) instead of Compound 26 at Step (i) in Reference example 8, and each appropriate starting compound (Material B) instead of cyclopropane-carboxylic acid at Step (iii) in Reference example 8.

Reference example 115: 4-{5-[(1S,2S)-2-fluorocyclopropyl]-1,2,4-oxadiazol-3-yl}-4-methylpiperidine Reference example 116: 4-{5-[(1R,2R)-2-fluorocyclopropyl]-1,2,4-oxadiazol-3-yl}-4-methylpiperidine Reference example 117: 4-(5-cyclobutyl-1,2,4-oxadiazol-3-yl)-4-methylpiperidine monohydrochloride Reference example 118: 4-ethyl-4-{5-[(1S,2S)-2-fluorocyclopropyl]-1,2,4-oxadiazol-3-yl}piperidine

| Reference example | Material A | Material B | Chemical structure | Instrumental analytical data |
|---|---|---|---|---|
| 115 | | | 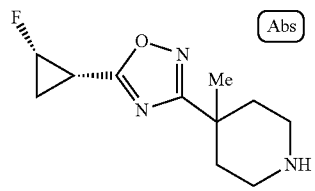 [SMILES: CC1(c2noc([C@@H]3C[C@@H]3F)n2)CCNCC1] | LCMS: [M + H]⁺/Rt (min): 226/0.29 (Method C) |
| 116 | | | 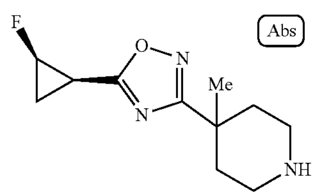 [SMILES: CC1(c2noc([C@H]3C[C@H]3F)n2)CCNCC1] | LCMS: [M + H]⁺/Rt (min): 226/0.29 (Method C) |
| 117 | | | 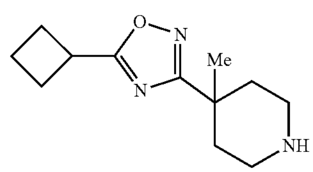 [SMILES: CC1(c2noc(C3CCC3)n2)CCNCC1] | LCMS: [M + H]⁺/Rt (min): 222/0.43 (Method C) |
| 118 | | | 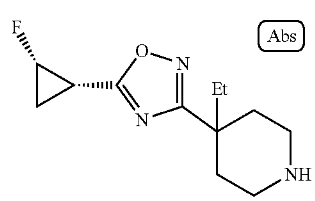 [SMILES: CCC1(c2noc([C@@H]3C[C@@H]3F)n2)CCNCC1] | LCMS: [M + H]⁺/Rt (min): 240/0.39 (Method C) |

Reference Example 119

(1R,6S)-2,2-Difluoro-6-{[2-(propan-2-yl)pyrimidin-4-yl]oxy}cyclohexan-1-amine

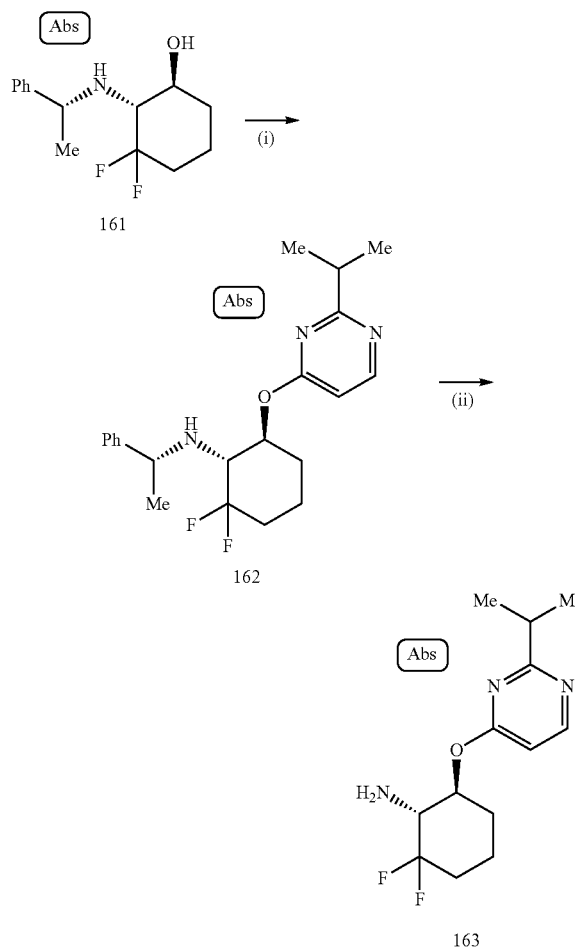

Step (i):

To a solution of Compound 161 (148 mg) known in literature in THF (3 ml) were added sodium hydride (55%, 30 mg) at 0° C., and then 4-chloro-2-(propan-2-yl)pyrimidine. The reaction solution was warmed to room temperature and stirred. After the reaction was completed, water was added to the reaction mixture, and the mixture was extracted with chloroform. The organic layer was dried over anhydrous sodium sulfate, concentrated in vacuo, and then the obtained residue was purified by silica gel column chromatography (eluate: hexane/ethyl acetate) to give the title compound 162 (209 mg).

Step (ii):

To a solution of Compound 162 (113 mg) in ethyl acetate (2 mL) was added palladium hydroxide (17 mg) at room temperature, and the mixture was stirred under hydrogen atmosphere. After the reaction was terminated as judged by LC-MS, the reaction mixture was filtrated with Celite, and the filtrate was concentrated in vacuo to give the title compound 163 (33.5 mg).

LCMS: [M+H]$^+$/Rt (min): 272/0.47

Reference Example 120

(1R,6S)-2,2-Difluoro-N-methyl-6-[4-(propan-2-yl)piperazin-1-yl]cyclohexan-1-amine

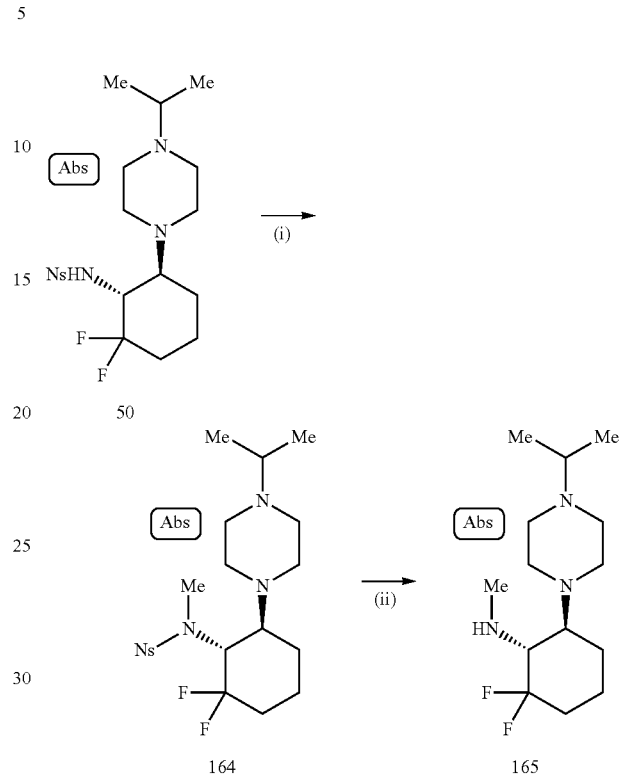

Step (i):

To a solution of Compound 50 (173 mg) in DMF (3 mL) were added cesium carbonate (253 mg) and methyl iodide (72 mg) at 0° C., and then the reaction mixture was warmed to room temperature and stirred. After the reaction was completed, water was added to the reaction mixture, and the mixture was extracted with diethy ether. The organic layer was dried over anhydrous sodium sulfate, concentrated in vacuo, and then the obtained residue was purified by amino silica gel column chromatography (eluate: hexane/ethyl acetate) to give the title compound 164 (159 mg).

Step (ii):

The title compound 165 (71 mg) was prepared in the same manner as Step (iii) in Reference example 18 by using Compound 164 (134 mg).

LCMS: [M+H]$^+$/Rt (min): 276/0.15

Reference Example 121 rac-(1S,6S)-2,2-Dimethyl-6-[4-(propan-2-yl)piperazin-1-yl]cyclohexan-1-amine

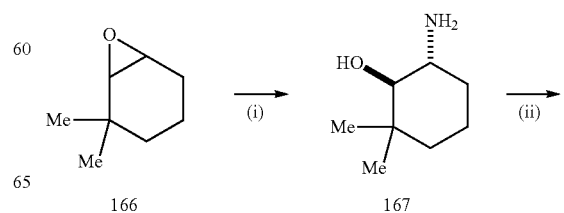

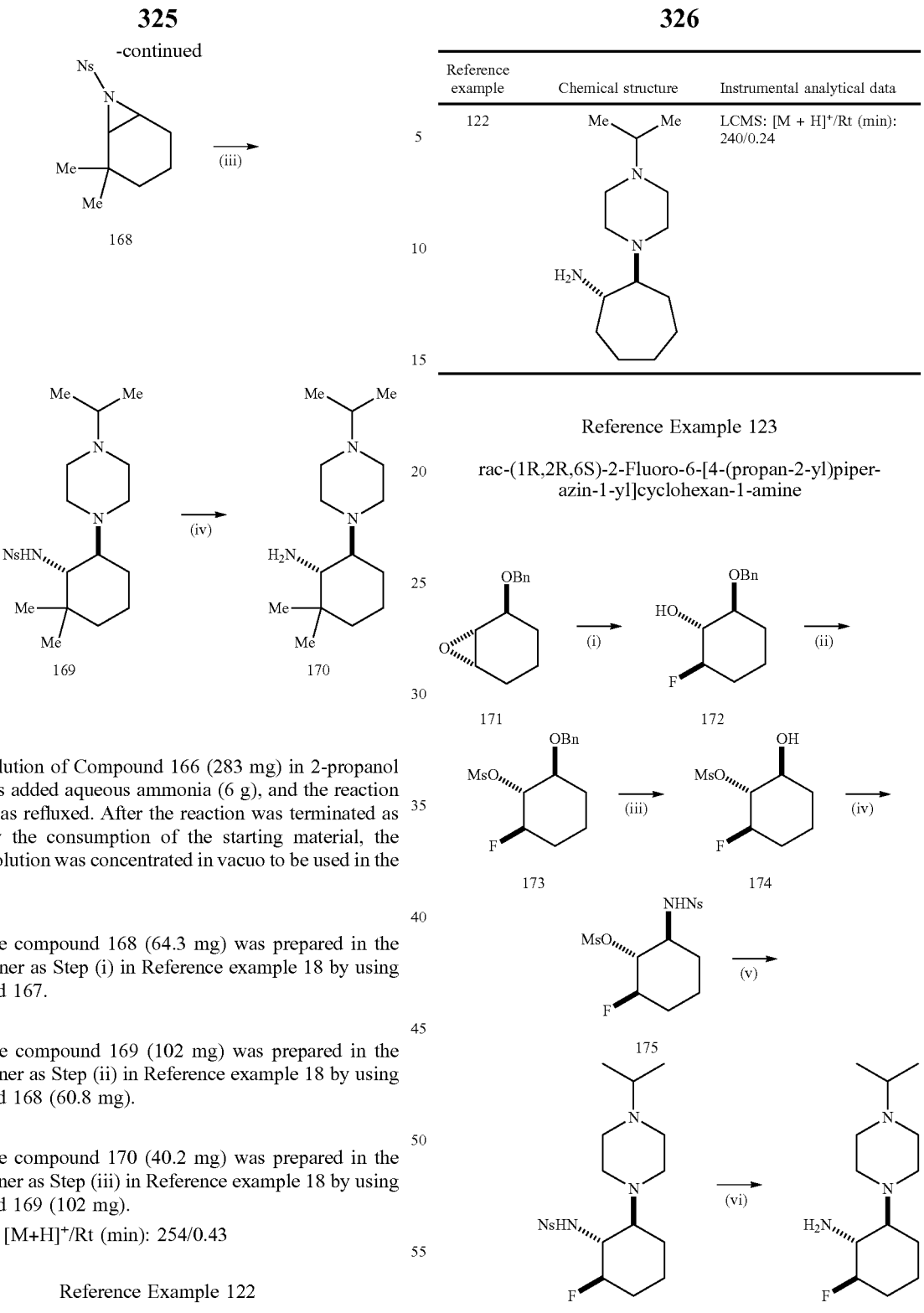

Step (i):

To a solution of Compound 166 (283 mg) in 2-propanol (8 ml) was added aqueous ammonia (6 g), and the reaction mixture was refluxed. After the reaction was terminated as judged by the consumption of the starting material, the reaction solution was concentrated in vacuo to be used in the next step.

Step (ii):

The title compound 168 (64.3 mg) was prepared in the same manner as Step (i) in Reference example 18 by using Compound 167.

Step (iii):

The title compound 169 (102 mg) was prepared in the same manner as Step (ii) in Reference example 18 by using Compound 168 (60.8 mg).

Step (iv):

The title compound 170 (40.2 mg) was prepared in the same manner as Step (iii) in Reference example 18 by using Compound 169 (102 mg).

LCMS: [M+H]⁺/Rt (min): 254/0.43

Reference Example 122 rac-(1S,2S)-2-[4-(Propan-2-yl)piperazin-1-yl]cyclo-heptan-1-amine

The compounds of Reference examples shown in the table below were prepared according to the process in the above Reference example 120, by using 8-oxabicyclo[5.1.0]octane instead of Compound 166 at Step (i) in Reference example 120.

| Reference example | Chemical structure | Instrumental analytical data |
|---|---|---|
| 122 | (structure) | LCMS: [M + H]⁺/Rt (min): 240/0.24 |

Reference Example 123 rac-(1R,2R,6S)-2-Fluoro-6-[4-(propan-2-yl)piper-azin-1-yl]cyclohexan-1-amine

Step (i):

A solution of Compound 171 (403 mg) and tetrabutylam-monium dihydrogen trifluoride (1.78 g) in toluene (1 mL) was heated at 150° C. with a microwave device. After the reaction was completed, water was added to the reaction mixture, and the mixture was extracted with diethyl ether. The organic layer was dried over anhydrous sodium sulfate, concentrated in vacuo, and then the obtained residue was purified by amino silica gel column chromatography (eluate: hexane/ethyl acetate) to give the title compound 172 (323 mg).

Step (ii):

Compound 172 (457 mg) was dissolved in THF (4.1 mL). To the solution were added triethylamine (1.13 mL) and methanesulfonyl chloride (0.318 mL) under ice temperature, and the reaction mixture was stirred. After the reaction was terminated as judged by the consumption of the starting material, water was added to the reaction mixture, and the mixture was extracted with ethyl acetate. The organic layer was dried over anhydrous sodium sulfate, concentrated in vacuo, and then the obtained residue was purified by amino silica gel column chromatography (eluate: hexane/ethyl acetate) to give the title compound 173 (578 mg).

Step (iii):

To a solution of Compound 173 (571 mg) in ethanol (3.5 mL) was added palladium hydroxide (20%, 133 mg) at room temperature, and the mixture was stirred under hydrogen atmosphere. After the reaction was completed, the reaction mixture was filtrated with Celite, and the filtrate was concentrated in vacuo. The obtained residue was purified by silica gel column chromatography (eluate: hexane/ethyl acetate) to give the title compound 174 (400 mg).

Step (iv):

Compound 174 (176 mg) was dissolved in 1,4-dioxane (3.5 mL). To the solution was added DBU (0.25 mL), and the reaction mixture was stirred at 85° C. After the reaction was terminated as judged by the consumption of the starting material, the reaction mixture was subsequently reacted in the same manner as Step (i) in Reference example 121, and methanesulfonylated in the same manner as the present Step (ii). Water was added to the reaction mixture, and the mixture was extracted with chloroform. The organic layer was dried over anhydrous sodium sulfate and concentrated in vacuo to give the title compound 175 (86 mg).

Step (v):

The title compound 176 (92.8 mg) was prepared according to the cyclization condition of Step (ii) in Reference example 121 followed by the same manner as Step (ii) in Reference example 18 by using Compound 175 (86 mg).

Step (vi):

The title compound 177 (35.1 mg) was prepared in the same manner as Step (iii) in Reference example 18 by using Compound 176 (86.1 mg).

LCMS: [M+H]$^+$/Rt (min): 244/0.19

Reference Example 124 rac-(1R,2S,6S)-2-Fluoro-6-[4-(propan-2-yl)piperazin-1-yl]cyclohexan-1-amine

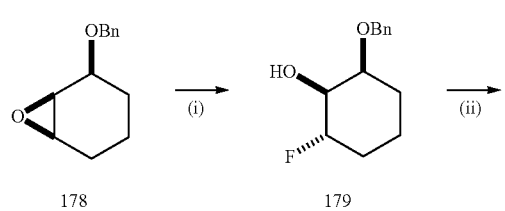

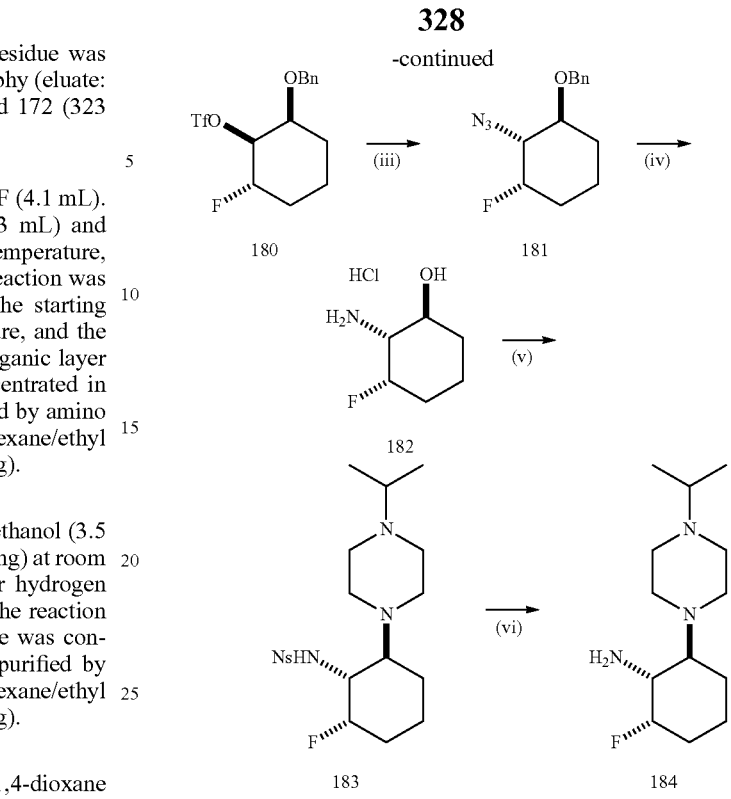

Step (i):

The title compound 179 (953 mg) was prepared in the same manner as Step (i) in Reference example 123 by using Compound 178 (929 mg).

Step (ii):

Compound 179 (283 mg) was dissolved in chloroform (6 mL). To the solution were added pyridine (0.51 mL) and trifluoromethanesulfonic anhydride (0.256 mL) under ice temperature, and the reaction mixture was stirred. After the reaction was terminated as judged by the consumption of the starting material, aqueous sodium bicarbonate was added to the reaction mixture, and the mixture was extracted with chloroform. The organic layer was dried over anhydrous sodium sulfate, concentrated in vacuo, and then the obtained residue was purified by silica gel column chromatography (eluate: hexane/ethyl acetate) to give the title compound 180 (424 mg).

Step (iii):

To a solution of Compound 180 (418 mg) in DMF (4 mL) was added sodium azide (229 mg), and the reaction solution was stirred at room temperature. After the reaction was completed, water was added to the reaction mixture, and the mixture was extracted with diethy ether. The organic layer was dried over anhydrous sodium sulfate, concentrated in vacuo, and then the obtained residue was purified by silica gel column chromatography (eluate: hexane/ethyl acetate) to give the title compound 181 (102 mg).

Step (iv):

To a solution of Compound 181 (102 mg) in ethanol (2 mL) was added palladium hydroxide (20%, 58 mg) at room temperature, and the mixture was stirred under hydrogen atmosphere. The reaction mixture was filtrated with Celite, and the filtrate was concentrated in vacuo. The obtained residue was dissolved in ethanol (2 mL) again, and aqueous hydrogen chloride (cyclopentylmethyl solution, 5 M, 0.327 mL) and palladium carbon (10%, 71 mg) were added thereto. The mixture was stirred under hydrogen atmosphere. After the reaction was completed, the reaction mixture was filtrated with Celite, and the filtrate was concentrated in vacuo to give the title compound 182 (76.8 mg).

Step (v):

The title compound 183 (69 mg) was prepared in the same manner as Step (i) and Step (ii) in Reference example 18 by using Compound 182 (103 mg).

Step (vi):

The title compound 184 (34.3 mg) was prepared in the same manner as Step (iii) in Reference example 18 by using Compound 183 (72 mg).

LCMS: [M+H]$^+$/Rt (min): 244/0.14

Reference Example 125

(1S,2R)-2-Amino-3,3-difluorocyclohexyl 4-(propan-2-yl)piperazine-1-carboxylate

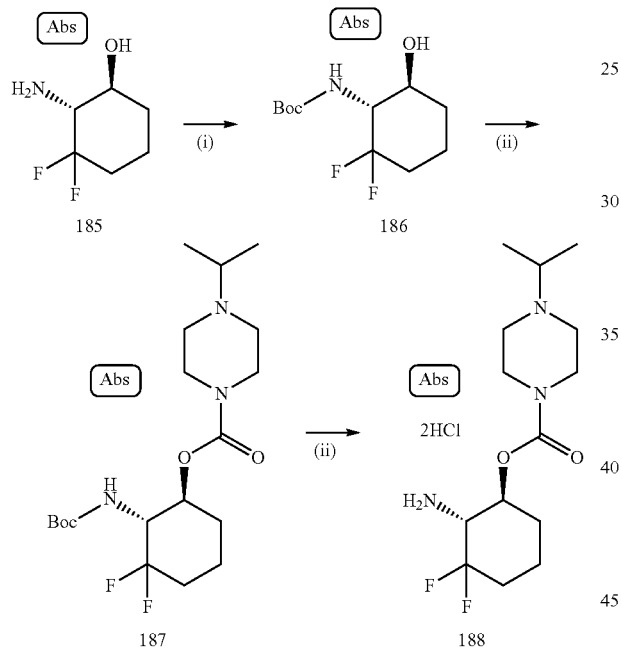

Step (i):

To a solution of Compound 185 known in literature in acetonitrile (3 mL) was added Boc$_2$O (238 mg), and the reaction solution was stirred at room temperature. After the reaction was completed, the reaction mixture was concentrated in vacuo, and the obtained residue was purified by silica gel column chromatography (eluate: hexane/ethyl acetate) to give the title compound 186 (216 mg).

Step (ii):

The title compound 187 (118 mg) was prepared in the same manner as Step (iii) in Reference example 2 by using Compound 186 (95.7 mg).

Step (iii):

The title compound 188 (99.7 mg) was prepared in the same manner as Step (iv) in Reference example 2 by using Compound 187 (118 mg).

LCMS: [M+H]$^+$/Rt (min): 306/0.25

Reference Example 126

N-{(1S,6S)-2,2-Difluoro-6-[1-(propan-2-yl)piperidine-4-sulfonyl]cyclohexyl}-4-nitrobenzene-1-sulfonamide

[化1]

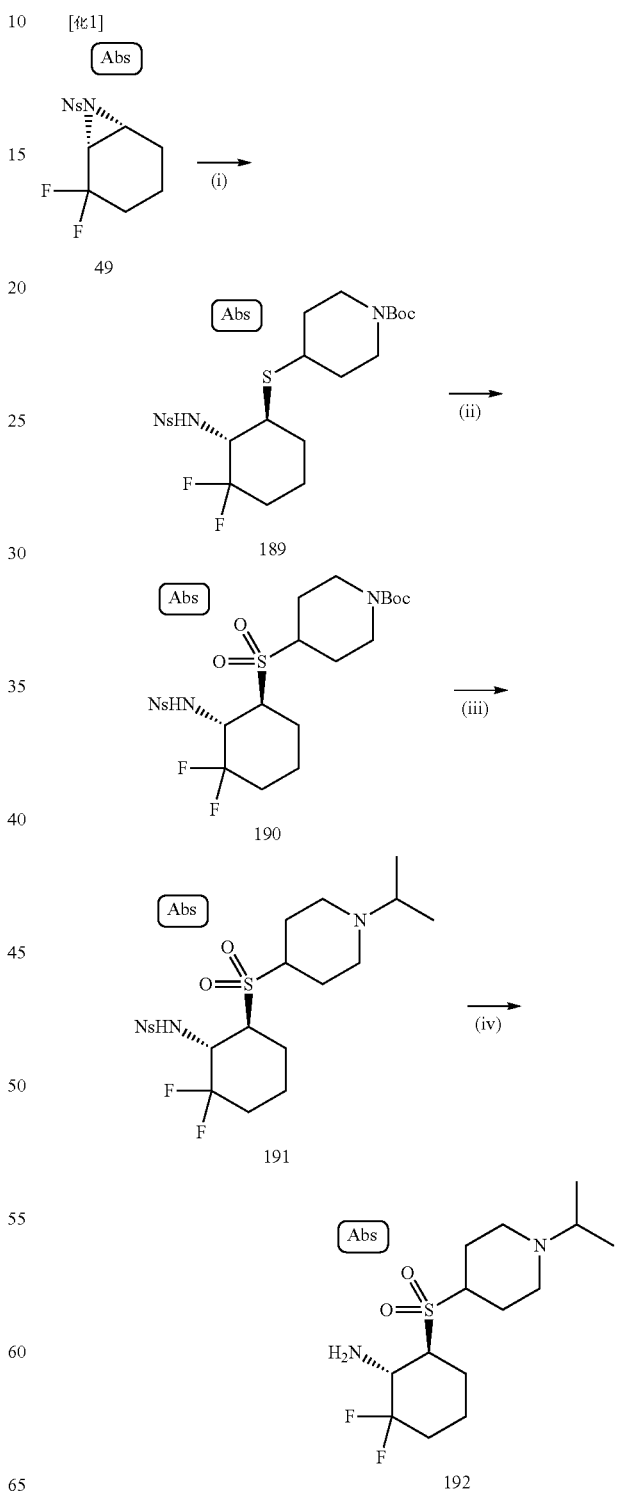

Step (i):

The title compound 189 (402 mg) was prepared in the same manner as Step (ii) in Reference example 18 by using Compound 49 (399 mg) and tert-butyl 4-sulfanylpiperidine-1-carboxylate (300 mg).

Step (ii):

To a solution of Compound 189 (210 mg) in chloroform (2 mL) was added m-CPBA (242 mg), and the reaction solution was stirred at room temperature. After the reaction was completed, aqueous sodium thiosulfate was added to the reaction mixture, and the mixture was extracted with chloroform. The organic layer was dried over anhydrous sodium sulfate, concentrated in vacuo, and then the obtained residue was purified by amino silica gel column chromatography (eluate: chloroform/methanol) to give the title compound 190 (250 mg).

Step (iii):

The title compound 191 (223 mg) was prepared in the same manner as Step (i) and Step (ii) in Reference example 53 by using Compound 190 (250 mg).

Step (iv):

The title compound 192 (102 mg) was prepared in the same manner as Step (iii) in Reference example 18 by using Compound 191 (223 mg).

LCMS: $[M+H]^+$/Rt (min): 325/0.21

Test 1: Evaluation of Agonist Activity for Orexin Receptor Type 2

Human orexin receptor type 2 and apoaequorin were transiently expressed in CHO cells, and the agonist activity was evaluated based on intracellular calcium mobilization with ligand stimulation. The CHO cells transiently-expressed human orexin receptor type 2 and apoaequorin were seeded on a 384-well plate by 2,000 cells/well, and then incubated for 16-22 hours. After the plate was returned to room temperature, Coelenterazine hcp (final concentration: 1 µM) was added to the plate, and the plate was allowed to stand at room temperature for 2 hours. And then, Orexin A (PEPTIDE INSTITUTE, INC., Lot. 641114) or each test compound was added to the plate, and the luminescence of the cells was measured with FDSS7000 (Hamamatsu Photonics K.K.), wherein Orexin A and each test compound were dissolved in DMSO (final concentration: 0.1%), and diluted with a buffer (Hanks, 20 mM HEPES,0.1% BSA). The agonist activity of each test compound for orexin receptor type 2 was calculated as relative percentage of luminescence for the luminescence (100%) of Orexin A (100 pM).

Result:

The results that each compound obtained in Examples was evaluated about the agonist activity for orexin receptor type 2 showed that the present compounds have agonist activity for orexin receptor type 2. Each agonist activity of the example compounds is shown in the table below as relative percentage of luminescence for the luminescence (100%) of Orexin A (100 µM).

| Example | agonist activity (%) |
|---|---|
| 1 | 137 |
| 2 | 58 |
| 3 | 67 |
| 4 | 62 |
| 5 | 103 |
| 6 | 43 |
| 7 | 75 |
| 8 | 207 |
| 9 | 207 |
| 10 | 213 |
| 11 | 211 |
| 12 | 178 |
| 13 | 56 |
| 14 | 178 |
| 15 | 62 |
| 16 | 39 |
| 17 | 72 |
| 18 | 73 |
| 19 | 167 |
| 20 | 160 |
| 21 | 153 |
| 22 | 163 |
| 23 | 104 |
| 24 | 210 |
| 25 | 165 |
| 26 | 198 |
| 27 | 162 |
| 28 | 190 |
| 29 | 109 |
| 30 | 128 |
| 31 | 168 |
| 32 | 176 |
| 33 | 123 |
| 34 | 183 |
| 35 | 165 |
| 36 | 114 |
| 37 | 45 |
| 38 | 142 |
| 39 | 157 |
| 41 | 23 |
| 42 | 141 |
| 43 | 146 |
| 44 | 148 |
| 45 | 150 |
| 46 | 136 |
| 47 | 163 |
| 48 | 156 |
| 49 | 151 |
| 50 | 154 |
| 51 | 149 |
| 52 | 113 |
| 53 | 143 |
| 54 | 146 |
| 55 | 95 |
| 56 | 140 |
| 57 | 155 |
| 58 | 150 |
| 59 | 164 |
| 60 | 151 |
| 61 | 169 |
| 62 | 174 |
| 63 | 149 |
| 64 | 204 |
| 65 | 155 |
| 66 | 144 |
| 67 | 175 |
| 68 | 156 |
| 69 | 161 |
| 70 | 141 |
| 71 | 199 |
| 72 | 146 |
| 73 | 185 |
| 74 | 174 |
| 75 | 141 |
| 76 | 145 |
| 77 | 158 |

| Example | agonist activity (%) |
|---|---|
| 78 | 36 |
| 79 | 191 |
| 80 | 178 |
| 81 | 57 |

Test 2: Evaluation of Agonist Activity for Orexin Receptor Type 2

Human orexin receptor type 2 and apoaequorin were transiently expressed in CHO cells, and the agonist activity was evaluated, based on intracellular calcium mobilization with ligand stimulation. The CHO cells transiently-expressed human orexin receptor type 2 and apoaequorin were seeded on a 384-well plate by 2,000 cells/well, and then incubated for 16-22 hours. After the plate was returned to room temperature, Coelenterazine hcp (final concentration: 1 µM) was added to the plate, and the plate was allowed to stand at room temperature for 2 hours. And then, Orexin A (PEPTIDE INSTITUTE, INC., Lot. 671009) or each test compound was added to the plate, and the luminescence of the cells was measured with FDSS7000 (Hamamatsu Photonics K.K.), wherein Orexin A and each test compound were dissolved in DMSO (final concentration: 0.1%), and diluted with a buffer (Hanks, 20 mM HEPES, 0.1% BSA). The agonist activity of each test compound for orexin receptor type 2 was calculated as relative percentage of luminescence for the luminescence (100%) of Orexin A (100 pM).

Result:

The results that each compound obtained in Examples was evaluated about the agonist activity for orexin receptor type 2 showed that the present compounds have agonist activity for orexin receptor type 2. Each agonist activity of the example compounds is shown in the table below as relative percentage of luminescence for the luminescence (100%) of Orexin A (100 pM).

| Example | agonist activity (%) |
|---|---|
| 82 | 69 |
| 83 | 371 |
| 84 | 372 |
| 85 | 360 |
| 86 | 367 |
| 87 | 226 |
| 88 | 201 |
| 89 | 0 |
| 90 | 112 |
| 91 | 243 |
| 92 | 16 |
| 93 | 365 |
| 94 | 382 |
| 95 | 447 |
| 96 | 493 |
| 97 | 486 |
| 98 | 271 |
| 99 | 499 |
| 100 | 340 |
| 101 | 326 |
| 102 | 374 |
| 103 | 369 |
| 104 | 289 |
| 105 | 359 |
| 106 | 220 |
| 107 | 363 |
| 108 | 292 |
| 109 | 359 |
| 110 | 380 |
| 111 | 382 |
| 112 | 376 |
| 113 | 374 |
| 114 | 438 |
| 115 | 403 |
| 116 | 488 |
| 117 | 465 |
| 118 | 524 |
| 119 | 378 |
| 120 | 387 |
| 121 | 379 |
| 122 | 369 |
| 123 | 366 |
| 124 | 391 |
| 125 | 402 |
| 126 | 394 |
| 127 | 367 |
| 128 | 402 |
| 129 | 435 |
| 130 | 450 |
| 131 | 461 |
| 132 | 166 |
| 133 | 506 |
| 134 | 456 |
| 135 | 396 |
| 136 | 346 |
| 137 | 376 |
| 138 | 385 |
| 139 | 351 |
| 140 | 249 |
| 141 | 405 |
| 142 | 407 |
| 143 | 444 |
| 144 | 399 |
| 145 | 403 |
| 146 | 23 |
| 147 | 373 |
| 148 | 391 |
| 149 | 419 |
| 150 | 437 |
| 151 | 368 |
| 152 | 470 |
| 153 | 350 |
| 154 | 493 |
| 155 | 167 |
| 156 | 323 |
| 157 | 392 |
| 158 | 389 |
| 159 | 392 |
| 160 | 410 |
| 161 | 374 |

INDUSTRIAL APPLICABILITY

The compounds of the present invention exhibit a potent agonist activity for orexin receptor, thereby they are useful as a medicament for treating or preventing narcolepsy, idiopathic hypersomnia, hypersomnia, sleep apnea syndrome, narcolepsy syndrome involving narcolepsy-like symptom, hypersomnia associated with Parkinson's disease, hypersomnia associated with dementia with Lewy body, etc.

The invention claimed is:
1. A compound or a pharmaceutically acceptable salt thereof, which is selected from the group consisting of:

a) 4-(5-cyclopropyl-1,2,4-oxadiazol-3-yl)-N-{(1R,6S)-2,2-difluoro-6-[4-(propan-2-yl)pierazin-1-yl]cyclohexyl}-4-methylpiperidine-1-carboxamide having the formula:

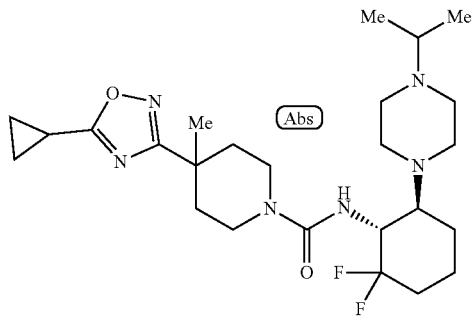 [SMILES: CC(C)N1CCN([C@H]2CCCC(F)(F)[C@@H]2NC(=O)N2CCC(C)(c3noc(C4CC4)n3)CC2)CC1]

b) N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide having the formula:

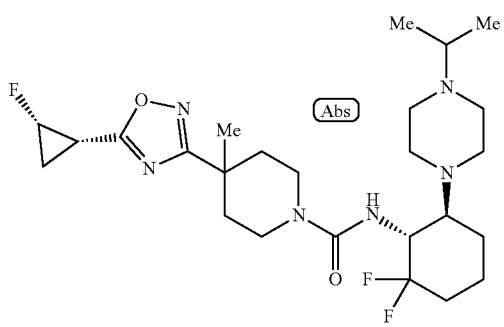 [SMILES: CC(C)N1CCN([C@H]2CCCC(F)(F)[C@@H]2NC(=O)N2CCC(C)(c3noc([C@@H]4C[C@@H]4F)n3)CC2)CC1]

c) N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl} piperidine-1-carboxamide having the formula:

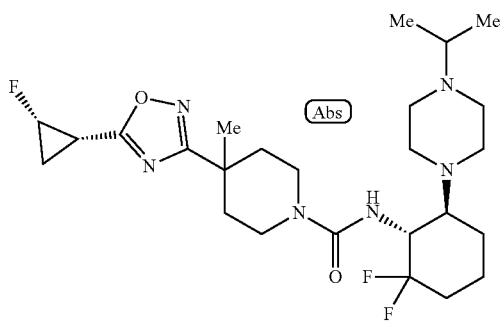 [SMILES: CC(C)N1CCN([C@H]2CCCC(F)(F)[C@@H]2NC(=O)N2CCC(C)(c3noc([C@@H]4C[C@@H]4F)n3)CC2)CC1]

d) N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide having the formula:

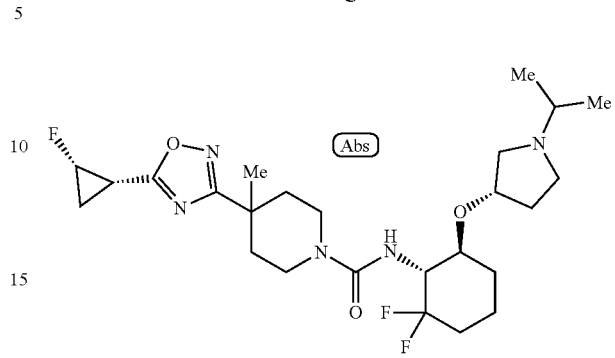

e) N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide having the formula:

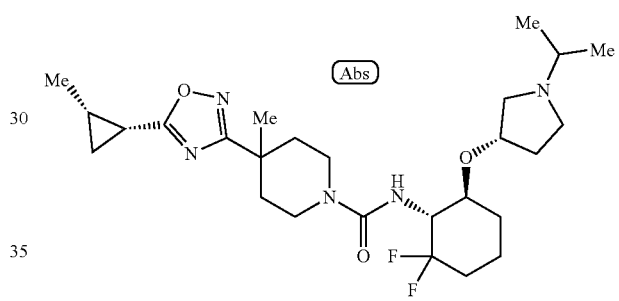

f) N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide having the formula:

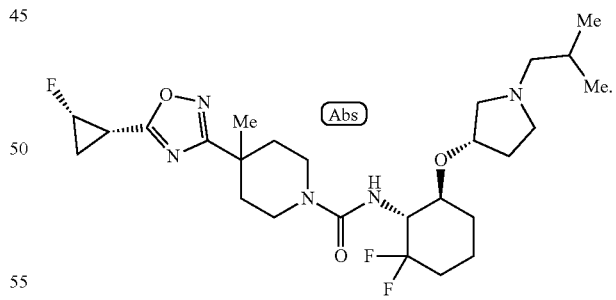

2. The compound of claim 1 which is 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide, or a pharmaceutically acceptable salt thereof.

3. The compound of claim 1 which is N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide, or a pharmaceutically acceptable salt thereof.

4. The compound of claim 1 which is N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide, or a pharmaceutically acceptable salt thereof.

5. The compound of claim 1 which is N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

6. The compound of claim 1 which is N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide, or a pharmaceutically acceptable salt thereof.

7. The compound of claim 1 which is N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

8. A pharmaceutical composition comprising a compound or a pharmaceutically acceptable salt thereof, and a pharmaceutically acceptable additive agent, wherein the compound is selected from the group consisting of:

a) 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide having the formula:

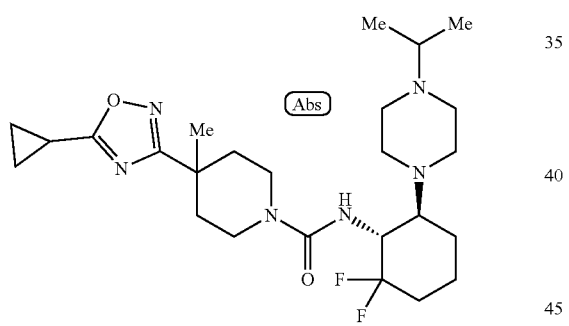

b) N-{(1R,6S)-2,2-difluoro-6-[4-(propan-2-yl) piperazin-1-yl]cyclohexyl}-4-{5-[(1S,2S)-2-fluorocyclopropyl]-1,2,4-oxadiazol-3-yl}-4-methylpiperidine-1-carboxamide having the formula:

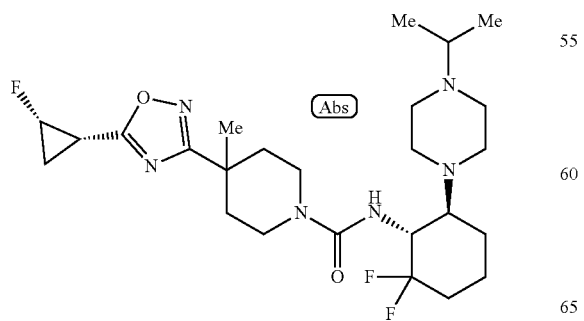

c) N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl} piperidine-1-carboxamide having the formula:

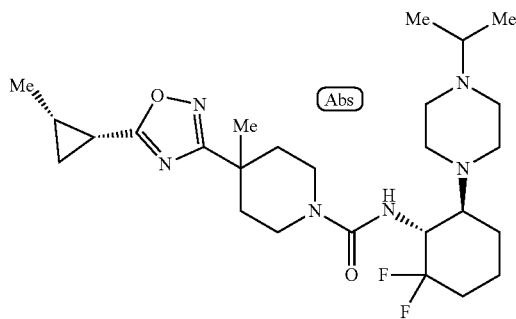 [SMILES: CC(C)N1CCN([C@H]2CCCC(F)(F)[C@@H]2NC(=O)N2CCC(C)(c3noc([C@@H]4C[C@@H]4C)n3)CC2)CC1]

d) N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide having the formula:

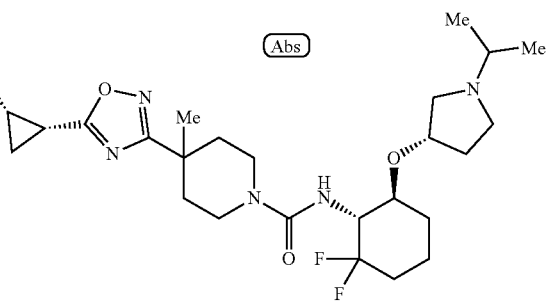

e) N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide having the formula:

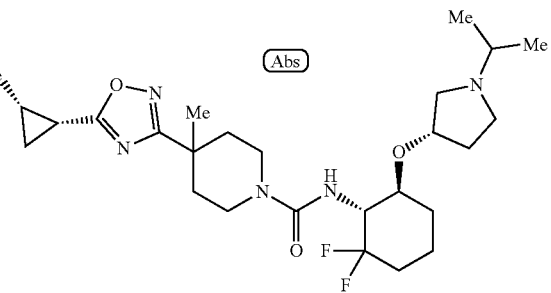

f) N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide having the formula:

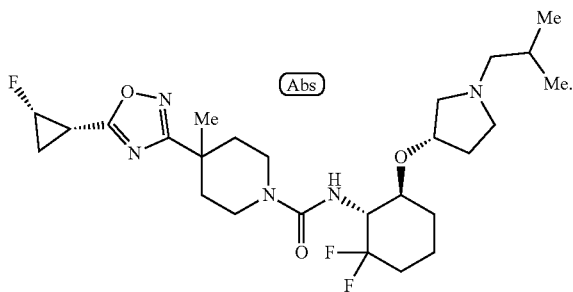 [SMILES: CC(C)CN1CC[C@H](O[C@H]2CCCC(F)(F)[C@@H]2NC(=O)N2CCC(C)(c3noc([C@@H]4C[C@@H]4F)n3)CC2)C1]

9. The pharmaceutical composition of claim 8 wherein the compound is 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide, or a pharmaceutically acceptable salt thereof.

10. The pharmaceutical composition of claim 8 wherein the compound is N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide, or a pharmaceutically acceptable salt thereof.

11. The pharmaceutical composition of claim 8 wherein the compound is N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide, or a pharmaceutically acceptable salt thereof.

12. The pharmaceutical composition of claim 8 wherein the compound is N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

13. The pharmaceutical composition of claim 8 wherein the compound is N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide, or a pharmaceutically acceptable salt thereof.

14. The pharmaceutical composition of claim 8 wherein the compound is N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

15. A method for treating narcolepsy, idiopathic hypersomnia, hypersomnia, sleep apnea syndrome, narcolepsy syndrome involving narcolepsy-like symptom, hypersomnia associated with Parkinson's disease, or hypersomnia associated with dementia with Lewy body, comprising administering a therapeutically effective amount of the compound of claim 1 or a pharmaceutically acceptable salt thereof to a patient in need thereof.

16. The method of claim 15 wherein the compound is 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide, or a pharmaceutically acceptable salt thereof.

17. The method of claim 15 wherein the compound is N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide, or a pharmaceutically acceptable salt thereof.

18. The method of claim 15 wherein the compound is N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide, or a pharmaceutically acceptable salt thereof.

19. The method of claim 15 wherein the compound is N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

20. The method of claim 15 wherein the compound is N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide, or a pharmaceutically acceptable salt thereof.

21. The method of claim 15 wherein the compound is N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

22. A method for treating narcolepsy comprising administering a therapeutically effective amount of the compound of claim 1 or a pharmaceutically acceptable salt thereof to a patient in need thereof.

23. The method of claim 22 wherein the compound is 4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide, or a pharmaceutically acceptable salt thereof.

24. The method of claim 22 wherein the compound is N-{(1R,6S)-2,2-difluoro-6-[4-(propan-2-yl)piperazin-1-yl]cyclohexyl}-4-{5-[(1S,2S)-2-fluorocyclopropyl]-1,2,4-oxadiazol-3-yl}-4-methylpiperidine-1-carboxamide, or a pharmaceutically acceptable salt thereof.

25. The method of claim 22 wherein the compound is N-{(1R,6S)-2,2-difluoro-6-[4-(propan-2-yl)piperazin-1-yl]cyclohexyl}-4-methyl-4-{5-[(1R,2S)-2-methylcyclopropyl]-1,2,4-oxadiazol-3-yl}piperidine-1-carboxamide, or a pharmaceutically acceptable salt thereof.

26. The method of claim 22 wherein the compound is N-[(1R,6S)-2,2-difluoro-6-{[(3S)-1-(propan-2-yl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

27. The method of claim 22 wherein the compound is N-[(1R,6S)-2,2-difluoro-6-{[(3S)-1-(propan-2-yl)pyrrolidin-3-yl]oxy}cyclohexyl]-4-methyl-4-{5-[(1R,2S)-2-methylcyclopropyl]-1,2,4-oxadiazol-3-yl}piperidine-1-carboxamide, or a pharmaceutically acceptable salt thereof.

28. The method of claim 22 wherein the compound is N-[(1R,6S)-2,2-difluoro-6-{[(3S)-1-(2-methylpropyl)pyrrolidin-3-yl]oxy}cyclohexyl]-4-{5-[(1S,2S)-2-fluorocyclopropyl]-1,2,4-oxadiazol-3-yl}-4-methylpiperidine-1-carboxamide, or a pharmaceutically acceptable salt thereof.

* * * * *

UNITED STATES PATENT AND TRADEMARK OFFICE
CERTIFICATE OF CORRECTION

PATENT NO. : 11,352,357 B2
APPLICATION NO. : 17/526722
DATED : June 7, 2022
INVENTOR(S) : Eiji Ideue et al.

Page 1 of 1

It is certified that error appears in the above-identified patent and that said Letters Patent is hereby corrected as shown below:

In the Claims

Column 335, Lines 1-4, "4-(5-cyclopropyl-1,2,4-oxadiazol-3-yl)-N-{(1R,6S)-2,2-difluoro-6-[4-(propan-2-yl)pierazin -1-yl]cyclohexyl}-4-methylpiperidine-1-carboxamide" should read --4-(5-cyclopropyl-1,2,4-oxadiazol-3-yl)-N-{(1R,6S)-2,2-difluoro-6-[4-(propan-2-yl)piperazin-1-yl]cyclohexyl}-4-methylpiperidine-1-carboxamide--.

Column 335, Lines 52-66, " 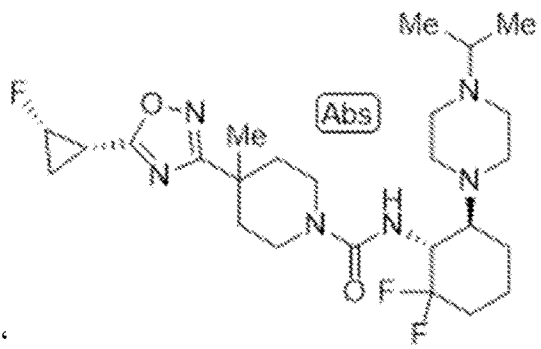 " should read

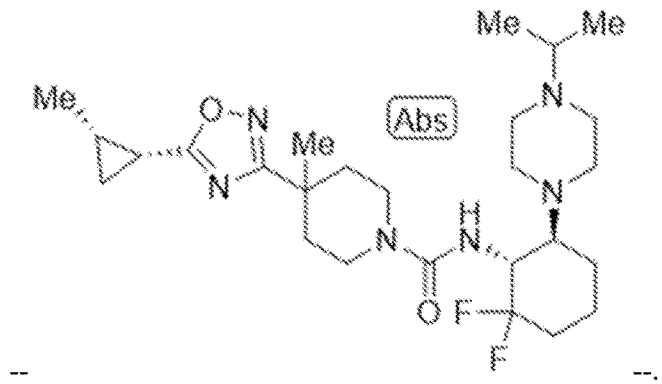

--.

Signed and Sealed this
Third Day of September, 2024

Katherine Kelly Vidal
*Director of the United States Patent and Trademark Office*